(12) United States Patent
Hennessy et al.

(10) Patent No.: US 9,517,259 B2
(45) Date of Patent: *Dec. 13, 2016

(54) WEST NILE VIRUS VACCINE

(71) Applicants: Kristina J. Hennessy, Leawood, KS (US); Phillip Wayne Hayes, Maurice, IA (US)

(72) Inventors: Kristina J. Hennessy, Leawood, KS (US); Phillip Wayne Hayes, Maurice, IA (US)

(73) Assignee: Boehringer Ingelheim Vetmedica, Inc., St. Joseph, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/250,436

(22) Filed: Apr. 11, 2014

(65) Prior Publication Data

US 2014/0328877 A1    Nov. 6, 2014

Related U.S. Application Data

(62) Division of application No. 12/937,504, filed as application No. PCT/US2009/055564 on Aug. 31, 2009, now Pat. No. 8,821,889.

(60) Provisional application No. 61/093,081, filed on Aug. 29, 2008, provisional application No. 61/117,086, filed on Nov. 21, 2008.

(51) Int. Cl.

| A61K 39/12 | (2006.01) |
|---|---|
| C12N 7/00 | (2006.01) |
| A61K 39/08 | (2006.01) |
| A61K 39/193 | (2006.01) |
| C07K 14/005 | (2006.01) |
| A61K 39/00 | (2006.01) |

(52) U.S. Cl.
CPC ............... *A61K 39/12* (2013.01); *A61K 39/08* (2013.01); *A61K 39/193* (2013.01); *C07K 14/005* (2013.01); *C12N 7/00* (2013.01); *A61K 2039/521* (2013.01); *A61K 2039/5252* (2013.01); *A61K 2039/552* (2013.01); *A61K 2039/55566* (2013.01); *A61K 2039/70* (2013.01); *C12N 2710/16734* (2013.01); *C12N 2760/16134* (2013.01); *C12N 2770/24122* (2013.01); *C12N 2770/24134* (2013.01); *C12N 2770/36134* (2013.01)

(58) Field of Classification Search
None
See application file for complete search history.

(56) References Cited

U.S. PATENT DOCUMENTS

| 6,235,282 | B1 | 5/2001 | Riviere et al. | |
|---|---|---|---|---|
| 6,812,219 | B2 | 11/2004 | LaColla et al. | |
| 6,878,372 | B2 | 4/2005 | Monath et al. | |
| 7,101,861 | B2 | 9/2006 | Sommadossi et al. | |
| 7,105,493 | B2 | 9/2006 | Sommadossi et al. | |
| 7,148,206 | B2 | 12/2006 | Sommadossi et al. | |
| 7,153,513 | B2 * | 12/2006 | Chu | 424/218.1 |
| 7,163,929 | B2 | 1/2007 | Sommadossi et al. | |
| 7,227,011 | B2 | 6/2007 | Chang | |
| 7,244,430 | B2 | 7/2007 | Throsby et al. | |
| 7,425,437 | B2 | 9/2008 | UytdeHaag et al. | |
| 7,445,787 | B2 | 11/2008 | Chu | |
| 7,455,842 | B2 | 11/2008 | Yamshchikov | |
| 7,459,163 | B2 | 12/2008 | Yamshchikov | |
| 7,482,017 | B2 | 1/2009 | Barrett et al. | |
| 7,507,415 | B2 | 3/2009 | Arroyo et al. | |
| 7,556,812 | B2 | 7/2009 | Tangy et al. | |
| 7,585,621 | B2 | 9/2009 | Beall et al. | |
| 8,133,712 | B2 | 3/2012 | Sterner et al. | |
| 8,821,889 | B2 * | 9/2014 | Hennessy | 424/201.1 |
| 2003/0091595 | A1 | 5/2003 | Chu | |
| 2003/0104008 | A1 | 6/2003 | Loosmore et al. | |
| 2003/0148261 | A1 | 8/2003 | Fikrig et al. | |
| 2008/0279891 | A1 | 11/2008 | Johnston et al. | |
| 2009/0130146 | A1 | 5/2009 | Broeker | |
| 2011/0159033 | A1 | 6/2011 | Hennessy et al. | |
| 2014/0328877 | A1 * | 11/2014 | Hennessy et al. | 424/218.1 |

FOREIGN PATENT DOCUMENTS

| WO | 02067899 A1 | 9/2002 |
|---|---|---|
| WO | 03061555 A2 | 7/2003 |
| WO | 2007002470 A2 | 1/2007 |
| WO | 2007051763 A1 | 5/2007 |
| WO | 2010025469 A1 | 3/2010 |

OTHER PUBLICATIONS

Malkinson et al., "Use of Live and Inactivated Vaccines in the Control of West Nile Fever in Domestic Geese". Annals of the New York Academy of Sciences, 2001, pp. 255-261.
Wang et al., "Immunization of Mice Again West Nile Virus with Recombinant Envelope Protein".The Journal of Immunology, vol. 167, 2001, pp. 5273-5277.
"West Nile Innovator + EWT"., Ft. Dodge Material Safety Data Sheet, Fort Dodge Animal Health—A Division of Wyeth Corporation, Jan. 23, 2004, pp. 1-5.
"West Nile Innovator + VEWT"., Fort Dodge Material Safety Data Sheet, Fort Dodge Animal Health, Apr. 10, 2007, pp. 1-6.
Blood-Horse Staff, "Fort Dodge Releases West Nile DNA Vaccine"., BloodHorse.com, Jul. 19, 2005, 1 page. [Accessed at http://www.bloodhorse.com/horse-racing/articles/29112/fort-dodge-releases-west-nile- . . . on Apr. 9, 2013.]

(Continued)

Primary Examiner — Shanon A Foley
(74) Attorney, Agent, or Firm — Michael P. Morris; Joyce L. Morrison

(57) ABSTRACT

The invention provides for immunogenic compositions against West Nile Virus. The immunogenic compositions, in alternate embodiments, also include other equine pathogens. The West Nile Virus composition of the present invention advantageously provides for protection against North American Dominant West Nile Virus strains or isolates.

4 Claims, 120 Drawing Sheets

(56) References Cited

OTHER PUBLICATIONS

Cohen, Bettina, "The Golden Age of Horse Health". BloodHorse.com, Nov. 22, 2004, 4 pages. [Accessed at: http://www.bloodhorse.com/horse-racing/articles/25516/the-golden-age-of-horse-healt . . . on Apr. 8, 2013.]
Davis et al., "Phylogenetic analysis of North American West Nile virus isolates, 2001-2004: Evidence for the emergence of a dominant genotype". 2005, Virology, vol. 342, pp. 252-265.
Ebel et al., "Genetic and Phenotypic Variation of West Nile Virus in New York, 2000-2003". 2004, American Journal of Tropical Medicine and Hygiene, vol. 71, No. 4, pp. 493-500.
Eckels et al., "Formalin-Inactivated Whole Virus and Recombinant Subunit Flavivirus Vaccines". 2003, Advances in Virus Research, vol. 61, pp. 395-418.
Hilgers et al., "Alkyl-esters of polyacrylic acid as vaccine adjuvants". 1998, Vaccine, vol. 16, No. 16, pp. 1575-1581.
Imam et al., "Challenge of Hamsters With Japanese B, St. Louis and Murray Valley Encephalitis Viruses After Immunization by West Nile Infection Plus Specific Vaccine". 1957, The Journal of Immunology, vol. 79, pp. 243-252.
International Search Report for PCT/US2009/055564 mailed Dec. 3, 2009.
Konishi et al., "Dengue tetravalet DNA vaccine inducing neutralizing antibody and anamnestic responses to four serotypes in mice". 2006, Vaccine, vol. 24, pp. 2200-2207.
Kramer et al., "West Nile virus"., The Lancet Neurology, vol. 6, 2007, pp. 171-181.
Lanciotti et al., "Origin of the West Nile Virus Responsible for the Outbreak of Encephalitis in the Northeastern United States". Science, vol. 286, No. 17, Dec. 1999, pp. 2333-2337. [Accessed at www.sciencemag.org on Dec. 20, 2010].
Minke et al., "Equine viral vaccines: the past, the present and future". Veterinary Research, vol. 35, 2004, pp. 425-443.
Price et al., "Live and Inactivated Vaccines of Group B Arboviruses: Role of Neutralizing Antibody and Serum Protective Factor". Jun. 1969, Nature, vol. 222, pp. 1294-1295.
Snapinn et al., "Declining Growth Rate of West Nile Virus in North America". Mar. 2007, Journal of Virology, vol. 81, No. 5, pp. 2531-2534.
Steele et al., "Pathology of Fatal West Nile Virus Infections in Native and Exotic Birds during the 1999 Outbreak in New York City, New York". 2000, Veterinary Pathology, vol. 37, pp. 208-224.
Van Hoof, J. "Manufacturing Issues Related to Combining Different Antigens: An Industry Perspective". Clinical Infectious Diseases, Suppl. 4, vol. 33, 2001, p. S346-S350.
Wilson, J.H., "Vaccine Efficacy and Controversies". American Asssociation of Equine Practicioners Annual Proceedings, vol. 51, 2005, pp. 409-420.
Written Opinion of the International Searching Authority for PCT/US2009/055564 mailed Dec. 3, 2009.
Anderson et al., "Isolation of West Nile Virus from Mosquitoes, Crows and a Cooper's Hawk in Connecticut". Science, vol. 286, Dec. 1999, pp. 2331-2333.
Lustig et al., "A Live Attenuated West Nile Virus Strain as a Potential Veterinary Vaccine". Viral Immunology, vol. 13, No. 4, 2000, pp. 401-410.
Monath et al., "West Nile Virus Vaccine". Current Drug Targets-Infectious Disorders, vol. 1, No. 1, 2001, pp. 37-50.
Arroyo et al., "ChimerVax-West Nile Virus Live-Attenuated Vaccine: Preclinical Evaluation of Safety, Immogenicity, and Efficacy". Journal of Virology, vol. 78, No. 22, Nov. 2004, pp. 12497-12507.
Liljeqvist et al., "Production of Recombinant Subunit Vaccines: Protein Immunogens, Live Delivery Systems and Nucleic Acid Vaccines". Journal of Biotechnology, vol. 73, 1999, pp. 1-33.
Dauphin et al., "West Nile Virus: Recent Trends in Diagnosis and Vaccine Development". Vaccine, vol. 25, 2007, pp. 5563-5576.
Hall et al., "West Nile Virus Vaccines". Expert Opinion on Biological Therapy, vol. 4, No. 8, 2004, pp. 1295-1305.
"Scientific Discussion". EMEA, 2008, pp. 1-17.
Moudy et al., "A Newly Emergent Genotype of West Nile Virus is transmitted Earlier and More Efficiently by Culex Mosquitoes". The American Journal of Tropical Medicine and Hygiene, vol. 77, No. 2, 2007, pp. 365-370.

\* cited by examiner

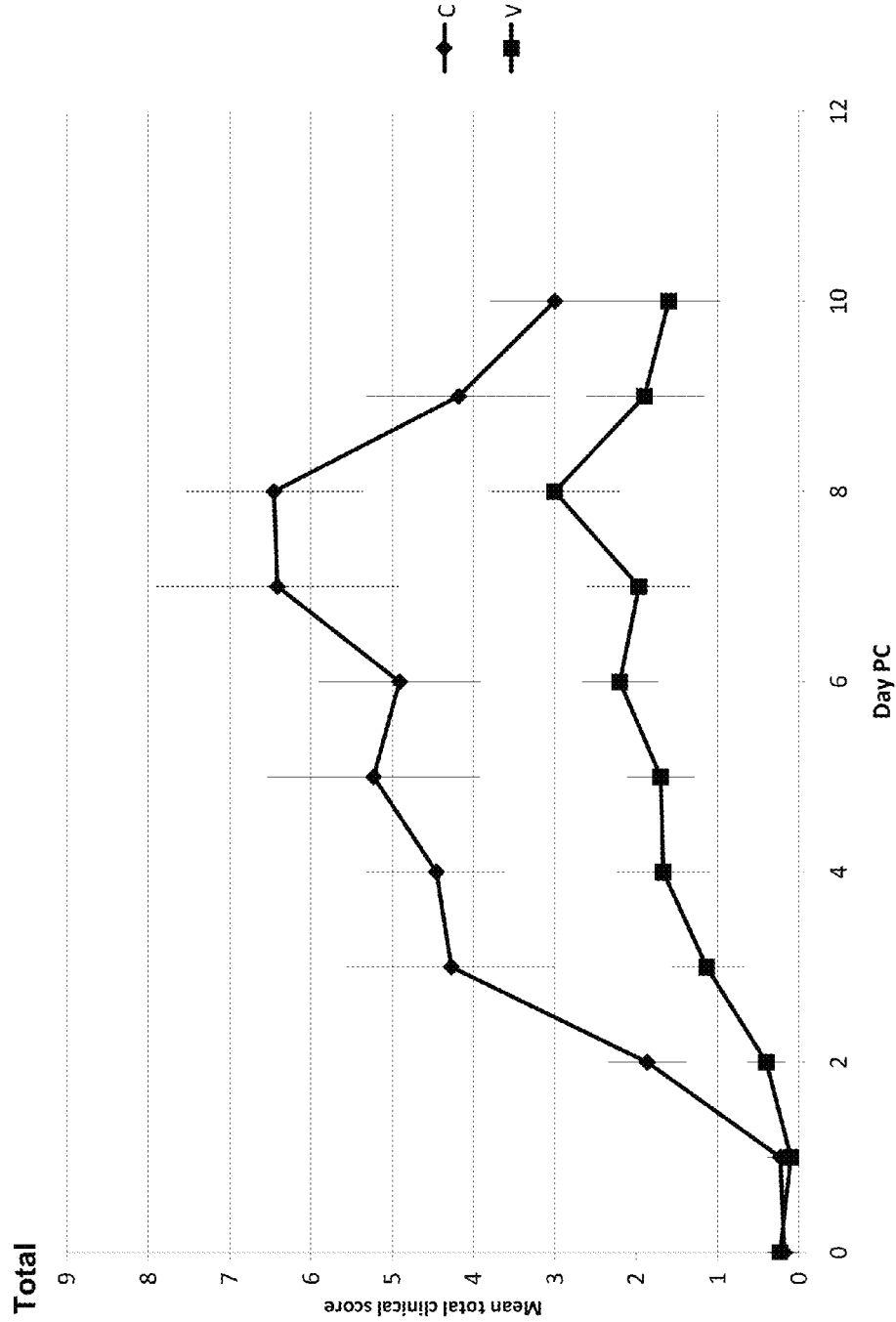

Fig. 2    Mean +/- SEM — virus shedding (*control versus vaccinated, P < 0.05)

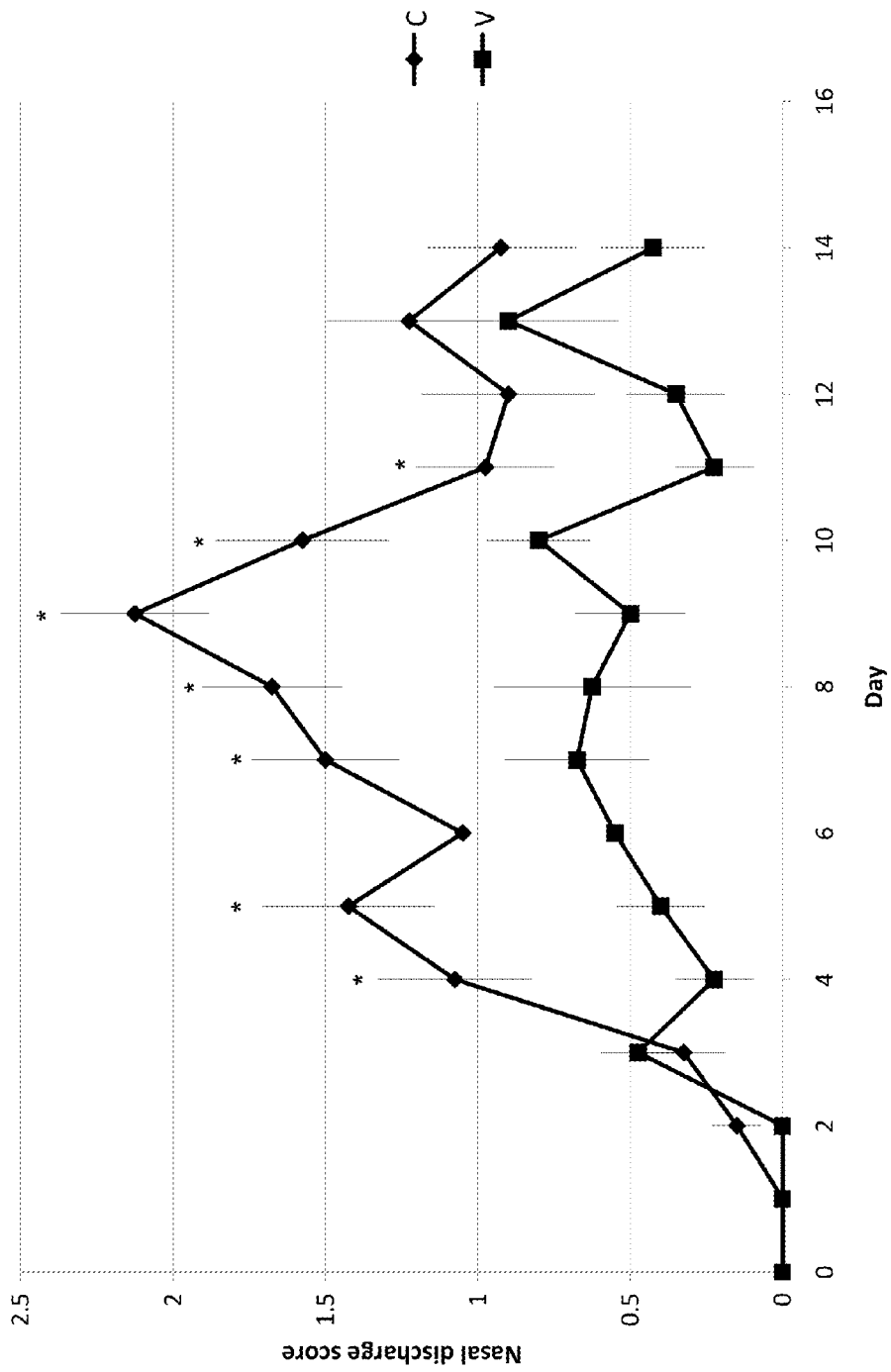
Fig. 3　Mean +/- SEM – nasal discharge score (*control versus vaccinated, P < 0.05)

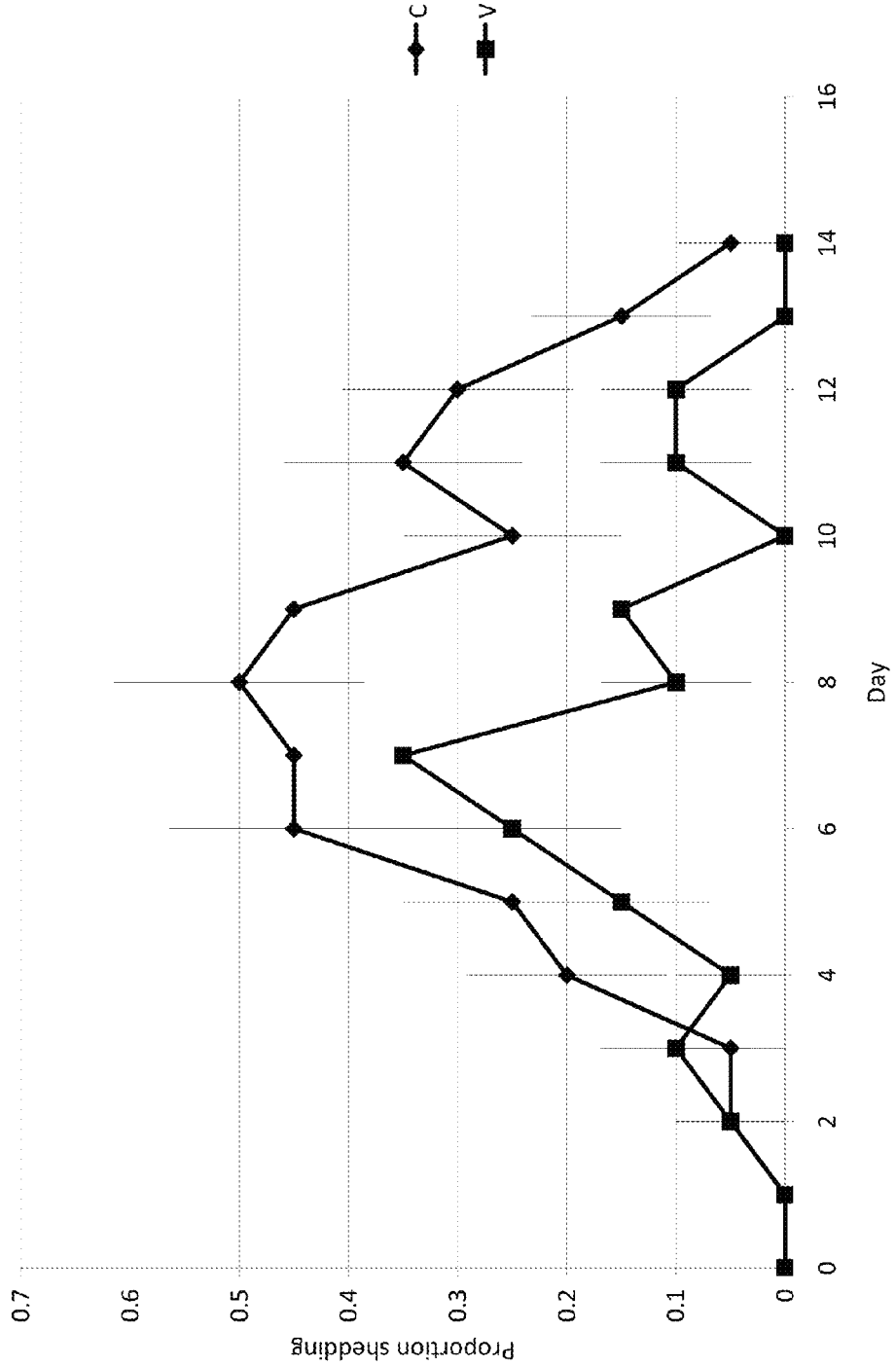

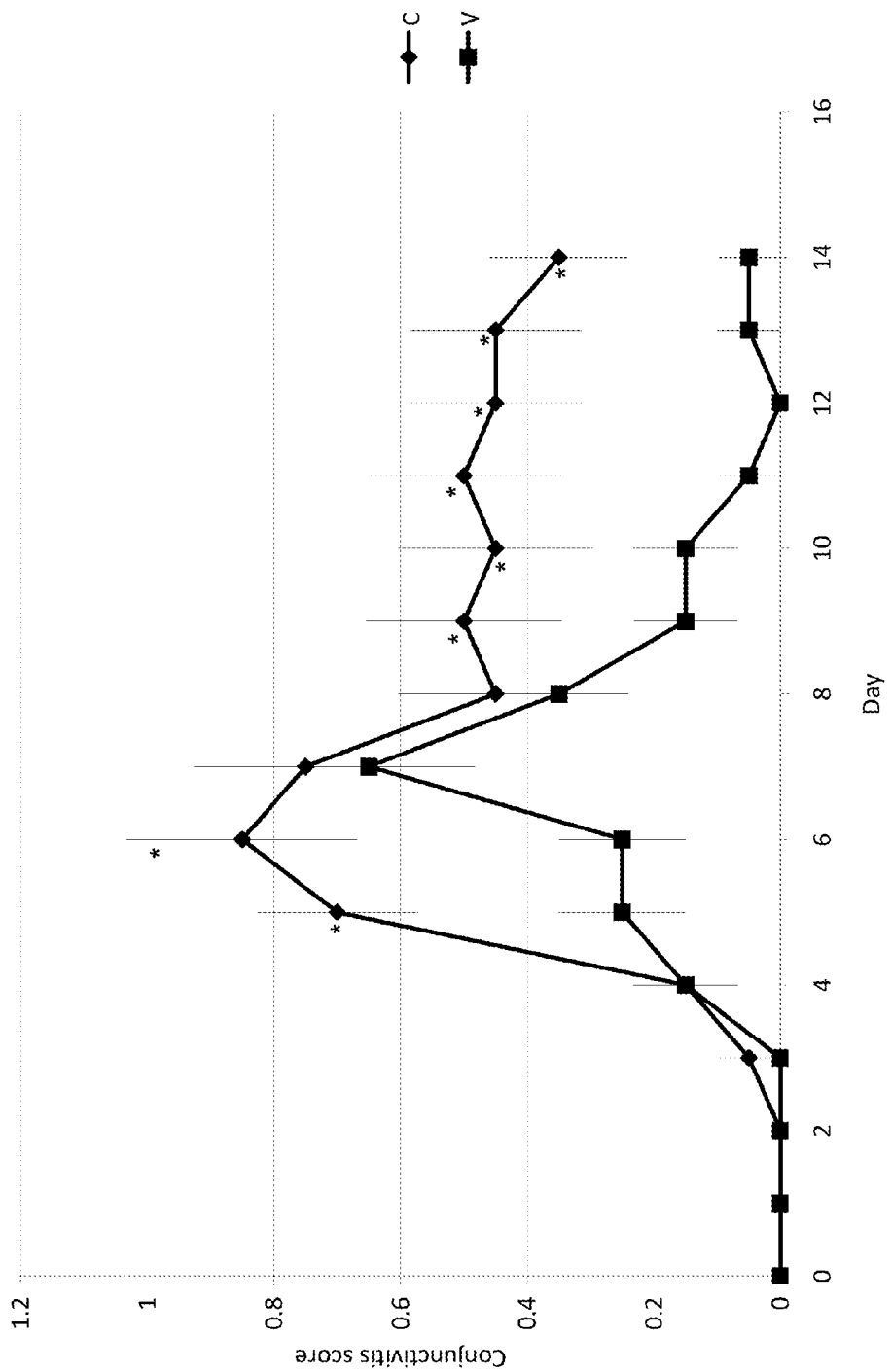
Fig. 5  Mean +/- SEM – conjunctivitis score (*control versus vaccinated, $P < 0.05$)

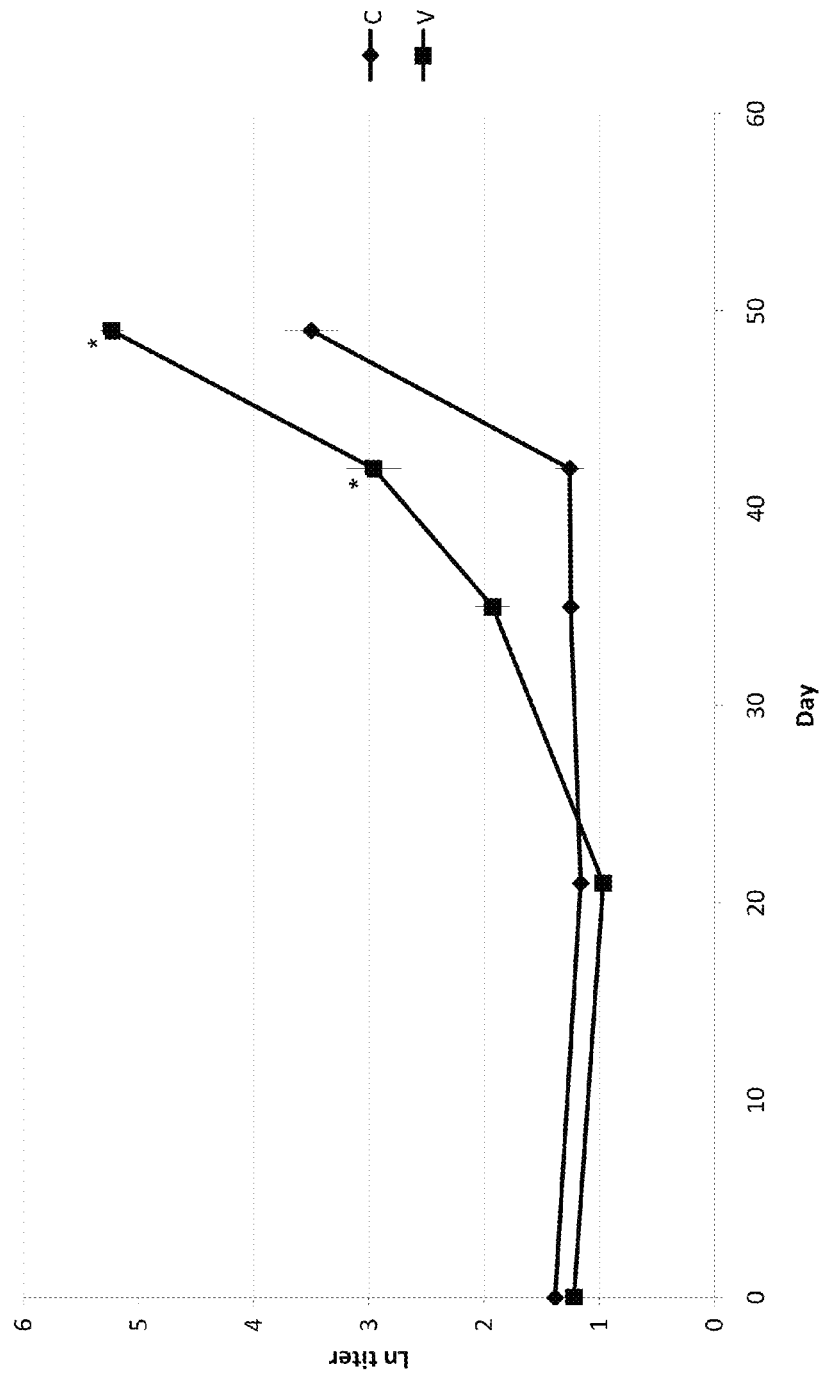
Fig. 6   Mean +/- SEM – serum neutralization (log titers, *control versus vaccinated, P< 0.05)

Fig. 7  Mean proportion positive (buffy coat): EHV-1 virus (+/- SEM)

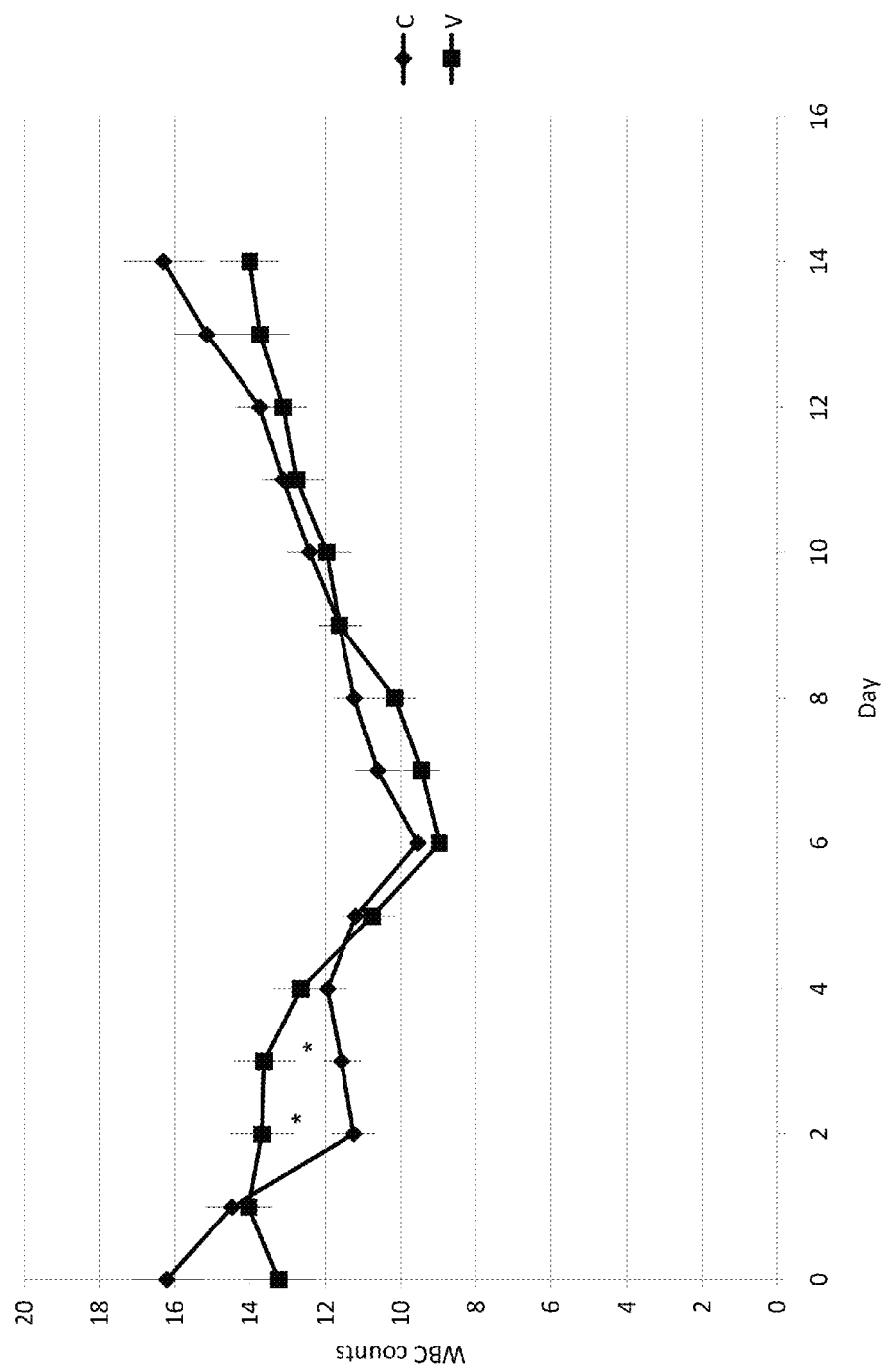

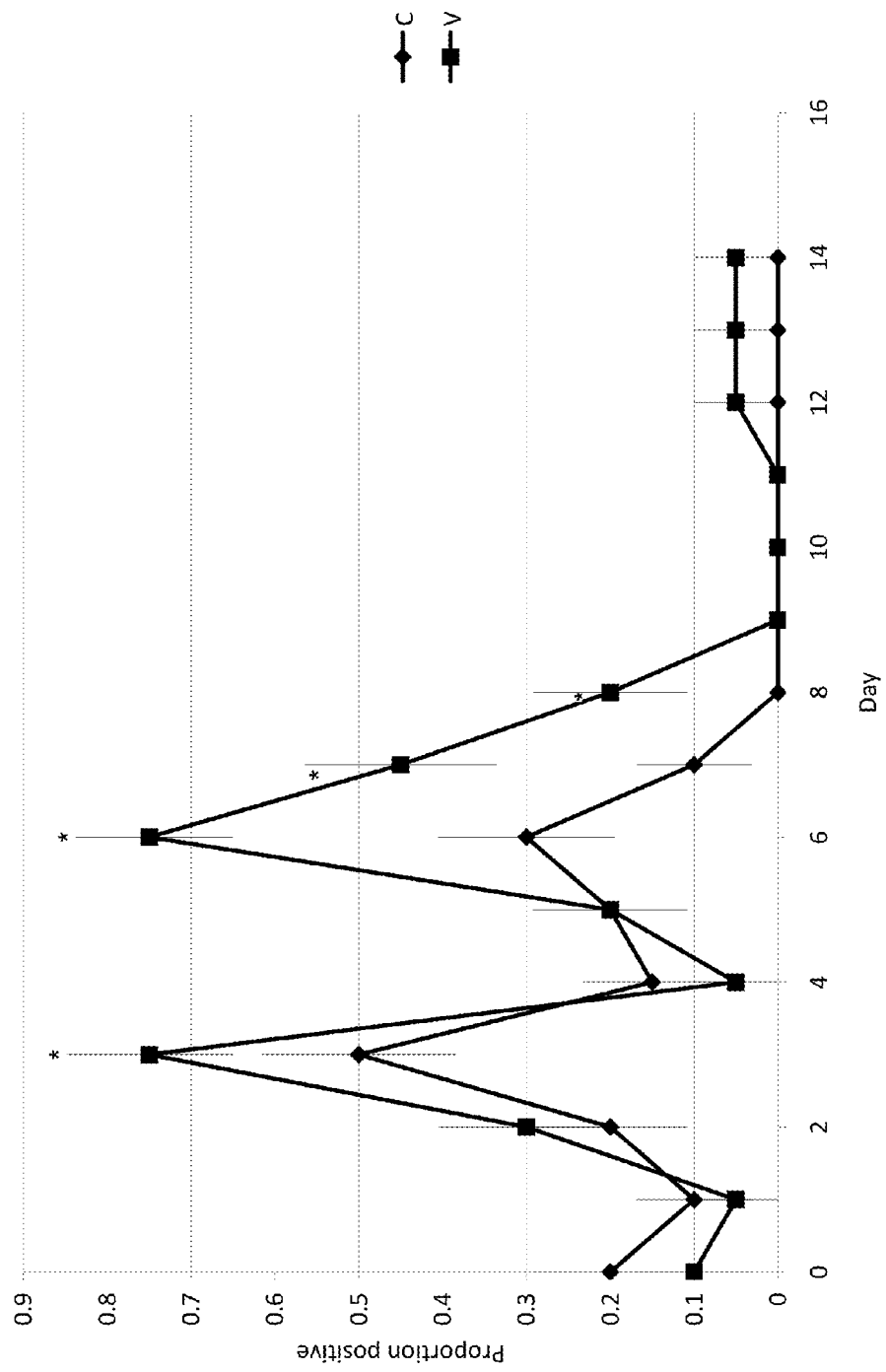

| | | | | |
|---|---|---|---|---|
| NY99 E | TACTACGTGA | TGACTGTTGG | AACAAAGACG | 630 |
| WN02 E | TACTACGTGA | TGACTGTTGG | AACAAAGACG | 630 |
| HEF1 | TACTATGTGA | TGACTGTTGG | AACAAAGACG | 507 |
| HEF3 | TACTATGTGA | TGACTGTTGG | AACAAAGACG | 226 |
| HER3 rev | -----TNTGA | TGACTGTNGG | AACAAAGACG | 25 |
| HER4 rev | ---------- | ---------- | ---------- | |
| Consensus | TACTATGTGA | TGACTGTTGG | AACAAAGACG | |

100% Conservation 0%

| | | | | |
|---|---|---|---|---|
| NY99 E | TTCTTGGTCC | ATCGTGAGTG | GTTCATGGAC | 660 |
| WN02 E | TTCTTGGTCC | ATCGTGAGTG | GTTCATGGAC | 660 |
| HEF1 | TTCTTGGTCC | ATCGTGAGTG | GTTCATGGAC | 537 |
| HEF3 | TTCTTGGTCC | ATCGTGAGTG | GTTCATGGAC | 256 |
| HER3 rev | TTCTNNNTCC | ATCGTGAGTN | NTTCATGGAC | 55 |
| HER4 rev | ---------- | ---------- | ---------- | |
| Consensus | TTCTTGGTCC | ATCGTGAGTG | GTTCATGGAC | |

100% Conservation 0%

| | | | | |
|---|---|---|---|---|
| NY99 E | CTCAACCTCC | CTTGGAGCAG | TGCTGG-AAG | 689 |
| WN02 E | CTCAACCTCC | CTTGGAGCAG | TGCTGG-AAG | 689 |
| HEF1 | CTCAACCTCC | CTTGGAGCAG | TGCTGG-AAG | 566 |
| HEF3 | CTCAACCTCC | CTTGGAGCAG | TGCTGG-AAG | 285 |
| HER3 rev | CTCAACCTCC | CTTGGAGCAG | TGCTGG-AAG | 84 |
| HER4 rev | ---------- | ----NAGCAG | TGCTGGNANG | 16 |
| Consensus | CTCAACCTCC | CTTGGAGCAG | TGCTGG-AAG | |

100% Conservation 0%

| | | | | |
|---|---|---|---|---|
| NY99 E | TACTGTGTGG | AGGAACAGAG | AGACGTTAAT | 719 |
| WN02 E | TACTGTGTGG | AGGAACAGAG | AGACGTTAAT | 719 |
| HEF1 | TACTGTGTGG | AGGAACAGAG | AGACGTTAAT | 596 |
| HEF3 | TACTGTGTGG | AGGAACAGAG | AGACGTTAAT | 315 |
| HER3 rev | TACTGTGTGG | AGGAACAGAG | AGACGTTAAT | 114 |
| HER4 rev | TACTGTGTGG | AGGAACAGAG | AGACGTTAAT | 46 |
| Consensus | TACTGTGTGG | AGGAACAGAG | AGACGTTAAT | |

100% Conservation 0%

Fig. 10F

```
NY99 E     GTTGACGTCG  GGTCATTTGA  AGTGTAGAGT  869
WN02 E     GTTGACGTCG  GGTCATTTGA  AGTGTAGAGT  869
HEF1       GTTGACGTCN  GGTCATTTGA  AGTGTAGAGT  746
HEF3       GTTGACGTCG  GGTCATTTGA  AGTGTAGAGT  465
HER3 rev   GTTGACGTCG  GGTCATTTGA  AGTGTAGAGT  264
HER4 rev   GTTGACGTCG  GGTCATTTGA  AGTGTAGAGT  196
Consensus  GTTGACGTCG  GGTCATTTGA  AGTGTAGAGT NY99 E     GAAGATGGAA  AAATTGCAGT  TGAAGGGAAC  899
WN02 E     GAAGATGGAA  AAATTGCAGT  TGAAGGGAAC  899
HEF1       GAAGATGGAA  AAATTGCAGT  TGAAGGGAAC  776
HEF3       GAAGATGGAA  AAATTGCAGT  TGAAGGGAAC  495
HER3 rev   GAAGATGGAA  AAATTGCAGT  TGAAGGGAAC  294
HER4 rev   GAAGATGGAA  AAATTGCAGT  TGAAGGGAAC  226
Consensus  GAAGATGGAA  AAATTGCAGT  TGAAGGGAAC NY99 E     AACCTATGGC  GTCTGTTCAA  AGGCTTTCAA  929
WN02 E     AACCTATGGC  GTCTGTTCAA  AGGCTTTCAA  929
HEF1       AACCTATGGC  GTCTGTTCAA  AGGCTTTCAA  806
HEF3       AACCTATGGC  GTCTGTTCAA  AGGCTTTCAA  525
HER3 rev   AACCTATGGC  GTCTGTTCAA  AGGCTTTCAA  324
HER4 rev   AACCTATGGC  GTCTGTTCAA  AGGCTTTCAA  256
Consensus  AACCTATGGC  GTCTGTTCAA  AGGCTTTCAA NY99 E     GTTTCTTGGG  ACTCCCGCAG  ACACAGGTCA  959
WN02 E     GTTTCTTGGG  ACTCCCGCAG  ACACAGGTCA  959
HEF1       GTTTCTTGGG  ACTCCCGCAG  ACACNNNTCA  836
HEF3       GTTTCTTGGG  ACTCCCGCAG  ACACAGGTCA  555
HER3 rev   GTTTCTTGGG  ACTCCCGCAG  ACACAGGTCA  354
HER4 rev   GTTTCTTGGG  ACTCCCGCAG  ACACAGGTCA  286
Consensus  GTTTCTTGGG  ACTCCCGCAG  ACACAGGTCA
```

Fig. 10H

| | | | | |
|---|---|---|---|---|
| NY99 E | CGGCACTGTG | GTGTTGGAAT | TGCAGTACAC | 989 |
| WN02 E | CGGCACTGTG | GTGTTGGAAT | TGCAGTACAC | 989 |
| HEF1 | CNGCACTGTG | GTGTTGGNAT | TGCAGTACAC | 866 |
| HEF3 | CGGCACTGTG | GTGTTGGAAT | TGCAGTACAC | 585 |
| HER3 rev | CGGCACTGTG | GTGTTGGAAT | TGCAGTACAC | 384 |
| HER4 rev | CGGCACTGTG | GTGTTGGAAT | TGCAGTACAC | 316 |
| Consensus | CGGCACTGTG | GTGTTGGAAT | TGCAGTACAC | |
| 100% Conservation 0% | | | | |
| NY99 E | TGG-CACGGA | TGGACCTTGC | AAAGTTCCTA | 1018 |
| WN02 E | TGG-CACGGA | TGGACCTTGC | AAAGTTCCTA | 1018 |
| HEF1 | TGGGCACGGA | TGGACCTTGC | AAAGTTNCTA | 896 |
| HEF3 | TGG-CACGGA | TGGACCTTGC | AAAGTTCCTA | 614 |
| HER3 rev | TGG-CACGGA | TGGACCTTGC | AAAGTTCCTA | 413 |
| HER4 rev | TGG-CACGGA | TGGACCTTGC | AAAGTTCCTA | 345 |
| Consensus | TGG-CACGGA | TGGACCTTGC | AAAGTTCCTA | |
| 100% Conservation 0% | | | | |
| NY99 E | TCTCGTCAGT | GGCTTCATTG | AACGACCTAA | 1048 |
| WN02 E | TCTCGTCAGT | GGCTTCATTG | AACGACCTAA | 1048 |
| HEF1 | TCTCGTCAGT | NGCTTCATTG | NACGANCTAA | 926 |
| HEF3 | TCTCGTCAGT | GGCTTCATTG | AACGACCTAA | 644 |
| HER3 rev | TCTCGTCAGT | GGCTTCATTG | AACGACCTAA | 443 |
| HER4 rev | TCTCGTCAGT | GGCTTCATTG | AACGACCTAA | 375 |
| Consensus | TCTCGTCAGT | GGCTTCATTG | AACGACCTAA | |
| 100% Conservation 0% | | | | |
| NY99 E | CGCCAGTGGG | CAGATTGGTC | ACTGTCAACC | 1078 |
| WN02 E | CGCCAGTGGG | CAGATTGGTC | ACTGTCAACC | 1078 |
| HEF1 | CNNCNGTGGG | NAGANNNGN- | ---------- | 945 |
| HEF3 | CGCCNGTGGG | CAGATTGGTC | ACTGTCAACC | 674 |
| HER3 rev | CGCCAGTGGG | CAGATTGGTC | ACTGTCAACC | 473 |
| HER4 rev | CGCCAGTGGG | CAGATTGGTC | ACTGTCAACC | 405 |
| Consensus | CGCCAGTGGG | CAGATTGGTC | ACTGTCAACC | |
| 100% Conservation 0% | | | | |

Fig. 10I

```
NY99 E     CTTTTGTTTC  AGTGGCCACG  GCCAACGCTA  1108
WN02 E     CTTTTGTTTC  AGTGGCCACG  GCCAACGCTA  1108
HEF1       ----------  ----------  ----------  945
HEF3       CTTTTGTTTC  AGTGGCCACG  GCCAACGCTN  704
HER3 rev   CTTTTGTTTC  AGTGGCCACG  GCCAACGCTA  503
HER4 rev   CTTTTGTTTC  AGTGGCCACG  GCCAACGCTA  435
Consensus  CTTTTGTTTC  AGTGGCCACG  GCCAACGCTA NY99 E     AGGTCCTGAT  TGAATTGGAA  CCACCCTTTG  1138
WN02 E     AGGTCCTGAT  TGAATTGGAA  CCACCCTTTG  1138
HEF1       ----------  ----------  ----------  945
HEF3       AGGTCCTGAT  TGAATTGGAA  CCACCCTTTG  734
HER3 rev   AGGTCCTGAT  TGAATTGGAA  CCACCCTTTG  533
HER4 rev   AGGTCCTGAT  TGAATTGGAA  CCACCCTTTG  465
Consensus  AGGTCCTGAT  TGAATTGGAA  CCACCCTTTG NY99 E     GAGACTCATA  CATAGTGGTG  GGCAGAGGAG  1168
WN02 E     GAGACTCATA  CATAGTGGTG  GGCAGAGGAG  1168
HEF1       ----------  ----------  ----------  945
HEF3       GAGACTCATA  CATAGTGGTG  GGCAGANGAG  764
HER3 rev   GAGACTCATA  CATAGTGGTG  GGCAGAGGAG  563
HER4 rev   GAGACTCATA  CATAGTGGTG  GGCAGAGGAG  495
Consensus  GAGACTCATA  CATAGTGGTG  GGCAGAGGAG NY99 E     AACAACAGAT  CAATCACCAT  TGGCACAAGT  1198
WN02 E     AACAACAGAT  CAATCACCAT  TGGCACAAGT  1198
HEF1       ----------  ----------  ----------  945
HEF3       AACAACAGAT  CAATCACCAT  TGGCACNAGT  794
HER3 rev   AACAACAGAT  CAATCACCAT  TGGCACAAGT  593
HER4 rev   AACAACAGAT  CAATCACCAT  TGGCACAAGT  525
Consensus  AACAACAGAT  CAATCACCAT  TGGCACAAGT
```

Fig. 10J

| | | | | |
|---:|---|---|---|---:|
| NY99 E | CTGGAAGCAG | CATTGGCAAA | GCCTTTACAA | 1228 |
| WN02 E | CTGGAAGTAG | CATTGGCAAA | GCCTTTACAA | 1228 |
| HEF1 | ---------- | ---------- | ---------- | 945 |
| HEF3 | CTGGAAGCAG | CATTGGCAAA | GCCTTTACNA | 824 |
| HER3 rev | CTGGAAGCAG | CATTGGCAAA | GCCTTTACAA | 623 |
| HER4 rev | CTGGAAGCAG | CATTGGCAAA | GCCTTTACAA | 555 |
| Consensus | CTGGAAGCAG | CATTGGCAAA | GCCTTTACAA | |

| | | | | |
|---:|---|---|---|---:|
| NY99 E | CCACCCTCAA | AGGAGCGCAG | AGACTAGCCG | 1258 |
| WN02 E | CCACCCTCAA | AGGAGCGCAG | AGACTAGCCG | 1258 |
| HEF1 | ---------- | ---------- | ---------- | 945 |
| HEF3 | CCACCCTCAA | AGGANCGCAN | ANACTAGCCG | 854 |
| HER3 rev | CCACCCTCAA | AGGAGCGCAG | AGACTAGCCG | 653 |
| HER4 rev | CCACCCTCAA | AGGAGCGCAG | AGACTAGCCG | 585 |
| Consensus | CCACCCTCAA | AGGAGCGCAG | AGACTAGCCG | |

| | | | | |
|---:|---|---|---|---:|
| NY99 E | CTCTAGGAGA | CACAGCTTGG | GACTTTGGAT | 1288 |
| WN02 E | CTCTAGGAGA | CACAGCTTGG | GACTTTGGAT | 1288 |
| HEF1 | ---------- | ---------- | ---------- | 945 |
| HEF3 | C--------- | ---------- | ---------- | 855 |
| HER3 rev | CTCTAGGAGA | CACAGCTTGG | GACTTTGGAT | 683 |
| HER4 rev | CTCTAGGAGA | CACAGCTTGG | GACTTTGGAT | 615 |
| Consensus | CTCTAGGAGA | CACAGCTTGG | GACTTTGGAT | |

| | | | | |
|---:|---|---|---|---:|
| NY99 E | CAGTTGGAGG | GGTGTTCACC | TCAGTTGGGA | 1318 |
| WN02 E | CAGTTGGAGG | GGTGTTCACC | TCAGTTGGGA | 1318 |
| HEF1 | ---------- | ---------- | ---------- | 945 |
| HEF3 | ---------- | ---------- | ---------- | 855 |
| HER3 rev | CAGTTGGAGG | GGTGTTCACC | TCAGTTGGGA | 713 |
| HER4 rev | CAGTTGGAGG | GGTGTTCACC | TCAGTTGGGA | 645 |
| Consensus | CAGTTGGAGG | GGTGTTCACC | TCAGTTGGGA | |

Fig. 10K

| | | | | |
|---|---|---|---|---|
| NY99 E | AGGCTGTCCA | TCAAGTGTTC | GGAGGAGCAT | 1348 |
| WN02 E | AGGCTGTCCA | TCAAGTGTTC | GGAGGAGCAT | 1348 |
| HEF1 | ---------- | ---------- | ---------- | 945 |
| HEF3 | ---------- | ---------- | ---------- | 855 |
| HER3 rev | AGGCTGTCCA | TCAAGTGTTC | GGAGGAGCAT | 743 |
| HER4 rev | AGGCTGTCCA | TCAAGTGTTC | GGAGGAGCAT | 675 |
| Consensus | AGGCTGTCCA | TCAAGTGTTC | GGAGGAGCAT | |
| NY99 E | TCCGCTCACT | GTTCGGAGGC | ATGTCCTGGA | 1378 |
| WN02 E | TCCGCTCACT | GTTCGGAGGC | ATGTCCTGGA | 1378 |
| HEF1 | ---------- | ---------- | ---------- | 945 |
| HEF3 | ---------- | ---------- | ---------- | 855 |
| HER3 rev | TCCGCTCACT | GTTCGGAGGC | ATGTCCTGGA | 773 |
| HER4 rev | TCCGCTCACT | GTTCGGAGGC | ATGTCCTGGA | 705 |
| Consensus | TCCGCTCACT | GTTCGGAGGC | ATGTCCTGGA | |
| NY99 E | TAACGCAAGG | ATTGCTGGGG | GCTCTCCTGT | 1408 |
| WN02 E | TAACGCAAGG | ATTGCTGGGG | GCTCTCCTGT | 1408 |
| HEF1 | ---------- | ---------- | ---------- | 945 |
| HEF3 | ---------- | ---------- | ---------- | 855 |
| HER3 rev | TAACGCAAGG | ATTGCTGGGG | GCTCTCCTGT | 803 |
| HER4 rev | TAACGCAAGG | ATTGCTGGGG | GCTCTCCTGT | 735 |
| Consensus | TAACGCAAGG | ATTGCTGGGG | GCTCTCCTGT | |
| NY99 E | TGTGGATGGG | CATCAATGCT | CGTGATAGGT | 1438 |
| WN02 E | TGTGGATGGG | CATCAATGCT | CGTGATAGGT | 1438 |
| HEF1 | ---------- | ---------- | ---------- | 945 |
| HEF3 | ---------- | ---------- | ---------- | 855 |
| HER3 rev | TGTGGATGGG | CATCAATGCT | CGTGATAGGT | 833 |
| HER4 rev | TGTGGATGGG | CATCAATGCT | CGTGATAGGT | 765 |
| Consensus | TGTGGATGGG | CATCAATGCT | CGTGATAGGT | |

Fig. 10L

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| HEF1 | - - - - - - - - - - | - - - - - - - - - - | - - - - - - - - - - | 945 |
| HEF3 | - - - - - - - - - - | - - - - - - - - - - | - - - - - - - - - - | 855 |
| HER3 rev | - - - - - - - - - - | - - - - - - - - - - | - - - - - - - - - - | 940 |
| HER4 rev | TGTTCATACA | CAATGATGTG | GAGGCTTGGA | 915 |
| Consensus | - - - - - - - - - - | - - - - - - - - - - | - - - - - - - - - - | |

100% Conservation 0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| HEF1 | - - - - - - - - - - | - - - - - - - - - - | - - - - - - - - - - | 945 |
| HEF3 | - - - - - - - - - - | - - - - - - - - - - | - - - - - - - - - - | 855 |
| HER3 rev | - - - - - - - - - - | - - - - - - - - - - | - - - - - - - - - - | 940 |
| HER4 rev | TGGACCGGTA | CAAGTATTAC | CCTGAAACGC | 945 |
| Consensus | - - - - - - - - - - | - - - - - - - - - - | - - - - - - - - - - | |

100% Conservation 0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| HEF1 | - - - - - - - - - - | - - - - - - - - - - | - - - - - - - - - - | 945 |
| HEF3 | - - - - - - - - - - | - - - - - - - - - - | - - - - - - - - - - | 855 |
| HER3 rev | - - - - - - - - - - | - - - - - - - - - - | - - - - - - - - - - | 940 |
| HER4 rev | CACAAGGCCT | AGCCAAGATC | ATTCAGAAAG | 975 |
| Consensus | - - - - - - - - - - | - - - - - - - - - - | - - - - - - - - - - | |

100% Conservation 0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| HEF1 | - - - - - - - - - - | - - - - - - - - - - | - - - - - - - - - - | 945 |
| HEF3 | - - - - - - - - - - | - - - - - - - - - - | - - - - - - - - - - | 855 |
| HER3 rev | - - - - - - - - - - | - - - - - - - - - - | - - - - - - - - - - | 940 |
| HER4 rev | CTCATAAGGA | AGGAGTGTGC | GNTCTACGAT | 1005 |
| Consensus | - - - - - - - - - - | - - - - - - - - - - | - - - - - - - - - - | |

100% Conservation 0%

Fig. 10N

| | | | | |
|---|---|---|---|---|
| NY99 E | TTCAACTGCC | TTGGAATGAG | CAACAGAGAC | 30 |
| WN02 E | TTCAACTGCC | TTGGAATGAG | CAACAGAGAC | 30 |
| DEF1 | ---------- | ---------- | ---------- | - |
| DEF3 | ---------- | ---------- | ---------- | - |
| DER3 rev | ---------- | ---------- | ---------- | - |
| DER4 rev | ---------- | ---------- | ---------- | - |
| Consensus | ---------- | ---------- | ---------- | |
| 100% Conservation 0% | | | | |
| NY99 E | TTCTTGGAAG | GAGTGTCTGG | AGCAACATGG | 60 |
| WN02 E | TTCTTGGAAG | GAGTGTCTGG | AGCAACATGG | 60 |
| DEF1 | ---------- | ---------- | ---------- | - |
| DEF3 | ---------- | ---------- | ---------- | - |
| DER3 rev | ---------- | ---------- | ---------- | - |
| DER4 rev | ---------- | ---------- | ---------- | - |
| Consensus | ---------- | ---------- | ---------- | |
| 100% Conservation 0% | | | | |
| NY99 E | GTGGATTTGG | TTCTCGAAGG | CGACAGCTGC | 90 |
| WN02 E | GTGGATTTGG | TTCTCGAAGG | CGACAGCTGC | 90 |
| DEF1 | ---------- | ---------- | ---------- | - |
| DEF3 | ---------- | ---------- | ---------- | - |
| DER3 rev | ---------- | ---------- | ---------- | - |
| DER4 rev | ---------- | ---------- | ---------- | - |
| Consensus | ---------- | ---------- | ---------- | |
| 100% Conservation 0% | | | | |
| NY99 E | GTGACTATCA | TGTCTAAGGA | CAAGCCTACC | 120 |
| WN02 E | GTGACTATCA | TGTCTAAGGA | CAAGCCTACC | 120 |
| DEF1 | ---------- | ---------- | ---------- | - |
| DEF3 | ---------- | ---------- | ---------- | - |
| DER3 rev | ---------- | ---------- | ---------- | - |
| DER4 rev | ---------- | ---------- | ---------- | - |
| Consensus | ---------- | ---------- | ---------- | |
| 100% Conservation 0% | | | | |

Fig. 11A

```
NY99 E      ATCGATGTGA  AGATGATGAA  TATGGAGGCG  150
WN02 E      ATCGATGTGA  AGATGATGAA  TATGGAGGCG  150
DEF1        --CGATGTGN  -GANGANGAA  TATGGAGGCG  27
DEF3        ----------  ----------  ----------  -
DER3 rev    ----------  ----------  ----------  -
DER4 rev    ----------  ----------  ----------  -
Consensus   --CGATGTG-  -GA-GA-GAA  TATGGAGGCG
100%
Conservation
0%

NY99 E      GCCAACCTGG  CAGAGGTCCG  CAGTTATTGC  180
WN02 E      GCCAACCTGG  CAGAGGTCCG  CAGTTATTGC  180
DEF1        GCCAACCTGG  CAGAGGTCCG  CAGTTATTGC  57
DEF3        ----------  ----------  ----------  -
DER3 rev    ----------  ----------  ----------  -
DER4 rev    ----------  ----------  ----------  -
Consensus   GCCAACCTGG  CAGAGGTCCG  CAGTTATTGC
100%
Conservation
0%

NY99 E      TATTTGGCTA  CCGTCAGCGA  TCTCTCCACC  210
WN02 E      TATTTGGCTA  CCGTCAGCGA  TCTCTCCACC  210
DEF1        TATTTGGCTA  CCGTCAGCGA  TCTCTCCACC  87
DEF3        ----------  ----------  ----------  -
DER3 rev    ----------  ----------  ----------  -
DER4 rev    ----------  ----------  ----------  -
Consensus   TATTTGGCTA  CCGTCAGCGA  TCTCTCCACC
100%
Conservation
0%

NY99 E      AAAGCTGCGT  GCCCGACCAT  GGGAGAAGCT  240
WN02 E      AAAGCTGCGT  GCCCGACCAT  GGGAGAAGCT  240
DEF1        AAAGCTGCGT  GCCCGACCAT  GGGAGAAGCT  117
DEF3        ----------  ----------  ----------  -
DER3 rev    ----------  ----------  ----------  -
DER4 rev    ----------  ----------  ----------  -
Consensus   AAAGCTGCGT  GCCCGACCAT  GGGAGAAGCT
100%
Conservation
0%
```

Fig. 11B

| | | | | |
|---|---|---|---|---|
| NY99 E | CACAATGACA | AACGTGCTGA | CCCAGCTTTT | 270 |
| WN02 E | CACAATGACA | AACGTGCTGA | CCCAGCTTTT | 270 |
| DEF1 | CACAATGACA | AACGTGCTGA | CCCAGCTTTT | 147 |
| DEF3 | ---------- | ---------- | ---------- | - |
| DER3 rev | ---------- | ---------- | ---------- | - |
| DER4 rev | ---------- | ---------- | ---------- | - |
| Consensus | CACAATGACA | AACGTGCTGA | CCCAGCTTTT | |
| NY99 E | GTGTGCAGAC | AAGGAGTGGT | GGACAGGGGC | 300 |
| WN02 E | GTGTGCAGAC | AAGGAGTGGT | GGACAGGGGC | 300 |
| DEF1 | GTGTGCAGAC | AAGGAGTGGT | GGACAGGGGC | 177 |
| DEF3 | ---------- | ---------- | ---------- | - |
| DER3 rev | ---------- | ---------- | ---------- | - |
| DER4 rev | ---------- | ---------- | ---------- | - |
| Consensus | GTGTGCAGAC | AAGGAGTGGT | GGACAGGGGC | |
| NY99 E | TGGGGCAACG | GCTGCGGACT | ATTTGGCAAA | 330 |
| WN02 E | TGGGGCAACG | GCTGCGGACT | ATTTGGCAAA | 330 |
| DEF1 | TGGGGCAACG | GCTGCGGACT | ATTTGGCAAA | 207 |
| DEF3 | ---------- | ---------- | ---------- | - |
| DER3 rev | ---------- | ---------- | ---------- | - |
| DER4 rev | ---------- | ---------- | ---------- | - |
| Consensus | TGGGGCAACG | GCTGCGGACT | ATTTGGCAAA | |
| NY99 E | GGAAGCATTG | ACACATGCGC | CAAATTTGCC | 360 |
| WN02 E | GGAAGCATTG | ACACATGCGC | CAAATTTGCC | 360 |
| DEF1 | GGAAGCATTG | ACACATGCGC | CAAATTTGCC | 237 |
| DEF3 | ---------- | ---------- | ---------- | - |
| DER3 rev | ---------- | ---------- | ---------- | - |
| DER4 rev | ---------- | ---------- | ---------- | - |
| Consensus | GGAAGCATTG | ACACATGCGC | CAAATTTGCC | |

Fig. 11C

| | | | | |
|---|---|---|---|---|
| NY99 E | TGCTCTACCA | AGGCAATAGG | AAGAACCATC | 390 |
| WN02 E | TGCTCTACCA | AGGCAATAGG | AAGAACCATC | 390 |
| DEF1 | TGCTCTACCA | AGGCAATAGG | AAGAACCATC | 267 |
| DEF3 | ---------- | ---------- | ---------- | |
| DER3 rev | ---------- | ---------- | ---------- | |
| DER4 rev | ---------- | ---------- | ---------- | |
| Consensus | TGCTCTACCA | AGGCAATAGG | AAGAACCATC | |
| NY99 E | TTGAAAGAGA | ATATCAAGTA | CGAAGTGGCC | 420 |
| WN02 E | TTGAAAGAGA | ATATCAAGTA | CGAAGTGGCC | 420 |
| DEF1 | TTGAAAGAGA | ATATCAAGTA | CGAAGTGGCC | 297 |
| DEF3 | ---------- | ----CAAGTA | CGAAGTGGCC | 16 |
| DER3 rev | ---------- | ---------- | ---------- | |
| DER4 rev | ---------- | ---------- | ---------- | |
| Consensus | TTGAAAGAGA | ATATCAAGTA | CGAAGTGGCC | |
| NY99 E | ATTTTTGTCC | ATGGACCAAC | TACTGTGGAG | 450 |
| WN02 E | ATTTTTGTCC | ATGGACCAAC | TACTGTGGAG | 450 |
| DEF1 | ATTTTTGTCC | ATGGACCAAC | TACTGTGGAG | 327 |
| DEF3 | ATTTTTGTCC | ATGGACCAAC | TACTGTGGAG | 46 |
| DER3 rev | ---------- | ---------- | ---------- | |
| DER4 rev | ---------- | ---------- | ---------- | |
| Consensus | ATTTTTGTCC | ATGGACCAAC | TACTGTGGAG | |
| NY99 E | TCGCACGGAA | ACTACTCCAC | ACAGGTTGGA | 480 |
| WN02 E | TCGCACGGAA | ACTATTCCAC | ACAGGCTGGA | 480 |
| DEF1 | TCGCACGGAA | ACTACTCCAC | ACAGGCTGGA | 357 |
| DEF3 | TCGCACGGAA | ACTACTCCAC | ACAGGCTGGA | 76 |
| DER3 rev | ---------- | ---------- | ---------- | |
| DER4 rev | ---------- | ---------- | ---------- | |
| Consensus | TCGCACGGAA | ACTACTCCAC | ACAGGCTGGA | |

Fig. 11D

```
NY99 E      GCCACTCAGG  CAGGGAGATT  CAGCATCACT  510
WN02 E      GCCACTCAGG  CAGGGAGATT  CAGCATCACT  510
  DEF1      GCCACTCAGG  CAGGGAGATT  CAGCATCACT  387
  DEF3      GCCACTCAGG  CAGGGAGATT  CAGCATCACT  106
DER3 rev    ----------  ----------  ----------
DER4 rev    ----------  ----------  ----------
Consensus   GCCACTCAGG  CAGGGAGATT  CAGCATCACT
  100%
Conservation ▮▮▮▮▮▮▮▮▮▮ ▮▮▮▮▮▮▮▮▮▮ ▮▮▮▮▮▮▮▮▮▮
   0%

NY99 E      CCTGCGGCGC  CTTCACACAC  ACTAAAGCTT  540
WN02 E      CCTGCGGCGC  CTTCATACAC  ACTAAAGCTT  540
  DEF1      CCTGCGGCGC  CTTCATACAC  ACTAAAGCTT  417
  DEF3      CCTGCGGCGC  CTTCATACAC  ACTAAAGCTT  136
DER3 rev    ----------  ----------  ----------
DER4 rev    ----------  ----------  ----------
Consensus   CCTGCGGCGC  CTTCATACAC  ACTAAAGCTT
  100%
Conservation ▮▮▮▮▮▮▮▮▮▮ ▮▮▮▮▮.▮▮▮▮ ▮▮▮▮▮▮▮▮▮▮
   0%

NY99 E      GGAGAATATG  GAGAGGTGAC  AGTGGACTGT  570
WN02 E      GGAGAATATG  GAGAGGTGAC  AGTGGACTGT  570
  DEF1      GGAGAATATG  GAGAGGTGAC  AGTGGACTGT  447
  DEF3      GGAGAATATG  GAGAGGTGAC  AGTGGACTGT  166
DER3 rev    ----------  ----------  ----------
DER4 rev    ----------  ----------  ----------
Consensus   GGAGAATATG  GAGAGGTGAC  AGTGGACTGT
  100%
Conservation ▮▮▮▮▮▮▮▮▮▮ ▮▮▮▮▮▮▮▮▮▮ ▮▮▮▮▮▮▮▮▮▮
   0%

NY99 E      GAACCACGGT  CAGGGATTGA  CACCAATGCA  600
WN02 E      GAACCACGGT  CAGGGATTGA  CACCAATGCA  600
  DEF1      GAACCACGGT  CAGGGATTGA  CACCAATGCA  477
  DEF3      GAACCACGGT  CAGGGATTGA  CACCAATGCA  196
DER3 rev    ----------  ----------  -----ATGCN  5
DER4 rev    ----------  ----------  ----------
Consensus   GAACCACGGT  CAGGGATTGA  CACCAATGCA
  100%
Conservation ▮▮▮▮▮▮▮▮▮▮ ▮▮▮▮▮▮▮▮▮▮ ▮▮▮▮▮▮▮▮▮▮
   0%
```

Fig. 11E

```
NY99 E    TACTACGTGA  TGACTGTTGG  AACAAAGACG  630
WN02 E    TACTACGTGA  TGACTGTTGG  AACAAAGACG  630
 DEF1     TACTACGTGA  TGACTGTTGG  AACAAAGACG  507
 DEF3     TACTACGTGA  TGACTGTTGG  AACAAAGACG  226
DER3 rev  NACTACGTGA  TGACTNNGAN  AAGANNNNNN   35
DER4 rev  ----------  ----------  ----------   -
Consensus TACTACGTGA  TGACTGTTGG  AACAAAGACG NY99 E    TTCTTGGTCC  ATCGTGAGTG  GTTCATGGAC  660
WN02 E    TTCTTGGTCC  ATCGTGAGTG  GTTCATGGAC  660
 DEF1     TTCTTGGTCC  ATCGTGAGTG  GTTCATGGAC  537
 DEF3     TTCTTGGTCC  ATCGTGAGTG  GTTCATGGAC  256
DER3 rev  T-------CC  ATCGTGAGNN  N--CATGGAN   56
DER4 rev  ----------  ----------  ----------   -
Consensus TTCTTGGTCC  ATCGTGAGTG  GTTCATGGAC NY99 E    CTCAACCTCC  CTTGGAGCAG  TGCTGGAAGT  690
WN02 E    CTCAACCTCC  CTTGGAGCAG  TGCTGGAAGT  690
 DEF1     CTCAACCTCC  CTTGGAGCAG  TGCTGGAAGT  567
 DEF3     CTCAACCTCC  CTTGGAGCAG  TGCTGGAAGT  286
DER3 rev  CTCANCCTNC  CNNGGAGCAG  TGCTGGAAGT   86
DER4 rev  ----------  ----------  ----------   -
Consensus CTCAACCTCC  CTTGGAGCAG  TGCTGGAAGT NY99 E    ACTGTGTGGA  GGAACAGAGA  GACGTTAATG  720
WN02 E    ACTGTGTGGA  GGAACAGAGA  GACGTTAATG  720
 DEF1     ACTGTGTGGA  GGAACAGAGA  GACGTTAATG  597
 DEF3     ACTGTGTGGA  GGAACAGAGA  GACGTTAATG  316
DER3 rev  ACTGNGTGGA  GGAACAGAGA  GACGTTAATG  116
DER4 rev  ----------  ----------  ----------   -
Consensus ACTGTGTGGA  GGAACAGAGA  GACGTTAATG
```

Fig. 11F

```
   NY99 E  GAGTTTGAGG  AACCACACGC  CACGAAGCAG  750
   WN02 E  GAGTTTGAGG  AACCACACGC  CACGAAGCAG  750
    DEF1   GAGTTTGAGG  AACCACACGC  CACGAAGCAG  627
    DEF3   GAGTTTGAGG  AACCACACGC  CACGAAGCAG  346
 DER3 rev  GAGTTTGAGN  AACCNCNCGC  CACGAAGCAG  146
 DER4 rev  ----------  ----------  -------CAG    3
 Consensus GAGTTTGAGG  AACCACACGC  CACGAAGCAG
```

100%
Conservation
0%

```
   NY99 E  TCTGTGATAG  CATTGGGCTC  ACAAGAGGGA  780
   WN02 E  TCTGTGATAG  CATTGGGCTC  ACAAGAGGGA  780
    DEF1   TCTGTGATAG  CATTGGGCTC  ACAAGAGGGA  657
    DEF3   TCTGTGATAG  CATTGGGCTC  ACAAGAGGGA  376
 DER3 rev  TCTGTGATAG  CATTGGGCTC  ACAAGAGGGA  176
 DER4 rev  TNNGTGATAN  CNTGG-CTC   ANAN-AGGNA   31
 Consensus TCTGTGATAG  CATTGGGCTC  ACAAGAGGGA
```

100%
Conservation
0%

```
   NY99 E  GCTCTGCAGC  AAGCTTTGGC  TGGAGCCATT  810
   WN02 E  GCTCTGCATC  AAGCTTTGGC  TGGAGCCATT  810
    DEF1   GCTCTGCATC  AAGCTTTGGC  TGGAGCCATT  687
    DEF3   GCTCTGCATC  AAGCTTTGGC  TGGAGCCATT  406
 DER3 rev  GCTNTGCATC  AAGCTTTGGC  NGGAGCCATT  206
 DER4 rev  GNTNTGCATC  AAGCTTTGGC  NGGAGCCATT   61
 Consensus GCTCTGCATC  AAGCTTTGGC  TGGAGCCATT
```

100%
Conservation
0%

```
   NY99 E  CCTGTGGAAT  TTTCAAGCAA  CACTGTCAAG  840
   WN02 E  CCTGTGGAAT  TTTCAAGCAA  CACTGTCAAG  840
    DEF1   CCTGTGGAAT  TTTCAAGCAA  CACTGTCAAG  717
    DEF3   CCTGTGGAAT  TTTCAAGCAA  CACTGTCAAG  436
 DER3 rev  CCTGTGGAAT  TTTCAAGCAA  CACTGTCAAG  236
 DER4 rev  NCTGTGGAAT  TTTCAAGCAA  CACTGTCAAG   91
 Consensus CCTGTGGAAT  TTTCAAGCAA  CACTGTCAAG
```

100%
Conservation
0%

Fig. 11G

```
   NY99 E    TTGACGTCGG  GTCATTTGAA  GTGTAGAGTG  870
   WN02 E    TTGACGTCGG  GTCATTTGAA  GTGTAGAGTG  870
    DEF1     TTGACGTCGG  GTCATTTGAA  GTGTAGAGTG  747
    DEF3     TTGACGTCGG  GTCATTTGAA  GTGTAGAGTG  466
  DER3 rev   TNGACGTCGG  NTCATTTGAA  GTGTAGAGTG  266
  DER4 rev   TTGACGTCGG  GTCATTTGAA  GTGTAGAGTG  121
  Consensus  TTGACGTCGG  GTCATTTGAA  GTGTAGAGTG
     100%
Conservation
      0%
   NY99 E    AAGATGGAAA  AATTGCAGTT  GAAGGGAACA  900
   WN02 E    AAGATGGAAA  AATTGCAGTT  GAAGGGAACA  900
    DEF1     AAGATGGAAA  AATTGCAGTT  GAAGGGAACA  777
    DEF3     AAGATGGAAA  AATTGCAGTT  GAAGGGAACA  496
  DER3 rev   AAGATGGAAA  AATTGCAGTT  GAAGGGAACA  296
  DER4 rev   AAGATGGAAA  AATTGCAGTT  GAAGGGAACA  151
  Consensus  AAGATGGAAA  AATTGCAGTT  GAAGGGAACA
     100%
Conservation
      0%
   NY99 E    ACCTATGGCG  TCTGTTCAAA  GGCTTTCAAG  930
   WN02 E    ACCTATGGCG  TCTGTTCAAA  GGCTTTCAAG  930
    DEF1     ACCTATGGCG  TCTGTTCAAA  GGCTTTCAAG  807
    DEF3     ACCTATGGCG  TCTGTTCAAA  GGCTTTCAAG  526
  DER3 rev   ACNTATGGCG  TCTGTTCAAA  GGCTTTCAAG  326
  DER4 rev   ACNTATGGCG  TCTGTTCAAA  GGCTTTCAAG  181
  Consensus  ACCTATGGCG  TCTGTTCAAA  GGCTTTCAAG
     100%
Conservation
      0%
   NY99 E    TTTCTTGGGA  CTCCCGCAGA  CACAGGTCAC  960
   WN02 E    TTTCTTGGGA  CTCCCGCAGA  CACAGGTCAC  960
    DEF1     TTTCTTGGGA  CTCCCGCAGA  CACAGGTCAC  837
    DEF3     TTTCTTGGGA  CTCCCGCAGA  CACAGGTCAC  556
  DER3 rev   TTTCTTGGGA  CTCCCGCAGA  CACAGGTCAC  356
  DER4 rev   TTTCTTGGGA  CTCCCGCAGA  CACAGGTCAC  211
  Consensus  TTTCTTGGGA  CTCCCGCAGA  CACAGGTCAC
     100%
Conservation
      0%
```

Fig. 11H

```
NY99 E     TTTGTTTCAG  TGGCCACGGC  CAACGCTAAG  1110
WN02 E     TTTGTTTCAG  TGGCCACGGC  CAACGCTAAG  1110
DEF1       ----------  ----------  ----------  944
DEF3       TTTGTTTCAG  TGGCCACGGC  CAACGCTAAG  706
DER3 rev   TTTGTTTCAG  TGGCCACGGC  CAACGCTAAG  506
DER4 rev   TTTGTTTCAG  TGGCCACGGC  CAACGCTAAG  361
Consensus  TTTGTTTCAG  TGGCCACGGC  CAACGCTAAG
100%
Conservation
0%
NY99 E     GTCCTGATTG  AATTGGAACC  ACCCTTTGGA  1140
WN02 E     GTCCTGATTG  AATTGGAACC  ACCCTTTGGA  1140
DEF1       ----------  ----------  ----------  944
DEF3       GTCCTGATTG  AATTGGAACC  ACCCTTTGGA  736
DER3 rev   GTCCTGATTG  AATTGGAACC  ACCCTTTGGA  536
DER4 rev   GTCCTGATTG  AATTGGAACC  ACCCTTTGGA  391
Consensus  GTCCTGATTG  AATTGGAACC  ACCCTTTGGA
100%
Conservation
0%
NY99 E     GACTCATACA  TAGTGGTGGG  CAGAGGAGAA  1170
WN02 E     GACTCATACA  TAGTGGTGGG  CAGAGGAGAA  1170
DEF1       ----------  ----------  ----------  944
DEF3       GACTCATACA  TAGTGGTGGG  CAGAGGAGAA  766
DER3 rev   GACTCATACA  TAGTGGTGGG  CAGAGGAGAA  566
DER4 rev   GACTCATACA  TAGTGGTGGG  CAGAGGAGAA  421
Consensus  GACTCATACA  TAGTGGTGGG  CAGAGGAGAA
100%
Conservation
0%
NY99 E     CAACAGATCA  ATCACCATTG  GCACAAGTCT  1200
WN02 E     CAACAGATCA  ATCACCATTG  GCACAAGTCT  1200
DEF1       ----------  ----------  ----------  944
DEF3       CAACAGATCA  ATCACCATTG  GCACAAGTCT  796
DER3 rev   CAACAGATCA  ATCACCATTG  GCACAAGTCT  596
DER4 rev   CAACAGATCA  ATCACCATTG  GCACAAGTCT  451
Consensus  CAACAGATCA  ATCACCATTG  GCACAAGTCT
100%
Conservation
0%
```

| | | | | |
|---|---|---|---|---|
| NY99 E | GGCTGTCCAT | CAAGTGTTCG | GAGGAGCATT | 1349 |
| WN02 E | GGCTGTCCAT | CAAGTGTTCG | GAGGAGCATT | 1349 |
| DEF1 | ---------- | ---------- | ---------- | 944 |
| DEF3 | GGNTGTCCAT | CAAGTGNTCG | GAGGAGCATT | 946 |
| DER3 rev | GGCTGTCCAT | CAAGTGTTCG | GAGGAGCATT | 745 |
| DER4 rev | GGCTGTCCAT | CAAGTGTTCG | GAGGAGCATT | 600 |
| Consensus | GGCTGTCCAT | CAAGTGTTCG | GAGGAGCATT | |

| | | | | |
|---|---|---|---|---|
| NY99 E | -CCGCTCACT | GTTCGGAGGC | ATGTCCTGGA | 1378 |
| WN02 E | -CCGCTCACT | GTTCGGAGGC | ATGTCCTGGA | 1378 |
| DEF1 | ---------- | ---------- | ---------- | 944 |
| DEF3 | NCCGCTCACT | GNTCGGAGGC | ATGTNCGGN | 976 |
| DER3 rev | -CCGCTCACT | GTTCGGAGGC | ATGTCCTGGA | 774 |
| DER4 rev | -CCGCTCACT | GTTCGGAGGC | ATGTCCTGGA | 629 |
| Consensus | -CCGCTCACT | GTTCGGAGGC | ATGTCCTGGA | |

| | | | | |
|---|---|---|---|---|
| NY99 E | TAACGCAAGG | ATTGCTGGGG | GCTCTCCTGT | 1408 |
| WN02 E | TAACGCAAGG | ATTGCTGGGG | GCTCTCCTGT | 1408 |
| DEF1 | ---------- | ---------- | ---------- | 944 |
| DEF3 | NNACGCAAGG | NTNGNTGGGG | G--------- | 997 |
| DER3 rev | TAACGCAAGG | ATTGCTGGGG | GCTCTCCTGT | 804 |
| DER4 rev | TAACGCAAGG | ATTGCTGGGG | GCTCTCCTGT | 659 |
| Consensus | TAACGCAAGG | ATTGCTGGGG | GCTCTCCTGT | |

| | | | | |
|---|---|---|---|---|
| NY99 E | TGTGGATGGG | CATCAATGCT | CGTGATAGGT | 1438 |
| WN02 E | TGTGGATGGG | CATCAATGCT | CGTGATAGGT | 1438 |
| DEF1 | ---------- | ---------- | ---------- | 944 |
| DEF3 | ---------- | ---------- | ---------- | 997 |
| DER3 rev | TGTGGATGGG | CATCAATGCT | CGTGATAGGT | 834 |
| DER4 rev | TGTGGATGGG | CATCAATGCT | CGTGATAGGT | 689 |
| Consensus | TGTGGATGGG | CATCAATGCT | CGTGATAGGT | |

Fig. 11L

| | | | | |
|---|---|---|---|---|
| NY99 E | CCATAGCTCT | CACGTTTCTC | GCAGTTGGAG | 1468 |
| WN02 E | CCATAGCTCT | CACGTTTCTC | GCAGTTGGAG | 1468 |
| DEF1 | ---------- | ---------- | ---------- | 944 |
| DEF3 | ---------- | ---------- | ---------- | 997 |
| DER3 rev | CCATAGCTCT | CACGTTTCTC | GCAGTTGGAG | 864 |
| DER4 rev | CCATAGCTCT | CACGTTTCTC | GCAGTTGGAG | 719 |
| Consensus | CCATAGCTCT | CACGTTTCTC | GCAGTTGGAG | |

| | | | | |
|---|---|---|---|---|
| NY99 E | GAGTTCTGCT | CTTCCTCTCC | GTGAACGTGC | 1498 |
| WN02 E | GAGTTCTGCT | CTTCCTCTCC | GTGAACGTGC | 1498 |
| DEF1 | ---------- | ---------- | ---------- | 944 |
| DEF3 | ---------- | ---------- | ---------- | 997 |
| DER3 rev | GAGTTCTGCT | CTTCCTCTCC | GTGAACGTGC | 894 |
| DER4 rev | GAGTTCTGCT | CTTCCTCTCC | GTGAACGTGC | 749 |
| Consensus | GAGTTCTGCT | CTTCCTCTCC | GTGAACGTGC | |

| | | | | |
|---|---|---|---|---|
| NY99 E | ACGCT----- | ---------- | ---------- | 1503 |
| WN02 E | ATGCT----- | ---------- | ---------- | 1503 |
| DEF1 | ---------- | ---------- | ---------- | 944 |
| DEF3 | ---------- | ---------- | ---------- | 997 |
| DER3 rev | ATGCTGACAC | TGGGTGTGCC | ATAGACATCA | 924 |
| DER4 rev | ATGCTGACAC | TGGGTGTGCC | ATAGACATCA | 779 |
| Consensus | ATGCT----- | ---------- | ---------- | |

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | GCCGGCAAGA | GCTGAG---- | ---------- | 940 |
| DER4 rev | GCCGGCAAGA | GCTGAGATGT | GGAAGTGGAG | 809 |
| Consensus | ---------- | ---------- | ---------- | |

Fig. 11M

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | TGTTCATACA | CAATGATGTG | GAGGCTTGGA | 839 |
| Consensus | ---------- | ---------- | ---------- | |

Conservation 100% – 0%

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | TGGACCGGTA | CAAGTATTAC | CCTGAAACGC | 869 |
| Consensus | ---------- | ---------- | ---------- | |

Conservation 100% – 0%

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | CACAAGGCCT | AGCCAAGATC | ATTCAGAAAG | 899 |
| Consensus | ---------- | ---------- | ---------- | |

Conservation 100% – 0%

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | CTCATAAGGA | AGGAGTGTGC | GGTCTACGAT | 929 |
| Consensus | ---------- | ---------- | ---------- | |

Conservation 100% – 0%

Fig. 11N

```
NY99 E     - -  1503
WN02 E     - -  1503
 DEF1      - -   944
 DEF3      - -   997
DER3 rev   - A   941
DER4 rev   C A   931
Consensus  - -
     100%
Conservation
      0%
```

Fig. 11O

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| D NS5F2 | C - - - - - - - - - | - - - - - - - - - - | - - - - - - - - - - | 1 |
| D NS5F5 | TCTCNCGGAT | TCCNCGCACG | AGATGTATTG | 30 |
| D NS5R3 rev | - - - - - - - - - - | - - - - - - - - - - | - - - - - - - - - - | - |
| D NS5R5 rev | - - - - - - - - - - | - - - - - - - - - - | - - - - - - - - - - | - |
| Consensus | - - - - - - - - - - | - - - - - - - - - - | - - - - - - - - - - | |

Conservation 100% / 0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| D NS5F2 | - - - - - - - - - - | - - - - - - - - - - | - - - - - - - - - - | 1 |
| D NS5F5 | GGTGAGTCGA | GCTTCAGGCA | ATGTGGTACA | 60 |
| D NS5R3 rev | - - - - - - - - - - | - - - - - - - - - - | - - - - - - - - - - | - |
| D NS5R5 rev | - - - - - - - - - - | - - - - - - - - - - | - - - - - - - - - - | - |
| Consensus | - - - - - - - - - - | - - - - - - - - - - | - - - - - - - - - - | |

Conservation 100% / 0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| D NS5F2 | - - - - - - - - - - | - - - - - - - - - - | - - - - - - - - - - | 1 |
| D NS5F5 | TTCAGTGAAT | ATGACCAGCC | AGGTGCTCCT | 90 |
| D NS5R3 rev | - - - - - - - - - - | - - - - - - - - - - | - - - - - - - - - - | - |
| D NS5R5 rev | - - - - - - - - - - | - - - - - - - - - - | - - - - - - - - - - | - |
| Consensus | - - - - - - - - - - | - - - - - - - - - - | - - - - - - - - - - | |

Conservation 100% / 0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| D NS5F2 | - - - - - - - - - - | - - - - - - - - - - | - - - - - - - - - - | 1 |
| D NS5F5 | AGGAAGAATG | GAAAAAGGA | CCTGGAAGGG | 120 |
| D NS5R3 rev | - - - - - - - - - - | - - - - - - - - - - | - - - - - - - - - - | - |
| D NS5R5 rev | - - - - - - - - - - | - - - - - - - - - - | - - - - - - - GGG | 3 |
| Consensus | - - - - - - - - - - | - - - - - - - - - - | - - - - - - - - - - | |

Conservation 100% / 0%

Fig. 12A

```
    NY99 NS5   - - - - - - - - - -  - - - - - - - - - -  - - - - - - - - - -   -
    WN02 NS5   - - - - - - - - - -  - - - - - - - - - -  - - - - - - - - - -   -
     D NS5F2   - - - - - - - - - -  - - - - - - - - - -  - - - - - - - - - -   1
     D NS5F5   T T C G A C G T G G  C A C C A C G A T G  A G A A C C A C C C  270
  D NS5R3 rev  - - - - - - - - - -  - - - - - - - - - -  - - - - - - - - - -   -
  D NS5R5 rev  T T C G A C G T G G  C A C C A C G A T G  A G A A C C A C C C  149
   Consensus   - - - - - - - - - -  - - - - - - - - - -  - - - - - - - - - -
        100%
Conservation
          0%

NY99 NS5   - - - - - - - - - -  - - - - - - - - - -  - - - - - - - - - -   -
    WN02 NS5   - - - - - - - - - -  - - - - - - - - - -  - - - - - - - - - -   -
     D NS5F2   - - - - - - - - - -  - - - - - - - - - -  - - - - - - - - - -   1
     D NS5F5   A T A T A G A A C C  T G G A A C T A T C  A C G G C A G T T A  300
  D NS5R3 rev  - - - - - - - - - -  - - - - - - - - - -  - - - - - - - - - -   -
  D NS5R5 rev  A T A T A G A N C N  N G G A A C T A T C  A C G G C A G T T A  179
   Consensus   - - - - - - - - - -  - - - - - - - - - -  - - - - - - - - - -
        100%
Conservation
          0%

NY99 NS5   - - - - - - - - - -  - - - - - - - - - -  - - - - - - - - - -   -
    WN02 NS5   - - - - - - - - - -  - - - - - - - - - -  - - - - - - - - - -   -
     D NS5F2   - - - - - - - - - -  - - - - - - - - - -  - - - - - - - - - -   1
     D NS5F5   T G A T G T G A A G  C C C A C A G G C T  C C G C C A G T T C  330
  D NS5R3 rev  - - - - - - - - - -  - - - - - - - - - -  - - - - - - - T T C   3
  D NS5R5 rev  T G A T G T G A A G  C C C A C A G G C T  C C G C C A G T T C  209
   Consensus   - - - - - - - - - -  - - - - - - - - - -  - - - - - - - T T C
        100%
Conservation
          0%

NY99 NS5   - - - - - - - - - -  - - - - - - - - - -  - - - - - - - - - -   -
    WN02 NS5   - - - - - - - - - -  - - - - - - - - - -  - - - - - - - - - -   -
     D NS5F2   - - - - - - - - - -  - - - - - - - - - -  - - - - - - - - - -   1
     D NS5F5   G C T G G T C A A T  G G A G T G G T C A  G G C T C C T C T C  360
  D NS5R3 rev  G C T N G T C A A T  G G A G T N G T C A  G G C T C C T C T C   33
  D NS5R5 rev  G C T G G T C A A T  G G A G T G G T C A  G G C T C C T C T C  239
   Consensus   G C T - G T C A A T  G G A G T - G T C A  G G C T C C T C T C
        100%
Conservation
          0%
```

Fig. 12C

| | | | | |
|---|---|---|---|---|
| NY99 NS5     | ---------- | ---------- | ---------- | - |
| WN02 NS5     | ---------- | ---------- | ---------- | - |
| D NS5F2      | ---------- | ---------- | ---------- | 1 |
| D NS5F5      | GAGTGAAGTA | CGTGCTCAAC | GAGACCACCA | 509 |
| D NS5R3 rev  | GAGTGAAGTA | CGTGCTCAAC | GAGACCACCA | 182 |
| D NS5R5 rev  | GAGTGAAGTA | CGTGCTCAAC | GAGACCACCA | 388 |
| Consensus 100% | GAGTGAAGTA | CGTGCTCAAC | GAGACCACCA | |

| | | | | |
|---|---|---|---|---|
| NY99 NS5     | ---------- | ---------- | ---------- | - |
| WN02 NS5     | ---------- | ---------- | ---------- | - |
| D NS5F2      | ---------- | ---------- | ---------- | 1 |
| D NS5F5      | ACTGGTTGTG | GGCGTTTTTG | GCCAGAGAAA | 539 |
| D NS5R3 rev  | ACTGGTTGTG | GGCGTTTTTG | GCCAGAGAAA | 212 |
| D NS5R5 rev  | ACTGGTTGTG | GGCGTTTTTG | GCCAGAGAAA | 418 |
| Consensus 100% | ACTGGTTGTG | GGCGTTTTTG | GCCAGAGAAA | |

| | | | | |
|---|---|---|---|---|
| NY99 NS5     | ---------- | ---------- | ---------- | - |
| WN02 NS5     | ---------- | ---------- | ---------- | - |
| D NS5F2      | ---------- | ---------- | ---------- | 1 |
| D NS5F5      | AACGTCCCAG | AATGTGCTCT | CGAGAGGAAT | 569 |
| D NS5R3 rev  | AACGTCCCAG | AATGTGCTCT | CGAGAGGAAT | 242 |
| D NS5R5 rev  | AACGTCCCAG | AATGTGCTCT | CGAGAGGAAT | 448 |
| Consensus 100% | AACGTCCCAG | AATGTGCTCT | CGAGAGGAAT | |

| | | | | |
|---|---|---|---|---|
| NY99 NS5     | ---------- | ---------- | ---------- | - |
| WN02 NS5     | ---------- | ---------- | ---------- | - |
| D NS5F2      | ---------- | -----ACAGC | AATGCAGCTT | 16 |
| D NS5F5      | TCATAAGAAA | GGTCAACAGC | AATGCAGCTT | 599 |
| D NS5R3 rev  | TCATNAGAAA | GGTCAACAGC | AATGCAGCTT | 272 |
| D NS5R5 rev  | TCATAAGAAA | GGTCAACAGC | AATGCAGCTT | 478 |
| Consensus 100% | TCAT-AGAAA | GGTCAACAGC | AATGCAGCTT | |

Fig. 12E

| | | | | |
|---|---|---|---|---|
| NY99 NS5 | CTTGCATTTA | CAACATGATG | GGAAAGAGAG | 46 |
| WN02 NS5 | CTTGCATTTA | CAACATGATG | GGAAAGAGAG | 46 |
| D NS5F2 | CTTGCATTTA | CAACATGATG | GGAAAGAGAG | 166 |
| D NS5F5 | CTTGCATTTA | CAACATGATG | GGAAAGAGAG | 749 |
| D NS5R3 rev | CTTGCATTTA | CAACATGATG | GGAAAGAGAG | 422 |
| D NS5R5 rev | CTTGCATTTA | CAACATGATG | GGAAAGAGAG | 628 |
| Consensus | CTTGCATTTA | CAACATGATG | GGAAAGAGAG | |

| | | | | |
|---|---|---|---|---|
| NY99 NS5 | AGAAAAAACC | CGGAGAATTC | GGAAAGGCCA | 76 |
| WN02 NS5 | AGAAAAAACC | CGGAGAGTTC | GGAAAGGCCA | 76 |
| D NS5F2 | AGAAAAAACC | CGGAGAGTTC | GGAAAGGCCA | 196 |
| D NS5F5 | AGAAAAAACC | CGGAGAGTTC | GGAAAGGCCA | 779 |
| D NS5R3 rev | AGAAAAAACC | CGGAGAGTTC | GGAAAGGCCA | 452 |
| D NS5R5 rev | AGAAAAAACC | CGGAGAGTTC | GGAAAGGCCA | 658 |
| Consensus | AGAAAAAACC | CGGAGAGTTC | GGAAAGGCCA | |

| | | | | |
|---|---|---|---|---|
| NY99 NS5 | AGGGAAGCAG | AGCCATTTGG | TTCATGTGGC | 106 |
| WN02 NS5 | AGGGAAGCAG | AGCCATTTGG | TTCATGTGGC | 106 |
| D NS5F2 | AGGGAAGCAG | AGCCATTTGG | TTCATGTGGC | 226 |
| D NS5F5 | AGGGAAGCAG | AGCCATTTGG | TTCATGTGGC | 809 |
| D NS5R3 rev | AGGGAAGCAG | AGCCATTTGG | TTCATGTGGC | 482 |
| D NS5R5 rev | AGGGAAGCAG | AGCCATTTGG | TTCATGTGGC | 688 |
| Consensus | AGGGAAGCAG | AGCCATTTGG | TTCATGTGGC | |

| | | | | |
|---|---|---|---|---|
| NY99 NS5 | TCGGAGCTCG | CTTTCTGGAG | TTCGAGGCTC | 136 |
| WN02 NS5 | TCGGAGCTCG | CTTTCTGGAG | TTCGAGGCTC | 136 |
| D NS5F2 | TCGGAGCTCG | CTTTCTGGAG | TTCGAGGCTC | 256 |
| D NS5F5 | TCGGANCTCG | CTTTCTGGAG | TTCGAGGCTC | 839 |
| D NS5R3 rev | TCGGAGCTCG | CTTTCTGGAG | TTCGAGGCTC | 512 |
| D NS5R5 rev | TCGGAGCTCG | CTTTCTGGAG | TTCGAGGCTC | 718 |
| Consensus | TCGGAGCTCG | CTTTCTGGAG | TTCGAGGCTC | |

Fig. 12G

| | | | | |
|---|---|---|---|---|
| NY99 NS5 | TGGGTTTTCT | CAATGAAGAC | CACTGGCTTG | 166 |
| WN02 NS5 | TGGGTTTTCT | CAATGAAGAC | CACTGGCTTG | 166 |
| D NS5F2 | TGGGTTTTCT | CAATGAAGAC | CACTGGCTTG | 286 |
| D NS5F5 | TGGGTTTTCT | CAATGAAGAC | CACTGGCTTG | 869 |
| D NS5R3 rev | TGGGTTTTCT | CAATGAAGAC | CACTGGCTTG | 542 |
| D NS5R5 rev | TGGGTTTTCT | CAATGAAGAC | CACTGGCTTG | 748 |
| Consensus | TGGGTTTTCT | CAATGAAGAC | CACTGGCTTG | |
| NY99 NS5 | GAAGAAAGAA | CTCAGGAGGA | GGTGTCGAGG | 196 |
| WN02 NS5 | GAAGAAAGAA | CTCAGGAGGA | GGTGTCGAGG | 196 |
| D NS5F2 | GAAGAAAGAA | CTCAGGAGGA | GGTGTCGAGG | 316 |
| D NS5F5 | GAAGNNN-AA | CTCNNNNGA | GGTGTCGAGG | 898 |
| D NS5R3 rev | GAAGAAAGAA | CTCAGGAGGA | GGTGTCGAGG | 572 |
| D NS5R5 rev | GAAGAAAGAA | CTCAGGAGGA | GGTGTCGAGG | 778 |
| Consensus | GAAGAAAGAA | CTCAGGAGGA | GGTGTCGAGG | |
| NY99 NS5 | GCTTGGGCCT | CCAAAAACTG | GGTTACATCC | 226 |
| WN02 NS5 | GCTTGGGCCT | CCAAAAACTG | GGTTACATCC | 226 |
| D NS5F2 | GCTTGGGCCT | CCAAAAACTG | GGTTACATCC | 346 |
| D NS5F5 | GCTTNNNC-T | CCAAAAACTG | GGTTACATCC | 927 |
| D NS5R3 rev | GCTTGGGCCT | CCAAAAACTG | GGTTACATCC | 602 |
| D NS5R5 rev | GCTTGGGCCT | CCAAAAACTG | GGTTACATCC | 808 |
| Consensus | GCTTGGGCCT | CCAAAAACTG | GGTTACATCC | |
| NY99 NS5 | TGCGTGAAGT | TGGCACCCGG | CCTGGGGGCA | 256 |
| WN02 NS5 | TGCGTGAAGT | TGGCACCCGG | CCTGGGGGCA | 256 |
| D NS5F2 | TGCGTGAAGT | TGGCACCCGG | CCTGGGGGCA | 376 |
| D NS5F5 | NGCGTGAAGT | NG-CACCCNG | NCTGGGGGC- | 955 |
| D NS5R3 rev | TGCGTGAAGT | TGGCACCCGG | CCTGGGGGCA | 632 |
| D NS5R5 rev | TGCGTGAAGT | TGGCACCCGG | CCTGGGGGCA | 838 |
| Consensus | TGCGTGAAGT | TGGCACCCGG | CCTGGGGGCA | |

Fig. 12H

| | | | | |
|---|---|---|---|---|
| NY99 NS5 | AGATCTATGC | TGATGACACA | GCTGGCTGGG | 286 |
| WN02 NS5 | AGATCTATGC | TGATGACACA | GCTGGCTGGG | 286 |
| D NS5F2 | AGATCTATGC | TGATGACACA | GCTGGCTGGG | 406 |
| D NS5F5 | ---------- | ---------- | ---------- | 955 |
| D NS5R3 rev | AGATCTATGC | TGATGACACA | GCTGGCTGGG | 662 |
| D NS5R5 rev | AGATCTATGC | TGATGACACA | GCTGGCTGGG | 868 |
| Consensus | AGATCTATGC | TGATGACACA | GCTGGCTGGG | |

| | | | | |
|---|---|---|---|---|
| NY99 NS5 | ACACCCGCAT | CACGAGAGCT | GACTTGGAAA | 316 |
| WN02 NS5 | ACACCCGCAT | CACGAGTGCT | GACTTGGAAA | 316 |
| D NS5F2 | ACACCCGCAT | CACGAGAGCT | GACTTGGAAA | 436 |
| D NS5F5 | ---------- | ---------- | ---------- | 955 |
| D NS5R3 rev | ACACCCGCAT | CACGAGAGCT | GACTTGGAAA | 692 |
| D NS5R5 rev | ACACCCGCAT | CACGAGAGCT | GACTTGGAAA | 898 |
| Consensus | ACACCCGCAT | CACGAGAGCT | GACTTGGAAA | |

| | | | | |
|---|---|---|---|---|
| NY99 NS5 | ATGAAGCTAA | GGTGCTTGAG | CTGCTTGATG | 346 |
| WN02 NS5 | ATGAAGCTAA | GGTGCTTGAG | TTGCTTGATG | 346 |
| D NS5F2 | ATGAAGCTAA | GGTGCTTGAG | TTGCTTGATG | 466 |
| D NS5F5 | ---------- | ---------- | ---------- | 955 |
| D NS5R3 rev | ATGAAGCTAA | GGTGCTTGAG | TTGCTTGATG | 722 |
| D NS5R5 rev | ATGAAGCTAA | GGTGCTTGAG | TTGCTTGATG | 928 |
| Consensus | ATGAAGCTAA | GGTGCTTGAG | TTGCTTGATG | |

| | | | | |
|---|---|---|---|---|
| NY99 NS5 | GGGAACATCG | GCGTCTTGCC | AGGGCCATCA | 376 |
| WN02 NS5 | GGGAACATCG | GCGTCTTGCC | AGGGCCATCA | 376 |
| D NS5F2 | GGGAACATCG | GCGTCTTGCC | AGGGCCATCA | 496 |
| D NS5F5 | ---------- | ---------- | ---------- | 955 |
| D NS5R3 rev | GGGAACATCG | GCGTCTTGCC | AGGGCCATCA | 752 |
| D NS5R5 rev | GGGAACATCG | GCGTCTTGCC | AGGGCCATCA | 958 |
| Consensus | GGGAACATCG | GCGTCTTGCC | AGGGCCATCA | |

Fig. 12I

| | | | | |
|---|---|---|---|---|
| NY99 NS5 | TTGAGCTCAC | CTATCGTCAC | AAAGTTGTGA | 406 |
| WN02 NS5 | TTGAGCTCAC | CTATCGTCAC | AAAGTTGTGA | 406 |
| D NS5F2 | TTGAGCTCAC | CTATCGTCAC | AAAGTTGTGA | 526 |
| D NS5F5 | ---------- | ---------- | ---------- | 955 |
| D NS5R3 rev | TTGAGCTCAC | CTATCGTCAC | AAAGTTGTGA | 782 |
| D NS5R5 rev | TTGAGCTCAC | CNA------- | ---------- | 971 |
| Consens

```
NY99 NS5    CCCTAAACAC  TTTCACCAAC  CTGGCCGTCC  526
WN02 NS5    CCCTAAACAC  TTTCACCAAC  CTGGCCGTCC  526
D NS5F2     CCCTAAACAC  TTTCACCAAC  CTGGCCGTCC  646
D NS5F5     ----------  ----------  ----------  955
D NS5R3 rev CCCTAAACAC  TTTCACCAAC  CTGGCCGTCC  902
D NS5R5 rev ----------  ----------  ----------  971
Consensus   CCCTAAACAC  TTTCACCAAC  CTGGCCGTCC NY99 NS5    AGCTGGTGAG  GATGATGGAA  GGGGAA-GGA  555
WN02 NS5    AGCTGGTGAG  GATGATGGAA  GGGGAA-GGA  555
D NS5F2     AGCTGGTGAG  GATGATGGAA  GGGGAANGGA  676
D NS5F5     ----------  ----------  ----------  955
D NS5R3 rev AGCTGGTGAG  GATGATGGAA  GGGGAA-GGA  931
D NS5R5 rev ----------  ----------  ----------  971
Consensus   AGCTGGTGAG  GATGATGGAA  GGGGAA-GGA NY99 NS5    GTGATTGGCC  CAGATGATGT  GGAGAAACTC  585
WN02 NS5    GTGATTGGCC  CAGATGATGT  GGAGAAACTC  585
D NS5F2     GTGATTGGCC  CAGATGATGT  GGAGAAACTC  706
D NS5F5     ----------  ----------  ----------  955
D NS5R3 rev GTGATTGGCC  CAGATGATGT  GGAGAAACTC  961
D NS5R5 rev ----------  ----------  ----------  971
Consensus   GTGATTGGCC  CAGATGATGT  GGAGAAACTC NY99 NS5    ACAAAAGGGA  AAGGACCCAA  AGT-------  608
WN02 NS5    ACAAAAGGGA  AAGGACCCAA  AGT-------  608
D NS5F2     ACAAAAGGGA  AAGGACCCAA  AGTCAGGACC  736
D NS5F5     ----------  ----------  ----------  955
D NS5R3 rev ACAAAAGG--  ----------  ----------  969
D NS5R5 rev ----------  ----------  ----------  971
Consensus   ACAAAAGGGA  AAGGACCCAA  AGT-------
```

Fig. 12K

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| D NS5F2 | TGGCTGTTTG | AGAATGGGGA | AGAAAGACTC | 766 |
| D NS5F5 | - - - - - - - - - - | - - - - - - - - - - | - - - - - - - - - - | 955 |
| D NS5R3 rev | - - - - - - - - - - | - - - - - - - - - - | - - - - - - - - - - | 969 |
| D NS5R5 rev | - - - - - - - - - - | - - - - - - - - - - | - - - - - - - - - - | 971 |
| Consensus | - - - - - - - - - - | - - - - - - - - - - | - - - - - - - - - - | |

Conservation 100% / 0%

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| D NS5F2 | AGCCGCATGG | CTGTCAGTGG | AGATGACTGT | 796 |
| D NS5F5 | - - - - - - - - - - | - - - - - - - - - - | - - - - - - - - - - | 955 |
| D NS5R3 rev | - - - - - - - - - - | - - - - - - - - - - | - - - - - - - - - - | 969 |
| D NS5R5 rev | - - - - - - - - - - | - - - - - - - - - - | - - - - - - - - - - | 971 |
| Consensus | - - - - - - - - - - | - - - - - - - - - - | - - - - - - - - - - | |

Conservation 100% / 0%

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| D NS5F2 | GTGGTAAAGC | CCCTGGACGA | TCGCTTTGCC | 826 |
| D NS5F5 | - - - - - - - - - - | - - - - - - - - - - | - - - - - - - - - - | 955 |
| D NS5R3 rev | - - - - - - - - - - | - - - - - - - - - - | - - - - - - - - - - | 969 |
| D NS5R5 rev | - - - - - - - - - - | - - - - - - - - - - | - - - - - - - - - - | 971 |
| Consensus | - - - - - - - - - - | - - - - - - - - - - | - - - - - - - - - - | |

Conservation 100% / 0%

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| D NS5F2 | ACCTCGCTCC | ACTTCCTCAA | TGCTATGTCA | 856 |
| D NS5F5 | - - - - - - - - - - | - - - - - - - - - - | - - - - - - - - - - | 955 |
| D NS5R3 rev | - - - - - - - - - - | - - - - - - - - - - | - - - - - - - - - - | 969 |
| D NS5R5 rev | - - - - - - - - - - | - - - - - - - - - - | - - - - - - - - - - | 971 |
| Consensus | - - - - - - - - - - | - - - - - - - - - - | - - - - - - - - - - | |

Conservation 100% / 0%

Fig. 12L

| | | | | |
|---|---|---|---|---|
| NY99 NS5 | ---------- | ---------- | ---------- | 608 |
| WN02 NS5 | ---------- | ---------- | ---------- | 608 |
| D NS5F2 | AANNNTCGCA | AAGACATCCA | AGAGTGGAAA | 886 |
| D NS5F5 | ---------- | ---------- | ---------- | 955 |
| D NS5R3 rev | ---------- | ---------- | ---------- | 969 |
| D NS5R5 rev | ---------- | ---------- | ---------- | 971 |
| Consensus | ---------- | ---------- | ---------- | |

| | | | | |
|---|---|---|---|---|
| NY99 NS5 | ---------- | ---------- | ---------- | 608 |
| WN02 NS5 | ---------- | ---------- | ---------- | 608 |
| D NS5F2 | CCGTCAACTG | GATGGTATGA | TTGGCAGCNG | 916 |
| D NS5F5 | ---------- | ---------- | ---------- | 955 |
| D NS5R3 rev | ---------- | ---------- | ---------- | 969 |
| D NS5R5 rev | ---------- | ---------- | ---------- | 971 |
| Consensus | ---------- | ---------- | ---------- | |

| | | | | |
|---|---|---|---|---|
| NY99 NS5 | ---------- | ---------- | ---------- | 608 |
| WN02 NS5 | ---------- | ---------- | ---------- | 608 |
| D NS5F2 | GTTCCATTTT | GCTCAAACCA | TTTNNCTGAA | 946 |
| D NS5F5 | ---------- | ---------- | ---------- |

| | | | | |
|---|---|---|---|---|
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | AAAACC-ATG | GGACACCATC | ACGAATGTTA | 389 |
| H NS5R3 rev | AAAACCNTG | GGACNCCATC | NCGAANNNNC | 109 |
| H NS5R5 rev | AAAACC-ATG | GGACACCATC | ACGAATGTTA | 314 |
| Consensus 100% | AAAACC--TG | GGAC-CCATC | -CGAA----- | |
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | CCACCATGGC | CATGACTGAC | ACTACTCCC- | 418 |
| H NS5R3 rev | CACCATNGNC | CATGACTGNC | ACTACTCCCN | 139 |
| H NS5R5 rev | CCACCATGGC | CATGACTGAC | ACTACTCCC- | 343 |
| Consensus 100% | C--C---G-C | CATGACTG-C | ACTACTCCC- | |
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | TTCGGGCAGC | AGCGAGTGTT | CAAAGAGAAG | 448 |
| H NS5R3 rev | TTCGGGCAGC | AGCGAGTGTT | CAAAGAGAAG | 169 |
| H NS5R5 rev | TTCGGGCAGC | AGCGAGTGTT | CAAAGAGAAG | 373 |
| Consensus 100% | TTCGGGCAGC | AGCGAGTGTT | CAAAGAGAAG | |
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | GTGGACACGA | AAGCTCCTGA | ACCGCCAGAA | 478 |
| H NS5R3 rev | GTGGACACGA | AAGCTCNNGA | ACCGCCAGAA | 199 |
| H NS5R5 rev | GTGGACACGA | AAGCTCCTGA | ACCGCCAGAA | 403 |
| Consensus 100% | GTGGACACGA | AAGCTC--GA | ACCGCCAGAA | |

Fig. 13D

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | GGAGTGAAGT | ACGTGCTCAA | CGAGACCACC | 508 |
| H NS5R3 rev | GGAGTGAAGT | ACGTGCTCAA | CGAGACCACC | 229 |
| H NS5R5 rev | GGAGTGAAGT | ACGTGCTCAA | CGAGACCACC | 433 |
| Consensus | GGAGTGAAGT | ACGTGCTCAA | CGAGACCACC | |

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | AACTGGTTGT | GGGCGTTTTT | GGCCAGAGAA | 538 |
| H NS5R3 rev | AACTGGTTGT | GGGCGTTTTT | GGCCAGAGAA | 259 |
| H NS5R5 rev | AACTGGTTGT | GGGCGTTTTT | GGCCAGAGAA | 463 |
| Consensus | AACTGGTTGT | GGGCGTTTTT | GGCCAGAGAA | |

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | AAACGTCCCA | GAATGTGCTC | TCGAGAGGAA | 568 |
| H NS5R3 rev | AAACGTCCCA | GAATGTGCTC | TCGAGAGGAA | 289 |
| H NS5R5 rev | AAACGTCCCA | GAATGTGCTC | TCGAGAGNNN | 493 |
| Consensus | AAACGTCCCA | GAATGTGCTC | TCGAGAG - - - | |

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - CACAG | CAATGCAGCT | 15 |
| H NS5F5 | TTCATAAGAA | AGGTCAACAG | CAATGCAGCT | 598 |
| H NS5R3 rev | TTCATNAGAA | AGGTCAACAG | CAATGCAGCT | 319 |
| H NS5R5 rev | NNNATAAGAA | AGGTCAACAG | CAATGCAGCT | 523 |
| Consensus | - - -AT-AGAA | AGGTCAACAG | CAATGCAGCT | |

Fig. 13E

| | | | | |
|---|---|---|---|---|
| NY99 NS5 | ---------- | ---------- | ---------- | |
| WN02 NS5 | ---------- | ---------- | ---------- | |
| H NS5F2 | TTGGGTGCCN | TGTTTGAAGA | GCAGAATCAA | 45 |
| H NS5F5 | TTGGGTGCCA | TGTTTGAAGA | GCAGAATCAA | 628 |
| H NS5R3 rev | TTGGGTGCCA | TGTTTGAAGA | GCAGAATCAA | 349 |
| H NS5R5 rev | TTGGGTGCCA | TGTTTGAAGA | GCAGAATCAA | 553 |
| Consensus | TTGGGTGCCA | TGTTTGAAGA | GCAGAATCAA | |

| | | | | |
|---|---|---|---|---|
| NY99 NS5 | ---------- | ---------- | ---------- | |
| WN02 NS5 | ---------- | ---------- | ---------- | |
| H NS5F2 | TGGAGGAGCG | CCAGAGAAGC | AGTTGAAGAT | 75 |
| H NS5F5 | TGGAGGAGCG | CCAGAGAAGC | AGTTGAAGAT | 658 |
| H NS5R3 rev | TGGAGGAGCG | CCAGAGAAGC | AGTTGAAGAT | 379 |
| H NS5R5 rev | TGGAGGAGCG | CCAGAGAAGC | AGTTGAAGAT | 583 |
| Consensus | TGGAGGAGCG | CCAGAGAAGC | AGTTGAAGAT | |

| | | | | |
|---|---|---|---|---|
| NY99 NS5 | ---------- | ---------- | ---------- | |
| WN02 NS5 | ---------- | ---------- | ---------- | |
| H NS5F2 | CCAAAATTTT | GGGAGATGGT | GGATGAGGAG | 105 |
| H NS5F5 | CCAAAATTTT | GGGAGATGGT | GGATGAGGAG | 688 |
| H NS5R3 rev | CCAAAATTTT | GGGAGATGGT | GGATGAGGAG | 409 |
| H NS5R5 rev | CCAAAATTTT | GGGAGATGGT | GGATGAGGAG | 613 |
| Consensus | CCAAAATTTT | GGGAGATGGT | GGATGAGGAG | |

| | | | | |
|---|---|---|---|---|
| NY99 NS5 | ---------- | -----CGGGG | GGAATGTCAC | 15 |
| WN02 NS5 | ---------- | -----CGGGG | GGAATGTCAC | 15 |
| H NS5F2 | CGCGAGGCAC | ATCTGCGGGG | GGAATGTCAC | 135 |
| H NS5F5 | CGCGAGGCAC | ATCTGCGGGG | GGAATGTCAC | 718 |
| H NS5R3 rev | CGCGAGGCAC | ATCTGCGGGG | GGAATGTCAC | 439 |
| H NS5R5 rev | CGCGAGGCAC | ATCTGCGGGG | GGAATGTCAC | 643 |
| Consensus | CGCGAGGCAC | ATCTGCGGGG | GGAATGTCAC | |

Fig. 13F

| | | | | |
|---|---|---|---|---|
| NY99 NS5 | CTGGGTTTTC | TCAATGAAGA | CCACTGGCTT | 165 |
| WN02 NS5 | CTGGGTTTTC | TCAATGAAGA | CCACTGGCTT | 165 |
| H NS5F2 | CTGGGTTTTC | TCAATGAAGA | TCACTGGCTT | 285 |
| H NS5F5 | CTNGGTTTTC | TCAATGAAGA | TCACTGGCTT | 868 |
| H NS5R3 rev | CTGGGTTTTC | TCAATGAAGA | TCACTGGCTT | 589 |
| H NS5R5 rev | CTGGGTTTTC | TCAATGAAGA | TCACTGGCTT | 793 |
| Consensus | CTGGGTTTTC | TCAATGAAGA | TCACTGGCTT | |
| NY99 NS5 | GGAAGAAAGA | ACTCAGGAGG | AGGTGTCGAG | 195 |
| WN02 NS5 | GGAAGAAAGA | ACTCAGGAGG | AGGTGTCGAG | 195 |
| H NS5F2 | GGAAGAAAGA | ACTCAGGAGG | AGGTGTCGAG | 315 |
| H NS5F5 | GGAAGAAAGA | ACTCNNNANG | AGGTGTCGAG | 898 |
| H NS5R3 rev | GGAAGAAAGA | ACTCAGGAGG | AGGTGTCGAG | 619 |
| H NS5R5 rev | GGAAGAAAGA | ACTCAGGAGG | AGGTGTCGAG | 823 |
| Consensus | GGAAGAAAGA | ACTCAGGAGG | AGGTGTCGAG | |
| NY99 NS5 | GGCTTGGGCC | TCCAAAAACT | GGGTTACATC | 225 |
| WN02 NS5 | GGCTTGGGCC | TCCAAAAACT | GGGTTACATC | 225 |
| H NS5F2 | GGCTTGGGCC | TCCAAAAACT | GGGTTACATC | 345 |
| H NS5F5 | GGCTTGGGCC | TCCAAAAACT | GGGTTACATC | 928 |
| H NS5R3 rev | GGCTTGGGCC | TCCAAAAACT | GGGTTACATC | 649 |
| H NS5R5 rev | GGCTTGGGCC | TCCAAAAACT | GGGTTACATC | 853 |
| Consensus | GGCTTGGGCC | TCCAAAAACT | GGGTTACATC | |
| NY99 NS5 | CTGCGTGAAG | TTGGCACCCG | G-CCTGGGGG | 254 |
| WN02 NS5 | CTGCGTGAAG | TTGGCACCCG | G-CCTGGGGG | 254 |
| H NS5F2 | CTGCGTGAAG | TTGGCACCCG | G-CCTGGGGG | 374 |
| H NS5F5 | CTGCGTGAAG | TTGGCACCCN | GNCCTGGGGG | 958 |
| H NS5R3 rev | CTGCGTGAAG | TTGGCACCCG | G-CCTGGGGG | 678 |
| H NS5R5 rev | CTGCGTGAAG | TTGGCACCCG | G-CCTGGGGG | 882 |
| Consensus | CTGCGTGAAG | TTGGCACCCG | G-CCTGGGGG | |

Fig. 13H

| | | | | |
|---|---|---|---|---|
| NY99 NS5 | CAAGATCTAT | GCTGATGACA | CAGCTGGCTG | 284 |
| WN02 NS5 | CAAGATCTAT | GCTGATGACA | CAGCTGGCTG | 284 |
| H NS5F2 | CAAGATCTAT | GCTGATGACA | CAGCTGGCTG | 404 |
| H NS5F5 | CAAGATCTAT | GCTGATGACN | CAGCTGNNTG | 988 |
| H NS5R3 rev | CAAGATCTAT | GCTGATGACA | CAGCTGGCTG | 708 |
| H NS5R5 rev | CAAGATCTAT | GCTGATGACA | CAGCTGGCTG | 912 |
| Consensus | CAAGATCTAT | GCTGATGACA | CAGCTGGCTG | |
| NY99 NS5 | GGACACCCGC | ATCACGAGAG | CTGACTTGGA | 314 |
| WN02 NS5 | GGACACCCGC | ATCACGAGTG | CTGACTTGGA | 314 |
| H NS5F2 | GGACACCCGC | ATCACGAGAG | CTGACTTGGA | 434 |
| H NS5F5 | GGNNACCCNC | ATCACGAGNG | CTGANTTNNN | 1018 |
| H NS5R3 rev | GGACACCCGC | ATCACGAGAG | CTGACTTGGA | 738 |
| H NS5R5 rev | GGACACCCGC | ATCACGAGAG | CTGACTTGGA | 942 |
| Consensus | GGACACCCGC | ATCACGAGAG | CTGACTTGGA | |
| NY99 NS5 | AAATGAAGCT | AAGGTGCTTG | AGCTGCTTGA | 344 |
| WN02 NS5 | AAATGAAGCT | AAGGTGCTTG | AGTTGCTTGA | 344 |
| H NS5F2 | AAATGAAGCT | AAGGTGCTTG | AGCTGCTTGA | 464 |
| H NS5F5 | AAATGNAGC- | ---------- | ---------- | 1027 |
| H NS5R3 rev | AAATGAAGCT | AAGGTGCTTG | AGCTGCTTGA | 768 |
| H NS5R5 rev | AAATGAAGCT | AAGGTGCTTG | AGCTGCTTGA | 972 |
| Consensus | AAATGAAGCT | AAGGTGCTTG | AGCTGCTTGA | |
| NY99 NS5 | TGGGGAACAT | CGGCGTCTTG | CCAGGGCCAT | 374 |
| WN02 NS5 | TGGGGAACAT | CGGCGTCTTG | CCAGGGCCAT | 374 |
| H NS5F2 | TGGGGAACAT | CGGCGTCTTG | CCAGGGCCAT | 494 |
| H NS5F5 | ---------- | ---------- | ---------- | 1027 |
| H NS5R3 rev | TGGGGAACAT | CGGCGTCTTG | CCAGGGCCAT | 798 |
| H NS5R5 rev | TGGGGAACAT | CGGCGTCTTG | CCAGGGCCAT | 1002 |
| Consensus | TGGGGAACAT | CGGCGTCTTG | CCAGGGCCAT | |

Fig. 13I

| | | | | |
|---|---|---|---|---|
| NY99 NS5 | CATTGAGCTC | ACCTATCGTC | ACAAAGTTGT | 404 |
| WN02 NS5 | CATTGAGCTC | ACCTATCGTC | ACAAAGTTGT | 404 |
| H NS5F2 | CATTGAGCTC | ACCTATCGTC | ACAAAGTTGT | 524 |
| H NS5F5 | ---------- | ---------- | ---------- | 1027 |
| H NS5R3 rev | CATTGAGCTC | ACCTATCGTC | ACAAAGTTGT | 828 |
| H NS5R5 rev | CATTGAGCTC | ACC------- | ---------- | 1015 |
| Consensus | CATTGAGCTC | ACCTATCGTC | ACAAAGTTGT | |

| | | | | |
|---|---|---|---|---|
| NY99 NS5 | GAAAGTGATG | CGCCCGGCTG | CTGATGGAAG | 434 |
| WN02 NS5 | GAAAGTGATG | CGCCCGGCTG | CTGATGGAAG | 434 |
| H NS5F2 | GAAAGTGATG | CGCCCGGCTG | CTGATGGAAG | 554 |
| H NS5F5 | ---------- | ---------- | ---------- | 1027 |
| H NS5R3 rev | GAAAGTGATG | CGCCCGGCTG | CTGATGGAAG | 858 |
| H NS5R5 rev | ---------- | ---------- | ---------- | 1015 |
| Consensus | GAAAGTGATG | CGCCCGGCTG | CTGATGGAAG | |

| | | | | |
|---|---|---|---|---|
| NY99 NS5 | AACCGTCATG | GATGTTATCT | CCAGAGAAGA | 464 |
| WN02 NS5 | AACCGTCATG | GATGTTATCT | CCAGAGAAGA | 464 |
| H NS5F2 | AACCGTCATG | GATGTTATCT | CCAGAGAAGA | 584 |
| H NS5F5 | ---------- | ---------- | ---------- | 1027 |
| H NS5R3 rev | AACCGTCATG | GATGTTATCT | CCAGAGAAGA | 888 |
| H NS5R5 rev | ---------- | ---------- | ---------- | 1015 |
| Consensus | AACCGTCATG | GATGTTATCT | CCAGAGAAGA | |

| | | | | |
|---|---|---|---|---|
| NY99 NS5 | TCAGAGGGGG | AGTGGACAAG | TTGTCACCTA | 494 |
| WN02 NS5 | TCAGAGGGGG | AGTGGACAAG | TTGTCACCTA | 494 |
| H NS5F2 | TCAGAGGGGG | AGTGGACAAG | TTGTCACCTA | 614 |
| H NS5F5 | ---------- | ---------- | ---------- | 1027 |
| H NS5R3 rev | TCAGAGGGGG | AGTGGACAAG | TTGTCACCTA | 918 |
| H NS5R5 rev | ---------- | ---------- | ---------- | 1015 |
| Consensus | TCAGAGGGGG | AGTGGACAAG | TTGTCACCTA | |

Fig. 13J

```
      NY99 NS5   CGCCCTAAAC  ACTTTCACCA  ACCTGGCCGT   524
      WN02 NS5   CGCCCTAAAC  ACTTTCACCA  ACCTGGCCGT   524
       H NS5F2   CGCNCTAAAC  ACTTTCACCA  ACCTGGCCGT   644
       H NS5F5   ----------  ----------  ----------  1027
    H NS5R3 rev  CNCNCTAAAC  ACTTTCACCA  ACCTGGCCGT   948
    H NS5R5 rev  ----------  ----------  ----------  1015
     Consensus   CGCCCTAAAC  ACTTTCACCA  ACCTGGCCGT
         100%
  Conservation
           0%

NY99 NS5   CCAGCTGGTG  AGGATGATGG  AAGGGGAA-G   553
      WN02 NS5   CCAGCTGGTG  AGGATGATGG  AAGGGGAA-G   553
       H NS5F2   CCAGCTGGTG  AGGATGATGG  AAGGGGAANG   674
       H NS5F5   ----------  ----------  ----------  1027
    H NS5R3 rev  CCAGCTGGTG  AGGATGATGG  AAGGGGAA-G   977
    H NS5R5 rev  ----------  ----------  ----------  1015
     Consensus   CCAGCTGGTG  AGGATGATGG  AAGGGGAA-G
         100%
  Conservation
           0%

NY99 NS5   GAGTGATTGG  CCCAGATGAT  GTGGAGAAAC   583
      WN02 NS5   GAGTGATTGG  CCCAGATGAT  GTGGAGAAAC   583
       H NS5F2   GAGTGATTGG  CCCAGATGAT  GTGGAGAAAC   704
       H NS5F5   ----------  ----------  ----------  1027
    H NS5R3 rev  GAGTGATTGG  CCCAGATGAT  GTGGAGAAAC  1007
    H NS5R5 rev  ----------  ----------  ----------  1015
     Consensus   GAGTGATTGG  CCCAGATGAT  GTGGAGAAAC
         100%
  Conservation
           0%

NY99 NS5   TCACAAAAGG  GAAAGGACCC  AAAGT-----   608
      WN02 NS5   TCACAAAAGG  GAAAGGACCC  AAAGT-----   608
       H NS5F2   TCACAAAAGG  GAAAGGACCC  AAAGTCAGGA   734
       H NS5F5   ----------  ----------  ----------  1027
    H NS5R3 rev  TCACAAAAGG  GA--------  ----------  1019
    H NS5R5 rev  ----------  ----------  ----------  1015
     Consensus   TCACAAAAGG  GAAAGGACCC  AAAGT-----
         100%
  Conservation
           0%
```

Fig. 13K

| | | | | |
|---|---|---|---|---|
| NY99 NS5 | ---------- | ---------- | ---------- | 608 |
| WN02 NS5 | ---------- | ---------- | ---------- | 608 |
| H NS5F2 | CCTGGCTGTT | TGAGAATGGG | GAAGAAAGAC | 764 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

| | | | | |
|---|---|---|---|---|
| NY99 NS5 | ---------- | ---------- | ---------- | 608 |
| WN02 NS5 | ---------- | ---------- | ---------- | 608 |
| H NS5F2 | TCAGCCGCAT | GGCTGTCAGT | GGAGATGACT | 794 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

| | | | | |
|---|---|---|---|---|
| NY99 NS5 | ---------- | ---------- | ---------- | 608 |
| WN02 NS5 | ---------- | ---------- | ---------- | 608 |
| H NS5F2 | GTGTGGTAAA | GCCCCTGGAC | GATCGCTTTG | 824 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

| | | | | |
|---|---|---|---|---|
| NY99 NS5 | ---------- | ---------- | ---------- | 608 |
| WN02 NS5 | ---------- | ---------- | ---------- | 608 |
| H NS5F2 | CCACCTCGCT | CCACTTCCTC | AATGCTATGT | 854 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

Fig. 13L

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| H NS5F2 | CAAANGTTCG | CAAAGACATC | CAAGAGTGGN | 884 |
| H NS5F5 | - - - - - - - - - - | - - - - - - - - - - | - - - - - - - - - - | 1027 |
| H NS5R3 rev | - - - - - - - - - - | - - - - - - - - - - | - - - - - - - - - - | 1019 |
| H NS5R5 rev | - - - - - - - - - - | - - - - - - - - - - | - - - - - - - - - - | 1015 |
| Consensus | - - - - - - - - - - | - - - - - - - - - - | - - - - - - - - - - | |
| Conservation 100% 0% | | | | |
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| H NS5F2 | AACCGTCAAC | TGGATGGTAT | GATTGGCAGC | 914 |
| H NS5F5 | - - - - - - - - - - | - - - - - - - - - - | - - - - - - - - - - | 1027 |
| H NS5R3 rev | - - - - - - - - - - | - - - - - - - - - - | - - - - - - - - - - | 1019 |
| H NS5R5 rev | - - - - - - - - - - | - - - - - - - - - - | - - - - - - - - - - | 1015 |
| Consensus | - - - - - - - - - - | - - - - - - - - - - | - - - - - - - - - - | |
| Conservation 100% 0% | | | | |
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| H NS5F2 | NNNTCCATTT | TGCTCAAACC | ATTTCACTGA | 944 |
| H NS5F5 | - - - - - - - - - - | - - - - - - - - - - | - - - - - - - - - - | 1027 |
| H NS5R3 rev | - - - - - - - - - - | - - - - - - - - - - | - - - - - - - - - - | 1019 |
| H NS5R5 rev | - - - - - - - - - - | - - - - - - - - - - | - - - - - - - - - - | 1015 |
| Consensus | - - - - - - - - - - | - - - - - - - - - - | - - - - - - - - - - | |
| Conservation 100% 0% | | | | |
| NY99 NS5 | - | 608 | | |
| WN02 NS5 | - | 608 | | |
| H NS5F2 | A | 945 | | |
| H NS5F5 | - | 1027 | | |
| H NS5R3 rev | - | 1019 | | |
| H NS5R5 rev | - | 1015 | | |
| Consensus | - | | | |
| Conservation 100% 0% | | | | |

Fig. 13M

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | CGACGTGGCA | CCACGATGAG | AACCACCCAT | 270 |
| NS5R3 rev | - - - - - - - - - - | - - - - - - - - - - | - - - - - - - - - - | - |
| NS5R5 rev | CGACGTGGCA | CCACGATGAG | AACCACCCAT | 155 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | ATAGAACCTG | GAACTATCAC | GGCAGTTATG | 300 |
| NS5R3 rev | - - - - - - - - - - | - - - - - - - - - - | - - - - - - - - - - | - |
| NS5R5 rev | ATAGAACCTG | GAACTATCAC | GGCAGTTATG | 185 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | ATGTGAAGCC | CACAGGCTCC | GCCAGTTCGC | 330 |
| NS5R3 rev | - - - - - - - - - - | - - - - - - - - - - | - - - - - - - - - - | - |
| NS5R5 rev | ATGTGAAGCC | CACAGGCTCC | GCCAGTTCGC | 215 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | TGGTTAATGG | AGTGGTCAGG | CTCCTCTCAA | 360 |
| NS5R3 rev | - - - - -AATGG | AGNGGTCAGG | CTCCTCTCAA | 25 |
| NS5R5 rev | TGGTTAATGG | AGTGGTCAGG | CTCCTCTCAA | 245 |
| Consensus | - - - - -AATGG | AG-GGTCAGG | CTCCTCTCAA | |

100%
Conservation
0%

Fig. 14C

| | | | | |
|---|---|---|---|---|
| NY99 NS5 | - - - - - - - - - | - - - - - - - - - - | - - - - - - - - - - | - |
| WN02 NS5 | - - - - - - - - - | - - - - - - - - - - | - - - - - - - - - - | - |
| NS5F2 | - - - - - - - - - | - - - - - - - - - - | - - - - - - - - - - | - |
| NS5F5 | AA - CCATGGG | ACACCATCAC | GAATGTTACC | 389 |
| NS5R3 rev | AACCCNTGGG | ACACCATCAC | GAATGNTACC | 55 |
| NS5R5 rev | AA - CCATGGG | ACACCATCAC | GAATGTTACC | 274 |
| Consensus | AA - CC - TGGG | ACACCATCAC | GAATG - TACC | |
| NY99 NS5 | - - - - - - - - - | - - - - - - - - - - | - - - - - - - - - - | - |
| WN02 NS5 | - - - - - - - - - | - - - - - - - - - - | - - - - - - - - - - | - |
| NS5F2 | - - - - - - - - - | - - - - - - - - - - | - - - - - - - - - - | - |
| NS5F5 | ACCATGGCCA | TGACTGACAC | TACTCCC - TT | 418 |
| NS5R3 rev | ACCATGGCCA | TGACTGACAC | TACTCCCNTT | 85 |
| NS5R5 rev | ACCATGGCCA | TGACTGACAC | TACTCCC - TT | 303 |
| Consensus | ACCATGGCCA | TGACTGACAC | TACTCCC - TT | |
| NY99 NS5 | - - - - - - - - - | - - - - - - - - - - | - - - - - - - - - - | - |
| WN02 NS5 | - - - - - - - - - | - - - - - - - - - - | - - - - - - - - - - | - |
| NS5F2 | - - - - - - - - - | - - - - - - - - - - | - - - - - - - - - - | - |
| NS5F5 | CGGGCAGCAG | CGAGTGTTCA | AAGAGAAGGT | 448 |
| NS5R3 rev | CGGGCAGCAG | CGAGTGTTCA | AAGAGAAGGT | 115 |
| NS5R5 rev | CGGGCAGCAG | CGAGTGTTCA | AAGAGAAGGT | 333 |
| Consensus | CGGGCAGCAG | CGAGTGTTCA | AAGAGAAGGT | |
| NY99 NS5 | - - - - - - - - - | - - - - - - - - - - | - - - - - - - - - - | - |
| WN02 NS5 | - - - - - - - - - | - - - - - - - - - - | - - - - - - - - - - | - |
| NS5F2 | - - - - - - - - - | - - - - - - - - - - | - - - - - - - - - - | - |
| NS5F5 | GGACACGAAA | GCTCCTGAAC | CGCCAGAAGG | 478 |
| NS5R3 rev | GGACACGAAA | GCTCNTGAAC | CGCCAGAAGG | 145 |
| NS5R5 rev | GGACACGAAA | GCTCCTGAAC | CGCCAGAAGG | 363 |
| Consensus | GGACACGAAA | GCTC - TGAAC | CGCCAGAAGG | |

Fig. 14D

| | | | | |
|---|---|---|---|---|
| NY99 NS5 | TTGCATTTAC | AACATGATGG | GAAAGAGAGA | 47 |
| WN02 NS5 | TTGCATTTAC | AACATGATGG | GAAAGAGAGA | 47 |
| NS5F2 | TTGCATTTAC | AACATGATGG | GAAAGAGAGA | 163 |
| NS5F5 | TTGCATTTAC | AACATGATGG | GAAAGAGAGA | 748 |
| NS5R3 rev | TTGCATTTAC | AACATGATGG | GAAAGAGAGA | 415 |
| NS5R5 rev | TTGCATTTAC | AACATGATGG | GAAAGAGAGA | 633 |
| Consensus | TTGCATTTAC | AACATGATGG | GAAAGAGAGA | |

| | | | | |
|---|---|---|---|---|
| NY99 NS5 | GAAAAACCC | GGAGAATTCG | GAAAGGCCAA | 77 |
| WN02 NS5 | GAAAAACCC | GGAGAGTTCG | GAAAGGCCAA | 77 |
| NS5F2 | GAAAAACCC | GGAGAGTTCG | GAAAGGCTAA | 193 |
| NS5F5 | GAAAAACCC | GGAGAGTTCG | GAAAGGCTAA | 778 |
| NS5R3 rev | GAAAAACCC | GGAGAGTTCG | GAAAGGCTAA | 445 |
| NS5R5 rev | GAAAAACCC | GGAGAGTTCG | GAAAGGCTAA | 663 |
| Consensus | GAAAAACCC | GGAGAGTTCG | GAAAGGCTAA | |

| | | | | |
|---|---|---|---|---|
| NY99 NS5 | GGGAAGCAGA | GCCATTTGGT | TCATGTGGCT | 107 |
| WN02 NS5 | GGGAAGCAGA | GCCATTTGGT | TCATGTGGCT | 107 |
| NS5F2 | GGGAAGCAGA | GCCATTTGGT | TCATGTGGCT | 223 |
| NS5F5 | GGGAAGCAGA | GCCATTTGGT | TCATGTGGCT | 808 |
| NS5R3 rev | GGGAAGCAGA | GCCATTTGGT | TCATGTGGCT | 475 |
| NS5R5 rev | GGGAAGCAGA | GCCATTTGGT | TCATGTGGCT | 693 |
| Consensus | GGGAAGCAGA | GCCATTTGGT | TCATGTGGCT | |

| | | | | |
|---|---|---|---|---|
| NY99 NS5 | CGGAGCTCGC | TTTCTGGAGT | TCGAGGCTCT | 137 |
| WN02 NS5 | CGGAGCTCGC | TTTCTGGAGT | TCGAGGCTCT | 137 |
| NS5F2 | CGGAGCTCGC | TTTCTGGAGT | TCGAGGCTCT | 253 |
| NS5F5 | CGGANCTCGC | TTTCTGGAGT | TCGAGGCTCT | 838 |
| NS5R3 rev | CGGAGCTCGC | TTTCTGGAGT | TCGAGGCTCT | 505 |
| NS5R5 rev | CGGAGCTCGC | TTTCTGGAGT | TCGAGGCTCT | 723 |
| Consensus | CGGAGCTCGC | TTTCTGGAGT | TCGAGGCTCT | |

Fig. 14G

| | | | | |
|---|---|---|---|---|
| NY99 NS5 | GATCTATGCT | GATGACACAG | CTGGCTGGGA | 287 |
| WN02 NS5 | GATCTATGCT | GATGACACAG | CTGGCTGGGA | 287 |
| NS5F2 | GATCTATGCT | GATGACACAG | CCGGCTGGGA | 403 |
| NS5F5 | GATCTATGCT | GATGACA- - - | - - - - - - - - - - | 975 |
| NS5R3 rev | GATCTATGCT | GATGACACAG | CCGGCTGGGA | 655 |
| NS5R5 rev | GATCTATGCT | GATGACACAG | CCGGCTGGGA | 873 |
| Consensus | GATCTATGCT | GATGACACAG | CCGGCTGGGA | |
| NY99 NS5 | CACCCGCATC | ACGAGAGCTG | ACTTGGAAAA | 317 |
| WN02 NS5 | CACCCGCATC | ACGAGTGCTG | ACTTGGAAAA | 317 |
| NS5F2 | CACCCGCATC | ACGAGAGCTG | ACTTGGAAAA | 433 |
| NS5F5 | - - - - - - - - - - | - - - - - - - - - - | - - - - - - - - - - | 975 |
| NS5R3 rev | CACCCGCATC | ACGAGAGCTG | ACTTGGAAAA | 685 |
| NS5R5 rev | CACCCGCATC | ACGAGAGCTG | ACTTGGAAAA | 903 |
| Consensus | CACCCGCATC | ACGAGAGCTG | ACTTGGAAAA | |
| NY99 NS5 | TGAAGCTAAG | GTGCTTGAGC | TGCTTGATGG | 347 |
| WN02 NS5 | TGAAGCTAAG | GTGCTTGAGT | TGCTTGATGG | 347 |
| NS5F2 | TGAAGCTAAG | GTGCTTGAGT | TGCTTGATGG | 463 |
| NS5F5 | - - - - - - - - - - | - - - - - - - - - - | - - - - - - - - - - | 975 |
| NS5R3 rev | TGAAGCTAAG | GTGCTTGAGT | TGCTTGATGG | 715 |
| NS5R5 rev | TGAAGCTAAG | GTGCTTGAGT | TGCTTGATGG | 933 |
| Consensus | TGAAGCTAAG | GTGCTTGAGT | TGCTTGATGG | |
| NY99 NS5 | GGAACATCGG | CGTCTTGCCA | GGGCCATCAT | 377 |
| WN02 NS5 | GGAACATCGG | CGTCTTGCCA | GGGCCATCAT | 377 |
| NS5F2 | GGAACATCGG | CGTCTTGCCA | GGGCCATCAT | 493 |
| NS5F5 | - - - - - - - - - - | - - - - - - - - - - | - - - - - - - - - - | 975 |
| NS5R3 rev | GGAACATCGG | CGTCTTGCCA | GGGCCATCAT | 745 |
| NS5R5 rev | GGAACATCGG | CGTCTTGCCA | GGGCCATC- - | 961 |
| Consensus | GGAACATCGG | CGTCTTGCCA | GGGCCATCAT | |

Fig. 14I

| | | | | |
|---|---|---|---|---|
| NY99 NS5 | TGAGCTCACC | TATCGTCACA | AAGTTGTGAA | 407 |
| WN02 NS5 | TGAGCTCACC | TATCGTCACA | AAGTTGTGAA | 407 |
| NS5F2 | TGAGCTCACC | TATCGTCACA | AAGTTGTGAA | 523 |
| NS5F5 | ---------- | ---------- | ---------- | 975 |
| NS5R3 rev | TGAGCTCACC | TATCGTCACA | AAGTTGTGAA | 775 |
| NS5R5 rev | ---------- | ---------- | ---------- | 961 |
| Consensus | TGAGCTCACC | TATCGTCACA | AAGTTGTGAA | |
| NY99 NS5 | AGTGATGCGC | CCGGCTGCTG | ATGGAAGAAC | 437 |
| WN02 NS5 | AGTGATGCGC | CCGGCTGCTG | ATGGAAGAAC | 437 |
| NS5F2 | AGTGATGCGC | CCGGCTGCTG | ATGGAAGAAC | 553 |
| NS5F5 | ---------- | ---------- | ---------- | 975 |
| NS5R3 rev | AGTGATGCGC | CCGGCTGCTG | ATGGAAGAAC | 805 |
| NS5R5 rev | ---------- | ---------- | ---------- | 961 |
| Consensus | AGTGATGCGC | CCGGCTGCTG | ATGGAAGAAC | |
| NY99 NS5 | CGTCATGGAT | GTTATCTCCA | GAGAAGATCA | 467 |
| WN02 NS5 | CGTCATGGAT | GTTATCTCCA | GAGAAGATCA | 467 |
| NS5F2 | CGTCATGGAT | GTTATCTCCA | GAGAAGATCA | 583 |
| NS5F5 | ---------- | ---------- | ---------- | 975 |
| NS5R3 rev | CGTCATGGAT | GTTATCTCCA | GAGAAGATCA | 835 |
| NS5R5 rev | ---------- | ---------- | ---------- | 961 |
| Consensus | CGTCATGGAT | GTTATCTCCA | GAGAAGATCA | |
| NY99 NS5 | GAGGGGGAGT | GGACAAGTTG | TCACCTACGC | 497 |
| WN02 NS5 | GAGGGGGAGT | GGACAAGTTG | TCACCTACGC | 497 |
| NS5F2 | GAGGGGGAGT | GGACAAGTTG | TCACCTACGC | 613 |
| NS5F5 | ---------- | ---------- | ---------- | 975 |
| NS5R3 rev | GAGGGGGAGT | GGACAAGTTG | TCACCTACGC | 865 |
| NS5R5 rev | ---------- | ---------- | ---------- | 961 |
| Consensus | GAGGGGGAGT | GGACAAGTTG | TCACCTACGC | |

Fig. 14J

```
     NY99 NS5  CCTAAACACT  TTCACCAACC  TGGCCGTCCA  527
     WN02 NS5  CCTAAACACT  TTCACCAACC  TGGCCGTCCA  527
        NS5F2  CCTAAACACT  TTCACCAACC  TGGCCGTCCA  643
        NS5F5  ----------  ----------  ----------  975
    NS5R3 rev  CCTAAACACT  TTCACCAACC  TGGCCGTCCA  895
    NS5R5 rev  ----------  ----------  ----------  961
    Consensus  CCTAAACACT  TTCACCAACC  TGGCCGTCCA
         100%
 Conservation
           0%
     NY99 NS5  GCTGGTGAGG  ATGATGGAAG  GGGAAGGAGT  557
     WN02 NS5  GCTGGTGAGG  ATGATGGAAG  GGGAAGGAGT  557
        NS5F2  GCTGGTGAGG  ATGATGGAAG  GGGAAGGAGT  673
        NS5F5  ----------  ----------  ----------  975
    NS5R3 rev  GCTGGTGAGG  ATGATGGAAG  GGGAAGGAGT  925
    NS5R5 rev  ----------  ----------  ----------  961
    Consensus  GCTGGTGAGG  ATGATGGAAG  GGGAAGGAGT
         100%
 Conservation
           0%
     NY99 NS5  GATTGGCCCA  GATGATGTGG  AGAAACTCAC  587
     WN02 NS5  GATTGGCCCA  GATGATGTGG  AGAAACTCAC  587
        NS5F2  GATTGGCCCA  GATGATGTGG  AGAAACTCAC  703
        NS5F5  ----------  ----------  ----------  975
    NS5R3 rev  GATTGGCCCA  GATGATGTGG  AGAAACTCAC  955
    NS5R5 rev  ----------  ----------  ----------  961
    Consensus  GATTGGCCCA  GATGATGTGG  AGAAACTCAC
         100%
 Conservation
           0%
     NY99 NS5  AAAAGGGAAA  GGACCCAAAG  T---------  608
     WN02 NS5  AAAAGGGAAA  GGACCCAAAG  T---------  608
        NS5F2  AAAAGGGAAA  GGACCCAAAG  TCAGGACCTG  733
        NS5F5  ----------  ----------  ----------  975
    NS5R3 rev  AA--------  ----------  ----------  957
    NS5R5 rev  ----------  ----------  ----------  961
    Consensus  AAAAGGGAAA  GGACCCAAAG  T---------
         100%
 Conservation
           0%
```

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| NS5F2 | GGTTCGCAAA | GACATCCAAG | AGTGGAAACC | 883 |
| NS5F5 | - - - - - - - - - - | - - - - - - - - - - | - - - - - - - - - - | 975 |
| NS5R3 rev | - - - - - - - - - - | - - - - - - - - - - | - - - - - - - - - - | 957 |
| NS5R5 rev | - - - - - - - - - - | - - - - - - - - - - | - - - - - - - - - - | 961 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - | 608 |
| WN02 NS5 | - - - - - - - - - - | - - - - - - - - - - | - - - - - - | 608 |
| NS5F2 | GTCAACTGGA | TGGTATGATT | GGCAGC | 909 |
| NS5F5 | - - - - - - - - - - | - - - - - - - - - - | - - - - - - | 975 |
| NS5R3 rev | - - - - - - - - - - | - - - - - - - - - - | - - - - - - | 957 |
| NS5R5 rev | - - - - - - - - - - | - - - - - - - - - - | - - - - - - | 961 |
| Consensus | - - - - - - - - - - | - - - - - - - - - - | - - - - - - | |

100%
Conservation
0%

Fig. 14M

| | | | | |
|---|---|---|---|---|
| NY99 E | TTCAACTGCC | TTGGAATGAG | CAACAGAGAC | 30 |
| WN02 E | TTCAACTGCC | TTGGAATGAG | CAACAGAGAC | 30 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |
| 100% Conservation 0% | | | | |
| NY99 E | TTCTTGGAAG | GAGTGTCTGG | AGCAACATGG | 60 |
| WN02 E | TTCTTGGAAG | GAGTGTCTGG | AGCAACATGG | 60 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |
| 100% Conservation 0% | | | | |
| NY99 E | GTGGATTTGG | TTCTCGAAGG | CGACAGCTGC | 90 |
| WN02 E | GTGGATTTGG | TTCTCGAAGG | CGACAGCTGC | 90 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |
| 100% Conservation 0% | | | | |
| NY99 E | GTGACTATCA | TGTCTAAGGA | CAAGCCTACC | 120 |
| WN02 E | GTGACTATCA | TGTCTAAGGA | CAAGCCTACC | 120 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |
| 100% Conservation 0% | | | | |

Fig. 15A

```
NY99 E      ATCGATGTGA  AGATGATGAA  TATGGAGGCG  150
WN02 E      ATCGATGTGA  AGATGATGAA  TATGGAGGCG  150
  EF1       ---GATGTGN  -GANGANGAA  TATGGAGGCG   26
  EF3       ----------  ----------  ----------    -
ER3 rev     ----------  ----------  ----------    -
ER4 rev     ----------  ----------  ----------    -
Consensus   ---GATGTG-  -GA-GA-GAA  TATGGAGGCG
    100%
Conservation
      0%

NY99 E      GCCAACCTGG  CAGAGGTCCG  CAGTTATTGC  180
WN02 E      GCCAACCTGG  CAGAGGTCCG  CAGTTATTGC  180
  EF1       GCCAACCTGG  CAGAGGTCCG  CAGTTATTGC   56
  EF3       ----------  ----------  ----------    -
ER3 rev     ----------  ----------  ----------    -
ER4 rev     ----------  ----------  ----------    -
Consensus   GCCAACCTGG  CAGAGGTCCG  CAGTTATTGC
    100%
Conservation
      0%

NY99 E      TATTTGGCTA  CCGTCAGCGA  TCTCTCCACC  210
WN02 E      TATTTGGCTA  CCGTCAGCGA  TCTCTCCACC  210
  EF1       TATTTGGCTA  CCGTCAGCGA  TCTCTCCACC   86
  EF3       ----------  ----------  ----------    -
ER3 rev     ----------  ----------  ----------    -
ER4 rev     ----------  ----------  ----------    -
Consensus   TATTTGGCTA  CCGTCAGCGA  TCTCTCCACC
    100%
Conservation
      0%

NY99 E      AAAGCTGCGT  GCCCGACCAT  GGGAGAAGCT  240
WN02 E      AAAGCTGCGT  GCCCGACCAT  GGGAGAAGCT  240
  EF1       AAAGCTGCGT  GCCCGACCAT  GGGAGAAGCT  116
  EF3       ----------  ----------  ----------    -
ER3 rev     ----------  ----------  ----------    -
ER4 rev     ----------  ----------  ----------    -
Consensus   AAAGCTGCGT  GCCCGACCAT  GGGAGAAGCT
    100%
Conservation
      0%
```

Fig. 15B

| | | | | |
|---|---|---|---|---|
| NY99 E | CACAATGACA | AACGTGCTGA | CCCAGCTTTT | 270 |
| WN02 E | CACAATGACA | AACGTGCTGA | CCCAGCTTTT | 270 |
| EF1 | CACAATGACA | AACGTGCTGA | CCCAGCTTTT | 146 |
| EF3 | ---------- | ---------- | ---------- | - |
| ER3 rev | ---------- | ---------- | ---------- | - |
| ER4 rev | ---------- | ---------- | ---------- | - |
| Consensus | CACAATGACA | AACGTGCTGA | CCCAGCTTTT | |
| NY99 E | GTGTGCAGAC | AAGGAGTGGT | GGACAGGGGC | 300 |
| WN02 E | GTGTGCAGAC | AAGGAGTGGT | GGACAGGGGC | 300 |
| EF1 | GTGTGCAGAC | AAGGAGTGGT | GGACAGGGGC | 176 |
| EF3 | ---------- | ---------- | ---------- | - |
| ER3 rev | ---------- | ---------- | ---------- | - |
| ER4 rev | ---------- | ---------- | ---------- | - |
| Consensus | GTGTGCAGAC | AAGGAGTGGT | GGACAGGGGC | |
| NY99 E | TGGGGCAACG | GCTGCGGACT | ATTTGGCAAA | 330 |
| WN02 E | TGGGGCAACG | GCTGCGGACT | ATTTGGCAAA | 330 |
| EF1 | TGGGGCAACG | GCTGCGGACT | ATTTGGCAAA | 206 |
| EF3 | ---------- | ---------- | ---------- | - |
| ER3 rev | ---------- | ---------- | ---------- | - |
| ER4 rev | ---------- | ---------- | ---------- | - |
| Consensus | TGGGGCAACG | GCTGCGGACT | ATTTGGCAAA | |
| NY99 E | GGAAGCATTG | ACACATGCGC | CAAATTTGCC | 360 |
| WN02 E | GGAAGCATTG | ACACATGCGC | CAAATTTGCC | 360 |
| EF1 | GGAAGCATTG | ACACATGCGC | CAAATTTGCC | 236 |
| EF3 | ---------- | ---------- | ---------- | - |
| ER3 rev | ---------- | ---------- | ---------- | - |
| ER4 rev | ---------- | ---------- | ---------- | - |
| Consensus | GGAAGCATTG | ACACATGCGC | CAAATTTGCC | |

Fig. 15C

```
NY99 E      TGCTCTACCA  AGGCAATAGG  AAGAACCATC  390
WN02 E      TGCTCTACCA  AGGCAATAGG  AAGAACCATC  390
  EF1       TGCTCTACCA  AGGCAATAGG  AAGAACCATC  266
  EF3       ----------  ----------  --------C-  1
ER3 rev     ----------  ----------  ----------
ER4 rev     ----------  ----------  ----------
Consensus   TGCTCTACCA  AGGCAATAGG  AAGAACCATC
   100%
Conservation
    0%

NY99 E      TTGAAAGAGA  ATATCAAGTA  CGAAGTGGCC  420
WN02 E      TTGAAAGAGA  ATATCAAGTA  CGAAGTGGCC  420
  EF1       TTGAAAGAGA  ATATCAAGTA  CGAAGTGGCC  296
  EF3       TTNANAGANA  ---TCAAGTA  CGAAGTGGCC  28
ER3 rev     ----------  ----------  ----------
ER4 rev     ----------  ----------  ----------
Consensus   TTGAAAGAGA  ATATCAAGTA  CGAAGTGGCC
   100%
Conservation
    0%

NY99 E      ATTTTTGTCC  ATGGACCAAC  TACTGTGGAG  450
WN02 E      ATTTTTGTCC  ATGGACCAAC  TACTGTGGAG  450
  EF1       ATTTTTGTCC  ATGGACCAAC  TACTGTGGAG  326
  EF3       ATTTTTGTCC  ATGGACCAAC  TACTGTGGAG  58
ER3 rev     ----------  ----------  ----------
ER4 rev     ----------  ----------  ----------
Consensus   ATTTTTGTCC  ATGGACCAAC  TACTGTGGAG
   100%
Conservation
    0%

NY99 E      TCGCACGGAA  ACTACTCCAC  ACAGGTTGGA  480
WN02 E      TCGCACGGAA  ACTATTCCAC  ACAGGCTGGA  480
  EF1       TCGCACGGAA  ACTACTCCAC  ACAGGCTGGA  356
  EF3       TCGCACGGAA  ACTACTCCAC  ACAGGCTGGA  88
ER3 rev     ----------  ----------  ----------
ER4 rev     ----------  ----------  ----------
Consensus   TCGCACGGAA  ACTACTCCAC  ACAGGCTGGA
   100%
Conservation
    0%
```

Fig. 15D

```
    NY99 E  GCCACTCAGG  CAGGGAGATT  CAGCATCACT  510
    WN02 E  GCCACTCAGG  CAGGGAGATT  CAGCATCACT  510
       EF1  GCCACTCAGG  CAGGGAGATT  CAGCATCACT  386
       EF3  GCCACTCAGG  CAGGGAGATT  CAGCATCACT  118
   ER3 rev  ----------  ----------  ----------
   ER4 rev  ----------  ----------  ----------
 Consensus  GCCACTCAGG  CAGGGAGATT  CAGCATCACT
      100%
Conservation
        0%

NY99 E  CCTGCGGCGC  CTTCACACAC  ACTAAAGCTT  540
    WN02 E  CCTGCGGCGC  CTTCATACAC  ACTAAAGCTT  540
       EF1  CCTGCGGCGC  CTTCATACAC  ACTAAAGCTT  416
       EF3  CCTGCGGCGC  CTTCATACAC  ACTAAAGCTT  148
   ER3 rev  ----------  ----------  ----------
   ER4 rev  ----------  ----------  ----------
 Consensus  CCTGCGGCGC  CTTCATACAC  ACTAAAGCTT
      100%
Conservation
        0%

NY99 E  GGAGAATATG  GAGAGGTGAC  AGTGGACTGT  570
    WN02 E  GGAGAATATG  GAGAGGTGAC  AGTGGACTGT  570
       EF1  GGAGAATATG  GAGAGGTGAC  AGTGGACTGT  446
       EF3  GGAGAATATG  GAGAGGTGAC  AGTGGACTGT  178
   ER3 rev  --AGANTATG  GAGNGNNGNC  AGTGGACTGT  28
   ER4 rev  ----------  ----------  ----------
 Consensus  GGAGAATATG  GAGAGGTGAC  AGTGGACTGT
      100%
Conservation
        0%

NY99 E  GAA-CCACGG  TCAGGGATTG  ACACCAATGC  599
    WN02 E  GAA-CCACGG  TCAGGGATTG  ACACCAATGC  599
       EF1  GAA-CCACGG  TCAGGGATTG  ACACCAATGC  475
       EF3  GAA-CCACGG  TCAGGGATTG  ACACCAATGC  207
   ER3 rev  GAANCCNCGG  TCAGGGATTG  ACACCAATGC  58
   ER4 rev  ----------  ----------  ----------
 Consensus  GAA-CCACGG  TCAGGGATTG  ACACCAATGC
      100%
Conservation
        0%
```

Fig. 15E

| | | | | |
|---|---|---|---|---|
| NY99 E | TGGAGTTTGA | GGAACCACAC | GCCACGAAGC | 748 |
| WN02 E | TGGAGTTTGA | GGAACCACAC | GCCACGAAGC | 748 |
| EF1 | TGGAGTTTGA | GGAACCACAC | GCCACGAAGC | 624 |
| EF3 | TGGAGTTTGA | GGAACCACAC | GCCACGAAGC | 356 |
| ER3 rev | TGGAGTTTGA | GGAACCACAC | GCCACGAAGC | 207 |
| ER4 rev | TGGAGTTTGA | GGAACCACAC | GCCACGAAGC | 74 |
| Consensus | TGGAGTTTGA | GGAACCACAC | GCCACGAAGC | |
| NY99 E | AGTCTGTGAT | AGCATTGGGC | TCACAAGAGG | 778 |
| WN02 E | AGTCTGTGAT | AGCATTGGGC | TCACAAGAGG | 778 |
| EF1 | AGTCTGTGAT | AGCATTGGGC | TCACAAGAGG | 654 |
| EF3 | AGTCTGTGAT | AGCATTGGGC | TCACAAGAGG | 386 |
| ER3 rev | AGTCTGTGAT | AGCATTGGGC | TCACAAGAGG | 237 |
| ER4 rev | AGTCTGTGAT | AGCATTGGGC | TCACAAGAGG | 104 |
| Consensus | AGTCTGTGAT | AGCATTGGGC | TCACAAGAGG | |
| NY99 E | GAGCTCTGCA | GCAAGCTTTG | GCTGGAGCCA | 808 |
| WN02 E | GAGCTCTGCA | TCAAGCTTTG | GCTGGAGCCA | 808 |
| EF1 | GAGCTCTGCA | TCAAGCTTTG | GCTGGAGCCA | 684 |
| EF3 | GAGCTCTGCA | TCAAGCTTTG | GCTGGAGCCA | 416 |
| ER3 rev | GAGCTCTGCA | TCAAGCTTTG | GCTGGAGCCA | 267 |
| ER4 rev | GAGCTCTGCA | TCAAGCTTTG | GCTGGAGCCA | 134 |
| Consensus | GAGCTCTGCA | TCAAGCTTTG | GCTGGAGCCA | |
| NY99 E | TTCCTGTGGA | ATTTTCAAGC | AACACTGTCA | 838 |
| WN02 E | TTCCTGTGGA | ATTTTCAAGC | AACACTGTCA | 838 |
| EF1 | TTCCTGTGGA | ATTTTCAAGC | AACACTGTCA | 714 |
| EF3 | TTCCTGTGGA | ATTTTCAAGC | AACACTGTCA | 446 |
| ER3 rev | TTCCTGTGGA | ATTTTCAAGC | AACACTGTCA | 297 |
| ER4 rev | TTCCTGTGGA | ATTTTCAAGC | AACACTGTCA | 164 |
| Consensus | TTCCTGTGGA | ATTTTCAAGC | AACACTGTCA | |

Fig. 15G

| | | | | |
|---|---|---|---|---|
| NY99 E | CTTTTGTTTC | AGTGGCCACG | GCCAACGCTA | 1108 |
| WN02 E | CTTTTGTTTC | AGTGGCCACG | GCCAACGCTA | 1108 |
| EF1 | CTTTTGTTTC | AGTG------ | ---------- | 968 |
| EF3 | CTTTTGTTTC | AGTGGCCACG | GCCAACGCTA | 716 |
| ER3 rev | CTTTTGTTTC | AGTGGCCACG | GCCAACGCTA | 567 |
| ER4 rev | CTTTTGTTTC | AGTGGCCACG | GCCAACGCTA | 434 |
| Consensus | CTTTTGTTTC | AGTGGCCACG | GCCAACGCTA | |
| NY99 E | AGGTCCTGAT | TGAATTGGAA | CCACCCTTTG | 1138 |
| WN02 E | AGGTCCTGAT | TGAATTGGAA | CCACCCTTTG | 1138 |
| EF1 | ---------- | ---------- | ---------- | 968 |
| EF3 | AGGTCCTGAT | TGAATTGGAA | CCACCCTTTG | 746 |
| ER3 rev | AGGTCCTGAT | TGAATTGGAA | CCACCCTTTG | 597 |
| ER4 rev | AGGTCCTGAT | TGAATTGGAA | CCACCCTTTG | 464 |
| Consensus | AGGTCCTGAT | TGAATTGGAA | CCACCCTTTG | |
| NY99 E | GAGACTCATA | CATAGTGGTG | GGCAGAGGAG | 1168 |
| WN02 E | GAGACTCATA | CATAGTGGTG | GGCAGAGGAG | 1168 |
| EF1 | ---------- | ---------- | ---------- | 968 |
| EF3 | GAGACTCATA | CATAGTGGTG | GGCAGAGGAG | 776 |
| ER3 rev | GAGACTCATA | CATAGTGGTG | GGCAGAGGAG | 627 |
| ER4 rev | GAGACTCATA | CATAGTGGTG | GGCAGAGGAG | 494 |
| Consensus | GAGACTCATA | CATAGTGGTG | GGCAGAGGAG | |
| NY99 E | AACAACAGAT | CAATCACCAT | TGGCACAAGT | 1198 |
| WN02 E | AACAACAGAT | CAATCACCAT | TGGCACAAGT | 1198 |
| EF1 | ---------- | ---------- | ---------- | 968 |
| EF3 | AACAACAGAT | CAATCACCAT | TGGCACAAGT | 806 |
| ER3 rev | AACAACAGAT | CAATCACCAT | TGGCACAAGT | 657 |
| ER4 rev | AACAACAGAT | CAATCACCAT | TGGCACAAGT | 524 |
| Consensus | AACAACAGAT | CAATCACCAT | TGGCACAAGT | |

Fig. 15J

| | | | | |
|---:|---|---|---|---:|
| NY99 E | CTGGAAGCAG | CATTGGCAAA | GCCTTTACAA | 1228 |
| WN02 E | CTGGAAGTAG | CATTGGCAAA | GCCTTTACAA | 1228 |
| EF1 | - - - - - - - - - - | - - - - - - - - - - | - - - - - - - - - - | 968 |
| EF3 | CTGGAAGCAG | CATTGGCAAA | GCCTTTACAA | 836 |
| ER3 rev | CTGGAAGCAG | CATTGGCAAA | GCCTTTACAA | 687 |
| ER4 rev | CTGGAAGCAG | CATTGGCAAA | GCCTTTACAA | 554 |
| Consensus | CTGGAAGCAG | CATTGGCAAA | GCCTTTACAA | |

| | | | | |
|---:|---|---|---|---:|
| NY99 E | CCACCCTCAA | AGGAGCGCAG | AGACTAGCCG | 1258 |
| WN02 E | CCACCCTCAA | AGGAGCGCAG | AGACTAGCCG | 1258 |
| EF1 | - - - - - - - - - - | - - - - - - - - - - | - - - - - - - - - - | 968 |
| EF3 | CCACCCTCAA | AGGAGCGCAG | AGACTAGCCG | 866 |
| ER3 rev | CCACCCTCAA | AGGAGCGCAG | AGACTAGCCG | 717 |
| ER4 rev | CCACCCTCAA | AGGAGCGCAG | AGACTAGCCG | 584 |
| Consensus | CCACCCTCAA | AGGAGCGCAG | AGACTAGCCG | |

| | | | | |
|---:|---|---|---|---:|
| NY99 E | CTCTAGGAGA | CACAGCTTGG | GACTTTGGAT | 1288 |
| WN02 E | CTCTAGGAGA | CACAGCTTGG | GACTTTGGAT | 1288 |
| EF1 | - - - - - - - - - - | - - - - - - - - - - | - - - - - - - - - - | 968 |
| EF3 | CTCTAGGAGA | CACAGCTTGG | GACTTTGGAT | 896 |
| ER3 rev | CTCTAGGAGA | CACAGCTTGG | GACTTTGGAT | 747 |
| ER4 rev | CTCTAGGAGA | CACAGCTTGG | GACTTTGGAT | 614 |
| Consensus | CTCTAGGAGA | CACAGCTTGG | GACTTTGGAT | |

| | | | | |
|---:|---|---|---|---:|
| NY99 E | CAGTTGGAGG | GGTGTTCACC | TCAGTTGGGA | 1318 |
| WN02 E | CAGTTGGAGG | GGTGTTCACC | TCAGTTGGGA | 1318 |
| EF1 | - - - - - - - - - - | - - - - - - - - - - | - - - - - - - - - - | 968 |
| EF3 | CAGTTGGAGG | GGTGTTCACC | TCAGTTGGGA | 926 |
| ER3 rev | CAGTTGGAGG | GGTGTTCACC | TCAGTTGGGA | 777 |
| ER4 rev | CAGTTGGAGG | GGTGTTCACC | TCAGTTGGGA | 644 |
| Consensus | CAGTTGGAGG | GGTGTTCACC | TCAGTTGGGA | |

Fig. 15K

| | | | | |
|---|---|---|---|---|
| NY99 E | AGGCTGTCCA | TCAAGTGTTC | GGAGGAGCAT | 1348 |
| WN02 E | AGGCTGTCCA | TCAAGTGTTC | GGAGGAGCAT | 1348 |
| EF1 | ---------- | ---------- | ---------- | 968 |
| EF3 | AGGCTGTCCA | TCAAGTGTTC | GGAGGAGCAT | 956 |
| ER3 rev | AGGCTGTCCA | TCAAGTGTTC | GGAGGAGCAT | 807 |
| ER4 rev | AGGCTGTCCA | TCAAGTGTTC | GGAGGAGCAT | 674 |
| Consensus | AGGCTGTCCA | TCAAGTGTTC | GGAGGAGCAT | |
| NY99 E | TCCGCTCACT | GTTCGGAGGC | ATGTCCTGGA | 1378 |
| WN02 E | TCCGCTCACT | GTTCGGAGGC | ATGTCCTGGA | 1378 |
| EF1 | ---------- | ---------- | ---------- | 968 |
| EF3 | TCCGCACACT | GTTCGGANGC | ATG------- | 979 |
| ER3 rev | TCCGCACACT | GTTCGGAGGC | ATGTCCTGGA | 837 |
| ER4 rev | TCCGCACACT | GTTCGGAGGC | ATGTCCTGGA | 704 |
| Consensus | TCCGCACACT | GTTCGGAGGC | ATGTCCTGGA | |
| NY99 E | TAACGCAAGG | ATTGCTGGGG | GCTCTCCTGT | 1408 |
| WN02 E | TAACGCAAGG | ATTGCTGGGG | GCTCTCCTGT | 1408 |
| EF1 | ---------- | ---------- | ---------- | 968 |
| EF3 | ---------- | ---------- | ---------- | 979 |
| ER3 rev | TAACGCAAGG | ATTGCTGGGG | GCTCTCCTGT | 867 |
| ER4 rev | TAACGCAAGG | ATTGCTGGGG | GCTCTCCTGT | 734 |
| Consensus | TAACGCAAGG | ATTGCTGGGG | GCTCTCCTGT | |
| NY99 E | TGTGGATGGG | CATCAATGCT | CGTGATAGGT | 1438 |
| WN02 E | TGTGGATGGG | CATCAATGCT | CGTGATAGGT | 1438 |
| EF1 | ---------- | ---------- | ---------- | 968 |
| EF3 | ---------- | ---------- | ---------- | 979 |
| ER3 rev | TGTGGATGGG | CATCAATGCT | CGTGATAGGT | 897 |
| ER4 rev | TGTGGATGGG | CATCAATGCT | CGTGATAGGT | 764 |
| Consensus | TGTGGATGGG | CATCAATGCT | CGTGATAGGT | |

Fig. 15L

```
     NY99 E  CCATAGCTCT  CACGTTTCTC  GCAGTTGGAG  1468
     WN02 E  CCATAGCTCT  CACGTTTCTC  GCAGTTGGAG  1468
        EF1  ----------  ----------  ----------   968
        EF3  ----------  ----------  ----------   979
    ER3 rev  CCATAGCTCT  CACGTTTCTC  GCAGTTGGAG   927
    ER4 rev  CCATAGCTCT  CACGTTTCTC  GCAGTTGGAG   794
  Consensus  CCATAGCTCT  CACGTTTCTC  GCAGTTGGAG
       100%
Conservation
         0%
     NY99 E  GAGTTCTGCT  CTTCCTCTCC  GTGAACGTGC  1498
     WN02 E  GAGTTCTGCT  CTTCCTCTCC  GTGAACGTGC  1498
        EF1  ----------  ----------  ----------   968
        EF3  ----------  ----------  ----------   979
    ER3 rev  GAGTTCTGCT  CTTCCTCTCC  GTGAACGTGC   957
    ER4 rev  GAGTTCTGCT  CTTCCTCTCC  GTGAACGTGC   824
  Consensus  GAGTTCTGCT  CTTCCTCTCC  GTGAACGTGC
       100%
Conservation
         0%
     NY99 E  ACGCT-----  ----------  ----------  1503
     WN02 E  ATGCT-----  ----------  ----------  1503
        EF1  ----------  ----------  ----------   968
        EF3  ----------  ----------  ----------   979
    ER3 rev  ATGCTGACAC  TGGGTGTGCC  ATAGACATCA   987
    ER4 rev  ATGCTGACAC  TGGGTGTGCC  ATAGACATCA   854
  Consensus  ATGCT-----  ----------  ----------
       100%
Conservation
         0%
     NY99 E  ----------  ----------  ----------  1503
     WN02 E  ----------  ----------  ----------  1503
        EF1  ----------  ----------  ----------   968
        EF3  ----------  ----------  ----------   979
    ER3 rev  GCCGGCAAGA  GCTGAG----  ----------  1003
    ER4 rev  GCCGGCAAGA  GCTGAGATGT  GGAAGTGGAG   884
  Consensus  ----------  ----------  ----------
       100%
Conservation
         0%
```

Fig. 15M

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | TGTTCATACA | CAATGATGTG | GAGGCTTGGA | 914 |
| Consensus | - - - - - - - - - - | - - - - - - - - - - | - - - - - - - - - - | |

Conservation 100% / 0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | TGGACCGGTA | CAAGTATTAC | CCTGAAACGC | 944 |
| Consensus | - - - - - - - - - - | - - - - - - - - - - | - - - - - - - - - - | |

Conservation 100% / 0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | CACAAGGCCT | AGCCAAGATC | ATTCAGAAAG | 974 |
| Consensus | - - - - - - - - - - | - - - - - - - - - - | - - - - - - - - - - | |

Conservation 100% / 0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | CTCATAAGGA | AGGAGTGTGC | GNTCTACGAN | 1004 |
| Consensus | - - - - - - - - - - | - - - - - - - - - - | - - - - - - - - - - | |

Conservation 100% / 0%

Fig. 15N

```
NY99 E      - -  1503
WN02 E      - -  1503
   EF1      - -   968
   EF3      - -   979
ER3 rev     - A  1004
ER4 rev     C A  1006
Consensus   - -
     100%
Conservation
       0%
```

Fig. 15O

| | | | | |
|---|---|---|---|---|
| AY369442.1 | .......... | .......... | .......... | . |
| AY369440.1 | .......... | .......... | .......... | . |
| H NS5 consensus | .......... | CTACTCCCTT | CGGGCAGCAG | CGAGTGTTCA 119 |
| D NS5 consensus | .......... | CTACTCCCTT | CGGGCAGCAG | CGAGTGTTCA 107 |
| H WN05 NS5 consensus | .......... | CTACTCCCTT | CGGGCAGCAG | CGAGTGTTCA 100 |
| Consensus | | CTACTCCCTT | CGGGCAGCAG | CGAGTGTTCA |
| Conservation 100% / 0% | | | | |

| | | | | |
|---|---|---|---|---|
| AY369442.1 | .......... | .......... | .......... | . |
| AY369440.1 | .......... | .......... | .......... | . |
| H NS5 consensus | AAGAGAAGGT | GGACACGAAA | GCTC-GAACC | 148 |
| D NS5 consensus | AAGAGAAGGT | GGACACGAAA | GCT--GAACC | 135 |
| H WN05 NS5 consensus | AAGAGAAGGT | GGACACGAAA | GCTCTGAACC | 130 |
| Consensus | AAGAGAAGGT | GGACACGAAA | GCT--GAACC | |
| Conservation 100% / 0% | | | | |

| | | | | |
|---|---|---|---|---|
| AY369442.1 | .......... | .......... | .......... | . |
| AY369440.1 | .......... | .......... | .......... | . |
| H NS5 consensus | GCCAGAAGGA | GTGAAGTACG | TGCTCAACGA | 178 |
| D NS5 consensus | GCCAGAAGGA | GTGAAGTACG | TGCTCAACGA | 165 |
| H WN05 NS5 consensus | GCCAGAAGGA | GTGAAGTACG | TGCTCAACGA | 160 |
| Consensus | GCCAGAAGGA | GTGAAGTACG | TGCTCAACGA | |
| Conservation 100% / 0% | | | | |

Fig. 16B

|                      |                      |                      |                      |      |
|----------------------|----------------------|----------------------|----------------------|------|
| AY369442.1           | ----------           | ----------           | ----------           |      |
| AY369440.1           | ----------           | ----------           | ----------           |      |
| H NS5 consensus      | GACCACCAAC           | TGGTTGTGGG           | CGTTTTTGGC           | 208  |
| D NS5 consensus      | GACCACCAAC           | TGGTTGTGGG           | CGTTTTTGGC           | 195  |
| H WN05 NS5 consensus | GACCACCAAC           | TGGTTGTGGG           | CGTTTTTGGC           | 190  |
| Consensus            | GACCACCAAC       | TGGTTGTGGG       | CGTTTTTGGC       |      |
| Conservation 100% 0% |                      |                      |                      |      |

|                      |                      |                      |                      |      |
|----------------------|----------------------|----------------------|----------------------|------|
| AY369442.1           | ----------           | ----------           | ----------           |      |
| AY369440.1           | ----------           | ----------           | ----------           |      |
| H NS5 consensus      | CAGAGAAAAA           | CGTCCCAGAA           | TGTGCTCTCG           | 238  |
| D NS5 consensus      | CAGAGAAAAA           | CGTCCCAGAA           | TGTGCTCTCG           | 225  |
| H WN05 NS5 consensus | CAGAGAAAAA           | CGTCCCAGAA           | TGTGCTCTCG           | 220  |
| Consensus            | CAGAGAAAAA       | CGTCCCAGAA       | TGTGCTCTCG       |      |
| Conservation 100% 0% |                      |                      |                      |      |

|                      |                      |                      |                      |      |
|----------------------|----------------------|----------------------|----------------------|------|
| AY369442.1           | ----------           | ----------           | ----------           |      |
| AY369440.1           | ----------           | ----------           | ----------           |      |
| H NS5 consensus      | AGAGATA---           | ----GAAAGG           | TCAACAGCAA           | 261  |
| D NS5 consensus      | AGAGGAATTC           | ATA-GAAAGG           | TCAACAGCAA           | 254  |
| H WN05 NS5 consensus | AGAGGAATTC           | ATAAGAAAGG           | TCAACAGCAA           | 250  |
| Consensus            | AGAGGAA---       | ----GAAAGG       | TCAACAGCAA       |      |
| Conservation 100% 0% |                      |                      |                      |      |

Fig. 16C

| | | | | |
|---|---|---|---|---|
| AY369442.1 | - - - - - | - - - - - | - - - - - | |
| AY369440.1 | - - - - - | - - - - - | - - - - - | |
| H NS5 consensus | TGCAGCTTTG | GGTGCCATGT | TTGAAGAGCA | 291 |
| D NS5 consensus | TGCAGCTTTG | GGTGCCATGT | TTGAAGAGCA | 284 |
| H WN05 NS5 consensus | TGCAGCTTTG | GGTGCCATGT | TTGAAGAGCA | 280 |
| Consensus | TGCAGCTTTG | GGTGCCATGT | TTGAAGAGCA | |
| Conservation 100% 0% | | | | |

| | | | | |
|---|---|---|---|---|
| AY369442.1 | - - - - - | - - - - - | - - - - - | |
| AY369440.1 | - - - - - | - - - - - | - - - - - | |
| H NS5 consensus | GAATCAATGG | AGGAGCGCCA | GAGAAGCAGT | 321 |
| D NS5 consensus | GAATCAATGG | AGGAGCGCCA | GAGAAGCAGT | 314 |
| H WN05 NS5 consensus | GAATCAATGG | AGGAGCGCCA | GAGAAGCAGT | 310 |
| Consensus | GAATCAATGG | AGGAGCGCCA | GAGAAGCAGT | |
| Conservation 100% 0% | | | | |

| | | | | |
|---|---|---|---|---|
| AY369442.1 | - - - - - | - - - - - | - - - - - | |
| AY369440.1 | - - - - - | - - - - - | - - - - - | |
| H NS5 consensus | TGAAGATCCA | AAATTTTGGG | AGATGGTGGA | 351 |
| D NS5 consensus | TGAAGATCCA | AAATTTTGGG | AGATGGTGGA | 344 |
| H WN05 NS5 consensus | TGAAGATCCA | AAATTTTGGG | AGATGGTGGA | 340 |
| Consensus | TGAAGATCCA | AAATTTTGGG | AGATGGTGGA | |
| Conservation 100% 0% | | | | |

Fig. 16D

| | | | |
|---|---|---|---|
| AY369442.1 | CTGGCTTGGA | AGAAAGAACT | CAGGAGGAGG 188 |
| AY369440.1 | CTGGCTTGGA | AGAAAGAACT | CAGGAGGAGG 188 |
| H NS5 consensus | CTGGCTTGGA | AGAAAGAACT | CAGGAGGAGG 561 |
| D NS5 consensus | CTGGCTTGGA | AGAAAGAACT | CAGGAGGAGG 554 |
| H WN05 NS5 consensus | CTGGCTTGGA | AGAAAGAACT | CAGGAGGAGG 550 |
| Consensus | CTGGCTTGGA | AGAAAGAACT | CAGGAGGAGG |
| Conservation 100% 0% | | | |
| AY369442.1 | TGTCGAGGGC | TTGGGCCTCC | AAAAACTGGG 218 |
| AY369440.1 | TGTCGAGGGC | TTGGGCCTCC | AAAAACTGGG 218 |
| H NS5 consensus | TGTCGAGGGC | TTGGGCCTCC | AAAAACTGGG 591 |
| D NS5 consensus | TGTCGAGGGC | TTGGGCCTCC | AAAAACTGGG 584 |
| H WN05 NS5 consensus | TGTCGAGGGC | TTGGGCCTCC | AAAAACTGGG 580 |
| Consensus | TGTCGAGGGC | TTGGGCCTCC | AAAAACTGGG |
| Conservation 100% 0% | | | |
| AY369442.1 | TTACATCCTG | CGTGAAGTTG | GCACCCGGCC 248 |
| AY369440.1 | TTACATCCTG | CGTGAAGTTG | GCACCCGGCC 248 |
| H NS5 consensus | TTACATCCTG | CGTGAAGTTG | GCACCCGGCC 621 |
| D NS5 consensus | TTACATCCTG | CGTGAAGTTG | GCACCCGGCC 614 |
| H WN05 NS5 consensus | TTACATCCTG | CGTGAAGTTG | GCACCCGACC 610 |
| Consensus | TTACATCCTG | CGTGAAGTTG | GCACCCGGCC |
| Conservation 100% 0% | | | |

Fig. 16G

| | | | |
|---|---|---|---|
| AY369442.1 | GCTTGATGGG | GAACATCGGC | GTCTTGCCAG 368 |
| AY369440.1 | GCTTGATGGG | GAACATCGGC | GTCTTGCCAG 368 |
| H NS5 consensus | GCTTGATGGG | GAACATCGGC | GTCTTGCCAG 741 |
| D NS5 consensus | GCTTGATGGG | GAACATCGGC | GTCTTGCCAG 734 |
| H WN05 NS5 consensus | GCTTGATGGG | GAACATCGGC | GTCTTGCCAG 730 |
| Consensus 100% | GCTTGATGGG | GAACATCGGC | GTCTTGCCAG |
| Conservation 0% | | | |
| AY369442.1 | GGCCATCATT | GAGCTCACCT | ATCGTCACAA 398 |
| AY369440.1 | GGCCATCATT | GAGCTCACCT | ATCGTCACAA 398 |
| H NS5 consensus | GGCCATCATT | GAGCTCACCT | ATCGTCACAA 771 |
| D NS5 consensus | GGCCATCATT | GAGCTCACCT | ATCGTCACAA 764 |
| H WN05 NS5 consensus | GGCCATCATT | GAGCTCACCT | ATCGTCACAA 760 |
| Consensus 100% | GGCCATCATT | GAGCTCACCT | ATCGTCACAA |
| Conservation 0% | | | |
| AY369442.1 | AGTTGTGAAA | GTGATGCGCC | CGGCTGCTGA 428 |
| AY369440.1 | AGTTGTGAAA | GTGATGCGCC | CGGCTGCTGA 428 |
| H NS5 consensus | AGTTGTGAAA | GTGATGCGCC | CGGCTGCTGA 801 |
| D NS5 consensus | AGTTGTGAAA | GTGATGCGCC | CGGCTGCTGA 794 |
| H WN05 NS5 consensus | AGTTGTGAAA | GTGATGCGCC | CGGCTGCTGA 790 |
| Consensus 100% | AGTTGTGAAA | GTGATGCGCC | CGGCTGCTGA |
| Conservation 0% | | | |

Fig. 16I

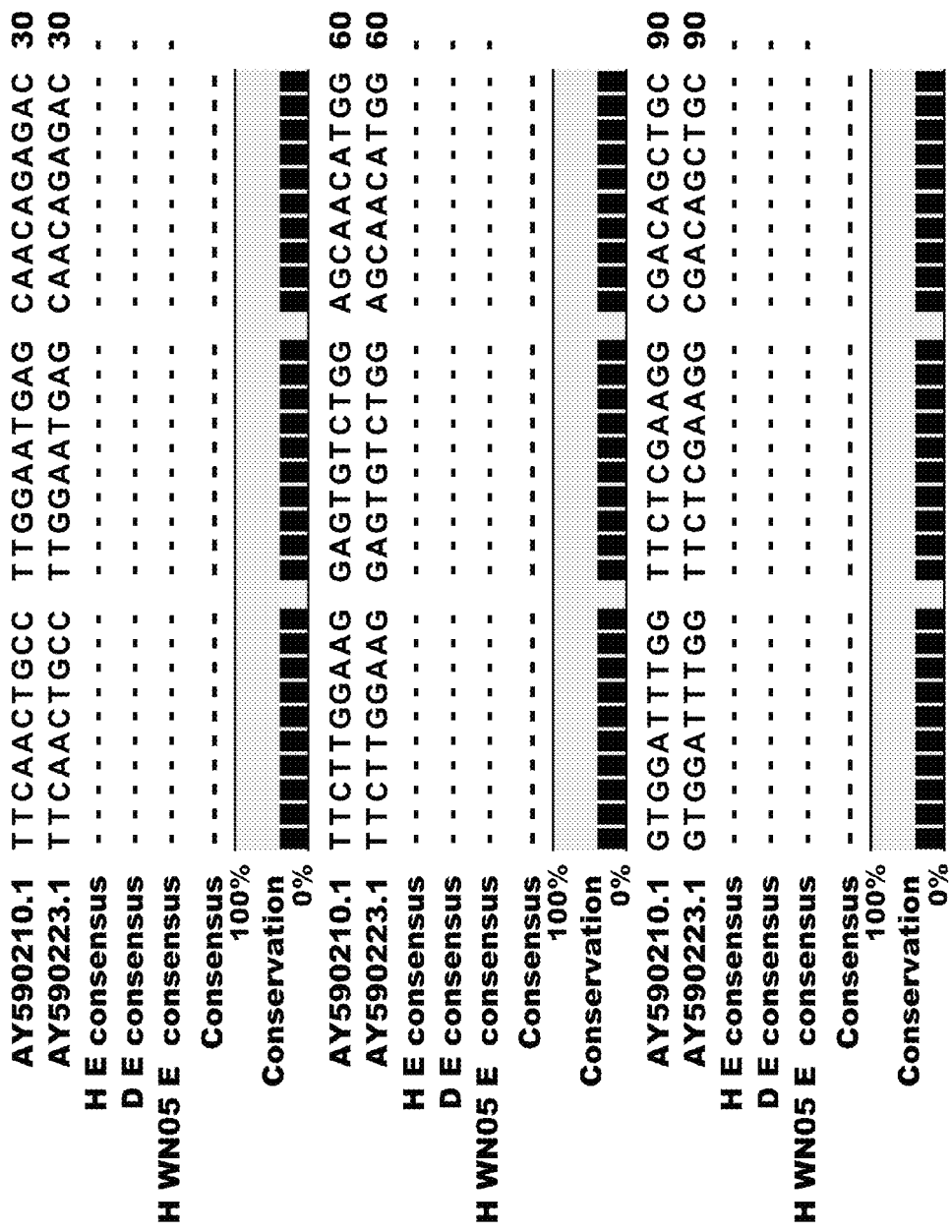

| | | | | |
|---|---|---|---|---|
| AY590210.1 | GTGACTATCA | TGTCTAAGGA | CAAGCCTACC | 120 |
| AY590223.1 | GTGACTATCA | TGTCTAAGGA | CAAGCCTACC | 120 |
| H E consensus | | | | |
| D E consensus | | | | |
| H WN05 E consensus | | | | |
| Consensus 100% | | | | |
| Conservation 0% | | | | |
| AY590210.1 | ATCGATGTGA | AGATGATGAA | TATGGAGGCG | 150 |
| AY590223.1 | ATCGATGTGA | AGATGATGAA | TATGGAGGCG | 150 |
| H E consensus | ---GATGTGG | AGA------ | ---GAA---- | 23 |
| D E consensus | ---GATGTGG | AGA------ | ---GAA---- | 23 |
| H WN05 E consensus | ---GATGTGG | AGA------ | ---GAA---- | 23 |
| Consensus 100% | ----GATGTGG | AGA------ | -GAA TATGGAGGCG | |
| Conservation 0% | | | | |
| AY590210.1 | GCCAACCTGG | CAGAGGTCCG | CAGTTATTGC | 180 |
| AY590223.1 | GCCAACCTGG | CAGAGGTCCG | CAGTTATTGC | 180 |
| H E consensus | GCCAACCTGG | CAGAGGTCCG | CAGTTATTGC | 53 |
| D E consensus | GCCAACCTGG | CAGAGGTCCG | CAGTTATTGC | 53 |
| H WN05 E consensus | GCCAACCTGG | CAGAGGTCCG | CAGTTATTGC | 53 |
| Consensus 100% | GCCAACCTGG | CAGAGGTCCG | CAGTTATTGC | |
| Conservation 0% | | | | |

Fig. 17B

WEST NILE VIRUS VACCINE

SEQUENCE LISTING

This application contains a sequence listing in accordance with 37 C.F.R. 1.821-1.825. The sequence listing accompanying this application has been submitted electronically in ASCII format and is hereby incorporated by reference in its entirety. Said ASCII copy, created on Dec. 14, 2015, is named 10-0111-US-4-SEQ-UP.txt and is 117,841 bytes in size.

BACKGROUND

West Nile Virus ("WNV") is in the family Flavivirade. Infection is usually contracted through a mosquito vector transferred through the insect's bite. West Nile infects all types of animals and birds across the globe. This virus was first discovered in the North American region in 1999 with the first diagnosis occurring in Canadian horses. Presently, West Nile Virus has become endemic in the United States affecting birds, humans, and animals of all types. In 2002, over 14,700 confirmed cases of West Nile Virus were reported in 43 states.

The spread of WNV has been influenced by several factors. Since the mosquito is the vector for the virus and perpetuates WNV, the ecological conditions conducive to growth and development of mosquito populations have had an impact of the spread of the WNV. There are several tactics that have been utilized to control populations of mosquitoes in an effort to prevent the spread of WNV. These tactics include the use of pesticides, repellants, physical barriers preventing contact between mosquitoes and animals, eliminating environments that perpetuate breeding of mosquitoes, and the use of immunizations. Typical signs of WNV include various symptoms affecting the central nervous system. Symptoms of encephalitis are often seen and include viremia, histopathologic lesions of the central nervous system, anorexia, depression, fever, weakness, abnormal gait, paralysis of hind limbs, impaired vision, ataxia, aimless wandering, convulsions, inability to swallow, coma, and death.

A few vaccines directed towards WNV have been introduced which are undesirable for various reasons. For example, one vaccine was produced from a canarypox-vectored West Nile Virus. Another set of vaccines were produced from a recombinant chimeric protein of West Nile Virus, wherein the chimeric protein vaccine was designed by fusing a modified version of bacterial flagellin (STF2 Delta) to the EIII domain of the WNV envelope protein. Another vaccine included an inactivated early North American West Nile strain that required a metabolizable oil as an adjuvant. Finally, a live, attenuated chimeric vaccine was produced from an infectious clone of yellow fever 17D virus in which the pre-membrane and envelope proteins have been replaced by the corresponding genes of WN(4).

There are several problems inherent in vaccines described above. Vaccines containing live viral organisms have the risk of infecting an animal with the virus through vaccination leading to sickness and even death. Chimeric protein vaccines, recombinantly expressed vaccines, and some sub-unit vaccines have the problem of limited immunological activity and effect related to the number of proteins included in the vaccine composition. The efficacy of these types of vaccines is usually limited and the risk of infection by the virus or reversion to wild type virus is prevalent. In addition, some of the adjuvants utilized in common vaccines are comprised of metabolizable oils which are removed relatively rapidly from the body and limit the duration during which the immune system of the vaccinated animal may respond to the immunogenically active composition. Other adjuvants can cause allergic reactions and unfavorable effects in the vaccinated animals. Additionally, these vaccines do not include antigens for stimulating immunity to other pathogens besides WNV, so they fail to protect animals against several diseases with both convenience and safety. Also, all previous vaccines were derived from an early isolate of WNV that is no longer present in the environment, and hence, can no longer infect animals and cause disease.

Accordingly, what is needed in the art is a vaccine that is safe for administration to animals of all ages, including pregnant animals, that includes adjuvants suitable for aiding the immunogenic effect and duration of the vaccine, and that is prepared from contemporary or dominant isolates of WNV that remain present in the natural environment and cause disease against which such vaccines would afford protection. What is further needed is a vaccine that reduces the incidence and/or severity of up to and including the elimination or prevention of clinical signs associated with the disease or infection by West Nile Virus. Additionally what is needed is a vaccine against West Nile virus, which includes West Nile Virus antigens in combination with antigens from other equine pathogens, thereby providing further protection by reducing the incidence of or severity of clinical signs of disease from both West Nile Virus and the other pathogen(s).

SUMMARY OF INVENTION

The present invention overcomes the problems inherent in the prior art and provides a distinct advance in the state of the art. More particularly, the present invention provides for a vaccine or immunogenic composition comprising an immunogenically active antigenic component comprised of one or more strains or isolates of West Nile Virus. In some preferred embodiments, the composition further comprises an adjuvant, preferably a carbomer, and a pharmaceutically acceptable carrier. Preferably, the West Nile Virus antigen is killed or inactivated. This composition induces an immunogenic response in animals susceptible to contraction of West Nile Virus and provides for a safe vaccine for animals of any age.

The present invention additionally provides for a vaccine composition, which is immunogenically active, and which overcomes the limitations of those previously described. The present invention provides an inactivated vaccine thereby providing unique safety for the vaccinated animals, including pregnant females. Additionally, the immunogenic composition of the present invention overcomes interference from passively acquired maternal immunity and stimulates active immunity in vaccinated animals. Advantageously, the present invention provides a broad and effective immunogenically active composition containing many or all relevant antigenic components and proteins of pathogenic WNV. The immunogenic composition of the present invention is unique in that it includes antigens of contemporary isolates or epidemiologically dominant isolates of WNV in the composition, providing protective immunogenic responses by reducing the incidence of and/or severity of clinical signs of WNV infection up to and including immunity against the most prevalent isolates seen in animals, including horses, today. In a preferred embodiment, those contemporary isolates of WNV include those isolates that are part of the North American West Nile Virus isolates or North American Dominant West Nile Virus isolates For purposes of the present invention, WN02 is a representative example of a WNV strain that can be referred to as a North American Dominant West Nile Virus strain or isolate. Specifically, North American Dominant strains and isolates are those having at least 1 nucleotide change resulting in an amino acid change from the WN99 isolates. Strain NY99 (GenBank accession no. AF196835) serves as a reference strain for determining if a strain or isolate is North American Dominant. In addition, these strains or isolates may have one or more silent amino acid changes. In a preferred embodiment, the nucleotide change results in an amino acid change in an envelope protein of the strain or isolate and, more preferably, the nucleotide change results in an amino acid change from valine to alanine. Preferably, this amino acid change is associated with a greater ability to replicate in the intermediate host, namely, the mosquito. More preferably, North American Dominant strains include either (and preferably both) a U to C mutation and a C to U mutation at positions 1442 and 2466 (in comparison to a North American strain, e.g. NY 99 and SEQ ID NO.23), respectively. Still more preferably, North American Dominant strains or isolates further include a mutation in the nucleotide sequence encoding the E protein and the C to U mutation at position 9352 in the sequence encoding the NS5 protein (again in comparison to a North American strain, e.g. NY 99 and SEQ ID NO. 23). These preferred mutations are shown in Example 10 and in Phylogenetic Analysis of North American West Nile Virus Isolates, 2001-2004: Evidence For the Emergence of a Dominant Genotype, C. Todd Davis, et. al, Virology 342, p. 252-265 (2005), the teaching and content of which is hereby incorporated by reference herein.

The present invention also provides for a method of making the immunogenic composition of the present invention. The method generally comprises the steps of combining a West Nile Virus antigen and an excipient or pharmaceutically or veterinary acceptable carrier. A preferred embodiment further comprises the step of adding one or more additional equine antigens. In another embodiment, the method further comprises the step of adding a suitable adjuvant to the composition.

In one preferred embodiment, the present invention includes WNV antigens and a non-metabolizable oil adjuvant, preferably mineral oil, to extend the duration during which the immune system of the vaccinated animal may respond to the immunogenically active composition. The non-metabolizable oil is understood to be an oil that, when administered with an antigen, does not metabolize in the body after administration. A preferred non-metabolizable oil is mineral oil. In other preferred forms, both a carbomer adjuvant and non-metabolizable oil (preferably mineral oil) are present in addition to the WNV antigens. The adjuvant(s) can be used in any of the compositions described herein.

In an additional embodiment, the composition of the present invention contains WNV antigens, preferably an inactivated or killed WNV from a North American dominant strain, and essentially no oil or oil-based adjuvants. In such an embodiment, other adjuvants, preferably carbomer, can be included.

In another embodiment, a vaccine composition comprised of WNV antigens in combination with other antigens from equine microbial pathogens is provided in order to confer a broad scope of protection to the animal. In such embodiments, the WNV antigens are in any form as described above.

In one preferred embodiment, the present invention provides a vaccine composition comprising WNV antigens as described above in combination with one or more immunologically effective amounts of antigenic components selected from the group consisting of Venezuelan Equine Encephalomyelitis (VEE), Eastern Equine Encephalomyelitis (EEE), Western Equine Encephalomyelitis (WEE), Tetanus toxoid (T), Equine herpes viruses (EHV) including types 1 and 4, Equine influenza viruses (EIV), and combinations thereof, along with a pharmaceutically acceptable carrier. Preferably such embodiments will include an adjuvant, preferably carbomer, and a pharmaceutically acceptable carrier. Additionally, a non-metabolizable oil, preferably mineral oil, may be present, however, such an oil is not required.

Preferred embodiments also include WNV antigens, as described above, in combination with: Eastern Equine Encephalomyelitis; Western Equine Encephalomyelitis; Venezuelan Equine Encephalomyelitis; Tetanus Toxoid; Eastern Equine Encephalomyelitis and Western Equine Encephalomyelitis; Eastern Equine Encephalomyelitis and Venezuelan Equine Encephalomyelitis; Eastern Equine Encephalomyelitis and Tetanus Toxoid; Eastern Equine Encephalomyelitis, Western Equine Encephalomyelitis, and Venezuelan Equine Encephalomyelitis; Eastern Equine Encephalomyelitis, Western Equine Encephalomyelitis, and Tetanus Toxoid; Eastern Equine Encephalomyelitis, Western Equine Encephalomyelitis, Venezuelan Equine Encephalomyelitis and Tetanus Toxoid; Western Equine Encephalomyelitis and Venezuelan Equine Encephalomyelitis; Western Equine Encephalomyelitis and Tetanus Toxoid; Western Equine Encephalomyelitis, Venezuelan Equine Encephalomyelitis, and Tetanus Toxoid; Venezuelan Equine Encephalomyelitis and Tetanus Toxoid; and Eastern Equine Encephalomyelitis, Venezuelan Equine Encephalomyelitis and Tetanus Toxoid. The most preferred combination of these specified combinations includes WNV antigens in combination with antigens or antigenic components of Eastern Equine Encephalomyelitis, Western Equine Encephalomyelitis, Venezuelan Equine Encephalomyelitis, and Tetanus Toxoid. In each such specified combination, an adjuvant or combination of adjuvants can be used, with carbomer, and even more preferably carbopol, being particularly preferred. In the most preferred forms of the combination of WNV and Eastern Equine Encephalomyelitis, Western Equine Encephalomyelitis, Venezuelan Equine Encephalomyelitis and Tetanus Toxoid, no oil (metabolizable or non-metabolizable) is present. The NJO strain of Eastern Equine Encephalomyelitis, the Fleming strain of Western Equine Encephalomyelitis strain, and the TC-83 strain of Venezuelan Equine Encephalomyelitis strain are all representative strains of these vaccine components.

Further preferred embodiments of the present invention can be made using each of the specified combination vaccines listed above and adding in antigens from Equine Herpesvirus, preferably type 1, type 4, (EHV1 and/or EHV4) or combinations thereof.

Still further variations of each of the specified combination vaccines listed above, including those that include EHV1 and/or EHV4 can be made by adding in antigens from Equine influenza virus (EIV). Preferred embodiments incorporating Equine influenza virus include: West Nile Virus, at least one strain of Equine Influenza Virus, and Tetanus Toxoid; West Nile Virus, at least one strain of Equine Influenza Virus, Tetanus Toxoid, and Eastern Equine Encephalomyelitis; West Nile Virus, at least one strain of Equine Influenza Virus, Tetanus Toxoid, Eastern Equine Encephalomyelitis, and Western Equine Encephalomyelitis; West Nile Virus, at least one strain of Equine Influenza Virus, Tetanus Toxoid, Eastern Equine Encephalomyelitis, Western Equine Encephalomyelitis; and Venezuelan Equine Encephalomyelitis; West Nile Virus, at least one strain of Equine Influenza Virus, and Eastern Equine Encephalomyelitis; West Nile Virus, at least one strain of Equine Influenza Virus, and Western Equine Encephalomyelitis; West Nile Virus, at least one strain of Equine Influenza Virus, and Venezuelan Equine Encephalomyelitis; West Nile Virus, at least one strain of Equine Influenza Virus, Eastern Equine Encephalomyelitis, and Western Equine Encephalomyelitis; West Nile Virus, at least one strain of Equine Influenza Virus, Eastern Equine Encephalomyelitis, and Venezuelan Equine Encephalomyelitis; West Nile Virus, at least one strain of Equine Influenza Virus, Western Equine Encephalomyelitis, and Venezuelan Equine Encephalomyelitis; West Nile Virus, at least one strain of Equine Influenza Virus, Western Equine Encephalomyelitis, and tetanus toxoid; West Nile Virus, at least one strain of Equine Influenza Virus, Venezuelan Equine Encephalomyelitis, and tetanus toxoid; West Nile Virus, at least one strain of Equine Influenza Virus, Venezuelan Equine Encephalomyelitis, Western Equine Encephalomyelitis, and tetanus toxoid; and West Nile Virus, at least one strain of Equine Influenza Virus, Venezuelan Equine Encephalomyelitis, Eastern Equine Encephalomyelitis, and tetanus toxoid. In each specified embodiment any one or more strains or isolates of Equine Influenza may be present. Preferred strains of Equine Influenza virus include Influenza A/equine-2/Ohio/03, Influenza A/equine-2/New Market/2/93, Influenza A/equine-2/Kentucky/95, and combinations thereof. In all of the combinations listed above, it is preferred to use at least two strains of Equine Influenza and still more preferred to use at least 3 strains of Equine Influenza. Preferred embodiments incorporating Equine Herpes Virus include: West Nile Virus, at least one strain of Equine Influenza Virus, Tetanus Toxoid, and Equine Herpes Virus; West Nile Virus, at least one strain of Equine Influenza Virus, Tetanus Toxoid, Eastern Equine Encephalomyelitis, and Equine Herpes Virus; West Nile Virus, at least one strain of Equine Influenza Virus, Tetanus Toxoid, Eastern Equine Encephalomyelitis, Western Equine Encephalomyelitis, and Equine Herpes Virus; West Nile Virus, at least one strain of Equine Influenza Virus, Tetanus Toxoid, Eastern Equine Encephalomyelitis, Western Equine Encephalomyelitis, Venezuelan Equine Encephalomyelitis, and Equine Herpes Virus; West Nile Virus, at least one strain of Equine Influenza Virus, and Eastern Equine Encephalomyelitis; West Nile Virus, at least one strain of Equine Influenza Virus, Western Equine Encephalomyelitis and Equine Herpes Virus; West Nile Virus, at least one strain of Equine Influenza Virus, Venezuelan Equine Encephalomyelitis, and Equine Herpes Virus; West Nile Virus, at least one strain of Equine Influenza Virus, Eastern Equine Encephalomyelitis, Western Equine Encephalomyelitis, and Equine Herpes Virus; West Nile Virus, at least one strain of Equine Influenza Virus, Eastern Equine Encephalomyelitis, Venezuelan Equine Encephalomyelitis, and Equine Herpes Virus; West Nile Virus, at least one strain of Equine Influenza Virus, Western Equine Encephalomyelitis, Venezuelan Equine Encephalomyelitis, and Equine Herpes Virus; West Nile Virus, at least one strain of Equine Influenza Virus, Western Equine Encephalomyelitis, Tetanus Toxoid, and Equine Herpes Virus; West Nile Virus, at least one strain of Equine Influenza Virus, Venezuelan Equine Encephalomyelitis, tetanus toxoid, and Equine Herpes Virus; West Nile Virus, at least one strain of Equine Influenza Virus, Venezuelan Equine Encephalomyelitis, Western Equine Encephalomyelitis, Tetanus Toxoid, and Equine Herpes Virus; and West Nile Virus, at least one strain of Equine Influenza Virus, Venezuelan Equine Encephalomyelitis, Eastern Equine Encephalomyelitis, Tetanus Toxoid, and Equine Herpes Virus. In all of the combinations listed above, it is preferred to use at least two strains of Equine Influenza and still more preferred to use at least 3 strains of Equine Influenza. Additionally, in all combinations above, the "at least one" strain of Equine Herpesvirus is preferred to be selected from the group consisting of EHV-1 and EHV-4. In some preferred forms, both strains, EHV-1 and EHV-4, will be included in the immunogenic composition. In other preferred forms, just EHV-1 will be included. The WNV component of the combination will preferably be an inactivated or killed North American dominant strain as described herein.

The vaccine composition can be administered in any immunogenically effective dose. In a preferred embodiment, the vaccine composition is administered as a single dose. Preferably, the dose has a total volume between about 0.5 ml and 2.5 ml, more preferably between about 0.6 ml and 2.0 ml, even more preferably between about 0.7 ml and 1.75 ml, still more preferably between about 0.8 ml and 1.5 ml, even more preferably between about 0.9 ml and 1.25 ml, with a single 1.0 ml dose being the most preferred.

In another embodiment, the vaccine is administered with a first dose being administered prior to the administration of a second (booster) dose. Preferably, the second dose is administered at least 15 days after the first dose. More preferably, the second dose is administered between 15 and 28 days after the first dose. Even more preferably, the second dose is administered at least 17 days after the first dose. Still more preferably, the second dose is administered between 17 and 25 days after the first dose. Even more preferably, the second dose is administered at least 19 days after the first dose. Still more preferably, the second dose is administered between 19 and 23 days after the first dose. Most preferably the second dose is administered at least 21 days after the first dose. In a preferred embodiment, both the first and second doses of the vaccine are in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these embodiments. Preferably, subsequent third, fourth, and fifth dose regimens are administered in the same amount as the first dose, with the time frame between the doses being consistent with the timing between the first and second doses mentioned above.

In an additional preferred embodiment, in each dose of the composition of the present invention, the WNV antigen comprises at least $10^{2.0}TCID_{50}$/dose. More preferably, the WNV antigen comprises between about $10^{2.0}TCID_{50}$/dose to $10^{10.0}TCID_{50}$/dose. Still more preferably, the WNV antigen comprises at least $10^{2.5}TCID_{50}$/dose. Even more preferably, the WNV antigen comprises between about $10^{2.5}TCID_{50}$/dose to about $10^{9.5}TCID_{50}$/dose. Still more preferably, the WNV antigen comprises at least $10^{3.0}TCID_{50}$/dose. Even more preferably, the WNV antigen comprises between about $10^{3.0}TCID_{50}$/dose to about $10^{9.0}TCID_{50}$/dose. Still more preferably, the WNV antigen comprises at least $10^{3.5}TCID_{50}$/dose. Even more preferably, the WNV antigen comprises between about $10^{3.5}TCID_{50}$/dose to about $10^{9.0}TCID_{50}$/dose. Most preferably, the WNV antigen comprises between $10^{7.0}TCID_{50}$/dose and $10^{9.0}TCID_{50}$/dose. The $TCID_{50}$ values of an inactivated WNV vaccine or any other inactivated vaccine refer in general to the antigen content in the final vaccine that however is equivalent to the antigen content calculated for the vaccine composition prior to the inactivation of its antigen. Preferably, the immunogenic composition of the present invention stimulates serum neutralizing antibodies to WNV at a titer of 1:4 or higher when determined in a commercial available detection assay or using the procedures known to those of skill in the art with a representative example provided herein. In a preferred embodiment, in each dose of an embodiment of the present invention that comprises additional equine antigen, the amount of Eastern Equine Encephalomyelitis or Venezuelan Equine Encephalomyelitis in any dose is preferably at least $10^{5.5}TCID_{50}$/dose. Even more preferably, the dose is between about $10^{5.5}TCID_{50}$/dose and $10^{9.5}TCID_{50}$/dose. Still more preferably, the dose is at least $10^{6.0}TCID_{50}$/dose. Still more preferably, the dose is between about $10^{6.0}TCID_{50}$/dose and $10^{9.0}TCID_{50}$/dose. Even more preferably, the dose is at least $10^{6.5}TCID_{50}$/dose. Still more preferably, the dose is between about $10^{6.5}TCID_{50}$/dose and $10^{9.5}TCID_{50}$/dose. Even more preferably, the dose is at least $10^{7.0}TCID_{50}$/dose. Most preferably, the dose is between $10^{6.7}TCID_{50}$ and $10^{9.2}TCID_{50}$/dose.

Preferably, the Western Equine Encephalomyelitis antigen, when present in the composition of the present invention, is in an amount of at least $10^{6.2}$ PFU/ml. Even more preferably, the amount is between $10^{6.2}$ PFU/ml and $10^{10.2}$ PFU/ml. Still more preferably, the amount is at least $10^{6.7}$ PFU/ml. Even more preferably, the amount is between $10^{6.5}$ PFU/ml and $10^{9.7}$ PFU/ml. Still more preferably, the amount is at least $10^{7.2}$ PFU/ml. Even more preferably, the amount is between about $10^{7.2}$ PFU/ml and $10^{9.2}$ PFU/ml. Still more preferably, the amount is at least $10^{7.7}$ PFU/ml with at between $10^{6.5}$ PFU/dose and $10^{9.0}$ PFU/ml being the most preferred.

In another preferred embodiment, the amount of tetanus toxoid, if present in the composition of the present invention, is in an amount of at least 3 CPU, more preferably, between about 3 CPU and 20 CPU, still more preferably, at least 4 CPU, and most preferably, at least 5 CPU but not more than 20 CPU.

In an alternate embodiment, where one or more strains of Equine Influenza Virus is present, the amount of Equine Influenza present in the composition is in an amount of at least $10^{5.0}TCID_{50}$/mL. More preferably, the Equine Influenza is in an amount of between about $10^{5.0}$ $TCID_{50}$/mL to $10^{9.0}TCID_{50}$/mL, and, more preferably, at least $10^{6.0}TCID_{50}$/mL. Still more preferably, the amount is between about $10^{6.0}TCID_{50}$/mL to $10^{8.0}TCID_{50}$/mL and, more preferably, the amount is at least $10^{6.5}TCID_{50}$/mL. Still more preferably, the amount is between about $10^{6.5}TCID_{50}$/mL to $10^{7.0}TCID_{50}$/mL, with the most preferred amount being between about $10^{6.7}TCID_{50}$/mL to $10^{7.0}$.

In an embodiment that comprises Equine Herpes Virus, the amount of Equine Herpes Virus in each dose is at least $10^{6.0}TCID_{50}$/mL. More preferably, Equine Herpes Virus is present in the composition in an amount of between $10^{6.0}TCID_{50}$/mL to $10^{9.5}TCID_{50}$/mL and, more preferably, in an amount of about $10^{7.0}TCID_{50}$/mL. Still more preferably, Equine Herpes Virus is present in an amount between $10^{7.5}TCID_{50}$/mL to $10^{9.0}TCID_{50}$/mL and, more preferably, in an amount of about $10^{8.0}TCID_{50}$/mL. Still more preferably, Equine Herpes Virus is present in an amount of between $10^{8.0}TCID_{50}$/mL to $10^{9.0}TCID_{50}$/mL and, most preferably, in an amount of about $10^{8.50}TCID_{50}$/mL.

In yet another preferred embodiment, a vaccine composition comprising the chronologically contemporary and epidemiologically prevalent strains of WNV is provided. Such a composition will generally improve the efficacy of the composition. Preferably, such a prevalent strain is isolated from the tissues of a horse. Such a source is a preferred source of WNV for preparing vaccine seed virus for an immunological composition for a species for which a comprehensively safe and effective WNV vaccine is particularly needed, namely, the horse. Further, the present invention discloses a vaccine composition comprising an inactivated low passage strain of WNV from the tissues of a horse, thereby overcoming the limitations of previous vaccines with the inappropriate limited repertoire of protein antigens found in either high passage attenuated vaccines, subunit vaccines, or other compositions produced by recombinant technology that express less than the full complement of proteins. This inactivated low passage WNV strain, isolated from horse tissues, overcomes deficiencies inherent in previous vaccines and provides a broad number of immunogenic proteins of most relevance by virtue of being produced from a highly virulent equine strain of low passage, thereby comprising a uniquely and comprehensively effective, yet safe, immunogenic composition not previously available for vaccination of the horse. Additionally, preferred chronologically contemporary and epidemiologically prevalent strains of WNV are North American dominant WNV strains, as defined herein.

The present invention provides for a broader scope of protection than traditional immunogenic or vaccine compositions, as the present invention provides protection against a broad range of isolates of a particular antigen. The challenge model used to evaluate the efficacy of the composition of the present invention utilized a heterologous challenge strain, evidencing the composition's ability to provide protection to isolates and strains outside of the particular strain or isolate used to vaccinate the animal. This is a unique feature of the present invention.

The present invention additionally provides for a method of reduction of the incidence and/or severity of clinical signs associated with West Nile Virus infection in an animal, preferably a horse, when compared to wild type infection. Such methods generally comprise the step of administering a vaccine composition comprising a killed or inactivated isolate of West Nile virus, preferably a North American dominant WNV strain, and a pharmaceutically acceptable carrier. In some preferred embodiments of the present application, an adjuvant is added to the composition, and in other preferred forms, no adjuvant is provided. In an alternate preferred embodiment, the method comprises administering a vaccine composition comprising one or more killed or inactivated isolate(s) of West Nile virus in combination with immunologically effective amounts of antigenic components from other equine pathogens. Preferably those isolates are selected from the group consisting of Eastern Equine Encephalomyelitis antigen, Western Equine Encephalomyelitis antigen, Venezuelan Equine Encephalomyelitis antigen, tetanus toxoid, and combinations thereof, and more preferably being those combinations described above. In another preferred embodiment, the vaccine of the present invention is combined with a suitable adjuvant, diluent, or pharmaceutically acceptable carrier.

The present invention provides for reduction of the incidence and/or severity of clinical symptoms associated with West Nile Virus infection in a herd, when compared to wild type infection. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to wild type infection by WNV. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms. Preferably, the WNV strain is a North American dominant strain of WNV. Advantageously, the present invention also provides protection from heterologous strains (relative to the strain used in the composition) of pathogens.

The present invention further provides a method of stimulating serum neutralizing or serum hemagglutination antibodies to a pathogen selected from the group consisting of WNV, WEE, VEE, EEE, EHV, EIV, and combinations thereof by administering a composition in accordance with the present invention described herein. Preferably the compositions of the present invention stimulate serum neutralizing antibodies to WNV at a titer of 1:4 or higher, thereby preventing or reducing WNV viremia.

The immunogenic composition of the present invention provides an extended duration of immunity against all antigens present in the vaccine. Preferably, the duration of immunity against West Nile is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EIV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EHV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Western Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Eastern Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Venezuelan Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Tetanus Toxoid is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity of at least 12 months further relates to any combination of antigens forming the immunogenic composition of the present invention.

In another preferred embodiment comprising EIV and/or EHV antigen, as described above, the immunogenic composition ameliorates shedding of infectious EIV or EHV to prevent spread of the virus to other susceptible animals.

In yet another preferred embodiment, compositions in accordance with the present invention described herein overcome interference from passively acquired maternal immunity and stimulates active immunity and a reduction in the incidence of or severity of clinical signs of EIV infection in vaccinated animals against EIV.

In another preferred embodiment of the present invention, an immunogenic composition comprising VEE, WEE, EEE, tetanus, WNV, equine rhinopneumonitis and equine influenza, all as described herein, demonstrates efficacy against VEE, WEE, EEE, tetanus, WNV, equine rhinopneumonitis and equine influenza after administration in accordance with the present invention. Preferably, such a composition will further include an adjuvant, preferably mineral oil and/or a carbomer, and a veterinary acceptable carrier. In preferred forms, the composition will be administered in a single, 1 ml dose.

Each of the immunogenic compositions described herein that include WNV antigen can be administered as described such that they reduce the incidence of or lessen the severity of clinical symptoms associated with West Nile Virus.

Each of the immunogenic compositions described herein that include EIV antigen can be administered as described such that they reduce the incidence of or lessen the severity of clinical symptoms associated with Equine Influenza.

The present invention also provides a method for reducing the incidence of or lessening the severity of clinical symptoms associated with Equine Herpes virus comprising the step of administering any one of the immunogenic compositions described above, that includes an Equine Herpes virus antigen, to an animal.

The present invention also provides a method for reducing the incidence of clinical symptoms associated with West Nile Virus comprising the step of administering any one of the immunogenic compositions that includes West Nile Virus antigen, as described herein, to an animal.

The present invention also provides a method for reducing the incidence of clinical symptoms associated with Equine Influenza Virus comprising the step of administering any one of the immunogenic compositions described above, that includes an Equine Influenza antigen, to an animal.

The present invention further provides a method for reducing the incidence of clinical symptoms associated with Equine Herpes Virus comprising the step of administering any one of the immunogenic compositions described above that includes an Equine Herpes virus antigen, to an animal.

The present invention also provides a method of reducing the incidence of clinical symptoms associated with Equine Influenza Virus comprising the step of administering any one of the immunogenic compositions described above to an animal, wherein the reduction in clinical signs, compared to animals not receiving the immunogenic composition, is at least a 10% reduction in clinical signs.

The present invention provides a method of reducing the incidence of infection in a herd comprising the step of administering any one of the immunogenic compositions described above to an animal.

The present invention provides a method of reducing the incidence of infection in a herd comprising the step of administering any one of the immunogenic compositions described above to an animal, wherein the reduction of incidence of infection, compared to herds not receiving the immunogenic composition, is from about 10%-50% reduction.

The present invention provides a method of reducing the incidence and severity of clinical symptoms of EHV in a herd, wherein the clinical symptoms are selected from the group consisting of respiratory disease, abortion, reproductive complications, neurological disease, central nervous system disease, and combinations thereof.

The present invention provides a method for reducing the incidence of or lessening the severity of clinical symptoms associated with Equine Herpes Virus comprising the step of administering any one of the immunogenic compositions described above, that includes an Equine Herpes Virus antigen, to an animal.

The present invention provides a method for reducing the severity of or lessening the severity of clinical symptoms associated with Equine Influenza in a herd, comprising the step of administering any one of the immunogenic compositions described above, that includes an Equine Influenza antigen, to an animal.

The present invention provides a method for reducing the incidence of or lessening the severity of clinical symptoms associated with West Nile Virus in a herd, comprising the step of administering any one of the immunogenic compositions described above, that includes a West Nile Virus antigen, to an animal.

The present invention provides a method for reducing the incidence of or lessening the severity of clinical symptoms associated with Eastern Equine Encephalomyelitis in a herd, comprising the step of administering any one of the immunogenic compositions described above that includes an Eastern Equine Encephalomyelitis antigen to an animal.

The present invention further provides a method for reducing the incidence of or lessening the severity of clinical symptoms associated with Western Equine Encephalomyelitis in a herd, comprising the step of administering any one of the immunogenic compositions described above, that includes an Western Equine Encephalomyelitis antigen, to an animal.

The present invention further provides a method for reducing the incidence of or lessening the severity of clinical symptoms associated with Venezuelan Equine Encephalomyelitis in a herd, comprising the step of administering any one of the immunogenic compositions described above, that includes a Venezuelan Equine Encephalomyelitis antigen, to an animal.

The present invention also provides a method of making any one of the immunogenic composition of the present invention as described above and herein, comprising the steps of combining a West Nile Virus antigen with a suitable excipient or pharmaceutical carrier. In preferred forms, this method further comprises the step of adding one or more equine antigens. A preferred group of equine antigens are selected from the group consisting of Western Equine Encephalomyelitis, Eastern Equine Encephalomyelitis, Venezuelan Equine Encephalomyelitis, Tetanus Toxoid, EHV, EIV, and combinations thereof. In some preferred forms, the methods described herein can further comprise a filtration step, wherein the final product is in a purified form.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.). John Wiley and Sons, NY, pp 51-94 (1995) and Todd et al., Vaccine 15:564-570 (1997). In a preferred embodiment the adjuvant is at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product. Of the possible adjuvants used in combination with the present invention, it is preferred to not use a metabolizable oil. In a preferred embodiment, the adjuvant is at least a non-metabolizable oil, preferably mineral oil. In an alternate preferred embodiment, the vaccine composition contains essentially no oil-based adjuvants. In a most preferred embodiment the vaccine composition contains both a non-metabolizable oil, preferably mineral oil, and carbomer as adjuvants.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, excipients, antibacterial and antifungal agents, antimicrobic agents, isotonic agents, adsorption delaying agents, and the like. In some preferred embodiments, and especially those that include lyophilized immunogenic compositions, stabilizing agents for use in the present invention include stabilizers for lyophilization or freeze-drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In a preferred embodiment, the immunogenic composition of the present invention is prepared comprising a preservative and a stabilizer; and, more preferably, the immunogenic composition of the present invention is prepared comprising gentamycin, EDTA, Glycerol, and combinations thereof.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

The term "in need of such administration" or "in need of such administration treatment", as used herein means that the administration/treatment is associated with the boosting or improvement in health or any other positive medicinal effect on health of the animals which receive the immunogenic composition in accordance with the present invention.

The term "West Nile Virus" antigen means, but is not limited to the components of the WNV virion that are immunogenic when present in an animal, and most particularly protein components, such as envelope and non-structural proteins, of the WNV that provoke humoral or cellular immune responses when present in an animal. Such antigens can include DNA, protein subunits, modified live virus, and killed or inactivated virus. In preferred forms of the invention, the WNV antigen or antigens comprise inactivated or killed, and even more preferably, North American dominant, WNV strains.

The term "North American West Nile Virus (strains)" refers to, but is not limited to any West Nile Virus strain or isolate that has ever been discovered on the North American continent. Preferably, a North American West Nile Virus strain has a sequence identity to the NY99 strain (GenBank accession no. AF196835 or NCBI reference sequence NC_00942.1 (SEQ ID No. 23) of at least 97%, even more preferably, at least 98%, still more preferably, at least 98.5%, more preferably, at least 99%, even more preferably, at least 99.2%, and, most preferably of at least 99.4%.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The term "North American Dominant West Nile Virus" strains and isolates refers to those strains or isolates defined as such in *Phylogenetic Analysis of North American West Nile Virus Isolates, 2001-2004: Evidence For the Emergence of a Dominant Genotype*, C. Todd Davis, et. al, Virology 342, p. 252-265 (2005), the teaching and content of which is hereby incorporated by reference herein. As noted therein, North American Dominant WNV strains or isolates have at least 1 nucleotide change resulting in an amino acid change from the WN99 isolates. Strain NY99 (GenBank accession no. AF196835), an example of which is provided in SEQ ID. NO. 23, serves as a reference strain for determining if a strain or isolate is North American Dominant. In a preferred embodiment, the nucleotide change results in an amino acid change in an envelope protein of the strain or isolate and, more preferably, the nucleotide change results in an amino acid change from valine to alanine at position 159 in the critical envelope protein or "E159". Preferably, this amino acid change is associated with a greater ability to replicate in the intermediate host, namely, the mosquito. In addition, these strains or isolates may have one or more silent amino acid changes. Preferably, North American Dominant strains also include either (and preferably both) a U to C mutation and a C to U mutation at positions 1442 and 2466 (in comparison to a North American strain, e.g. NY 99 and SEQ ID NO.23), respectively. Still more preferably, North American Dominant strains or isolates further include a mutation in the nucleotide sequence encoding the E protein and the C to U mutation at position 9352 in the sequence encoding the NS5 protein (again in comparison to a North American strain, e.g. NY 99 and SEQ ID NO. 23). These preferred mutations are shown in detail for specific regions in Example 10 and FIGS. 10-17. Representative North American Dominant WNV strains are listed in this application. Additionally, for purposes of the present invention North American Dominant and WN02 are used interchangeably.

For purposes of the present invention, Horse Origin 2005 strain North American Equine E159, E159 (Horse Origin), NAEE159, United States Department of Agriculture 1920 Dayton Avenue, Ames, Iowa 50010 Isolate 405330 (USDA 2005) Horse Origin, and E159 strain are used interchangeably. For purposes of the present invention, Donkey Origin 2004 strain, United States Department of Agricultures Isolate 292206 (USDA 2004) Donkey Origin, E159 (Donkey Origin), and North American Donkey E159 (NADE159) are used interchangeably. E159 indicates that the amino acid change in the envelope protein from valine to alanine occurs at position 159, as described above.

West Nile Virus strains or isolates, for purposes of the present invention, are not limited to horse and equine West Nile Virus strains but encompass, while not being limited to, those West Nile Virus strains of bird origin, donkey origin, pig origin, human origin, mammal origin, and equine origin.

For purposes of the present invention the terms "strain" and "isolate" have the same meaning and are used interchangeably.

As used herein, "a pharmaceutically" or "veterinary acceptable carrier" or "pharmaceutical carrier" includes any and all solvents, growth media, dispersion media, coatings, adjuvants, stabilizing agents, diluents, preservatives, antibacterial and antifungal agents, isotonic agents, adsorption delaying agents, and the like.

An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, and/or virus neutralizing antibodies directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration of clinical disease or higher viral antibody titer in the tissues or body fluids or excretions of the infected host, or lessened viremia in the blood, or lessened gross or histopathological lesions due to infection.

In addition, the immunogenic and vaccine compositions of the present invention can include one or more veterinary-acceptable carriers. As used herein, "a veterinary-acceptable carrier" includes any and all solvents, dispersion media, cell culture media and cell culture constituents, coatings, adjuvants, stabilizing agents, diluents, preservatives, antibacterial and antifungal agents, isotonic agents, adsorption delaying agents, and the like. "Diluents" can include water, saline, buffered saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Clinical signs" of West Nile Virus, for purposes of this invention, include, but are not limited to, symptoms or lesions associated with encephalitis, viremia, anorexia, depression, fever, weakness, abnormal gait, paralysis of hind limbs, impaired vision, ataxia, aimless wandering, convulsions, inability to swallow, coma, posterior weakness, paralysis, poor coordination, depression and related behavior, tremors, convulsions, paddling of the limbs, neurological problems, swelling of the central nervous system, death, and combinations thereof. The clinical signs exhibited by an infected animal vary depending on the severity of infection "Clinical Signs" of Equine Herpes virus, for purposes of this invention include, but are not limited to, abortion, neurological deficiencies, respiratory disease, reproductive system deficiencies and failure, and symptoms relating to the central nervous system. Additionally, clinical symptoms of EHV 1 include, but are not limited to, the phenomenon of foals infected with EHV1, exhibiting respiratory complications, passing the virus to the older members of the herd who then exhibit reproductive deficiencies, including abortion, and neurological deficiencies, normally exhibited in the central nervous system.

"Clinical Signs" of Eastern Equine Encephalomyelitis, Western Equine Encephalomyelitis, and Venezuelan Equine Encephalomyelitis, for purposes of the present invention are those symptoms normally known to be associated with encephalomyelitis, including, but not limited to fever, nervous signs such as sensitivity to sound, periods of excitement, and restlessness, brain lesions, drowsiness, drooping ears, circling, abnormal gait, paralysis, loss of appetite, depression, head pressing, lack of coordination, long-term disability, brain damage, death, and combinations thereof. "Safety" as used herein, refers to the absence of adverse consequences in the vaccinated animal following vaccination, including but not limited to, potential reversion of vaccine virus to virulence and clinically significant side effects, such as persistent systemic illness or unacceptable inflammation at the site of vaccine administration.

"Reduction of the incidence and/or severity of clinical signs" or "reduction in the incidence and/or severity of clinical symptoms", as referred to herein, means reducing the number of infected animals in a group, reducing or eliminating the number of animals exhibiting clinical signs of infection, or reducing the severity of any clinical signs that are present in the animals, in comparison to wild-type infection. For example, in the experiments herein, such clinical signs included viremia, fever, antibody response, and histopathology. Preferably, these are reduced in animals receiving the composition of the present invention by at least 10% in comparison to animals not receiving the vaccination which may become infected. More preferably, clinical signs are reduced in animals receiving the composition of the present invention by at least 20%, more preferably by at least 30%, even more preferably by at least 40%, and even more preferably by at least 50%.

"Duration of Immunity," as used herein, refers to the minimum number of days during which an animal produces an immunogenic response such that the animal will be relatively immune from contracting a virus and/or benefit from reduction of incidence and/or severity of clinical signs, as described herein.

The terms "strain" and "isolate", when used herein, are meant to be used interchangeably.

The terms "vaccine" and "immunogenic composition", when used herein, are meant to be used interchangeably.

Any West Nile Virus strain(s) or isolate(s) can be used in accordance with the present invention. In a preferred embodiment, the isolate is selected from one or more of the following: New York (Northeastern North American) Isolate (WN-NY 99), Horse Origin, 1999, New York (Northeastern North American) Isolate (WN-NY 99), Crow Origin, 1999, United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof, and in a more preferred embodiment the isolate is selected from one or more of the following: United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof. In a most preferred embodiment, the isolate is United States Department of Agriculture Isolate 405330 (USDA 2005), Horse Origin singularly or in combination with one or more isolates as listed above. In an additionally preferred embodiment, those isolates which are part of the North American West Nile Virus isolates are included. In yet another preferred embodiment North American Dominant West Nile Virus isolates are included. In addition to those listed above, specific isolates include, but are not limited to, WN02 and isolates which have at least 1, preferably at least 2, and even more preferably at least 3 nucleotide changes resulting in at least one amino acid change from the WN NY99 isolates, and most preferred are strains with the amino acid change from valine to alanine at position 159 of the envelope protein. Most preferred North American Dominant strains include, but are not limited to: NY2002Nassau, NY2002Clinton, NY2002Queens, GA20021, GA20022, TX20021, TX20022, IN2002, NY2003Albany, N.Y.2003Suffolk, NY2003Chatauqua, CO20031, CO20032, TX2003, TX2003Harris4, TX2003Harris6, TX2003Harris7, TX2003Harris10, AZ2004, and TX2004Harris4, and combinations thereof. The strains of West Nile Virus useful in the vaccine or immunogenic composition of the present invention can be any strain or isolate. In a preferred embodiment, the North American Dominant West Nile Virus strain used is either E-159 (Horse Origin) or E-159 (Donkey Origin). A representative strain of such a North American Dominant WNV strain includes the Horse Origin 2005 strain deposited with the ATCC (ATCC Accession No. PTA-9409), located at 10801 University Boulevard, Manassas, Va., 20110-2209, on Aug. 14, 2008, under the provisions of the Budapest Treaty. Equine Influenza strains useful in the vaccine or immunogenic composition of the present invention can be any strain or isolate. Representative strains include Equi-2/Ohio/03, deposited as ATCC Accession No. PTA-9522, Equi-2/Kentucky/95, deposited as ATCC Accession No. PTA-9523, and Equi-2/New Market/2/93, deposited as ATCC Accession No. PTA-9524. Representative strains ATCC Accession Nos. PTA-9522, PTA-9523, and PTA-9524 were each deposited with the ATCC at 10801 University Boulevard, Manassas, Va., 20110-2209 on Sep. 23, 2008, under the provisions of the Budapest Treaty.

Equine Herpes Virus ("EHV") strains useful in the vaccine or immunogenic composition of the present invention can be any strain or isolate. Representative strains include EHV Subtype 1, deposited as ATCC Accession No. PTA-9525, and EHV Subtype 4, deposited as ATCC Accession No. PTA-9526. Representative strains ATCC Accession Nos. PTA-9525 and PTA-9526 were each deposited with the ATCC at 10801 University Boulevard, Manassas, Va., 20110-2209 on Sep. 23, 2008, under the provisions of the Budapest Treaty.

Western Equine Encephalomyelitis strains useful in the vaccine or immunogenic composition of the present invention can be any strain or isolate. A representative strain includes the Fleming Strain, deposited with the ATCC (ATCC Accession No. PTA-9410), located at 10801 University Boulevard, Manassas, Va., 20110-2209, on Aug. 14, 2008, under the provisions of the Budapest Treaty.

Venezuelan Equine Encephalomyelitis strains useful in the vaccine or immunogenic composition of the present invention can be any strain or isolate. A representative strain includes the TC-83 strain, deposited with the ATCC (ATCC Accession No. PTA-9411), located at 10801 University Boulevard, Manassas, Va., 20110-2209, on Aug. 14, 2008, under the provisions of the Budapest Treaty.

Eastern Equine Encephalomyelitis strains useful in the vaccine or immunogenic composition of the present invention can be any strain or isolate. A representative strain includes the NJO strain, deposited with the ATCC (ATCC Accession No. PTA-9412), located at 10801 University Boulevard, Manassas, Va., 20110-2209, on Aug. 14, 2008, under the provisions of the Budapest Treaty.

Tetanus toxoid strains useful in the vaccine or immunogenic composition of the present invention can be any strain or isolate. A representative strain is that taken from a master seed of *Clostridium tetani* from The Massachusetts Department of Public Health Institute of Laboratories in Boston, Mass.

The vaccine of the present invention is safe for administration in WNV susceptible species, particularly equidae, at any age and at any stage of reproduction, including pregnant females. In a preferred embodiment, the present invention is safe for administration to foals 12 months of age or older, more preferably, it is safe for administration to foals 10 months of age or older, more preferably, it is safe for administration to foals 8 months or older, more preferably, it is safe for administration to foals 6 months of age or older, more preferably, is safe for administration to foals 4 months of age or older, more preferably, it is safe for administration to foals 2 months of age or older, more preferably, it is safe for administration to foals 1 month of age or older, even more preferably, it is safe for administration to foals between 1 day and 1 month of age, and, most preferably, it is safe for administration to foals 1 day of age or older.

The composition of the present invention can be administered in any conventional manner Examples of administration methods include any that afford access by cells of the immune system to the immunogenic composition including oral, transdermal/intradermal, intravenous, subcutaneous, intramuscular, intraocular, intraperitoneal, intrarectal, intravaginal, intranasal, intragastrical, intratracheal, intrapulmonarial, or any combination thereof. In a preferred embodiment, the vaccine is administered parenterally, preferably intranasally, subcutaneously, or intramuscularly, and in the most preferred embodiment the vaccine is administered intramuscularly.

BRIEF DESCRIPTION OF THE DRAWINGS

FIG. 1 is a graphical representation of the Mean Total Clinical Scores;

FIG. 2 is a graphical representation of the Proportion Shedding;

FIG. 3 is a graphical representation of the Nasal Discharge Score;

FIG. 4 is a graphical representation of Proportion Virus Shedding;

FIG. 5 is a graphical representation of Conjunctivitis Score;

FIG. 6 is a graphical representation of Serum Neutralization Titers;

FIG. 7 is a graphical representation of Proportion Positive for EHV-1;

FIG. 8 is a graphical representation of Mean White Blood Cell Count;

FIG. 9 is a graphical representation of Proportion Positive (pyrexic);

FIG. 12A through 12M is a nucleotide alignment of the D NS5 region of WNV isolates (SEQ ID NOS 1-2 and 33-36, respectively, in order of appearance);

FIG. 13A through 13M is a nucleotide alignment of the H NS5 region of WNV isolates (SEQ ID NOS 1-2 and 37-40, respectively, in order of appearance);

FIG. 14A through 14M is a nucleotide alignment of the H WN05 E NS5 region of WNV isolates (SEQ ID NOS 1-6, respectively, in order of appearance);

FIG. 16A through 16K is a nucleotide alignment of the NS5 region of WNV isolates (SEQ ID NOS 12-16, respectively, in order of appearance)

DETAILED DESCRIPTION

Examples

Figure 10A:
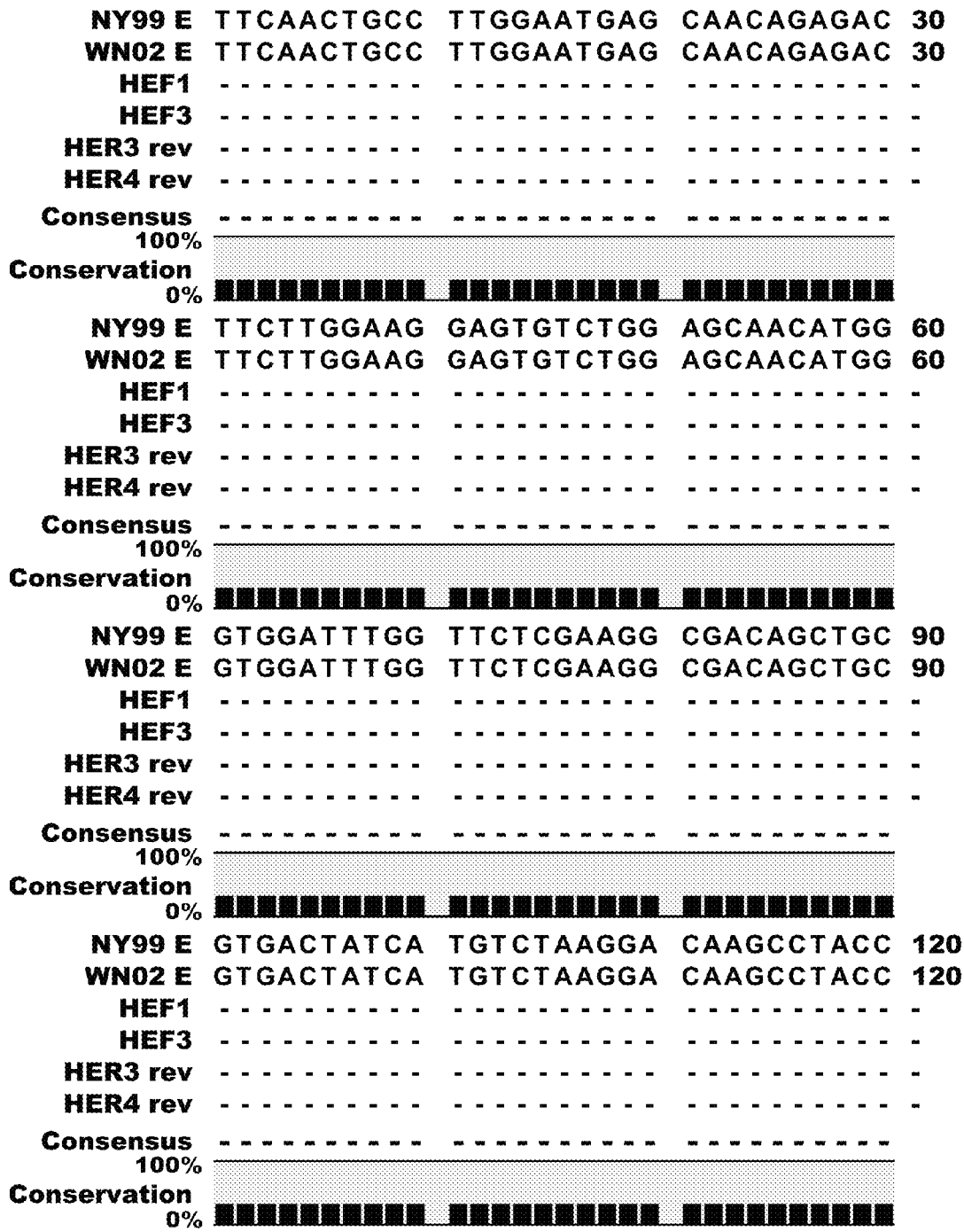
FIG. 10A through 10N is a nucleotide alignment of the HE region of WNV isolates (SEQ ID NOS 17-18 and 25-28, respectively, in order of appearance)

The following examples are set forth below to illustrate specific embodiments of the present invention. These examples are merely illustrative and are understood not to limit the scope or the underlying principles of the present invention.

Example 1

This example illustrates a preferred vaccine composition in accordance with the present invention.

Materials and Methods

For preparation of working cell stock, the Master Cell Stock (MCS), consisting of the Vero Cell Line known to propagate West Nile Virus, which was tested for purity, identity, and karyology, was thawed and used to inoculate a range of T25 up to T150 cm² vessels or 1050 cm² roller bottles, or bioreactors or other suitable sterile vessels. Thawed cells were suspended in growth medium at a rate of 0.0015 mL to 5.0 L per vessel, depending on vessel volume. Cells were then incubated at 36–38° C. for up to seven days. Cultures planted from frozen stock were re-fed with medium, if needed, within thirty-six hours after planting to remove residual DMSO. Cultures were re-fed with medium, if needed, during the growth period to remove excessive debris, or to stimulate the growth of cultures which have not reached confluence, or to maintain viability of confluent cultures.

Cells were passaged 1-20 times by decanting the spent medium and then by adding 5-500 mL of 0.25% Trypsin-EDTA Solution to each vessel, depending upon vessel volume. The vessels were agitated gently until the cells slough from the surface. The cells were then removed from the vessels by rinsing with growth medium and pooled together. Prior to inoculation, cell growth medium was decanted from Vero Working Cells that are at least 55% confluent. Virus growth medium described was added to each vessel at 0.15 to 0.4 mL per cm² surface area. A Multiplicity of Infection (MOI) of 0.000001-0.0002 was used for infection as determined by performing a cell count of at least two representative vessels. Roller bottle cultures infected were incubated at 36-38° C. for two to five days at 0.1-0.8 rpm.

During the growth period, cultures were checked for typical CPE microscopically and for gross contamination macroscopically. Unsuitable cultures were discarded after sterilization. Cultures may be attenuated using standard techniques or may be used without attenuation.

The microorganisms were then harvested for production purposes. Virus fluids were harvested when CPE reached 85% or greater. Roller bottles were swirled to remove loose cells, and fluids and then pooled into sterile 2-20 L glass, plastic, or PETG bottles, 20 L sterile polypropylene containers or 2-500 L sterile stainless steel tanks containers appropriate for clarification.

Next, the product was prepared. Clarified fluids were inactivated with Formaldehyde Solution, USP, 0.2% by volume, or another effective inactivating agent, transferred to a secondary container, and held at 20-25° C. (room temperature) with agitation for forty-eight hours. A sample of at least 12 mL of the inactivated fluids was taken for inactivation assurance testing (described below) prior to concentration. After inactivation was completed, inactivated lot material was held at 2-7° C. for up to sixty days prior to concentration. A number of suitable adjuvants may be added to the vaccine formulation, most preferably a non-metabolizable oil, preferably mineral oil, and/or a carbomer. Typical processing steps may be employed such as mixing, blending, microfluidization, and emulsification, of the adjuvant and/or the harvested virus antigens with other ingredients.

The product was then standardized. Sufficient volumes of clarified, inactivated, concentrated (optional) lots were combined to provide a calculated titer of at least $10^{4.0}$ TCID$_{50}$ per dose of each strain in the final product. Multiple lots may be blended to achieve the titer requirements per dose.

The product was then assembled to final formulation. Based on the desired final serial volume, the amounts of antigenic components, adjuvant, stabilizer and diluent were calculated as follows:

a. West Nile Virus, Horse Origin 2005 (ATCC No. PTA-9409): minimum $10^{4.0}$ TCID$_{50}$/dose
b. Adjuvant: The total adjuvant concentration, preferably a non metabolizable oil, and more preferably mineral oil and/or a carbomer, in a serial is at least 10% v/v and is added at time of serial batching/assembly.
c. Diluent: An appropriate volume of phosphate buffered saline (PBS) is added to bring the final volume to the desired volume.
d. Additional Formalin: An appropriate volume of 37% Formalin is added to maintain an appropriate level.
e. Gentamicin Sulfate The required amounts of adjuvant and PBS were combined in a sterile vessel. The pH of this mixture was adjusted to approximately 4.9-5.1 with 10N NaOH or 5N HCl if necessary. Clarified, killed, concentrated West Nile Virus, as well as Gentamicin, and Formalin were added and the pH adjusted to 6.9 to 7.1. This was mixed at 2-6° C. for at least 8 hours, not to exceed 48 hours.

The vaccine was given by typical hypodermic injection, with booster vaccinations if desired. Most preferably, the initial dose and the booster doses were 1 mL volume administered intramuscularly at 21-day intervals. The vaccination regimen of initial and booster dose was given at the most preferred 1 mL dose volume to horses, other equidae, and other WNV susceptible species to reduce the incidence of and or severity of clinical signs of WNV infection, and preferably to prevent infection by WNV as well as to prevent disease due to West Nile Virus infection for a sustained period following vaccination.

Results and Discussion

The vaccine was given by various appropriate parenteral routes, dose volumes, and dosing regimens to animals of varying immunological status for WNV, including naive and those with passive antibody, and provided for long duration of immunity up to and exceeding at least 2 years following vaccination. The vaccine was safe for administration in WNV susceptible species, particularly equidae, at any age and at any stage of reproduction, including pregnant females.

Example 2

This investigation was carried out to obtain an efficacy evaluation of a vaccine to protect horses from challenge with West Nile Virus (WNV).

Materials and Methods

A total of 30 horses were randomly divided into groups of 15 horses each. A total of 20 horses received 2 doses of vaccine at 21-day intervals and 10 horses were used for control. Each group of horses, Block 1 and Block 2, contained 10 vaccinated horses and 5 control horses. The vaccine was a combination including WNV antigen, specifically an inactivated or killed North American Dominant Strain of WNV, Horse Origin 2005 (ATCC Deposit No. PTA-9409) as well as antigenic components of Venezuelan Equine Encephalomyelitis, TC-83 strain (ATCC Deposit No. PTA-9411) Eastern Equine Encephalomyelitis, NJO strain (ATCC Deposit No. PTA-9412) Western Equine Encephalomyelitis, Fleming strain (ATCC Deposit No. PTA-9410) and Tetanus toxoid formulated approximately as follows:

| | |
|---|---|
| Eastern Equine Encephalomyelitis | $10^{6.7}$-$10^{9.2}$ TCID$_{50}$/mL |
| Western Equine Encephalomyelitis | $10^{6.7}$-$10^{9.2}$ PFU/mL |
| Venezuelan Equine Encephalomyelitis | $10^{6.7}$-$10^{9.2}$ TCID$_{50}$/mL |
| West Nile Virus | $10^{7.0}$-$10^{9.}$ TCID$_{50}$/mL |
| Tetanus Toxoid | 5-10 CPU/mL |
| Adjuvant | 100-200 µl/mL |
| Diluent - DMEM containing | q.s. |
| Gentamycin (30 µg/mL of diluent volume) | |
| Formaldehyde (0.1% of diluent volume) | |

All groups were challenged with intrathecal inoculation of 1 ml PBS containing approximately $10^5$ pfu of a heterologous strain of WNV (NY99, 4132, crow isolate). The challenge was conducted under ketamine-xylazine anesthesia.

Horses were monitored for a maximum of 14 days, then humanely euthanized. Those that developed severe disease prior to 14 days were euthanized prematurely.

The following data were collected to assess the effectiveness of the vaccine:
  Basic clinical evaluation
  Body temperature
  Assay for viremia
  Histopathology: two sections of brainstem were evaluated by a board-certified veterinary pathologist.

Sera collected on appropriate days were evaluated for characterization of serologic responses to challenge.

Results and Discussion

Viremia after challenge and serum neutralization titers were considered the primary outcome variables in this study. The first block of horses that had been vaccinated were 100% protected from viremia after challenge in this study. In comparison, 4 of the 5 control horses demonstrated viremia for 4-5 days post-challenge and 1 of 5 control horses demonstrated viremia for 1 timepoint. In addition, serum neutralization titers of vaccinated horses were statistically significantly higher than those of control horses at each time point examined after vaccination. Furthermore, the data establish that a WNV vaccine that provides a serum neutralization titer of 1:4 or higher is effective in preventing WNV viremia. The serum titers and viremia after challenge for Block 1 is summarized in Table 1 below:

TABLE 1

Serum Titers and Viremia for Block 1

| Horse Number | Treatment | Serum Titer Day of Challenge | Viremia After Challenge Highest Titer |
|---|---|---|---|
| 1 | Control | <2 | 390 |
| 2 | Vaccinate | 12 | <5 |
| 3 | Vaccinate | 12 | <5 |
| 4 | Control | <2 | 65 |
| 5 | Control | <2 | 1475 |
| 6 | Vaccinate | 6 | <5 |
| 7 | Vaccinate | 97 | <5 |
| 8 | Vaccinate | 10 | <5 |
| 9 | Vaccinate | 21 | <5 |
| 10 | Vaccinate | 35 | <5 |
| 11 | Vaccinate | 10 | <5 |
| 12 | Vaccinate | 24 | <5 |
| 13 | Vaccinate | 4 | <5 |
| 14 | Control | <2 | 235 |
| 15 | Control | <2 | 165 |

Viremia after challenge and serum neutralization titers were also considered the primary outcome variables in the second block of horses in this study. In the second block of horses only one vaccinate group horse displayed any timepoints of viremia throughout the challenge period. That horse had 3 separate timepoints on 3 mornings (not those same evenings) with minimal value readings of 5 (where <5 is negative). All control horses in the study (with the exception of one horse which exited the study prematurely but displayed definitive WNV histopathology and was excluded from evaluation) showed high levels of viremia for 1-8 timepoints after challenge.

Since viremia is a prerequisite before virus can cross the blood-brain barrier to cause WNV encephalitis, viremia is well justified as the primary parameter for evaluation of protection in an experimental study of this type.

This study demonstrated that 2 doses of the experimental combination vaccine administered to foals 4 to 5 months of age reliably and effectively stimulated protective serological serum neutralization titers. In addition the data confirm that post vaccination SN titers as low as 1:4 resulting from vaccination using an effectively batched antigen amount of West Nile Virus in this experimental combination vaccine protected vaccinated horses from viremia, clinical disease, and histopathology after a severe intrathecal challenge with a heterologous strain of West Nile Virus.

Histopathology also was different between the two groups with the likelihood of lesions in vaccinates being 40% less in Block 2 and 100% less in Block 1 than the likelihood of lesions in control animals challenged with virulent West Nile virus.

In addition a Control Group horse became weak on his hind legs on Day 9 post-challenge and got progressively worse until he was no longer able to stand. Histopathology of the pons and medulla from this horse showed severe encephalitis and myelitis consistent with WNV pathology that was more prevalent than signs of disease from any other horse in this study.

Two Block 2 control horses in this study displayed 3 days each of clinical signs relating to infection with West Nile Virus. One other control horse had a single timepoint of weakness due to disease. Another control horse did not display any timepoints of clinical signs, although it had multiple days of viremia. Although several vaccinated Block 2 horses in the study had mild to moderate histopathological changes in tissue as a result of the intrathecal challenge of WNV, only very mild clinical disease (mild head tremors) was noted for one vaccinate on one day of the study as compared to multiple days of clinical disease in 2 control horses and a single day of clinical disease in a third control horse.

The results demonstrated that the vaccine is effective and that an immunogenic reaction is induced in the animals that were administered the vaccine. The effectiveness of the vaccine was evidenced in this example by reduction in WNV viremia, by stimulation of high serum neutralization titers to WNV, and by prevention of WNV related clinical signs and histopathology in the brain and meninges. Because this vaccine is comprised of unique constituents, including a long lasting non-metabolizable adjuvant, it was formulated in a low 1 mL dose volume to provide a high degree of safety as a highly immunogenic low passage whole inactivated virus WNV isolate of recent origin and high epidemiological prevalence, and a WNV isolated from the tissues of an infected horse, it provides more comprehensive safety and effectiveness than other vaccines currently available. Additionally, it has the effect of providing a safe vaccine when administered to animals.

Example 3

This example illustrates the efficacy of the immunogenic composition of the present invention against infection by EHV-4

Materials and Methods

Thirty-seven (37) horses, 4-5 months of age, were used in this study. Horses were randomly assigned to either vaccinate or control groups by random number generator and then vaccinated. Twenty-four (24) horses served as vaccinates and thirteen (13) horses were mock-vaccinated control horses. All horses had low (≤1:14, avg.=1:7) EHV-4 serum neutralization (SN) titers prior to initiation of the study, indicative of horses susceptible to infection. The vaccine used was an experimental vaccine and had the following components:

The final formulated vaccine contains the following ingredients per 1 mL dose:

| | |
|---|---|
| EHV-1 (PTA-9525) | $10^{7.0-9.0}$ TCID$_{50}$/mL |
| Influenza A2/Ohio/03 (PTA-9522) | $10^{6.0-9.5}$ TCID$_{50}$/mL |
| Influenza A2/KY/95 (PTA-9523) | $10^{6.0-9.5}$ TCID$_{50}$/mL |
| Influenza A2/NewMarket/2/93 (PTA-9524) | $10^{6.0-9.5}$ TCID$_{50}$/mL |
| Tetanus Toxoid | 5-10 CPU |
| Eastern Equine Encephalomyelitis, (ATCC Deposit No. PTA-9412) | $10^{6.7-9.2}$ TCID$_{50}$/mL |
| Western Equine Encephalomyelitis, (ATCC Deposit No. PTA-9410) | $10^{6.7-9.2}$ PFU/mL |
| Venezuelan Equine Encephalomyelitis, (ATCC Deposit No. PTA-9411) | $10^{6.7-9.2}$ TCID$_{50}$/mL |
| West Nile Virus, Horse Origin 2005 (ATCC Deposit No. PTA-9409) | $10^{7.0-9.0}$ TCID$_{50}$/mL | transport medium (Dulbecco's Minimal Essential Medium (DMEM) supplemented with 2% FBS, 2× Pen/Strep, 2× Gentamicin, and 2× Amphotericin B).

For isolation of virus, the tubes were mixed, the swabs aseptically removed, and the medium centrifuged at 1500 rpm for 10 minutes to remove particulates. Medium was filtered through a 0.2μ syringe filter prior to inoculation on tissue culture cells. One mL of the clarified transport medium was used to inoculate a 2 cm$^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the adsorption period, an additional 1 mL of re-feed medium (DMEM containing 2-5% fetal bovine serum (FBS), 2 mM L-glutamine and 3× Gentamicin and 2× Amphotericin B) was added to each well. Following addition of re-feed media the plates were then incubated at 37° C. in a $CO_2$ incubator. Each test and control tissue culture well was examined microscopically for 7 days for signs of cytopathic effect (CPE) typical of the EHV-4 challenge virus. Wells that were negative at the end of the 7 day observation period were subcultured onto fresh cells and observed for an additional 7 days.

Serum Neutralization Testing Procedure

A standard microtiter serum neutralization test was employed in this study. All sera were tested in sterile flat bottom microtiter plates using 5 wells per dilution and an 8 well dilution series for each of the 5 test wells. Each of the 5 test wells contained 25 μl of serum dilution mixed with 25 μl of the indicator virus and 150 μl of a freshly planted ED cell suspension containing approximately $5\times10^4$ cells. The test indicator virus used was EHV-4 HRA005 Lot 033106 SN Stock Virus. In all tests the indicator virus back titration titers ranged between 68-149 $TCID_{50}/25$ μl. Serum neutralizing antibody titers are expressed as Reed-Muench $ID_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 All other wells contained 25 μl of DMEM (no FBS). Following serial dilution down the plate, 25 μl was discarded from the last row. 25 μl of a pre-determined dilution of the indicator virus was added to each test well. Plates were then mixed and incubated for one hour at 37° C. in 5% $CO_2$. On conclusion of the incubation period, 150 μl of a suspension containing $5\times10^4$ ED cells was added to each test and cell control well. The plates were incubated at 37° C. in a $CO_2$ incubator for 5-7 days, at which time plates were microscopically examined for CPE typical of EHV-4. However, any other commercial available test or any test described in the prior art could be used for this purpose.

Results and Conclusion

Nasal Exudate Evaluation

The vaccination group by day interaction was statistically significant for the nasal discharge scores (P<0.05, Table 1). Statistically significant group effects were seen on Days 6-10 and Day 14 post-challenge (lower nasal scores in the vaccinated group).

When the daily scores were summed over the post-challenge period, horses in the vaccinated group had lower total scores than those in the control group (P<0.05, Table 1). The mitigated fraction was estimated to be 0.824 (95% ASE CI: 0.629, 1.000).

TABLE 3

| Nasal Discharge Score | | | | |
|---|---|---|---|---|
| | Control | Vaccinate | P-value | Mitigated fraction (95% ASE CI) |
| Cumulative nasal discharge score | 28.9 | 13.6 | <0.0001 | 0.824 (0.629, 1.000) |

Conjunctivitis

The vaccination group by day interaction was statistically significant for the conjunctivitis scores. Statistically significant group effects were seen on Days 6, 7, 9, 10, 13 and 14 post-challenge (lower scores in the vaccinated group on 5 of the 6 days, P<0.05, FIG. 2).

Serological Studies

Titers were log transformed prior to the statistical analysis. The vaccination group by day interaction was statistically significant for SN titers. Statistically significant group effects were seen on Day 0 (pre-vaccination; control group titers>vaccinated group titers), Days 35 (the day of challenge) and 7 and 14 days post-challenge (study days 42 and 49). Horses in the vaccinated group had higher titers on Days 35, 42 and 49 than those in the control group (P<0.05, Table 4).

TABLE 4

| Titers | | | |
|---|---|---|---|
| Study day | Control | Vaccinated | P-value |
| 0 | 8.31 | 5.74 | 0.0303 |
| 21 | 8.25 | 6.51 | 0.1639 |
| 35 (day of challenge) | 6.12 | 8.56 | 0.0495 |
| 42 | 4.57 | 7.27 | 0.0069 |
| 49 | 4.87 | 13.12 | <0.0001 |

White Blood Cell Counts (WBC) and Lymphocyte Counts

The vaccination group by day interaction was statistically significant for WBC and lymphocyte counts. Statistically significant group effects were seen on Days 4-6 (WBC) and Days 4 and 5 (lymphocytes) post-challenge. Horses in the vaccinated group were protected from leucopenia due to EHV4 disease and had higher WBC and lymphocyte counts than those in the control group (P<0.05).

Discussion and Conclusions

In this study, moderate and adequate clinical signs of EHV-4 infection were seen after challenge. Significantly fewer clinical signs of nasal exudate were seen in vaccinated horses on Days 6-10 and Day 14 post-challenge. Conjunctivitis scores were significantly lower in vaccinated horses on Days 7, 9, 10, 13, and 14 post-challenge. Despite the adequate display of clinical signs following challenge, virus shedding in nasal swab samples was infrequent following this EHV-4 challenge. Nasal swabs were examined by virus isolation in cell culture.

Significant group effects for WBCs and lymphocytes were seen on Days 4-6 (WBC) and Days 4-5 (lymphocytes) with vaccinated animals showing higher WBC and lymphocyte counts than control horses. These values establish that control horses did succumb to the immunosuppression brought on by infection with Herpesvirus, and also demonstrate that vaccination with a cross-protective strain of EHV-1 allowed vaccinated horses to be more refractive to the immunosuppressive properties of Herpesvirus infection. Additionally, horses in the vaccinated group had higher serum neutralization titers on Days 35, 42 and 49 than those in the control group Data from this study confirm that horses vaccinated with a multi-component vaccine containing EHV-1 demonstrate cross-protective immunity when challenged with a heterologous EHV-4 challenge organism.

Example 4

This example is to illustrate the efficacy of the combination vaccine of the present invention as well as duration of immunity.

Materials and Methods

The influenza viral antigen used in the vaccine evaluated in this study was produced on Madin Darby Canine Kidney (MDCK) cells. Following growth, viral fluids were filtered, formalin inactivated, and concentrated. The inactivated viral fluids were tested for residual live virus after inactivation. On completion of satisfactory residual live virus testing the inactivated viral fluids were then used to formulate a vaccine which also contained inactivated Venezuelan, TC-83 strain (ATCC Accession No. PTA-9411), Eastern, NJO strain (ATCC Accession No. PTA-9412), and Western, Fleming strain (ATCC Accession No. PTA-9410), equine encephalomyelitis viruses, inactivated EHV-1 (ATCC Accession No. PTA-9525), inactivated influenza A/equine-2/Kentucky/95 (ATCC Accession No. PTA-9523) and influenza A/equine-2/NewMarket/2/93 (ATCC Accession No. PTA-9524) viruses, inactivated West Nile Virus, Horse Origin 2005 (ATCC Accession No. PTA-9409), and tetanus toxoid.

Vaccine was formulated to appropriate specifications for all antigens included in the product. Influenza A/equi-2/Ohio/03 (ATCC Accession No. PTA-9522) antigen was added to the vaccine at a pre-inactivation titer of $10^{6.7}$ $TCID_{50}$/mL.

The final formulated vaccine contains the following ingredients per 1 mL dose:

| | |
|---|---|
| EHV-1 | $10^{7.0-9.0}$ $TCID_{50}$/mL |
| Influenza A2/Ohio/03 | $10^{6.7-9.5}$ $TCID_{50}$/mL |
| Influenza A2/KY/95 | $10^{6.7-9.5}$ $TCID_{50}$/mL |
| Influenza A2/NewMarket/2/93 | $10^{6.7-9.5}$ $TCID_{50}$/mL |
| Tetanus Toxoid | 5-10 CPU |
| Eastern Equine Encephalomyelitis | $10^{6.7-9.2}$ $TCID_{50}$/mL |
| Western Equine Encephalomyelitis | $10^{6.7-9.2}$ PFU/mL |
| Venezuelan Equine Encephalomyelitis | $10^{6.7-9.2}$ $TCID_{50}$/mL |
| West Nile Virus | $10^{7.0-9.0}$ $TCID_{50}$/mL |
| Adjuvant (preferably mineral oil) | 100-200 µl |

-continued

| | |
|---|---|
| Glycerol | 100-200 µl |
| EDTA 240 mM solution | 10-20 µl |
| Diluent - DMEM containing | q.s. |
| Gentamicin (30 µg/mL of diluent volume) | |
| Formaldehyde (0.1-0.2% of diluent volume) | |

Twenty-six (26) horses, 4-5 months of age, were used in this study. Fifteen horses served as vaccinates and eleven horses were mock-vaccinated control horses.

Vaccine was administered intramuscularly in a 1 mL dose volume to each of 15 horses in the vaccinate group. Eleven horses in the control group received a 1 mL dose of adjuvanted DMEM (Lot 004) containing excipients used in the 9-way vaccine (Gentamicin and formaldehyde) but no antigens. Challenge inoculation of virulent influenza A/equi-2/Ohio/03 strain virus was performed 4 months post-booster vaccination.

Serum samples for serological evaluation were collected from the vaccinated and control horses prior to initial vaccination, at 21 days post first dose vaccination (day of booster vaccination), on the day of challenge, and at 7 and 14 days post challenge. Body temperature, whole blood samples, and nasal swabs were obtained from each horse on the day of challenge, and daily throughout the 10 day post-challenge observation period for a total of 11 observation days. Clinical data was also recorded daily for each horse for the 11-day observation period.

Challenge

The challenge virus seed of Influenza A/equi-2/Ohio/03 was produced in eggs. Challenge virus was diluted on the morning of challenge 1:20 with tissue culture media to affect a titer sufficient to cause clinical influenza in the non-vaccinated challenged horses.

SEDIVET® (romifidine hydrochloride), a sedative and analgesic, was administered intravenously to each horse prior to challenge at a dosage of 50 µg/kg of body weight. Each horse was then challenged with influenza A/equi-2/Ohio/03 virus. The challenge virus was administered intranasally as an aerosol produced by a nebulizer into an Equine AeroMask (Trudell Medical International, Ontario, Canada) by the following method:

Four milliliters of challenge virus were placed into the nebulizer cup in the AeroMask device. A pressure hose was fitted from an air compressor to the inlet port of the nebulizer. The outlet tube was then inserted into the AeroMask attached to the head of the horse being challenged and air pressure was applied to the inlet port. During this time approximately two milliliters of challenge virus fluid was aerosolized directly into the nostrils of the horse being challenged.

Temperature

Daily rectal temperatures were recorded for each of the 26 vaccinated and control horses on Day of Challenge and for 10 days post challenge by means of a calibrated, electronic thermometer (GSA Electronics) probe. The daily rectal temperatures were recorded in degrees Fahrenheit (° F.).

White Blood Cell Counts

Venous blood from each of the 26 vaccinated and control horses was collected daily on the Day of Challenge and for 10 days post-challenge directly into a vacutainer Disodium EDTA tube for WBC counts.

Nasal Exudate Evaluation

All nasal exudate observations were made prior to collection of nasopharyngeal swabs. On the Day of Challenge and for 10 days post challenge, the nasal passages and muzzle of each of the 26 vaccinated and control horses were examined and graded using the grading and scoring description listed below.

The scoring grades of 0 through 6 were assigned on the basis of the severity of the disease indicated by each of the following classification:

TABLE 5

Scoring Grades

| Score | Description of symptoms | Score sheet designation |
|---|---|---|
| 0 | Essentially normal indicates the horse was clean and essentially free of nasal exudate | EN |
| 1 | Slight clear serous discharge that may be frequently observed in both diseased and normal horses | C-1 |
| 2 | Moderate clear serous discharge is indicative of a definite increase in volume over that normally observed | C-2 |
| 3 | Copious clear serous discharge that is generally observed only in diseased horses | C-3 |
| 1.5 | Very slight mucopurulent discharge indicates that mucus was definitely present in small amounts in either one or both nostrils | VSM |
| 2 | Slightly mucopurulent is a discharge easily observed in one or both nostrils | SM |
| 4 | Moderately mucopurulent indicates that mucoid discharges were present in large quantities in both nostrils | MM |
| 6 | Heavy mucopurulent indicates that copious amounts of a mucoid discharge filled both nostrils | HM |

Coughing

Episodes of coughing on each observation day were counted for each horse during the entirety of the observation period, whether or not the individual animal was being examined by the investigator at that time. Observers other than the investigator recorded the number of episodes of coughing of each individual horse during the observation period. Scoring of coughing episodes was actual counts of coughing episodes per horse.

Conjunctivitis

Conjunctivitis was evaluated daily at the time of nasal exudate evaluation. Conjunctivitis scores were recorded as 0=normal; 1=mild to moderate conjunctivitis and 2=severe conjunctivitis.

Nasopharyngeal Viral Isolation/Hemagglutination (Ha) Methods

On each observation test day each nasal passage of each vaccinated and control was sampled deeply by means of sterile swabs. On collection, each of two swabs was immediately placed in a single tube containing 4 mL of chilled transport medium (Dulbecco's Minimal Essential Medium (DMEM) supplemented with 2% FBS, 2× Pen/Strep, 2× Amphotericin B).

For isolation of virus, the tubes were mixed, the swabs aseptically removed, and the medium centrifuged at 1500 rpm for 10 to 15 minutes to remove particulates. Medium was filtered through a 0.2μ syringe filter prior to inoculation on tissue culture cells. After filtration, 4-6% of sterile 85% sucrose solution was added to each sample for freezing at −80° C. in order for all samples to be tested concurrently.

All samples were tested in sterile flat bottom microtiter plates using five wells per dilution and a 4 well dilution series for each of the 5 test wells. Upon thawing, 22 μL of the clarified sample medium was used to inoculate one day old monolayer of MDCK-S cells from which the growth medium had been aseptically removed and replaced with 200 μl of influenza growth medium (DMEM containing 5-10 units/mL of 10,000 U stock solution Porcine Trypsin, 2 mM L-glutamine, 1× Pen-Strep and 1× Amphotericin B). The plates were then incubated at 35° C. in a $CO_2$ incubator for 5-7 days. After the 5-7 day incubation period, 50 μl from all wells of the titration plates were transferred directly into a labeled 96 well vinyl HA plate. Chicken red blood cells were added to each well and allowed to settle for 30-90 minutes at room temperature. Wells were read for positive agglutination as evidence of presence of equine influenza virus.

Hemagglutination Inhibition (Hi) Testing Procedure

Serum samples were prepared by dispensing 0.15 ml of each sample into a test tube and extracting with 0.3 mL of 0.01M Sodium Periodate Solution at room temperature for 15 minutes. Glycerol Solution 3% (0.125 mL) was added to each tube, mixed and incubated at room temperature for 15 minutes. All samples were then heat-inactivated at 56° C. for 30 minutes.

A 0.5% solution of chicken red blood cells was prepared in PBS (SAFC catalog number 59321C) and standardized to an optical density of 0.5 at 550 nm.

Extracted serum samples were tested in duplicate in U bottom polystyrene plates using a 2-fold dilution scheme in PBS ranging from 1:4 to 1:256, 25 ul per well. Influenza A/Equi2/Ohio03 stock virus (25 μL) was added to serum sample dilution. Plates were gently tapped to mix, and incubated at room temperature for 30 minutes. After incubation, chicken red blood cells were added to each well and incubated undisturbed at room temperature for 1 to 1.5 hours. Results were read by observing plates for presence or absence of agglutinated red blood cells in each well. Antibody titer was determined as the highest dilution of serum at which agglutination did not occur.

Results and Conclusions

When pooled across all timepoints post-challenge, vaccinated animals had lower total clinical scores than the control animals. When the total daily scores were summed over the post-challenge period, horses in the vaccinated group had lower total scores than those in the control group (P<0.05). The mitigated fraction was estimated to be 0.6485 (95% ASE CI: 0.3258, 0.9712).

TABLE 6

Total Clinical Score

| Outcome variable | Vaccination group | Day | Group by day interaction |
|---|---|---|---|
| Total clinical score[1] | <0.0001 | <0.0001 | 0.1321 |

[1]The GLIMMIX procedure would not converge, thus an ANOVA approach was used to evaluate the effect of vaccination over time after challenge. Results were interpreted through the bolded values.

TABLE 7

Mitigated fraction - total cumulative clinical score

| | Control | Vaccinate | P-value[1] | Mitigated fraction[2] (95% ASE CI) |
|---|---|---|---|---|
| Total cumulative clinical score[2] | 18.36[3] | 9.93 | 0.0055 | 0.6485 (0.3258, 0.9712) |

[1]P-value from Wilcoxon's rank sum test
[2]Nasal discharge score, conjunctivitis score and coughing score were summed with day and across all time points for each animal then ranked for the estimation of the mitigated fraction.
[3]Mean rank

Nasal Discharge

The main effect of vaccination was statistically significant and reduced nasal discharge due to the influenza challenge. When pooled across all time points post-challenge, vaccinated animals had lower nasal discharge scores than the control animals.

TABLE 8

Nasal Discharge Score

| Outcome variable | Vaccination group | Day | Group by day interaction |
|---|---|---|---|
| Nasal discharge score[1] | 0.0012 | <0.0001 | 0.4627 |

[1]The GLIMMIX procedure would not converge, thus an ANOVA approach was used to evaluate the effect of vaccination over time after challenge. Results were interpreted through the bolded values.

Conjunctivitis

For conjunctivitis, the main effect of vaccination was statistically significant. When pooled across all time points post-challenge, vaccinated animals had reduced conjunctivitis due to influenza infection as demonstrated by lower conjunctivitis scores than the control animals.

TABLE 9

Conjunctivitis Score

| Outcome variable | Vaccination group | Day | Group by day interaction |
|---|---|---|---|
| Conjunctivitis score[1] | 0.0187 | 0.0001 | 0.2498 |

[1]The GLIMMIX procedure would not converge, thus an ANOVA approach was used to evaluate the effect of vaccination over time after challenge. Results were interpreted through the bolded values.

Coughing

Vaccine also protected against the cough resulting from equine influenza infection. Vaccinated animals had lower scores (P<0.05,) on Days 3, 5, 7, 8, and 9 post-challenge than control animals.

TABLE 10

Coughing Score

| Outcome variable | Vaccination group | Day | Group by day interaction |
|---|---|---|---|
| Coughing score[1] | 0.0004 | 0.0009 | 0.0275 |

[1]The GLIMMIX procedure would not converge, thus an ANOVA approach was used to evaluate the effect of vaccination over time after challenge. Results were interpreted through the bolded values.

Virus Shedding (Nasal Swabs)

The vaccination also reduced the percent of horses shedding virus (P<0.05). The figure below represents that the percentage of vaccinated animals shedding virus was lower (P<0.05) on Days 3, 4, and 5 post-challenge than control animals.

TABLE 11

Mitigated fraction - days virus shedding

| | Control | Vaccinate | P-value[1] | Mitigated fraction[2] (95% ASE CI) |
|---|---|---|---|---|
| Days virus positive[2,3] | 2[3] | 0 | 0.0004 | 0.7939 (0.5343, 1.0000) |

[1]P-value from Wilcoxon's rank sum test
[2]The number of days of viral shedding was calculated then ranked for the estimation of the mitigated fraction. Asymptotic standard errors (ASE) were used to estimate the 95% confidence intervals (CI).
[3]The median number of days positive results was obtained from the virus isolation assay.

Hi Titers

The vaccine was also effective in eliciting protective antibody titers to equine influenza virus. Statistically significant higher titers in the vaccinated horses were seen on Day 36 (relative to vaccination), Day 154 (the day of challenge), 159 and 164. Horses in the vaccinated group had higher titers on each of these days than those in the control group (P<0.05).

WBC and Lymphocyte Counts

The vaccination also protected horses from reduction in white blood cell counts seen following influenza virus challenge. (P<0.05). Vaccination with the combination vaccine provided statistically significant protection that was seen on Days 2 and 7 for WBC counts, and Days 2, 6, 7, and 8 post-challenge. Horses in the vaccinated group had higher WBC and lymphocyte counts than those in the control group (P<0.05). A four month Duration of Immunity challenge was performed to demonstrate efficacy of the influenza virus fractions of a multi-component vaccine that included West Nile Virus vaccine (Encephalomyelitis-Rhinopneumonitis-Influenza-West Nile Virus Vaccine, Eastern, Western & Venezuelan, Killed Virus, Tetanus Toxoid) containing 3 Equine influenza A/equi-2 virus strains, ATCC Accession Nos. PTA-9522, PTA-9523, and PTA-9524, each of which is currently relevant in the equine population of the Americas, Europe and Asia. Twenty-six horses (15 vaccinates and 11 controls) were vaccinated twice in 3 week intervals with a 1 mL dose of vaccine, or were mock vaccinated with adjuvanted media components of the vaccine without viral antigen. Four months post-booster vaccination, horses were challenged with a virulent live Equine Influenza A/equi-2/Ohio03 virus. This virulent virus is the current Equine Influenza A/equi-2 strain recommended for inclusion into vaccines by OIE and is currently recognized as the most pertinent strain involved in outbreaks in the United States.

Results from this 4-month DOI challenge study show significant protective effects from challenge by vaccination with the test vaccine, a combination West Nile Virus vaccine with flu and other pertinent equine antigens. Importantly, vaccinated horses displayed statistically lower total clinical signs of influenza virus (nasal discharge, conjunctivitis, and coughing, P=0.0055) with a mitigated fraction estimated to be 0.6485 (95% ASE CI: 0.3258, 0.9712). Additionally, viral shedding was statistically lower in vaccinated horses than control horses (P=0.0004) with a mitigated fraction estimated to be 0.7939 (95% ASE CI: 0.5343, 1.0000). Hemagglutination inhibition titers were significantly higher in vaccinated horses than control horses, and white blood cell and lymphocyte counts remained significantly higher in vaccinated horses on multiple days of the study over those of control horses. No differences in rectal temperature were determined between the two groups.

In conclusion, the data from this study demonstrate that administration of 2×1 mL intramuscular doses of this West Nile Virus combination vaccine administered at a 21 day interval to foals 4 to 5 months of age protected against virulent challenge with the Equine Influenza A/equi-2/Ohio03 virus and provided a duration of immunity of at least 4 months for this product.

Example 5

This example illustrates the efficacy of an immunogenic composition of the present invention when challenged with (Equine Herpes Virus Type 1) EHV-1.

Materials and Methods

The EHV-1 viral antigen used in the vaccine evaluated in this study was produced on Madin Darby Bovine Kidney (MDBK) cells. Following growth, viral fluids were filtered, BPL inactivated, and concentrated. The inactivated viral fluids were tested for residual live virus after inactivation. On completion of satisfactory residual live virus testing, the inactivated viral fluids were then used to formulate a vaccine which also contained inactivated Venezuelan Equine Encephalomyelitis, TC-83 strain (ATCC Accession No. PTA-9411) Eastern Equine Encephalomyelitis, NJO strain (ATCC Accession No. PTA-9412) and Western Equine Encephalomyelitis, Fleming strain (ATCC Accession No. PTA-9410) viruses, inactivated influenza A/equine-2/Kentucky/95 (ATCC Accession No. PTA-9523), influenza A/equine-2/NewMarket/2/93 (ATCC Accession No. PTA-9524) and influenza A/equine-2/Ohio/03 (ATCC Accession No. PTA-9522) viruses, inactivated West Nile Virus (ATCC Accession No. PTA-9409) and tetanus toxoid.

Vaccine was formulated to minimum specifications for all antigens included in the product. EHV-1 antigen was added to the vaccine at a pre-inactivation titer of $10^{7.0}$ $TCID_{50}$/mL.

The final formulated vaccine contains the following ingredients per 1 mL dose:

| | |
|---|---|
| EHV-1 | $10^{7.0-9.0}$ $TCID_{50}$/mL |
| Influenza A2/Ohio/03 | $10^{6.7-9.5}$ $TCID_{50}$/mL |
| Influenza A2/KY/95 | $10^{6.7-9.5}$ $TCID_{50}$/mL |
| Influenza A2/NewMarket/2/93 | $10^{6.7-9.5}$ $TCID_{50}$/mL |
| Tetanus Toxoid | 5-10 CPU |
| Eastern Equine Encephalomyelitis | $10^{6.7-9.2}$ $TCID_{50}$/mL |
| Western Equine Encephalomyelitis | $10^{6.7-9.2}$ PFU/mL |
| Venezuelan Equine Encephalomyelitis | $10^{6.7-9.2}$ $TCID_{50}$/mL |
| West Nile Virus | $10^{7.0-9.0}$ $TCID_{50}$/mL |
| Adjuvant (preferably mineral oil) | 100-200 μl |
| Glycerol | 100-200 μl |
| EDTA 240 mM solution | 10-20 μl |
| Diluent - DMEM containing | q.s. |
| Gentamicin (30 μg/mL of diluent volume) | |
| Formaldehyde (0.1-0.2% of diluent volume) | |

Forty (40) horses, 4-5 months of age, were used in this study. Horses were randomly assigned to either vaccinate or control groups and were micro-chipped and then vaccinated. Twenty horses served as vaccinates and twenty horses were mock-vaccinated control horses. All horses had negative to low (<1:6) EHV-1 serum neutralization (SN) titers prior to initiation of the study, indicative of horses susceptible to infection.

Vaccine was administered intramuscularly in a 1 mL dose volume to each of 20 horses in the vaccinate group. Twenty horses in the control group received a 1 mL dose of adjuvanted DMEM (Lot 004) containing excipients used in the 9-way vaccine (Gentamycin and formaldehyde) but no antigens. Challenge inoculation of virulent EHV-1 A183 strain virus was performed 15 days post-booster vaccination.

Serum samples for serological evaluation were collected from the vaccinated and control horses prior to initial vaccination, at 21 days post first dose vaccination (day of booster vaccination), on the day of challenge, and at 7 and 14 days post challenge. Body temperature, whole blood samples, and nasal swabs were obtained from each horse on the day of challenge, and daily throughout the 14 day post-challenge observation period for a total of 15 observation days. Clinical data was also recorded daily for each horse for the 15-day observation period.

Challenge Procedure

Challenge Virus

The original challenge virus seed used in this challenge study was the first passage of the original seed virus on Equine Dermal (ED) cells. This challenge virus was harvested and frozen at a titer of $10^{6.2}$ $TCID_{50}$/mL.

Intranasal Challenge Method

SEDIVET® (romifidine hydrochloride), a sedative and analgesic, was administered intravenously to each horse prior to challenge at a dosage of 50 μg/kg of body weight.

Each horse was then challenged with approximately $10^{6.5}$ TCID$_{50}$ of EHV-1 strain. The challenge virus was administered intranasally as an aerosol produced by a nebulizer into an Equine AeroMask (Trudell Medical International, Ontario, Canada) by the following method:

A pressure hose was fitted from an air compressor to the inlet port of the nebulizer. The outlet tube was then inserted into the AeroMask attached to the head of the horse being challenged and approximately 10 psi of air pressure was applied to the inlet port for four minutes. During this time approximately two milliliters of a $10^{6.2}$ TCID$_{50}$/mL challenge virus fluid was aerosolized directly into the nostrils of the horse being challenged.

Pre and Post Challenge Evaluation Parameters

Temperature

Daily morning rectal temperatures were recorded for each of the 40 vaccinated and control horses on Day of Challenge and for 14 days post challenge by means of a calibrated, electronic thermometer (GSA Electronics) probe. The daily rectal temperatures were recorded in degrees Fahrenheit (° F.).

White Blood Cell Counts

Venous blood from each of the 40 vaccinated and control horses was collected daily on the Day of Challenge and for 14 days post-challenge directly into a vacutainer Disodium EDTA tube for WBC counts.

Nasal Exudate Evaluation

All nasal exudate observations were made prior to collection of nasopharyngeal swabs. On the Day of Challenge and for 14 days post challenge, the nasal passages and muzzle of each of the 40 vaccinated and control horses were examined and graded using the grading and scoring description listed below.

The scoring grades of 0 through 6 were assigned on the basis of the severity of the disease indicated by each of the following classification:

(EN) Essentially normal indicates the horse was clean and essentially free of nasal exudate, score, 0;

(C-1) Slight clear serous discharge that may be frequently observed in both diseased and normal horses, score 1;

(C-2) Moderate clear serous discharge is indicative of a definite increase in volume over that normally observed, score 2;

(C-3) Copious clear serous discharge that is generally observed only in diseased horses, score 3;

(VSM) Very slight mucopurulent discharge indicates that mucus was definitely present in small amounts in either one or both nostrils, score 1.5;

(SM) Slightly mucopurulent is a discharge easily observed in one or both nostrils, score 2;

(MM) Moderately mucopurulent indicates that mucoid discharges were present in large quantities in both nostrils, score 4; and (HM) Heavy mucopurulent indicates that copious amounts of a mucoid discharge filled both nostrils, score 6.

Nasopharyngeal Viral Isolation Methods

On each observation test day each nasal passage of each vaccinated and control was sampled deeply by means of a sterile swabs. On collection, each of two swabs were immediately placed in a single tube containing 4 mL of chilled transport medium (Dulbecco's Minimal Essential Medium (DMEM) supplemented with 2% FBS, 2× Pen/Strep, 2× Gentamicin, and 2× Amphotericin B).

For isolation of virus, the tubes were mixed, the swabs aseptically removed, and the medium centrifuged at 1500 rpm for 10 minutes to remove particulates. Medium was filtered through a 0.2μ syringe filter prior to inoculation on tissue culture cells. One mL of the clarified transport medium was used to inoculate a 2 cm$^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% CO$_2$ atmosphere. After the absorption period, an additional 1 mL of re-feed medium (DMEM containing 2-5% fetal bovine serum (FBS), 2 mM L-glutamine and 3× Gentamicin and 2× Amphotericin B) was added to each well. Following addition of re-feed media the plates were then incubated at 37° C. in a CO$_2$ incubator. Each test and control tissue culture well was examined microscopically for 7 days for signs of cytopathic effect (CPE) typical of the EHV-1 A183 challenge virus. Wells that were negative at the end of the 7 day observation period were subcultured onto fresh cells and observed for an additional 7 days.

WBC Buffy Coat Virus Isolation

Venous blood from each of the 40 vaccinated and control horses was collected on the Day of Challenge and daily for 14 days post-challenge by vacutainer into a Disodium EDTA tube. After permitting gravity sedimentation of the erythrocytes in the tube of EDTA anti-coagulated blood, the plasma and white blood cells were pipetted off and placed in a sterile 5 mL snap-cap tube. The plasma and white blood cell mixture was centrifuged at 1500 RPM for 10-15 minutes to pellet the white blood cells. The pellet was washed twice with 3 mL of phosphate buffered saline (PBS) containing 2× Pen/Strep, 2× Gentamicin, and 2× Amphotericin B. Cells were then suspended in 4 mL of DMEM supplemented with 2% fetal bovine serum (FBS) and 2× Pen/Strep, 2× Gentamicin, and 2× Amphotericin B. One mL buffy coat suspension was used to inoculate a 2 cm$^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% CO$_2$ atmosphere. After the adsorption period, an additional 1 mL of re-feed medium (DMEM containing 5-7% fetal bovine serum (FBS), 2 mM L-glutamine and 1× Gentamicin was added to each well. Following addition of re-feed media the plates were then incubated at 37° C. in a CO$_2$ incubator. Wells could not be observed microscopically due to large volume of white blood cells settled on the monolayer. Therefore, at the end of 7 days, all wells were subcultured onto fresh ED cells using 0.5 ml of the 1$^{st}$ passage as inoculum. The subculture was observed for 7 days for CPE typical of challenge virus infection.

Serum Neutralization Testing Procedure

A standard microtiter serum neutralization test was employed in this study. All sera were tested in sterile flat bottom microtiter plates using five wells per dilution and an 8 well dilution series for each of the 5 test wells. Each of the 5 test wells contained 25 µl of serum dilution mixed with 25 µl of the indicator virus and 150 µl of a freshly planted ED cell suspension containing approximately 5×10$^4$ cells. The test indicator virus used was EHV-1 subtype 1 strain A183. In all tests the indicator virus back titration titers ranged between 109 to 263 TCID$_{50}$/25 Serum neutralizing antibody titers are expressed as Reed-Muench ID$_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 µl. All other wells contained 25 µl of DMEM (no FBS). Following serial dilution down the plate, 25 µl was discarded from the last row. 25 µl of a pre-determined dilution of the indicator virus was added to each test well. Plates were then mixed and incubated for one hour at 37° C. in 5% $CO_2$. On conclusion of the incubation period, 150 µl of a suspension containing 5×10$^4$ ED cells was added to each test and cell control well. The plates were incubated at 37° C. in a $CO_2$ incubator for 3 days, at which time plates were microscopically examined for CPE typical of EHV-1. Alternatively, any conventional or commercial available assay can be used or those of skill in the art would be able to follow the guidance herein.

Results and Conclusion

Nasal discharge scores, nasal shedding of EHV-1 and conjunctivitis scores were considered the primary outcome variables. All other outcomes were considered secondary.

TABLE 12

Summary of the statistical analysis (P-values)

| Outcome variable | Vaccination group | Day | Group by day interaction |
|---|---|---|---|
| Nasal discharge score[1] | 0.0001 | <.0001 | <0.0001 |
| Virus shedding[1] | 0.0028 | <0.0001 | 0.0863 |
| Conjunctivitis score[1] | 0.0020 | <0.0001 | 0.0017 |
| SN Titers | <0.0001 | <0.0001 | <0.0001 |
| WBC | 0.3064 | <0.0001 | <0.0001 |

[1]The GLIMMIX procedure would not converge, thus an ANOVA approach was used to evaluate the effect of vaccination over time after challenge. Results were interpreted through the bolded values.

Nasal Exudate Evaluation

The vaccination group by day interaction was statistically significant for the nasal discharge scores (P<0.05). Statistically significant group effects were seen on Days 4, 5 and on Days 7-11 post-challenge (lower nasal scores in the vaccinated group, P<0.05,). When the daily scores were summed over the post-challenge period, horses in the vaccinated group had lower total scores than those in the control group (P<0.05). The mitigated fraction was estimated to be 0.7250 (95% ASE CI: 0.4886, 0.9614).

TABLE 13

Mitigated fraction - nasal discharge and conjunctivitis scores, nasal virus shedding (mean ranks)

| | Control | Vaccinate | P-value[1] | Mitigated fraction[2] (95% ASE CI) |
|---|---|---|---|---|
| Nasal discharge | 27.75 | 13.25 | <0.0001 | 0.7250 (0.4886, 0.9614) |
| Days shedding virus[2] | 24.43 | 15.78 | 0.0068 | 0.4925 (0.1896, 0.7954) |
| Conjunctivitis | 25.80 | 15.20 | 0.0038 | 0.5300 (0.2463, 0.8137) |

[1]P-value from Wilcoxon's rank sum test
[2]Nasal discharge and conjunctivitis scores were summed across all time points then ranked for the estimation of the mitigated fraction. The number of days of viral shedding was calculated then ranked for the estimation of the mitigated fraction. Asymptotic standard errors (ASE) were used to estimate the 95% confidence intervals (CI).

TABLE 14

Mean nasal discharge score (N = 20 horses per group)

| Days post-challenge | Control | Vaccinated | P-value[1] |
|---|---|---|---|
| 0 | 0.00 | 0.00 | 1.0000 |
| 1 | 0.00 | 0.00 | 1.0000 |
| 2 | 0.15 | 0.00 | 0.6029 |
| 3 | 0.33 | 0.48 | 0.6029 |
| 4 | 1.08 | 0.23 | 0.0033 |
| 5 | 1.43 | 0.40 | 0.0004 |
| 6 | 1.05 | 0.55 | 0.0833 |
| 7 | 1.50 | 0.68 | 0.0044 |
| 8 | 1.68 | 0.63 | 0.0003 |
| 9 | 2.13 | 0.50 | <.0001 |
| 10 | 1.58 | 0.80 | 0.0074 |
| 11 | 0.98 | 0.23 | 0.0095 |
| 12 | 0.90 | 0.35 | 0.0568 |
| 13 | 1.23 | 0.90 | 0.2599 |
| 14 | 0.93 | 0.43 | 0.0833 |

[1]The GLIMMIX procedure would not converge, thus an ANOVA approach was used to evaluate the effect of vaccination over time on the nasal discharge score.

Conjunctivitis

The vaccination group, by day interaction, was statistically significant for the conjunctivitis scores (P<0.05). Statistically significant group effects were seen on Days 5 and 6, and on Days 9-14 post-challenge (lower scores in the vaccinated group, P<0.05). When the daily scores were summed over the post-challenge period, horses in the vaccinated group had lower total scores than those in the control group (P<0.05). The mitigated fraction was estimated to be 0.5300 (95% ASE CI: 0.2463, 0.8137).

TABLE 15

Mean conjunctivitis score (N = 20 horses per group)

| Days post-challenge | Control | Vaccinated | P-value[1] |
|---|---|---|---|
| 0 | 0.00 | 0.00 | 1.0000 |
| 1 | 0.00 | 0.00 | 1.0000 |
| 2 | 0.00 | 0.00 | 1.0000 |
| 3 | 0.05 | 0.00 | 0.7321 |
| 4 | 0.15 | 0.15 | 1.0000 |
| 5 | 0.70 | 0.25 | 0.0022 |
| 6 | 0.85 | 0.25 | <.0001 |
| 7 | 0.75 | 0.65 | 0.4936 |
| 8 | 0.45 | 0.35 | 0.4936 |

TABLE 15-continued

Mean conjunctivitis score (N = 20 horses per group)

| Days post-challenge | Control | Vaccinated | P-value[1] |
|---|---|---|---|
| 9 | 0.50 | 0.15 | 0.0168 |
| 10 | 0.45 | 0.15 | 0.0403 |
| 11 | 0.50 | 0.05 | 0.0022 |
| 12 | 0.45 | 0.00 | 0.0022 |
| 13 | 0.45 | 0.05 | 0.0063 |
| 14 | 0.35 | 0.05 | 0.0403 |

[1]The GLIMMIX procedure would not converge, thus an ANOVA approach was used to evaluate the effect of vaccination over time.

Virus Isolation From Nasopharyngeal Swabs

The main effect of vaccination group was statistically significant (fewer animals shedding in the vaccinated group, P<0.05). When the number of days shedding was evaluated, horses in the vaccinated group had fewer days of virus shedding than those in the control group (P<0.05, Table 2). The mitigated fraction was estimated to be 0.4925 (95% ASE CI: 0.1896, 0.7954).

TABLE 16

Proportion virus shedding (nasal swab, N = 20 horses per group)

| Days post-challenge | Control | Vaccinated |
|---|---|---|
| 0 | 0.00 | 0.00 |
| 1 | 0.00 | 0.00 |
| 2 | 0.05 | 0.05 |
| 3 | 0.05 | 0.10 |
| 4 | 0.20 | 0.05 |
| 5 | 0.25 | 0.15 |
| 6 | 0.45 | 0.25 |
| 7 | 0.45 | 0.35 |
| 8 | 0.50 | 0.10 |
| 9 | 0.45 | 0.15 |
| 10 | 0.25 | 0.00 |
| 11 | 0.35 | 0.10 |
| 12 | 0.30 | 0.10 |
| 13 | 0.15 | 0.00 |
| 14 | 0.05 | 0.00 |

White Blood Cell Counts

The vaccination group by day interaction was statistically significant for WBC counts (P<0.05, Table 1). Statistically significant group effects were seen on Days 2 and 3 post-challenge. Horses in the vaccinated group had higher WBC counts than those in the control group, indicating the vaccine prevented the horses from suffering the leucopenia caused by infection with EHV 1 (P<0.05).

TABLE 17

Mean WBC counts (N = 20 horses per group)

| Days post-challenge | Control | Vaccinated | P-value[1] |
|---|---|---|---|
| 1 | 14.0413 | 14.4887 | 0.6081 |
| 2 | 10.7963 | 14.1287 | 0.0001 |
| 3 | 11.1263 | 14.0687 | 0.0008 |
| 4 | 11.5013 | 13.1037 | 0.0667 |
| 5 | 10.7413 | 11.1987 | 0.6001 |
| 6 | 9.1063 | 9.4187 | 0.7203 |
| 7 | 10.1563 | 9.9037 | 0.7721 |
| 8 | 10.7813 | 10.6037 | 0.8386 |
| 9 | 11.1813 | 12.0737 | 0.3065 |
| 10 | 11.9713 | 12.4187 | 0.6081 |

TABLE 17-continued

Mean WBC counts (N = 20 horses per group)

| Days post-challenge | Control | Vaccinated | P-value[1] |
|---|---|---|---|
| 11 | 12.6713 | 13.2137 | 0.5341 |
| 12 | 13.2913 | 13.5637 | 0.7549 |
| 13 | 14.7063 | 14.1737 | 0.5415 |
| 14 | 15.8463 | 14.4587 | 0.1121 |

[1]P-values from the ANOVA

Serological Studies

Titers were log transformed prior to the statistical analysis. The vaccination group by day interaction was statistically significant for SN titers (P<0.05). Statistically significant group effects were seen on Days 35 (the day of challenge) and 7 and 14 days post-challenge (study days 42 and 49). Horses in the vaccinated group had higher titers than those in the control group (P<0.05).

TABLE 18

Geometric mean - serum neutralization titers (N = 20 horses per group)

| Study day | Control | Vaccinated | P-value[1] |
|---|---|---|---|
| 0 | 3.987 | 3.384 | 0.4005 |
| 21 | 3.190 | 2.624 | 0.3168 |
| 35 (day of challenge) | 3.480 | 6.863 | 0.0006 |
| 42 | 3.519 | 19.252 | <0.0001 |
| 49 | 33.153 | 187.417 | <0.0001 |

[1]P-values from the ANOVA. Serum neutralization titers were log (natural) transformed prior to the statistical analysis.

Results and Discussion

Respiratory disease caused by equine herpesvirus type 1 is usually an epidemic disease of naive weanling and yearling horses that occurs in the first year of life, usually in the fall and winter months. Signs of acute infection include fever up to 106° F., viremia and leucopenia and/or neutropenia. Nasal discharge is usually evident during febrile periods of this first exposure. Natural infection by EHV-1 does not result in permanent immunity of the respiratory tract. Indeed, horses may be re-infected naturally every 3 to 6 months throughout life. After the first experience with this virus, re-infection results in production of virus, but usually without clinical signs of disease, resulting in carrier animals that act as natural reservoirs of the virus.

The equine herpesvirus-1 multi-component vaccine described in this report has been shown to be efficacious in reducing the respiratory manifestations, clinical symptoms and virus shedding from nasal exudate of horses challenged with a virulent heterologous strain of Equine Herpesvirus type 1. Reduction in shedding of virus from the respiratory route is important epidemiologically due to this being the natural route of exposure to naive animals as well as for re-infection of herd mates from those experiencing a natural infection. It was also a safe vaccine with no adverse reactions, either systemic or at the site of vaccine administration, observed following vaccine use in the study horses.

In this study, vaccination group by day interaction showed statistical significance for the primary outcome variables nasal discharge scores and conjunctivitis. Statistically significant group effects were seen in the vaccinate group for nasal discharge on Days 4, 5 and on Days 7-11 post-challenge. Group effects for conjunctivitis were also statistically significant on Days 5 and 6 and 9-14 with lower scores in the vaccinate group (P<0.05). This is significant epidemiologically because the EHV-1 virus is delicate and does not survive in the environment readily. Close contact is important for transmission of disease through nasal secretions containing virulent EHV-1 virus (Campbell and Studdert, 1983).

Importantly, another primary outcome variable in this study, virus shedding in nasal exudates, showed a main effect of vaccination as statistically significant (P<0.05). Horses in the vaccinated group also had statistically fewer days of virus shedding than those in the control group (P<0.05).

Serum neutralization titers were statistically significant after vaccination and throughout the challenge period in vaccinates versus control horses (P<0.05). Humoral immunity and mucosal antibodies may be important in determining whether an EHV-1 infection becomes a productive or limited infection event (Kidd, Smith, Hannant, et. al, 1994).

Example 6

This example illustrates the efficacy and 6 month duration of immunity of an immunogenic composition of the present invention when challenged with West Nile Virus.

Materials and Methods

The WNV viral antigen used in the vaccine evaluated in this study was produced on E vero cells as described in Example 1. A total of 15 horses were randomly divided into groups, one being a control group of 5 horses. The vaccinated group of 10 horses received 2 doses of vaccine at 21-day intervals cells. On completion of satisfactory residual live virus testing the inactivated viral fluids were then used to formulate a vaccine which also contained inactivated Venezuelan Equine Encephalomyelitis, TC-83 strain (ATCC Accession No. PTA-9411), Eastern Equine Encephalomyelitis, NJO strain (ATCC Accession No. PTA-9412), and Western Equine Encephalomyelitis, Fleming strain (ATCC Accession No. PTA-9410) viruses, inactivated influenza A/equine-2/Kentucky/95 (ATCC Accession No. PTA-9523), influenza A/equine-2/NewMarket/2/93 (ATCC Accession No. PTA-9524) and influenza A/equine-2/Ohio/03 (ATCC Accession No. PTA-9522) viruses, inactivated West Nile Virus (ATCC Accession No. 9409) and tetanus toxoid. Vaccine was formulated to minimum specifications for all antigens included in the product.

The final formulated vaccine contains the following ingredients per 1 mL dose:

| | |
|---|---|
| EHV-1 | $10^{7.0-9.0}$ TCID$_{50}$/mL |
| Influenza A2/Ohio/03 | $10^{6.7-9.5}$ TCID$_{50}$/mL |
| Influenza A2/KY/95 | $10^{6.7-9.5}$ TCID$_{50}$/mL |
| Influenza A2/NewMarket/2/93 | $10^{6.7-9.5}$ TCID$_{50}$/mL |
| Tetanus Toxoid | 5-10 CPU |
| Eastern Equine Encephalomyelitis | $10^{6.7-9.2}$ TCID$_{50}$/mL |
| Western Equine Encephalomyelitis | $10^{6.7-9.2}$ PFU/mL |
| Venezuelan Equine Encephalomyelitis | $10^{6.7-9.2}$ TCID$_{50}$/mL |
| West Nile Virus | $10^{7.0-9.0}$ TCID$_{50}$/mL |
| Adjuvant (preferably mineral oil) | 100-200 µl |
| Glycerol | 100-200 µl |
| EDTA 240 mM solution | 10-20 µl |
| Diluent - DMEM containing Gentamicin (30 µg/mL of diluent volume) Formaldehyde (0.1-0.2% of diluent volume) | q.s. |

Fifteen horses were used in this study. Horses were randomly assigned to either vaccinate or control groups and then vaccinated. Ten horses served as vaccinates and five horses were mock-vaccinated control horses.

The vaccine was administered intramuscularly in a 1 mL dose volume to each of the horses in the vaccinate group. Each control received a 1 mL dose of adjuvanted DMEM containing excipients used in the 9-way vaccine (gentamycin and formaldehyde) but no antigens.

All groups were challenged approximately 6 months following vaccination with intrathecal inoculation of 1 ml PBS containing approximately $10^5$ pfu of a heterologous strain of WNV (NY99, 4132, crow isolate). The challenge was conducted under ketamine-xylazine anesthesia.

Horses were monitored for a maximum of 14 days.

Results and Discussion

Viremia after challenge was considered the primary outcome variable in this study. The horses that had been vaccinated were 90% protected from viremia after challenge in this study. In comparison, all of the 5 control horses demonstrated viremia for 3-5 days post-challenge.

In addition, serum neutralization titers of vaccinated horses were significantly higher than those of control horses after vaccination. All the vaccinated horses developed measurable serum neutralization titers following vaccination, whereas none of the controls displayed any titer to WNV. This study demonstrated that 2 doses of the experimental combination vaccine reliably and effectively stimulated protective serological serum neutralization titers.

Since viremia is a prerequisite before virus can cross the blood-brain barrier to cause WNV encephalitis, viremia is well justified as the primary parameter for evaluation of protection in an experimental study of this type.

The results demonstrated that an immunogenic reaction is induced in the animals that were administered the vaccine, and that the vaccine is effective at providing protection for at least 6 months following vaccination. The effectiveness of the vaccine was evidenced in this example by reduction in WNV viremia and by stimulation of high serum neutralization titers to WNV. Because this vaccine is comprised of unique constituents including a long lasting non-metabolizable adjuvant, is formulated in a low 1 mL dose volume to provide a high degree of safety as a highly immunogenic low passage whole inactivated virus WNV isolate of recent origin and high epidemiological prevalence (a North American Dominant WNV strain), and a WNV isolated from the tissues of an infected horse, it provides more comprehensive safety and long lasting effectiveness of at least 6 months duration than other vaccines currently available. Additionally, it has the effect of providing a safe vaccine when administered to animals, and in particular to horses.

Example 7

This example illustrates the efficacy of one embodiment of the immunogenic composition of the present invention including encephalomyelitis antigens with tetanus toxoid antigen.

Materials and Methods

Host animal and laboratory animal immunization/serology were evaluated to demonstrate efficacy of encephalomyelitis antigens and the tetanus toxoid antigen fraction in an Encephalomyelitis-Rhinopneumonitis-Influenza-West Nile Virus Vaccine, including Eastern, Western, and Venezuelan Encephalomyelitis, Killed Virus, and Tetanus Toxoid. The efficacy and lack of interference on equine encephalitis virus vaccines and tetanus toxoid fractions can be unequivocally demonstrated by laboratory animal potency testing of the combination vaccine. Demonstration of serological response following vaccination of horses is also indicative of vaccine-toxoid efficacy. Hence, both lab animal potency and host animal serology were used in this study to confirm the efficacy of the experimental vaccine. The vaccine was also evaluated for safety in animals including horses.

Horses 4-5 months of age, from non-vaccinated mares, were vaccinated with an efficacy serial of WNV combination vaccine containing inactivated Venezuelan Equine Encephalomyelitis Virus, TC-83 strain (ATCC Accession No. PTA-9411) Eastern Equine Encephalomyelitis Virus, NJO strain (ATCC Accession No. PTA-9412) Western Equine Encephalomyelitis Virus, Fleming strain (ATCC Accession No. PTA-9410) West Nile Virus (WNV), Horse Origin 2005 (ATCC Accession No. PTA-9409) Equine Herpesvirus Type 1 (ATCC Accession No. PTA-9525) (EHV-1), Influenza A/equine-2/Ohio/03 (ATCC Accession No. PTA-9522), Influenza A/equine-2/Kentucky/95 (ATCC Accession No. PTA-9523), Influenza A/equine-2/NewMarket/2/93 (ATCC Accession No. PTA-9524) and Tetanus Toxoid. Horses were vaccinated on Day 0 and Day 21 of the study. Blood samples were collected at Day 0, Day 21 and Day 35. Day 0 and Day 35 serological results are reported herein.

In addition, the same WNV combination vaccine used to vaccinate horses was tested for potency in guinea pigs. Data presented in this report collectively and definitively establish the efficacy of each antigen tested (EEE, VEE, WEE, tetanus) in this study and also confirm the safety of a WNV combination vaccine.

Bulk lots of EEE, WEE, and VEE viruses and tetanus toxoid were produced. Following growth, viral fluids were filtered, formalin inactivated, and concentrated. The inactivated viral fluids were tested for residual live virus after inactivation.

Inactivated viral and toxoid fluids described above were used to formulate a vaccine that also contained inactivated Equine Herpesvirus Type 1, inactivated influenza A/equine-2/Kentucky/95, influenza A/equine-2/NewMarket/2/93 and influenza A/equine-2/Ohio/03 viruses.

The vaccine was formulated to specifications for all antigens included in the product.

The final formulated vaccine contained the following ingredients per 1 mL dose:

| | |
|---|---|
| EHV-1 | $10^{7.0-9.0}$ TCID$_{50}$/mL |
| Influenza A2/Ohio/03 | $10^{6.7-9.5}$ TCID$_{50}$/mL |
| Influenza A2/KY/95 | $10^{6.7-9.5}$ TCID$_{50}$/mL |
| Influenza A2/NewMarket/2/93 | $10^{6.7-9.5}$ TCID$_{50}$/mL |
| Tetanus Toxoid | 5-10 CPU |
| Eastern Equine Encephalomyelitis | $10^{6.7-9.2}$ TCID$_{50}$/mL |
| Western Equine Encephalomyelitis | $10^{6.7-9.2}$ PFU/mL |
| Venezuelan Equine Encephalomyelitis | $10^{6.7-9.2}$ TCID$_{50}$/mL |
| West Nile Virus | $10^{7.0-9.0}$ TCID$_{50}$/mL |
| Adjuvant (preferably mineral oil) | 100-200 μl |
| Glycerol | 100-200 μl |
| EDTA 240 mM solution | 10-20 μl |
| Diluent - DMEM containing | q.s. |
| Gentamicin (30 μg/mL of diluent volume) | |
| Formaldehyde (0.1-0.2% of diluent volume) | |

Forty horses, four to 5 months of age, were used in this study. Horses remained with their dams on pasture throughout the vaccination period and were weaned from their dams when the 2-week post-booster sera were collected. Horses were assigned to either one of the two treatment groups randomly as they were vaccinated intramuscularly (IM) with a 1.0 ml dose. The primary immunization was followed three weeks later by a 1.0 ml IM booster vaccination. Twenty horses received vaccine. Twenty horses received placebo.

Guinea pigs were also vaccinated with the same combination WNV vaccine.

Horses were vaccinated and serum samples collected using the following schedule:

TABLE 19

Vaccination and Serum Sampling Schedule

| Day of Test | Activity |
|---|---|
| 0 | Collect pre-vaccination blood and give primary vaccination |
| 21 | Collect blood and give booster vaccination |
| 35 | Collect blood for final serology |

Guinea pigs were vaccinated and serum collected using the schedule outlined by 9 CFR, 113.207(b) and 113.114(c.).

Sera from horses in this study were tested following general guidelines. The assay was modified to determine titers by testing at 1:2 and 1:10 dilutions for Day 0 samples and at 1:10 and 1:40 dilutions for the 2-week post-booster serum samples. Sera were tested for EEE, WEE and VEE antibody and were tested for Tetanus toxoid antibody.

Results and Discussion

Horse Serological Evaluation for EEE, WEE and VEE

At Day 0 of the Study, not all foals were sero-negative to encephalomyelitis viruses. Five of the vaccinated foals had significant (>1:10) residual maternal antibody to EEE virus. In addition, two of the vaccinated foals had residual maternal antibody (>1:10) to WEE virus. Despite existing and potentially interfering passively acquired, maternal antibody at the time of administration of the first dose of the WNV combination vaccine, titers for all three fractions increased substantially (>4 fold in 80% of horses tested for EEE, >4 fold in 90% of horses tested for WEE and >4 fold in 100% of horses tested for VEE) following vaccination, yet remained negative or low for the non-vaccinated foals. Individual foal data are presented below.

EEE, WEE and VEE Equine Serological Titers

TABLE 20

Plaque Reduction Neutralization Titration

| Horse ID | Test Article | Day 0 EEE | Day 35 EEE | Day 0 WEE | Day 35 WEE | Day 0 VEE | Day 35 VEE |
|---|---|---|---|---|---|---|---|
| 1 | V | >10 | >40 | 2 | >40 | <2 | >40 |
| 2 | V | <2 | >40 | <2 | 10 | <2 | 40 |
| 3 | V | <2 | >40 | <2 | <10 | <2 | >40 |
| 4 | V | <2 | >40 | <2 | 10 | <2 | >40 |
| 5 | V | >10 | >40 | >10 | >40 | <2 | >40 |
| 6 | V | >10 | >40 | <2 | >40 | NS | 10 |
| 7 | V | <2 | >40 | <2 | >40 | <2 | >40 |
| 8 | V | >10 | >40 | 2 | >40 | <2 | >40 |
| 9 | V | <2 | >40 | <2 | >40 | <2 | >40 |
| 10 | V | <2 | >40 | <2 | >40 | <2 | 10 |
| 11 | V | <2 | >40 | <2 | >40 | <2 | >40 |
| 12 | V | <2 | >40 | <2 | >40 | <2 | 40 |
| 13 | V | <2 | >40 | <2 | >40 | <2 | >40 |
| 14 | V | <2 | >40 | <2 | 10 | <2 | >40 |

TABLE 20-continued

Plaque Reduction Neutralization Titration

| Horse ID | Test Article | Day 0 EEE | Day 35 EEE | Day 0 WEE | Day 35 WEE | Day 0 VEE | Day 35 VEE |
|---|---|---|---|---|---|---|---|
| 15 | V | >10 | >40 | >10 | >40 | 2 | >40 |
| 16 | V | 2 | >40 | <2 | 10 | <2 | >40 |
| 17 | V | <2 | >40 | <2 | 10 | <2 | >40 |
| 18 | V | <2 | >40 | <2 | >40 | <2 | 40 |
| 19 | V | <2 | 10 | <2 | >40 | <2 | >40 |
| 20 | V | 2 | >40 | <2 | >40 | <2 | 10 |
| 21 | C | <2 | <10 | <2 | <10 | <2 | 10 |
| 22 | C | <2 | <10 | <2 | <10 | <2 | <10 |
| 23 | C | <2 | <10 | <2 | 10 | <2 | <10 |
| 24 | C | <2 | <10 | NS | <10 | <2 | <10 |
| 25 | C | <2 | <10 | <2 | <10 | <2 | <10 |
| 26 | C | <2 | <10 | <2 | 10 | <2 | <10 |
| 27 | C | <2 | <10 | <2 | <10 | <2 | <10 |
| 28 | C | 2 | <10 | <2 | <10 | <2 | 10 |
| 29 | C | 2 | <10 | <2 | 10 | <2 | <10 |
| 30 | C | <2 | <10 | <2 | <10 | <2 | <10 |
| 31 | C | <2 | <10 | <2 | <10 | <2 | <10 |
| 32 | C | <2 | <10 | <2 | <10 | <2 | <10 |
| 33 | C | >10 | >40 | <2 | 10 | <2 | <10 |
| 34 | C | <2 | <10 | <2 | <10 | <2 | <10 |
| 35 | C | >10 | 10 | 2 | <10 | <2 | 10 |
| 36 | C | 2 | <10 | <2 | <10 | <2 | <10 |
| 37 | C | <2 | <10 | <2 | <10 | <2 | <10 |
| 38 | C | <2 | <10 | 2 | <10 | <2 | <10 |
| 39 | C | <2 | 10 | <2 | <10 | <2 | <10 |
| 40 | C | <2 | >40 | <2 | <10 | <2 | <10 |

Guinea Pig Serological Evaluation for EEE, WEE, VEE and Tetanus toxoid

Nine of ten guinea pigs vaccinated with the combination vaccine seroconverted satisfactorily at (≥1:40) to EEE virus. Ten of ten guinea pigs had satisfactory titers for VEE virus (≥1:4) and ten of ten guinea pigs seroconverted satisfactorily to WEE virus (≥1:40). Also a serum pool from 10 vaccinated guinea pigs was tested for tetanus antibody and was shown to be satisfactory with a value of 4.3 anti-toxin units/ml (AU/ml).

Guinea pig potency tests were completed and found to be satisfactory for all four antigens including tetanus toxoid, EEE, VEE, and WEE.

The vaccine was also administered to horses (20 vaccinates and 20 controls) via primary immunization followed by booster immunization 3 weeks later. Fourteen days post-booster vaccination, horses were bled and serum collected for all serological testing. Equine response to encephalomyelitis antigens was tested utilizing 2 dilutions (1:2 and 1:10 for Day 0 samples and 1:10 and 1:40 for Day 35 samples) in 24-well plates to determine antibody titers.

The satisfactory guinea pig potency testing conclusively establishes the efficacy of 4 antigens (VEE, EEE, WEE and tetanus toxoid) in the West Nile Virus combination vaccine as a 9-antigen-containing vaccine-toxoid. Furthermore, satisfactory potency results are substantiated and confirmed by host animal horse serology data in which vaccinated horses demonstrated a substantial rise in titer to each encephalitis virus fraction following vaccination. Additionally, the absence of observation of any adverse reactions in any of the vaccinated horses or guinea pigs confirms the safety of the WNV combination vaccine in animals.

Example 8

This example illustrates that a vaccine or immunogenic composition in accordance with the present invention has a duration of immunity of at least one year.

Materials and Methods

Host animal vaccination and challenge at least 1 year post-booster vaccination was used to confirm duration of immunity for the West Nile Virus antigen fraction in an Encephalomyelitis-Rhinopneumonitis-Influenza-West Nile Virus Vaccine, Eastern, Western & Venezuelan, Killed Virus, Tetanus Toxoid prepared from a North American Dominant isolate of WNV designated North American Equine E159 (NAEE159).

TABLE 21

The final formulated vaccine contains the following ingredients per 1 mL dose:

| Ingredients | 1 mL Dose |
|---|---|
| Eastern Equine Encephalomyelitis | $10^{7.5-9.2}$ TCID$_{50}$/mL |
| Western Equine Encephalomyelitis | $10^{8.2-9.2}$ PFU/mL |
| Venezuelan Equine Encephalomyelitis | $10^{7.7-9.2}$ TCID$_{50}$/mL |
| West Nile Virus (North American Dominant prepared from NAEE159) | $10^{8.0-9.2}$ TCID$_{50}$/mL |
| EHV-1 | $10^{7.0-9.0}$ TCID$_{50}$/mL |
| Equine Influenza A2/Ohio/2003 | $10^{7.3-9.5}$ TCID$_{50}$/mL |
| Equine Influenza A2/Kentucky/95 | $10^{7.3-9.5}$ TCID$_{50}$/mL |
| Equine Influenza A2/NewMarket/2/93 | $10^{7.3-9.5}$ TCID$_{50}$/mL |
| Tetanus Toxoid | 5-10 CPU |
| Non-metabolizable Oil Adjuvant | 100-200 μL |
| Diluent - DMEM containing | q.s. |
| Gentamicin | 30 μg/mL of diluent volume |
| Formaldehyde | 0.1% of diluent volume |

Thirty horses (20 vaccinates and 10 controls), 4-5 months of age were used in this study. Horses were randomly assigned to one of two treatments and vaccinated intramuscularly (IM) with a 1.0 mL dose of the assigned vaccine or control product. The primary immunization was followed three weeks later by a 1.0 mL IM booster vaccination.

Horses were vaccinated once and then again about 30 days later. Horses were randomly assigned to either vaccine or control groups. Twenty horses received the vaccine group receiving VEWT/WNV/EHV-1/Influenza vaccine. Ten horses received adjuvanted DMEM containing excipients used in the vaccine (Gentamicin and formaldehyde) but no antigens. The non-metabolizable oil adjuvant used for all administrations was preferably mineral oil.

Challenge inoculation of the virulent heterologous WNV NY99 strain virus was performed 380 days post-booster vaccination. The second cohort of horses were challenged 408 days post-booster inoculation in a similar manner.

Serum samples for serological evaluation were collected from the vaccinated and control horses prior to initial vaccination, at 21 days post first dose vaccination (day of booster vaccination), monthly post-booster, on the day of challenge, and at 7 and 14 days post-challenge. Body temperature and serum samples were obtained from each horse on the day of challenge, twice daily on Days 1 through 6 post-challenge, and daily on Days 7-10 and Day 14 post-challenge. Clinical data was also recorded during those same time periods for the 15-day observation period.

The heterologous challenge virus, designated WNV NY99, was originally isolated from the brain of an infected crow (CDC, Ft. Collins, Colo.). On the day of challenge, the stock virus was thawed on ice and virus was diluted to the desired concentration in phosphate-buffered saline immediately prior to inoculation of horses.

Rectal temperatures were recorded for each of the vaccinated and control horses on the day before challenge, day of challenge and twice daily on days 1-14, then daily on Days 14-21 post challenge by means of a calibrated, electronic thermometer (GSA Electronics) probe. The daily rectal temperatures were recorded in degrees Fahrenheit (° F.).

Venous blood from each of the vaccinated and control horses was collected on the Day of Challenge, twice daily on Days 1-6, and daily on Days 7-10 and Day 14 days post-challenge by Vacutainer into an SST tube. After centrifugation, serum was aliquotted and frozen immediately.

Vero Cells were grown in 6-well plates to confluency. To perform the plaque assay, serial 10-fold dilutions of serum were prepared in 96-well plates in BA-1 medium (MEM salts containing 1% BSA, 250 mg/L sodium bicarbonate, 50 µl gentamicin and 2.5 µg amphotericin B/mL in 50 mM Tris, pH 7.6). Serum dilutions (0.1 mL) were inoculated into each well of the 6-well plate and incubated for 45-60 minutes with rocking every 15 minutes. After the incubation period, 2 mL of overlay (2× medium containing MEM without phenol red prepared at twice the normal concentration and supplemented with 4% FBS, 200 IU penicillin G/mL and 100 µg streptomycin/mL—warmed to 45° C.) was added to each well. Plates were incubated at 37° C.

Two days after inoculation, 2 mL of a second overlay containing 2× agarose prepared by mixing equal volumes of 2× medium and 2× agarose was added to each well. Plates were examined and plaque numbers recorded in each well on days 3, 4 and 5 following inoculation. The virus titer per mL of original material is calculated as the number of plaques in a well (or average of multiple wells inoculated with the same dilution) times the dilution for the well being counted multiplied by 10.

A standard microtiter serum neutralization test was employed in this study. All sera were tested in sterile flat bottom 96 well microtiter plates using five wells per dilution and an 8 well dilution series for each of the 5 test wells. Each of the 5 test wells contained 25 µL of serum dilution mixed with 25 µL of the indicator virus and 150 µL of a freshly planted Vero cell suspension containing approximately $4 \times 10^4$ cells. The test indicator virus used was WNV NY99. Serum neutralizing antibody titers are expressed as Reed-Muench $ID_{50}$ titers.

For performance of the test, two-fold dilutions of each test serum were made in a sterile flat bottom microtiter plate using five replicate wells per test serum and an 8 well dilution series. Dilutions were made with an adjustable volume single or multi-channel pipetting instrument using sterile microtiter tips. The volume of serum added to each of 5 wells of the first row was 50 µL. All other wells contained 25 µL of DMEM (no FBS). Following serial dilution down the plate, 25 µL was discarded from the last row. 25 µL of a pre-determined dilution of the indicator virus was added to each test well. Plates were then mixed and incubated for one hour at 37° C. in 5% $CO_2$. On conclusion of the incubation period, 150 µL of a suspension containing 4×104 Vero cells were added to each test and cell control well. The plates were incubated at 37° C. in a $CO_2$ incubator for 5-7 days, at which time plates were microscopically examined for CPE typical of WNV.

Histopathology was evaluated by a Board Certified Veterinary Pathologist. The scoring system used to describe defects in the pons or medulla was as follows:
Score:
0=no significant lesions in section
0.5=rare, small, multifocal glial nodules scattered throughout the parenchyma
1=mild, nonsuppurative encephalitis. This is characterized by mild multifocal perivascular cuffs with lymphocytes and plasma cells and a rare neutrophil and scattered multifocal glial nodules composed of glial cells with a few mononuclear inflammatory cells. Occasionally within this grade, there may be minimal perivascular cuffing and more moderate scattered glial nodules.
2=moderate nonsuppurative encephalitis characterized by moderate lymphoplasmacytic perivascular cuffs around many vessels and multifocal accumulations of glial nodules scattered throughout the parenchyma
3=severe nonsuppurative encephalitis characterized by severe and thick lymphoplasmacytic perivascular cuffing with multiple scattered glial nodules throughout the parenchyma Results and Discussion There were no adverse reactions to vaccine administration at either dosing time point. All 4 to 5 month old foals receiving the experimental vaccine were free of either systemic or injection site adverse reactions in the study. This confirms the excellent safety of the vaccine of the present invention against WNV containing North American Dominant WNV antigen prepared from isolate NAEE159.

Horse Challenge with Heterologous West Nile Virus

Viremia

Each of the 10 control horses (100%) were viremic for at least 1 day post-challenge, while only 2 of 20 horses (10%) in the WNV vaccine group were viremic.

Clinical Signs

Seven of the 10 horses (70%) in the control group developed signs of encephalomyelitis consistent with West Nile Virus infection. Each of these animals was viremic for at least one day during the challenge period. In the WNV vaccine group, 1 of the 20 horses (5%) developed signs consistent with West Nile Virus infection. Notably clinical signs progressed to death or euthanasia in 70% of the controls and only 5% of the vaccinates. All control mortalities were viremic, confirming fatal encephalitis due to WNV, whereas only one of two vaccinated animals that died was viremic during the challenge period.

Serum Neutralization Titers

All vaccinated horses responded favorably to the WNV vaccine by developing protective levels of serum neutralizing (SN) antibody following vaccination. Over one year following vaccination, 17 of 20 (85%) of vaccinated horses maintained protective SN titers. By contrast, none of the control horses developed rising SN titers prior to virulent WNV challenge. Also, all vaccinated horses displayed an anamnestic rise in SN titers following virulent WNV challenge Histopathology Severity scores were provided for both the medulla and pons. Also with regard to this efficacy parameter, WNV vaccine containing North American Dominant WNV antigen prepared from isolate NAEE159 proved highly effective.

Among the control horses, 50% displayed severe lesions of WNV encephalitis whereas only 10% of vaccinates were similarly affected.

Discussion and Conclusions

The WNV vaccine was prepared from a viral isolate (North American Equine E159) obtained from a horse in 2005 during the North American pandemic when a specific dominant WNV genotype emerged. This genotype is characterized by a specific valine to alanine amino acid change at the 159$^{th}$ amino acid in the envelope (E) protein of the virus (when compared to the publicly available sequence for the WNV-NY99 isolate having the ATCC Accession No. AF196835), which has made all such isolates more robust and prolific, thereby displacing other WNV isolates, and making this genotype dominant among disease-causing WNV isolates in North America. Because it was prepared from the dominant genotype, the vaccine used in this study is indicative of the unique safety and efficacy achievable with vaccine prepared from all such North American Dominant isolates with this E protein profile and resulting prolificacy. Notably, all previously tested WNV vaccines have been prepared from a less prolific isolate of differing genotype and E protein amino acid sequence, namely WNV NY99. Based on this difference in nucleic acid sequence, E protein amino acid sequence, viral prolificacy, and unique ability to cause a pandemic, the North American Dominant isolates are displacing or have displaced NY99 from the environment. The unique genotype and phenotype (prolificacy), and, most importantly, the overwhelming environmental presence of North American Dominant WNV isolates and the absence of WNV NY99 is compelling evidence for the superiority of the North American Dominant West Nile Virus vaccine. Such superiority is confirmed by the safety and efficacy of the vaccine as demonstrated in this challenge study using vaccine prepared from North American Dominant isolate North American Equine E159 (NAEE159) (ATCC Accession No PTA-9409).

In this study, 4 to 5 month old horses were safely and effectively vaccinated with a multi-component VEWT/WNV/EHV-1/Equine Influenza vaccine batched at an appropriate antigen amount with the WNV component being North American Dominant WNV antigen prepared from isolate NAEE159c(ATCC Accession No. PTA-9409).

Study horses were intrathecally challenged at least 380 days post-booster vaccination with $10^5$ PFU of a virulent heterologous West Nile Virus strain. Horses were evaluated for 14 days post-challenge for clinical signs (including temperature and mortality), viremia, serum neutralization titers, and histopathology scores from sections of the pons and medulla taken after euthanasia and necropsy.

Viremia after challenge and serum neutralization titers were key outcome variables in this study that were highly indicative of vaccine efficacy. Horses that had been vaccinated more than one year earlier with VEWT/WNV/EHV-1/Influenza Lot 916 were 90% protected from viremia after challenge in this study. In comparison, 100% of control horses demonstrated viremia post-challenge. Additionally, serum neutralization titers of vaccinated horses were significantly higher than those of control horses at 14 days post-challenge, and displayed an anamnestic response typical of an effective vaccine following heterologous, virulent WNV challenge.

In addition the vaccine containing North American Dominant WNV antigen prepared from isolate NAEE159 reduced clinical signs and mortality resulting from encephalomyelitis following heterologous challenge with virulent WNV. Vaccine efficacy at least one year following vaccination was also confirmed by reduction in lesions typical of WNV infection.

This study demonstrated for the first time that 2 doses of the experimental combination vaccine prepared at appropriate doses of antigen including North American Dominant WNV antigen prepared from isolate NAEE159 administered to foals 4 to 5 months of age safely, reliably and effectively stimulated protective serological serum neutralization titers that resulted in duration of immunity of at least one year with protection from viremia, clinical signs, mortality, and encephalitic lesions after virulent heterologous challenge with West Nile Virus.

Example 9

In this study, a combination vaccine was prepared using a North American Dominant isolate of WNV, North American Equine E159(NAEE159) (ATCC Accession No. PTA-9409). The 14-day post second-vaccination sera samples from the guinea pigs vaccinated with this Encephalomyelitis-Rhinopneumonitis-Influenza-West Nile Virus Vaccine, Eastern, Western & Venezuelan, Killed Virus, Tetanus Toxoid were collected and tested for West Nile Virus plaque reduction neutralization (PRN). The sera from the vaccinated guinea pigs were tested for neutralizing antibody to both a North American Dominant isolate of WNV and to WNV isolate NY99. Notably, the vaccine displayed superior activity in stimulating neutralizing antibodies to North American Dominant WNV, as opposed to NY99 WNV. These data support the conclusion of the superior efficacy of WNV vaccines prepared from North American Dominant WNV isolates as contrasted with earlier less effective vaccines prepared from or based on the NY99 WNV isolate.

Furthermore, a vaccine prepared from an additional North American Dominant isolate of WNV, North American Donkey E159 (NADE159) will similarly demonstrate, as described above, the superior efficacy of such vaccines over the former NY99 based vaccines. Hence, data from multiple North American Dominant isolates cultivated from different host species, originating from unique North American locations, and obtained at different times in North America will confirm the unexpected but superior efficacy of North American Dominant isolates of WNV for vaccine preparation.

The data from the plaque reduction neutralization assay also established that a vaccine prepared from a North American Dominant isolate of WNV that stimulates a titer of 1:12 or higher in vaccinated guinea pigs that provides 50% viral plaque reduction in at least 90% of vaccinated guinea pigs, correlates to vaccine protection against WNV challenge in the horse and provides for a duration of immunity of at least one year. West Nile Virus vaccination/challenge data in the horse at an antigen inclusion level of $10^{7.6-9.0}$TCID$_{50}$ or higher per dose correlated with these guinea pig PRN titer results and confirmed the WNV immunizing dose that provides 1 year or longer duration of immunity in the horse. The corresponding dose in guinea pigs also stimulates serum neutralizing antibodies to a titer of at least 1:12 against North American Dominant WNV in guinea pigs.

Data presented in this report collectively demonstrate the unexpected efficacy of vaccines prepared from North American Dominant isolates of WNV, define the correlation between vaccine efficacy in the horse and guinea pig serum levels of neutralizing antibody, confirm that a 1:12 titer or higher in guinea pigs identifies an effective equine vaccine providing at least one year duration of immunity, and quite notably, demonstrate the superior efficacy of vaccines prepared from North American Dominant WNV as contrasted with NY99 WNV.

Materials and Methods

In order to demonstrate efficacy of the West Nile Virus antigen, prepared using a North American Dominant isolate of WNV, North American Equine E159(NAEE159) (ATCC Accession No. PTA-9409), in an Encephalomyelitis-Rhinopneumonitis-Influenza-West Nile Virus Vaccine, Eastern, Western & Venezuelan, Killed Virus, Tetanus Toxoid and to establish an effective dose measurable in horses or guinea pigs, host animal vaccination/challenge studies were performed in conjunction with guinea pig vaccination/serology studies. In this study, 14-day post second-vaccination sera samples from guinea pigs vaccinated with Encephalomyelitis-Rhinopneumonitis-Influenza-West Nile Virus Vaccine, Eastern, Western & Venezuelan, Killed Virus, Tetanus Toxoid were collected and tested. Additionally, a plaque reduction neutralization assay was developed to measure the titer correlated to protection against challenge in the host animal. This titer was determined to be 1:12 or higher in the guinea pig.

Vaccine Formulations

Experimental Serials (Protective Dose Vaccine)
Experimental Serials were formulated to confirm protective antigen specifications for all antigens in the vaccine.

TABLE 22

The final formulated vaccines contained the following ingredients per 1 mL dose:

| Ingredients | 1 mL Dose |
|---|---|
| Eastern Equine Encephalomyelitis | $10^{7.5-9.2}$ TCID$_{50}$/mL |
| Western Equine Encephalomyelitis | $10^{8.2-9.2}$ PFU/mL |
| Venezuelan Equine Encephalomyelitis | $10^{7.7-9.2}$ TCID$_{50}$/mL |
| West Nile Virus (North American Dominant prepared from NAEE159) | $10^{7.3-9.2}$ TCID$_{50}$/mL |
| EHV-1 | $10^{7.0-9.0}$ TCID$_{50}$/mL |
| Equine Influenza A2/Ohio/2003 | $10^{7.3-9.5}$ TCID$_{50}$/mL |
| Equine Influenza A2/Kentucky/95 | $10^{7.3-9.5}$ TCID$_{50}$/mL |
| Equine Influenza A2/NewMarket/2/93 | $10^{7.3-9.5}$ TCID$_{50}$/mL |
| Tetanus Toxoid | 5-10 CPU |
| Non-metabolizable Oil Adjuvant | 100-200 µL |
| Diluent - DMEM containing | q.s. |
| Gentamicin | 30 µg/mL of diluent volume |
| Formaldehyde | 0.1% of diluent volume |

Experimental serial 916 was formulated for host animal vaccination studies. Experimental serial 916 is a multi-component vaccine containing VEWT-WNV-EHV-1 and 3 strains of equine influenza type A2 virus. Experimental serial 916 is batched at $10^{7.6-9.2}$ TCID$_{50}$/mL of West Nile Virus antigen North American Equine E159(NAEE159). It is a 1 mL dose vaccine in the horse.

This vaccine was also tested in guinea pigs at the time of host animal vaccinations to confirm the WNV efficacy and laboratory animal potency. Four replicate guinea pig sera dilution experiments were performed for experimental serial 916 to validate a guinea pig assay criterion for this one-year duration of immunity (DOI) vaccine.

Experimental Serial 507 (Comparative Efficacy Serial)

Data from Experimental Serial 507 is included in this report to demonstrate that serials formulated with a North American Dominant isolate of WNV antigen show superior efficacy, measured as guinea pig titers, of the relevant North American Dominant isolates of WNV as compared to the earlier NY99 isolate.

Guinea Pig Serological Evaluation

Sera were tested for WNV antibody as follows:
1) West Nile Virus Indicator Strain: North American Equine E159(NAEE159) (ATCC Accession No. PTA-9409) & North American Donkey E159 (NADE159)
2) Growth medium for Vero Cells is DMEM+5% FBS, 2 mM L-glutamine and 30 µg/mL gentamycin
3) Diluent for Test Serum is DMEM plus 30 µg/mL gentamycin
4) Diluent for indicator virus working solution is DMEM+ 10% normal guinea pig serum (specific to WNV assay)
5) Guinea pig test sera is diluted 1:12
7) Use 4 mL overlay instead of 3 mL (specific to WNV assay)
8) Titers are calculated using 50% plaque reduction
9) Nine of ten vaccinated guinea pigs must have an antibody titer of 1:12 to demonstrate efficacy, and negative guinea pigs must be <1:4 (same criteria as VEE assay in SAM).

Results and Discussion

Serological Evaluation for West Nile Virus

TABLE 23

Number of Plaques/Sera Dilution
Experimental Serial 916 Replicate I West Nile Guinea Pig Plaque Reduction Neutralization
Results Using North American Equine E159 (NAEE159) as Indicator Virus
The study was initiated and the guinea pigs were bled 25 days later.

| 916 (I) | 2 | 3 | 4 | 6 | 8 | 12 | 16 | 32 | 64 |
|---|---|---|---|---|---|---|---|---|---|
| GP1 | 0 | 2 | 2 | 4 | 5.5 | 2.5 | 17 | 14 | 11 |
| GP2 | 6.5 | 9.5 | 11 | 14 | 9 | 11.5 | 13 | 20 | 22.5 |
| GP3 | 7 | 5 | 6 | 9.5 | 10 | 9.5 | 11 | 10 | 16.5 |
| GP4 | 7 | 5 | 4 | 4 | 1 | 6 | 15.5 | 9.5 | 12.5 |
| GP5 | 6 | 4.5 | 9 | 7 | 17.5 | 13.5 | 12 | 16 | 17 |
| GP6 | 1 | 1 | 2.5 | 7.5 | 3 | 8 | 19.5 | 19.5 | 20.5 |
| GP7 | 9.5 | 8 | 8 | 15.5 | 17.5 | 21.5 | 36 | 17.5 | 20.5 |
| GP8 | 5 | 3.5 | 7.5 | 7.5 | 14.5 | 11 | 26.5 | 26.5 | 27.5 |
| GP9 | 0 | 2 | 7 | 6 | 7 | 12 | 9 | 10.5 | 11.5 |
| GP10 | 4.5 | 4.5 | 5.5 | 11 | 22 | 8.5 | 23 | 29 | 30.5 |
| # Passed | 10/10 | 10/10 | 10/10 | 10/10 | 10/10 | 10/10 | 10/10 | 10/10 | 10/10 |
| Neg. Control 1 | 68.5 | 64.5 | 72.5 | 93.5 | 68 | 82 | 89.5 | 78.5 | 71 |
| Neg. Control 2 | 72 | 61 | 87 | 69.5 | 70.5 | 85.5 | 77.5 | 69.5 | 88 |

Virus Control Values: 99. 70, 68, 88, 77, 64
Virus Control Average Plaques: 79
Virus Control 50% Reduction: 39.5

TABLE 24

Experimental Serial 916 Replicate II West Nile Guinea Pig
Plaque Reduction Neutralization
Results Using North American Equine E159(NAEE159) as Indicator Virus
Guinea Pigs were bled 35 days after the initiation of the study
Number of Plaques/Sera Dilution

| 916 (II) | 2 | 3 | 4 | 6 | 8 | 12 | 16 | 32 | 64 |
|---|---|---|---|---|---|---|---|---|---|
| GP1 | 1 | 3 | 6 | 6 | 14.5 | 6.5 | 13.5 | 18 | 17.5 |
| GP2 | 1.5 | 3.5 | 6.5 | 6.5 | 8.5 | 9.5 | 10.5 | 12.5 | 19 |
| GP3 | 12 | 5.5 | 22 | 21 | 41.5 | 34 | 41 | 41 | 43.5 |
| GP4 | 4 | 8.5 | 17.5 | 16.5 | 21 | 36.5 | 28 | 41.5 | 42.5 |
| GP5 | 3.5 | 4.5 | 9.5 | 15 | 26.5 | 25.5 | 13.5 | 23 | 40 |
| GP6 | 1 | 3 | 7 | 13.5 | 17.5 | 14 | 24.5 | 26 | 23 |
| GP7 | 8 | 5.5 | 14.5 | 11.5 | 21.5 | 15.5 | 34 | 26.5 | 28 |
| GP8 | 1 | 1.5 | 2.5 | 3.5 | 4 | 11 | 9 | 20 | 17.5 |
| GP9 | 13.5 | 18 | 25.5 | 29.5 | 29.5 | 35.5 | 28 | 37.5 | 43 |
| GP10 | 9 | 8 | 10.5 | 21.5 | 21 | 20.5 | 27 | 31.5 | 27.5 |
| # Passed | 10/10 | 10/10 | 10/10 | 10/10 | 9/10 | 10/10 | 9/10 | 8/10 | 6/10 |
| Neg. Control 1 | 69.5 | 67 | 71.5 | 69.5 | 72.5 | 73 | 83 | 68 | 78 |
| Neg. Control 2 | 68 | 70.5 | 69 | 72.5 | 82.5 | 66 | 75 | 76 | 74 |

Virus Control Values: 99. 70, 68, 88, 77, 64
Virus Control Average Plaques: 79
Virus Control 50% Reduction: 39.5

TABLE 25

Experimental Serial 916 Replicate III West Nile Guinea Pig
Plaque Reduction Neutralization
Results Using North American Equine E159(NAEE159) as Indicator Virus
Guinea Pigs were bled 35 days after initiation
Number of Plaques/Sera Dilution

| 916 (III) | 2 | 3 | 4 | 6 | 8 | 12 | 16 | 32 | 64 |
|---|---|---|---|---|---|---|---|---|---|
| GP1 | 0.5 | 1.5 | 0 | 0 | 0 | 1 | 4 | 6 | 3.5 |
| GP2 | 0 | 0 | 1 | 0.5 | 0 | 0 | 0 | 0 | 0 |
| GP3 | 7.5 | 9 | 9 | 16 | 17 | 13.5 | 12 | 18.5 | 23 |
| GP4 | 2.5 | 0 | 0 | 3 | 2 | 2 | 3.5 | 1 | 2.5 |
| GP5 | 13.5 | 15.5 | 18 | 18 | 19.5 | 24 | 16.5 | 21.5 | 33.5 |
| GP6 | 6.5 | 15.5 | 31.5 | 10 | 29.5 | 26.5 | 28.5 | 31.5 | 32 |
| GP7 | 14.5 | 12 | 17.5 | 20.5 | 19.5 | 29.5 | 21.5 | 16 | 22.5 |
| GP8 | 21 | 24.5 | 36 | 28 | 34.5 | 30.5 | 27.5 | 29 | 26 |
| GP9 | 0.5 | 0.5 | 3 | 4 | 6.5 | 5 | 10 | 9.5 | 18 |
| GP10 | 2.5 | 7.5 | 11 | 8 | 12.5 | 9 | 20 | 10.5 | 17 |
| # Passed | 10/10 | 10/10 | 8/10 | 10/10 | 9/10 | 10/10 | 10/10 | 9/10 | 8/10 |
| Neg. Control 1 | 73 | 61.5 | 79.5 | 53.5 | 58.5 | 78 | 57 | 70 | 63 |
| Neg. Control 2 | 55 | 54.5 | 64 | 52.5 | 58 | 68.5 | 66 | 67.5 | 79 |

Virus Control Values: 51, 58, 61, 66, 78
Virus Control Average Plaques: 62
Virus Control 50% Reduction: 31

TABLE 26

Experimental Serial 916 Replicate IV West Nile Guinea Pig
Plaque Reduction Neutralization
Results Using North American Equine E159(NAEE159) as Indicator Virus
Guinea Pigs were bled 30 days after the initiation of the study
Number of Plaques/Sera Dilution

| 916 (IV) | 2 | 3 | 4 | 6 | 8 | 12 | 16 | 32 | 64 |
|---|---|---|---|---|---|---|---|---|---|
| GP1 | 11.5 | 7 | 5.5 | 20.5 | 12 | 17.5 | 22.5 | 20 | 25 |
| GP2 | 31 | 21.5 | 20.5 | 36.5 | 32 | 30 | 27 | 15 | 28.5 |
| GP3 | 16 | 20.5 | 18 | 23.5 | 21.5 | 16 | 35.5 | 16.5 | 15 |
| GP4 | 1 | 2 | 6.5 | 7 | 11 | 15 | 19 | 14 | 18.5 |
| GP5 | 4 | 1 | 9.5 | 12 | 20 | 17 | 24.5 | 19.5 | 23.5 |
| GP6 | 0 | 0 | 0 | 1.5 | 2.5 | 2.5 | 0.5 | 3 | 3 |
| GP7 | 5.5 | 6.5 | 5.5 | 10 | 7 | 13 | 5.5 | 9.5 | 13 |
| GP8 | 1 | 4.5 | 0.5 | 3 | 7.5 | 4.5 | 13.5 | 17.5 | 11.5 |
| # Passed | 8/8 | 8/8 | 8/8 | 7/8 | 8/8 | 8/8 | 7/8 | 8/8 | 8/8 |

TABLE 26-continued

Experimental Serial 916 Replicate IV West Nile Guinea Pig
Plaque Reduction Neutralization
Results Using North American Equine E159(NAEE159) as Indicator Virus
Guinea Pigs were bled 30 days after the initiation of the study
Number of Plaques/Sera Dilution

| 916 (IV) | 2 | 3 | 4 | 6 | 8 | 12 | 16 | 32 | 64 |
|---|---|---|---|---|---|---|---|---|---|
| Neg. Control 1 | 48 | 39 | 46.5 | 39 | 48 | 54 | 39.5 | 54 | 67.5 |
| Neg. Control 2 | 40.5 | 53 | 44 | 44.5 | 54 | 48.5 | 59.5 | 61.5 | 45.5 |

Virus Control Values: 93, 53, 56, 92, 67, 44
Virus Control Average Plaques: 67.5
Virus Control 50% Reduction: 33.8

EXPERIMENTAL SERIAL 507(Demonstrating Superior Efficacy of North American Equine E159(NAEE159) Vaccines, and that other North American Dominant Vaccines, such as North American Donkey E159(NADE159 will provide superior efficacy to NY99 vaccines)

Guinea Pig Serological Evaluation for West Nile Virus

TABLE 27

Experimental Serial 507 West Nile Guinea Pig Plaque Reduction
Neutralization Results using WNV NY1999 Isolate as Indicator Virus
Number of Plaques/Sera Dilution

| Guinea Pig Number | 4 | 8 | 16 | 32 | 64 |
|---|---|---|---|---|---|
| GP1 | ≥10 | ≥15 | ≥15 | ≥14.5 | ≥10.5 |
| GP2 | 4.5 | 5 | 7.5 | 9.5 | 13 |
| GP3 | 1 | 3.5 | 3.5 | 6 | 6.5 |
| GP4 | 8 | 11.5 | ≥13.5 | ≥14.5 | ≥14.5 |
| GP5 | 6 | 7.5 | 7.5 | 8.5 | 9 |
| GP6 | 8.5 | 9.5 | 9.5 | 12 | 14 |
| GP7 | 7 | 8.5 | 9 | ≥10.5 | ≥14.5 |
| GP8 | 5 | 10.5 | 10.5 | 14 | 14 |
| GP9 | 5.5 | 7 | 7.5 | 10 | 10 |
| GP10 | 5.5 | 6.5 | 8.5 | ≥12.5 | 14 |
| # Passed | 9/10 | 6/10 | 5/10 | 2/10 | 1/10 |
| Neg. Control 1 | ≥13.5 | ≥13.5 | ≥13 | ≥13 | ≥14.5 |
| Neg. Control 2 | ≥15.5 | ≥14.5 | ≥16 | ≥17 | ≥16.5 |

Virus Control Values: ≥24, ≥15, ≥14, ≥16, ≥18, ≥20
Virus Control Average Plaques: ≥17.8
Virus Control 50% Reduction: ≥8.9

TABLE 28

Experimental Serial 507 West Nile Guinea Pig Plaque
Reduction Neutralization
Results Using North American Equine
E159(NAEE159) as Indicator Virus
Number of Plaques/Sera Dilution

| Guinea Pig Number | 2 | 4 | 8 | 16 | 32 | 64 |
|---|---|---|---|---|---|---|
| GP1 | 17 | 14 | 18.5 | 14.5 | 19.5 | 26 |
| GP2 | 2.5 | 3.5 | 2 | 6 | 17 | 15 |
| GP3 | 5.5 | 10 | 4.5 | 9 | 5 | 11.5 |
| GP4 | 11.5 | 10 | 15 | 15.5 | 19 | 19.5 |
| GP5 | 13 | 23 | 23.5 | 19.5 | 32.5 | 13 |
| GP6 | 5.5 | 8.5 | 12 | 11 | 13 | 14 |
| GP7 | 8.5 | 12 | 14 | 15 | 16 | 12 |
| GP8 | 14.5 | 14 | 18 | 19.5 | 25.5 | 27.5 |
| GP9 | 1.5 | 3 | 3 | 8.5 | 15.5 | 7 |
| GP10 | 12.5 | 12 | 7 | 18.5 | 14 | 13 |
| # Passed | 9/10 | 9/10 | 7/10 | 7/10 | 5/10 | 7/10 |

TABLE 28-continued

Experimental Serial 507 West Nile Guinea Pig Plaque
Reduction Neutralization
Results Using North American Equine
E159(NAEE159) as Indicator Virus
Number of Plaques/Sera Dilution

| Guinea Pig Number | 2 | 4 | 8 | 16 | 32 | 64 |
|---|---|---|---|---|---|---|
| Neg. Control 1 | 24.5 | 21 | 22 | 23.5 | 22 | 25 |
| Neg. Control 2 | 24 | 33 | 29 | 29 | 24.5 | 34.5 |

Virus Control Values: 40, 38, 34, 35, 28, 23
Virus Control Average: 33
Virus Control 50% Reduction: 16.5

Discussion and Conclusions

Guinea pigs were vaccinated and sera tested for West Nile Virus antibody. This assay established that a titer of 1:12 in vaccinated guinea pigs correlates to protection in a horse vaccination/challenge study that provides at least one year duration of immunity for WNV vaccine prepared using a North American Dominant isolate of WNV, such as North American Equine E159(NAEE159).

Concurrently with guinea pig vaccinations, WNV vaccine prepared using a North American Dominant isolate of WNV, North American Equine E159(NAEE159), was also administered to horses (20 vaccinates and 10 controls) via primary immunization followed by booster immunization 3 weeks later. More than one year post-booster vaccination, horses were subjected to virulent West Nile Virus challenge, and were protected when compared to non-vaccinated controls. Vaccinated horses were protected from viremia, clinical signs, mortality, and encephalitic lesions after virulent heterologous challenge with West Nile Virus.

In addition the data substantiate the superior efficacy of WNV vaccines prepared using North American Dominant WNV, as opposed to previously developed vaccines derived from WNV NY99. The sera from the vaccinated guinea pigs were tested for neutralizing antibody to both a North American Dominant isolate of WNV and to WNV isolate NY99. Titers to the isolate frequently occurring in North America, namely North American Dominant (NAEE159), were consistently higher in vaccinated guinea pigs as compared to titers to the isolate that is no longer reported to be present in nor causing disease in North America, WNV NY99. Hence, the vaccine displayed superior activity in stimulating neutralizing antibodies to North American Dominant WNV, as opposed to NY99 WNV. These data support the conclusion of the superior efficacy of WNV vaccines prepared from North American Dominant WNV isolates as contrasted with earlier less effective vaccines prepared from or based on the NY99 WNV isolate.

Example 10

This Example illustrates the genetic differences between North American WNV strains and North American Dominant WNV strains, as used in the present invention.

Materials and Methods

Relevant areas of the genome of WNV NY99 and the North American Dominant WNV isolates suitable for preparation of a novel, superior vaccine were sequenced and compared to confirm the key genetic differences. Examples of North American Dominant isolates used in vaccine preparation include North American Equine E159(NAEE159) (ATCC Accession No. PTA-9409) and North American Donkey E159 (NADE159).

Results and Conclusions

Figure 10B:
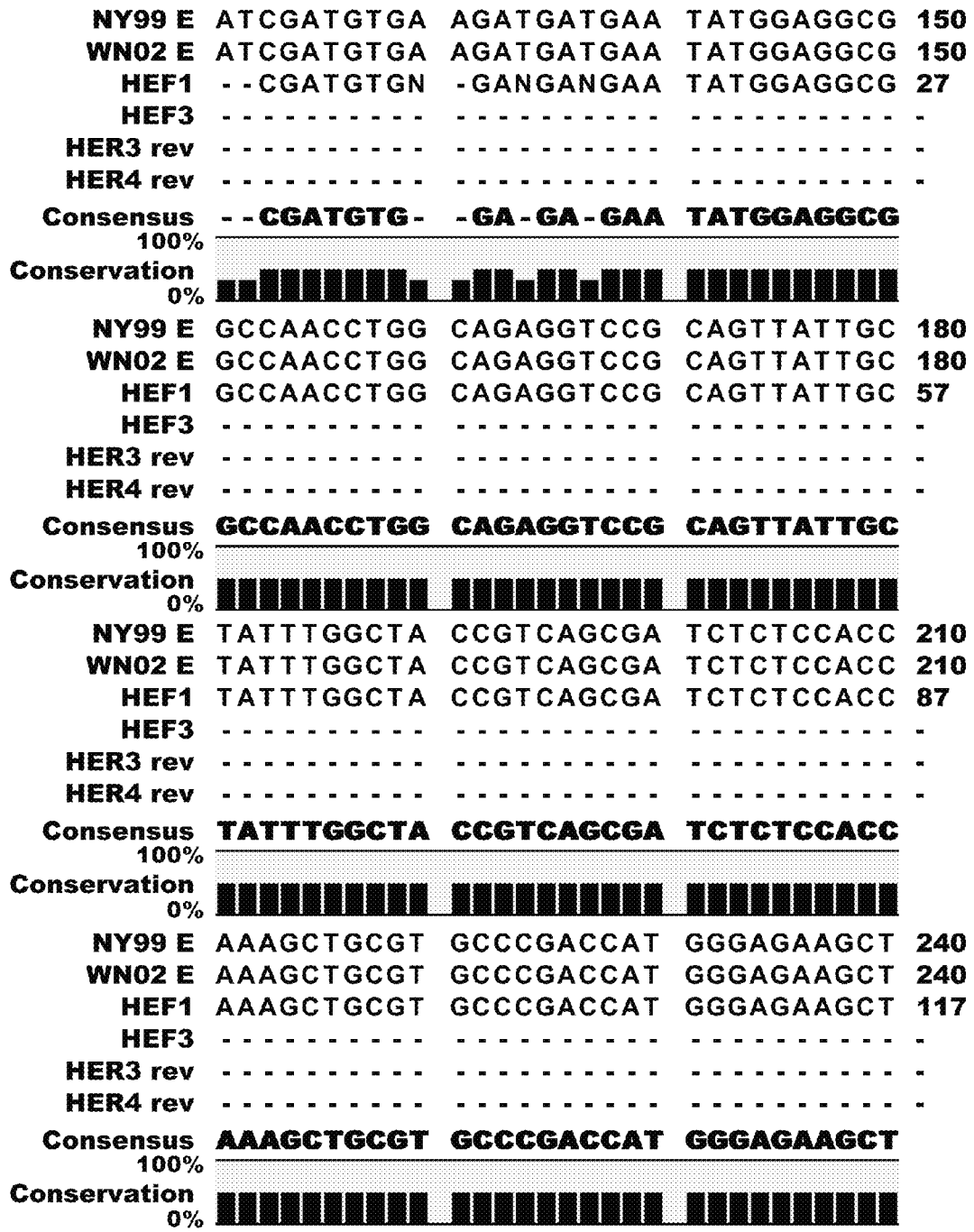
Figure 10C:
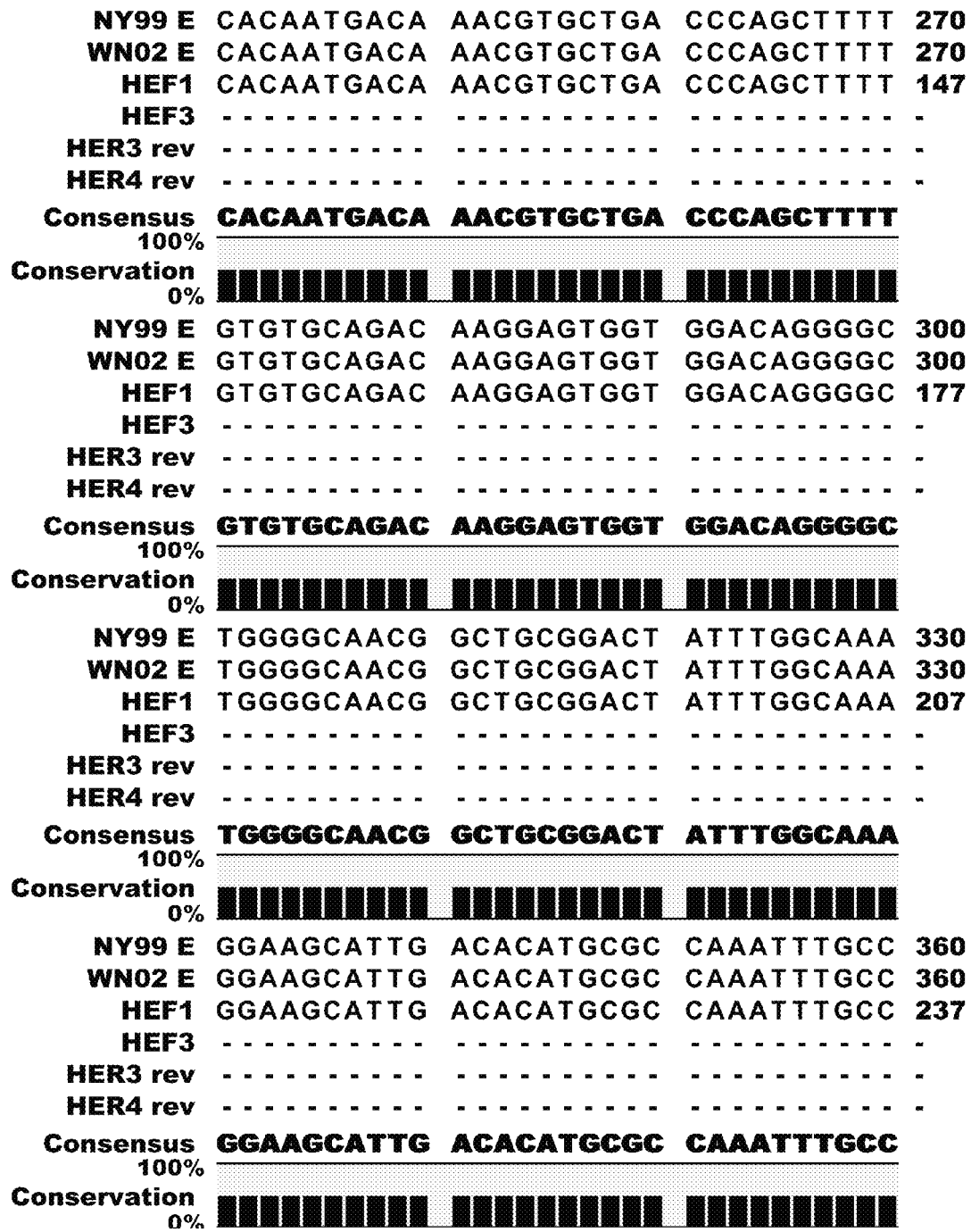
Figure 10D:
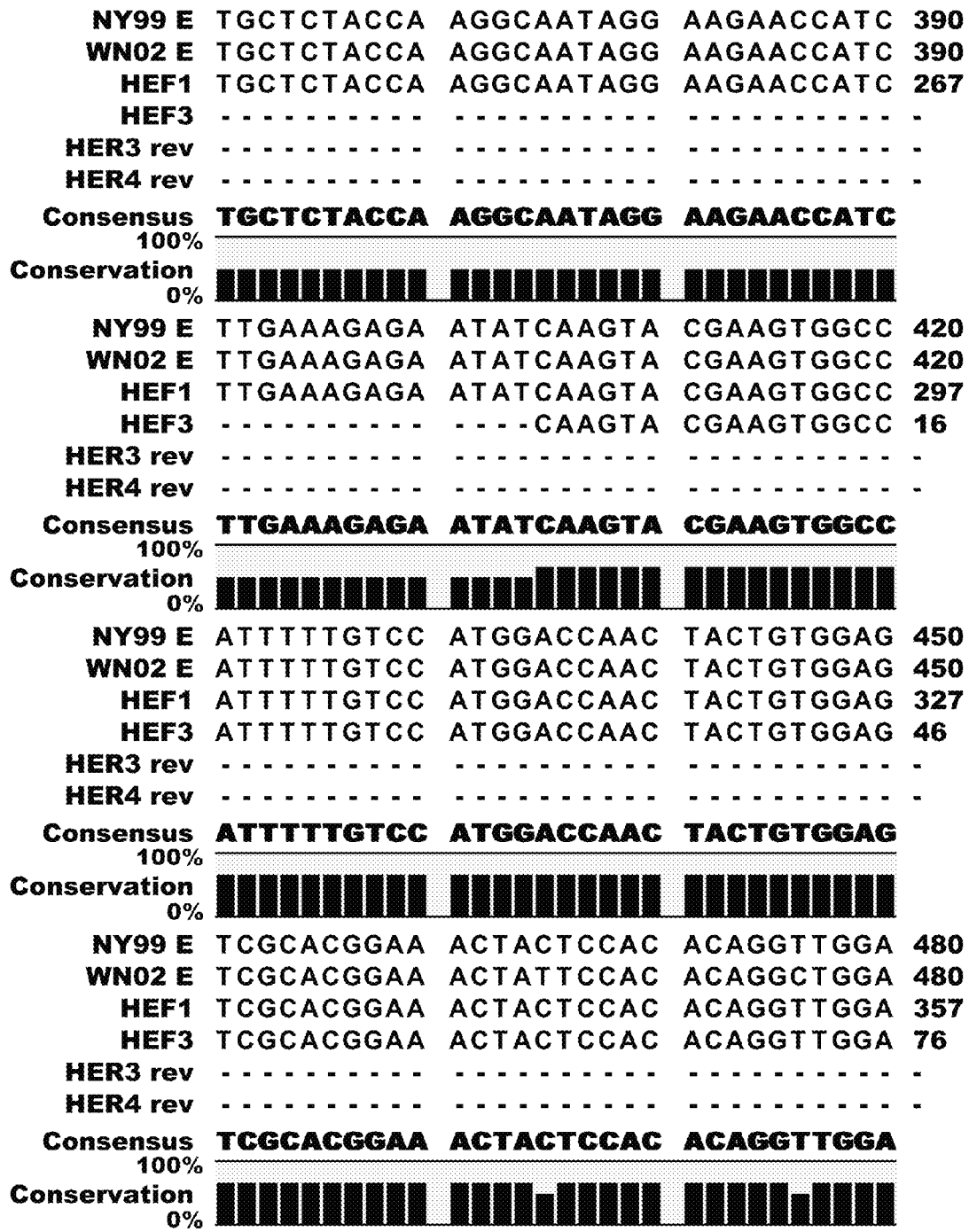
Figure 10E:
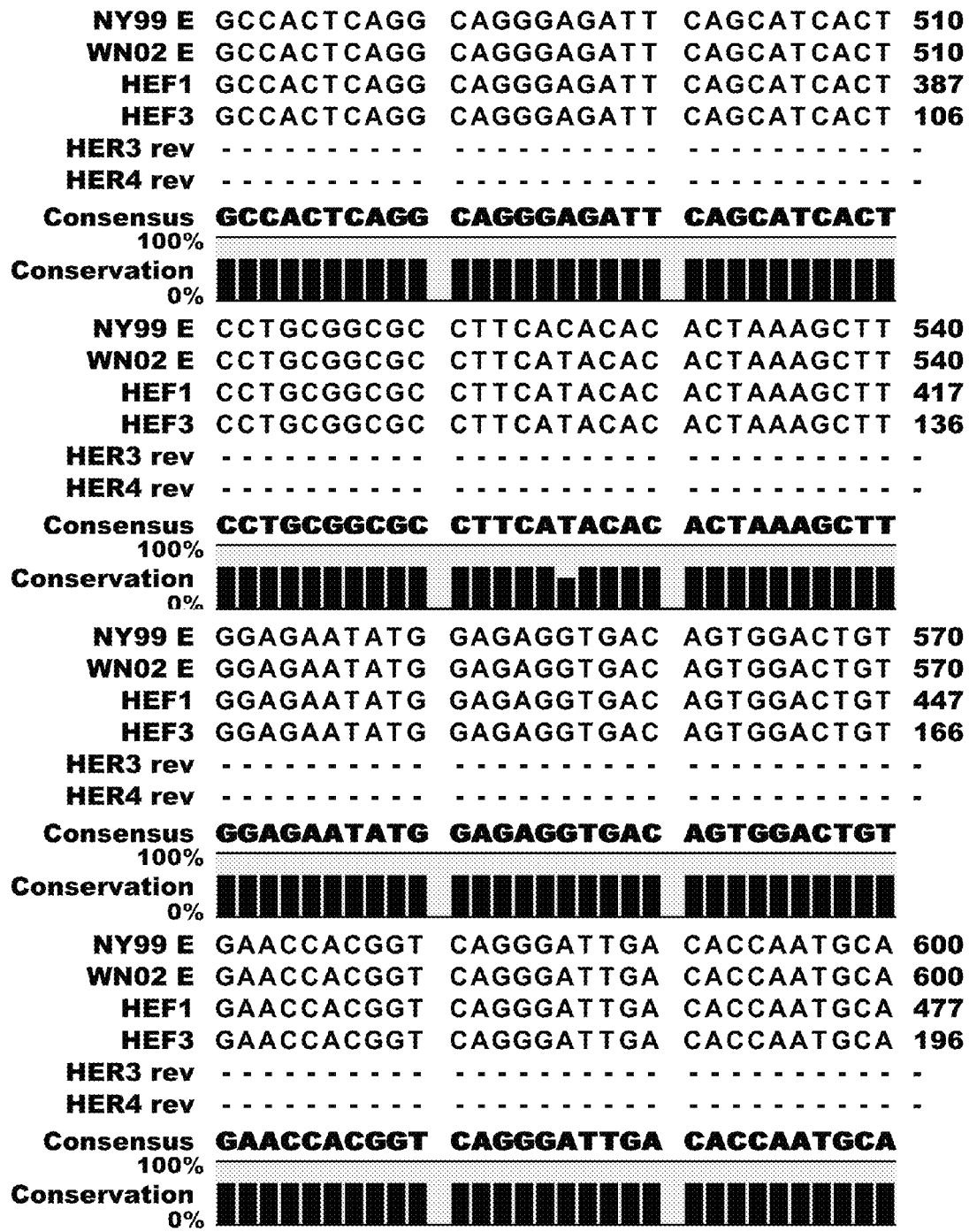
Figure 10G:
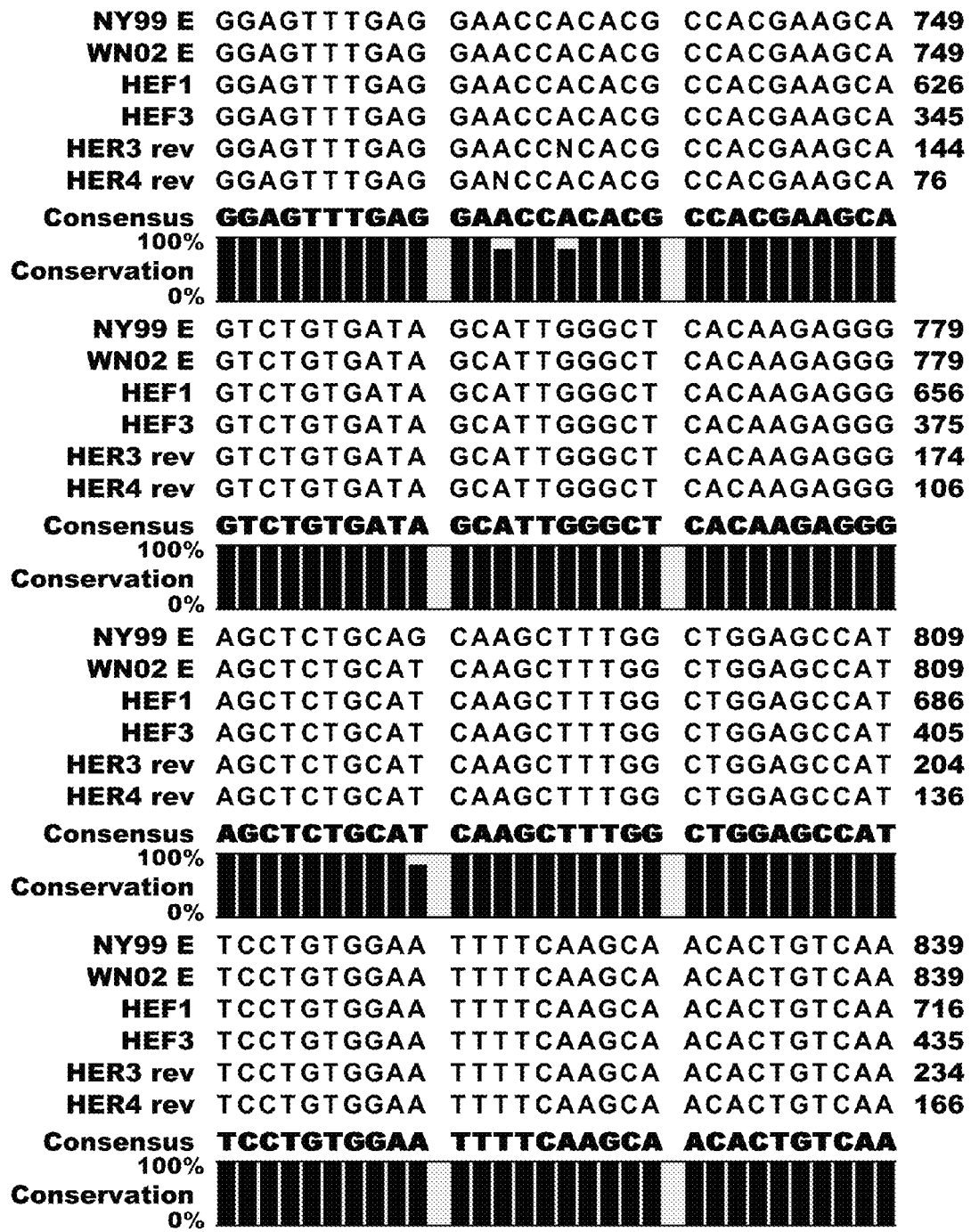
Figure 10M:
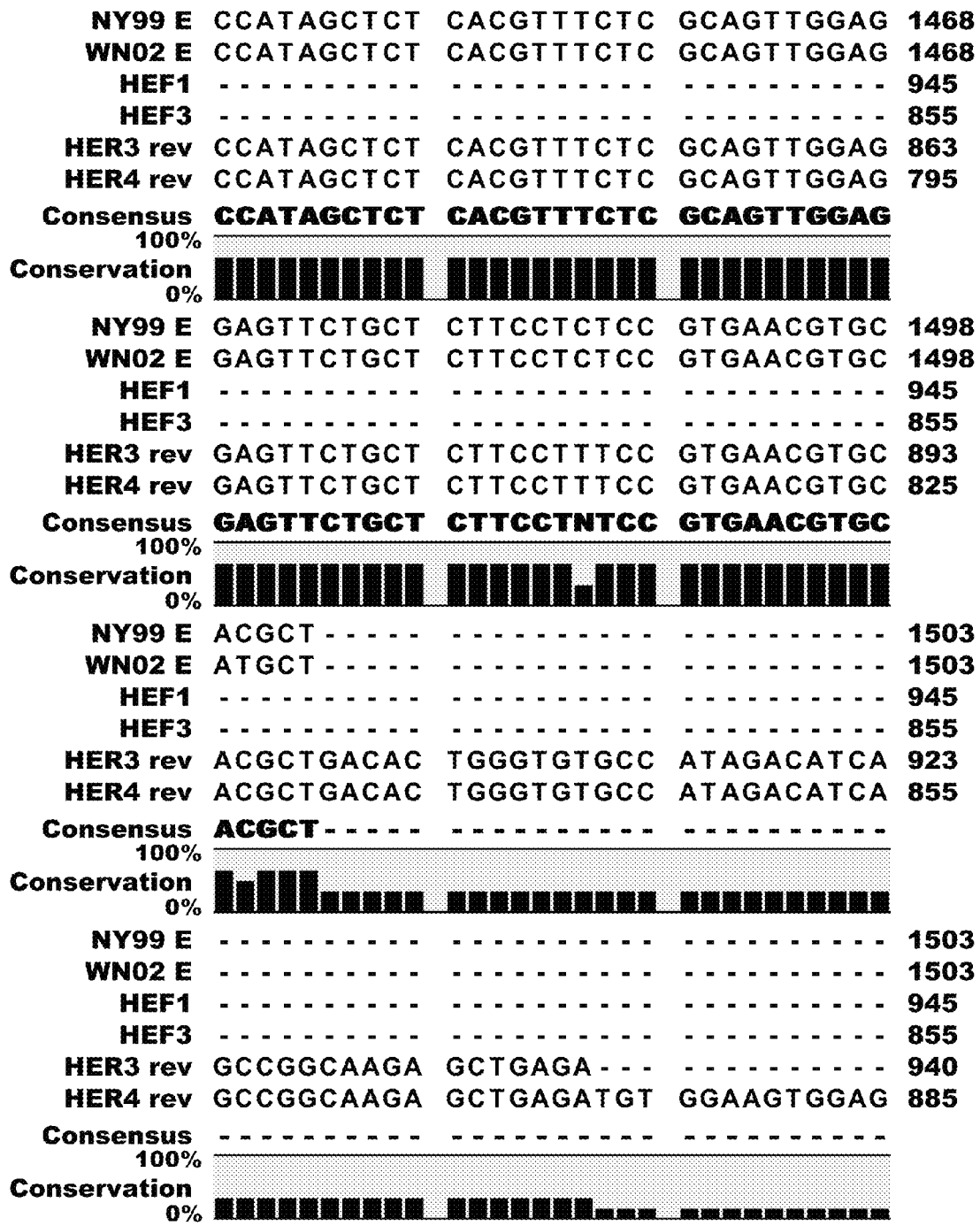
Figure 11L:
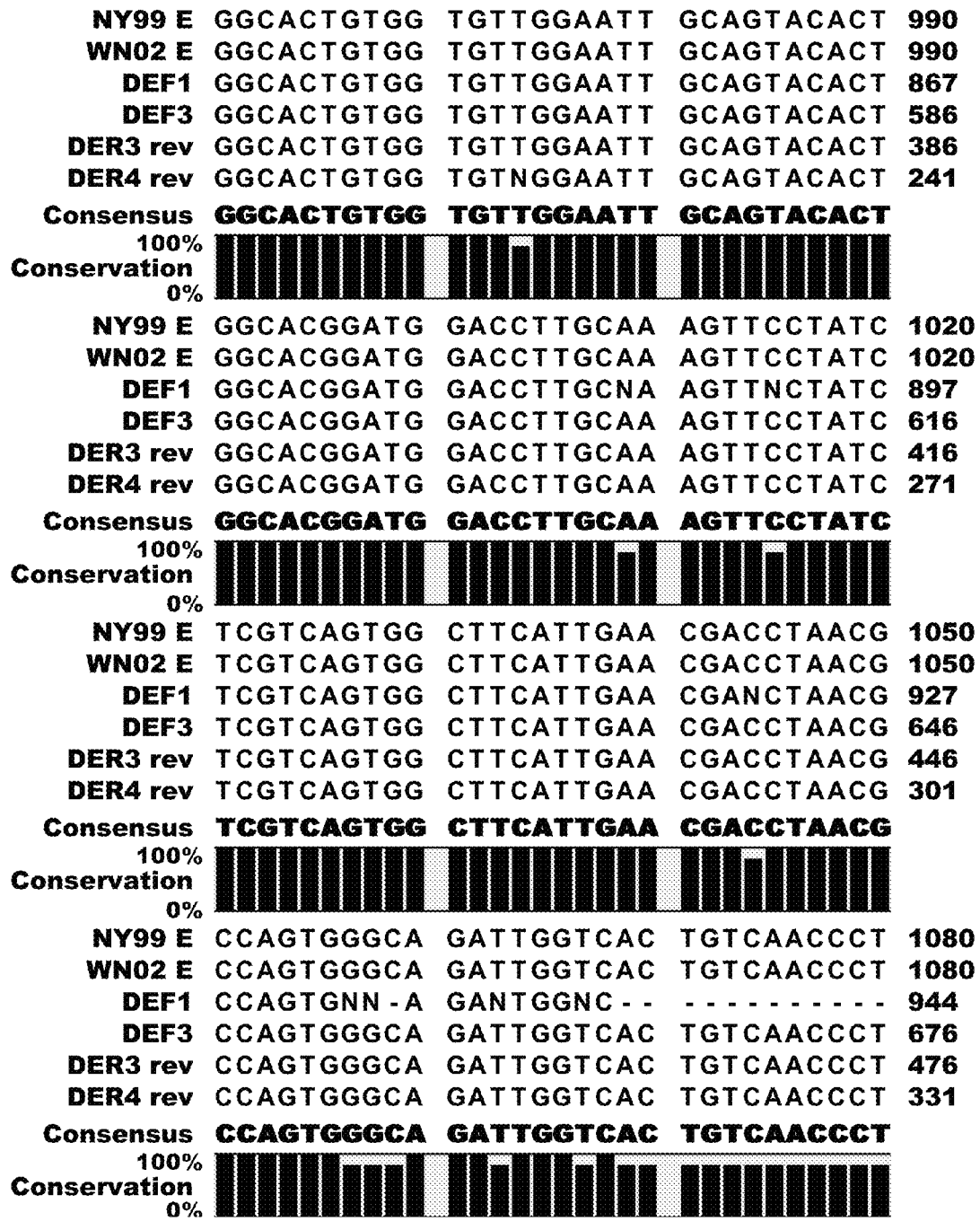
FIG. 11A through 11O is a nucleotide alignment of the DE region of WNV isolates (SEQ ID NOS 17-18 and 29-32, respectively, in order of appearance)
Figure 11K:
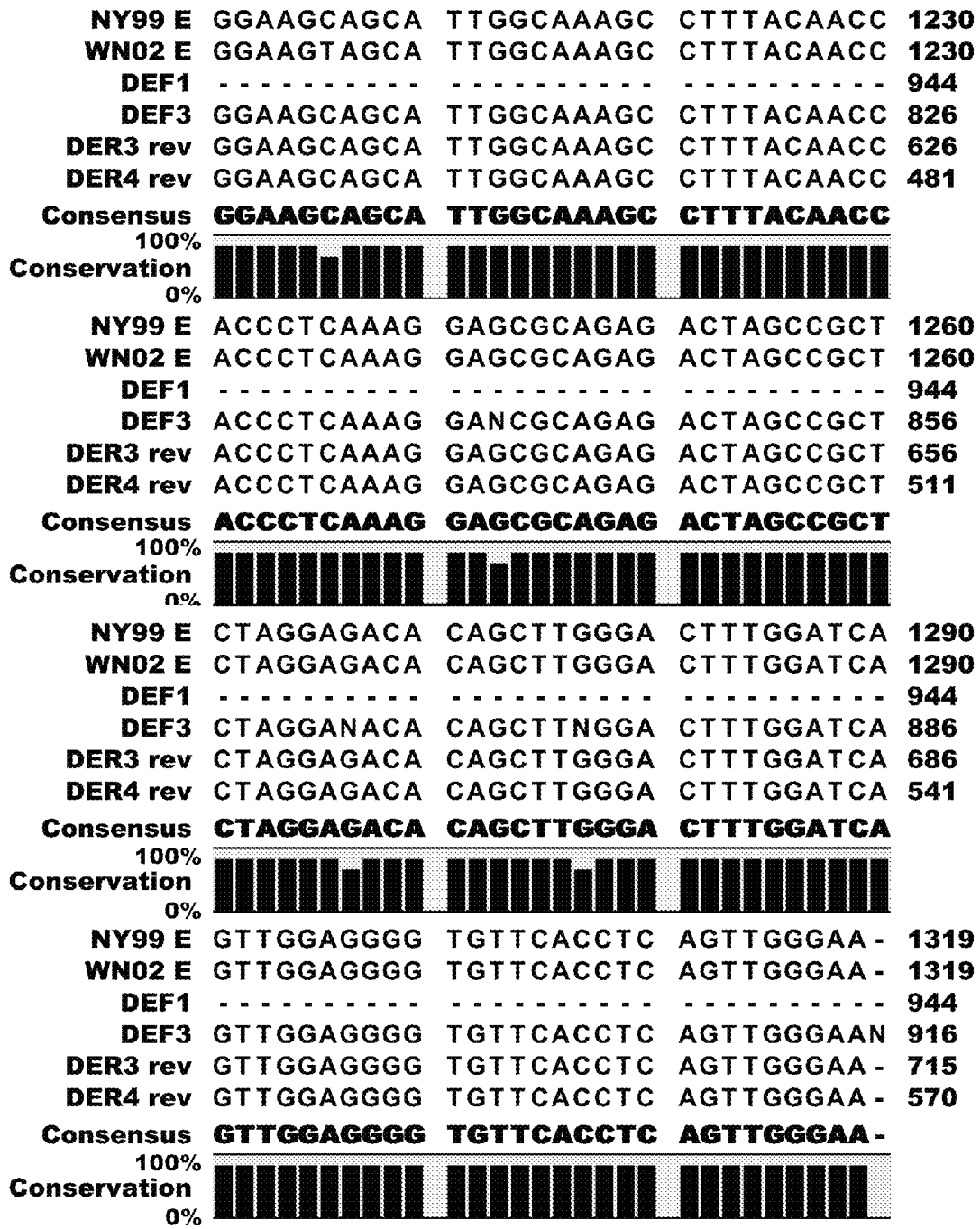
Figure 12B:
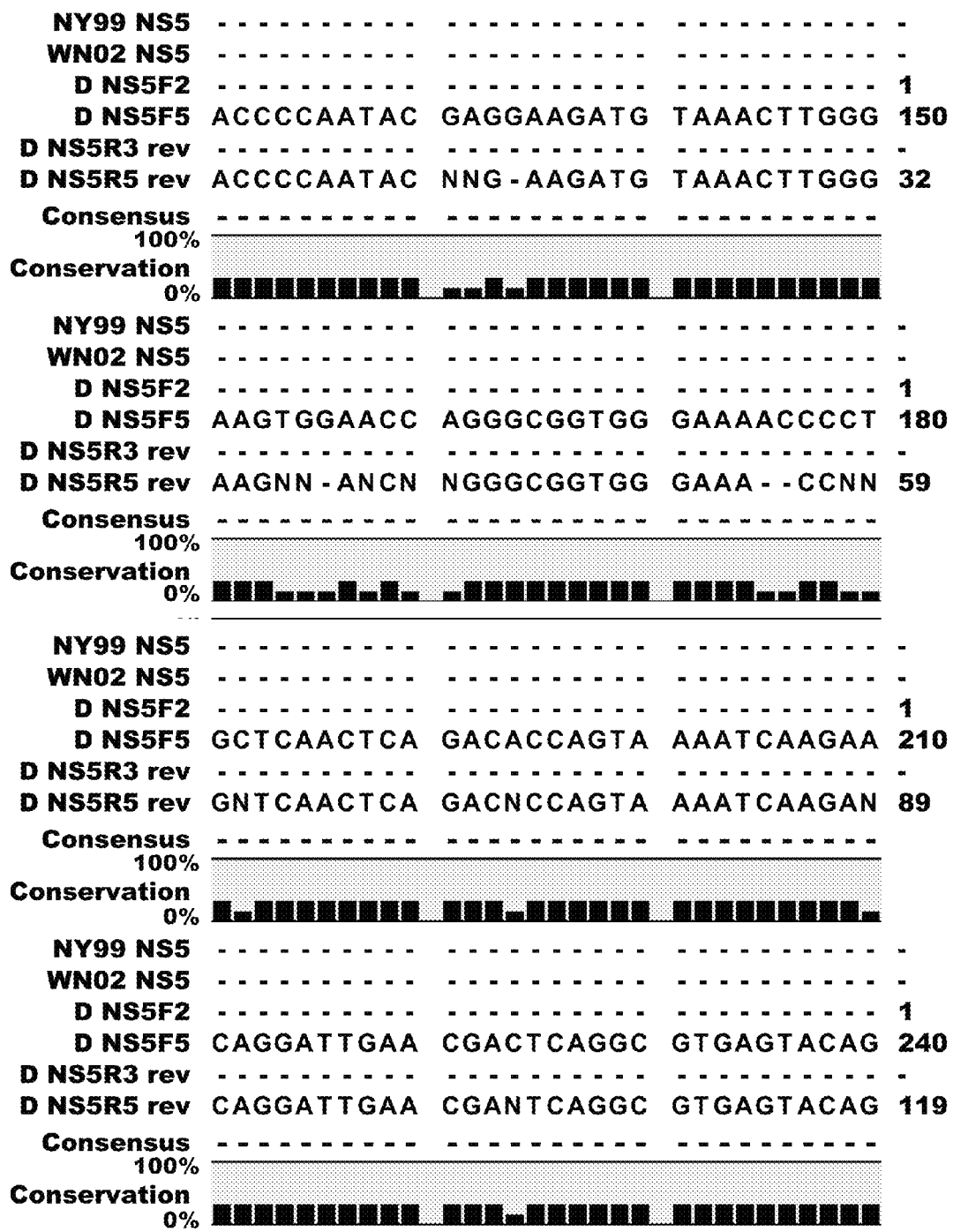
Figure 12D:
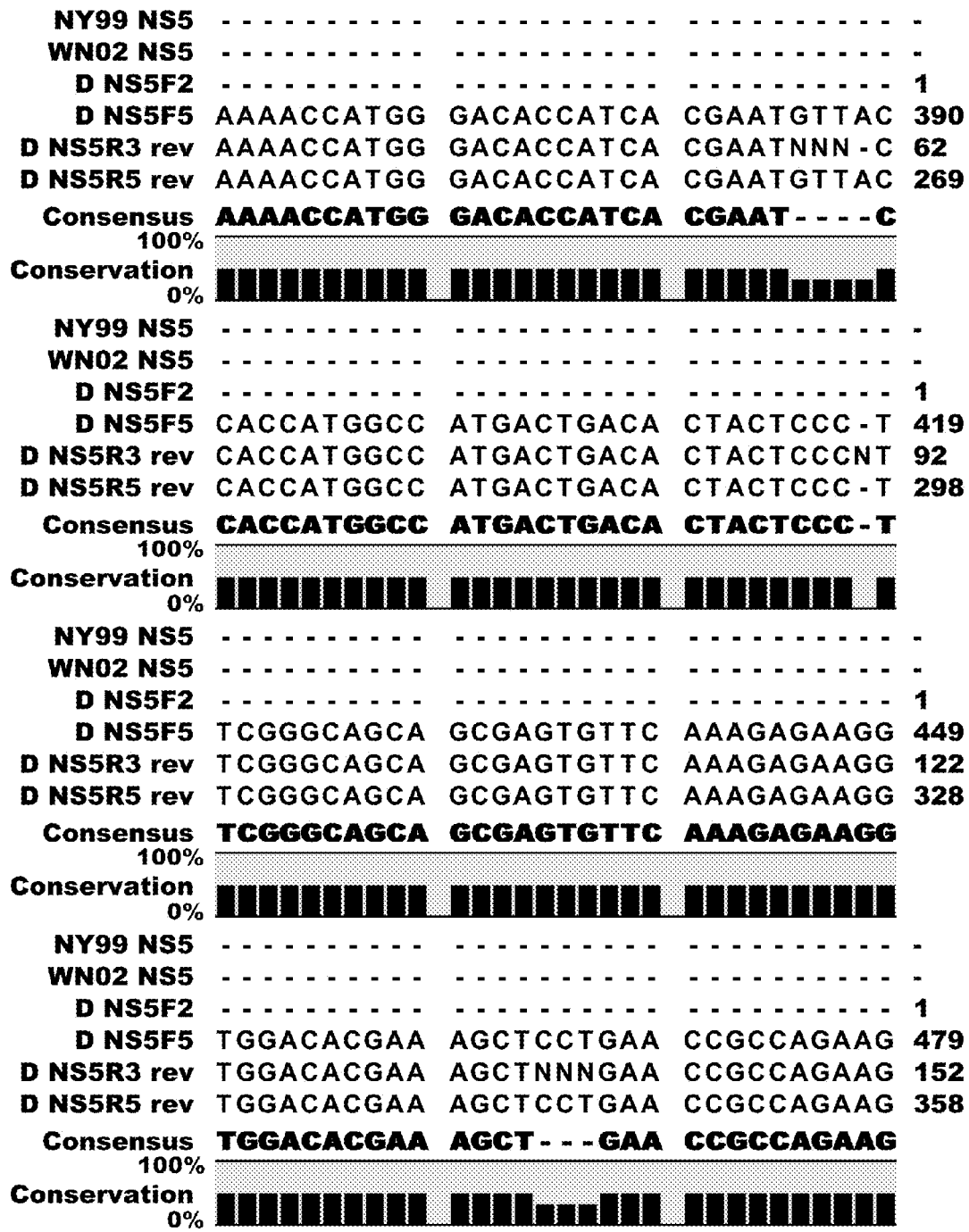
Figure 12F:
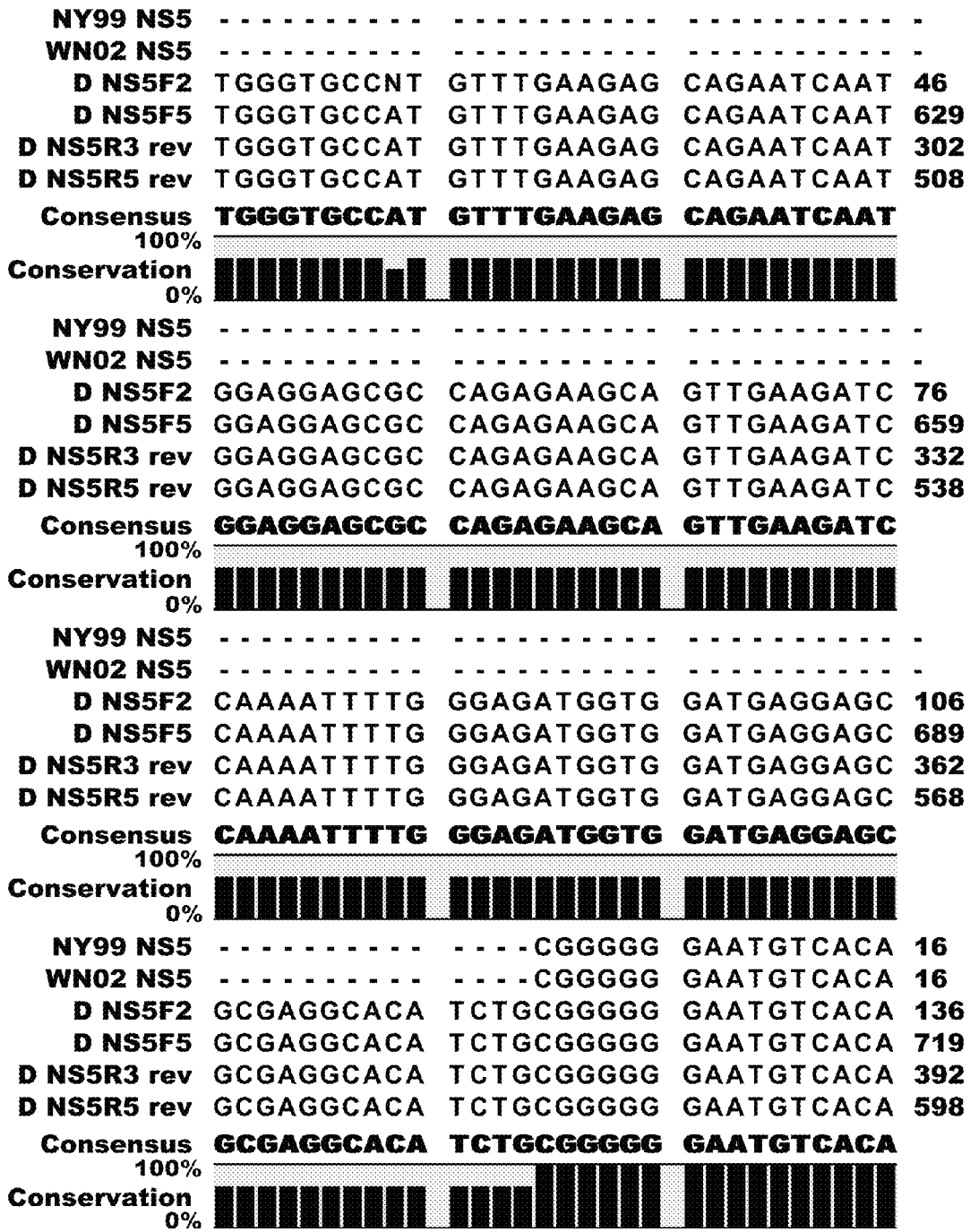
Figure 13A:
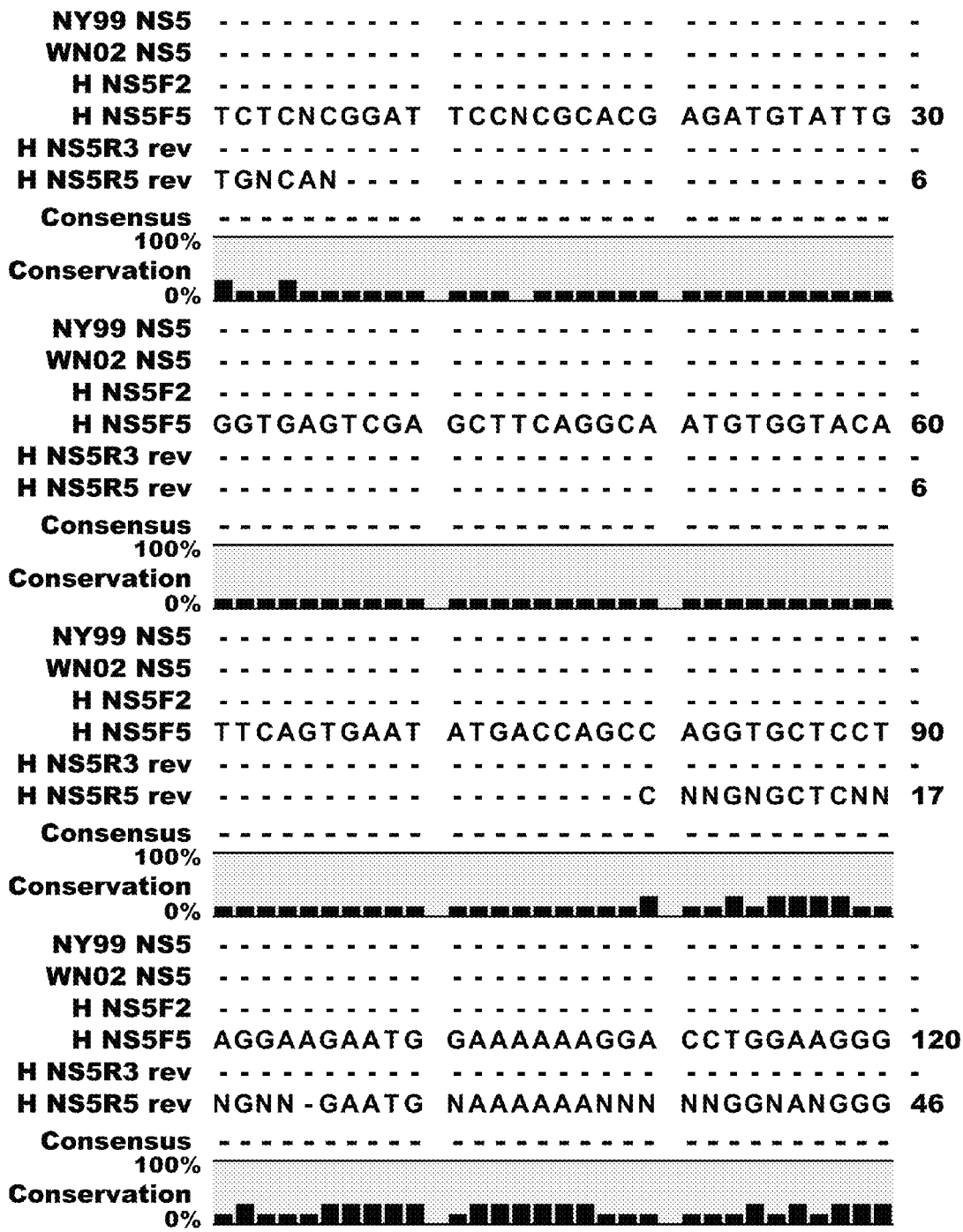
Figure 13B:
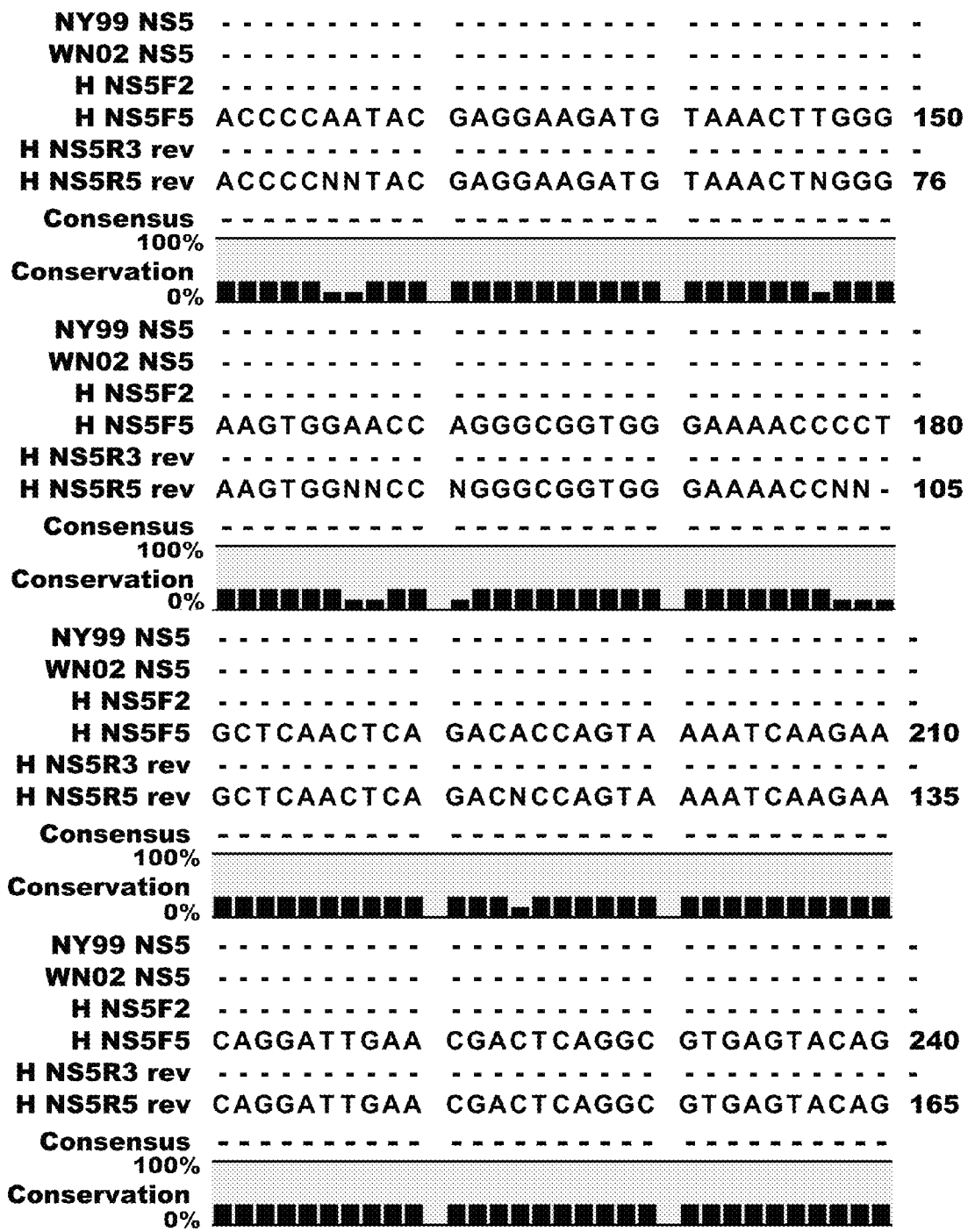
Figure 13C:
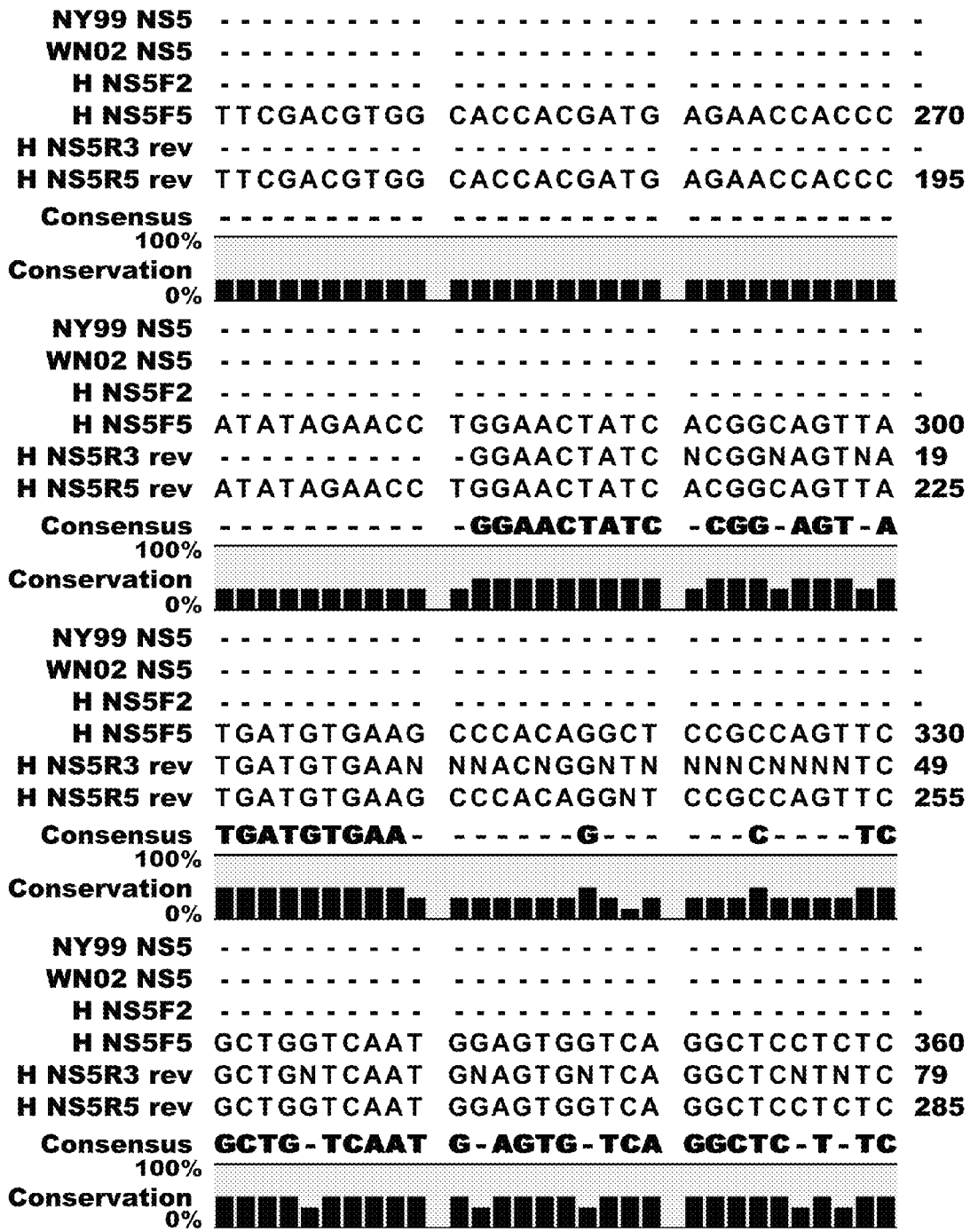
Figure 13G:
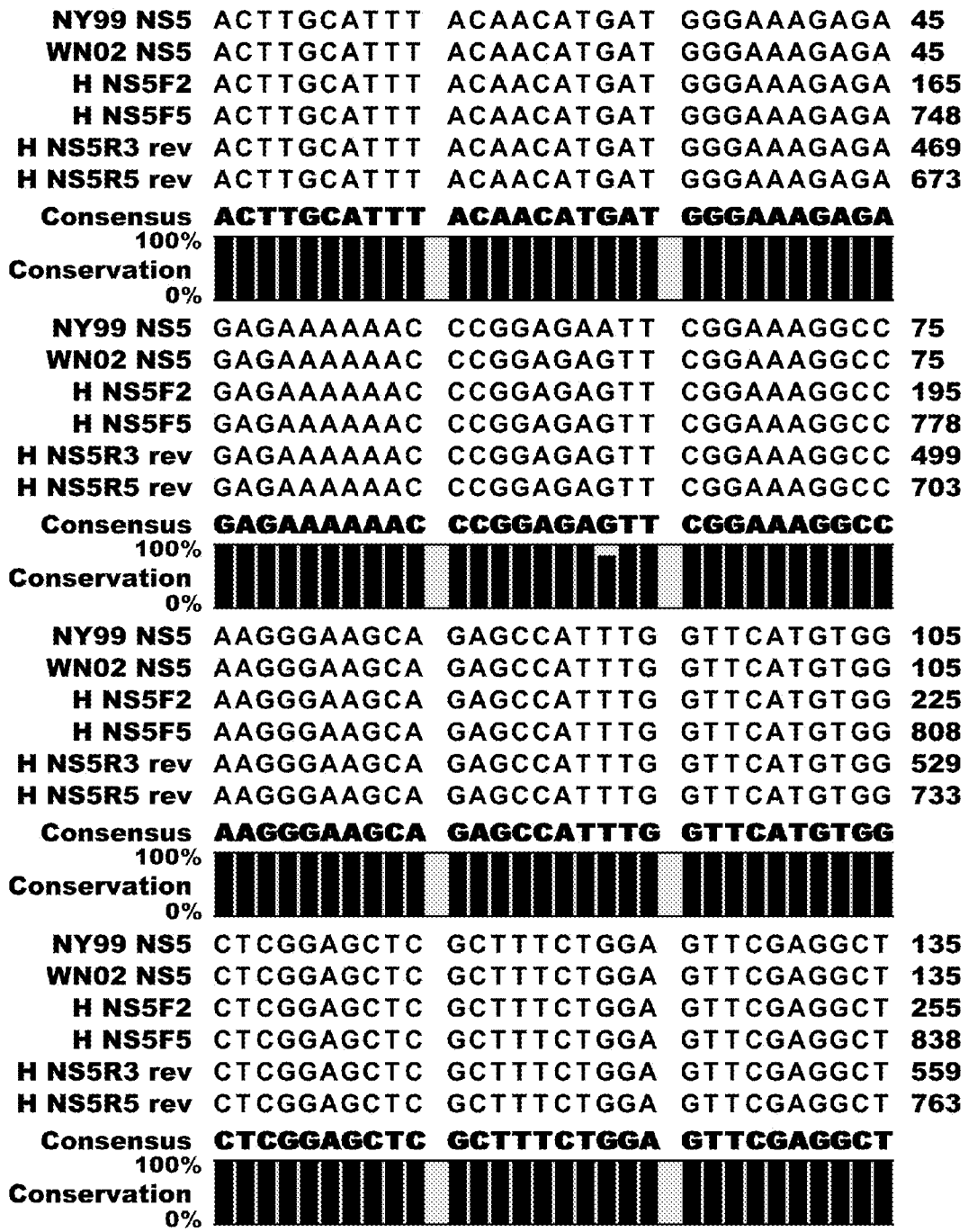
Figure 14A:
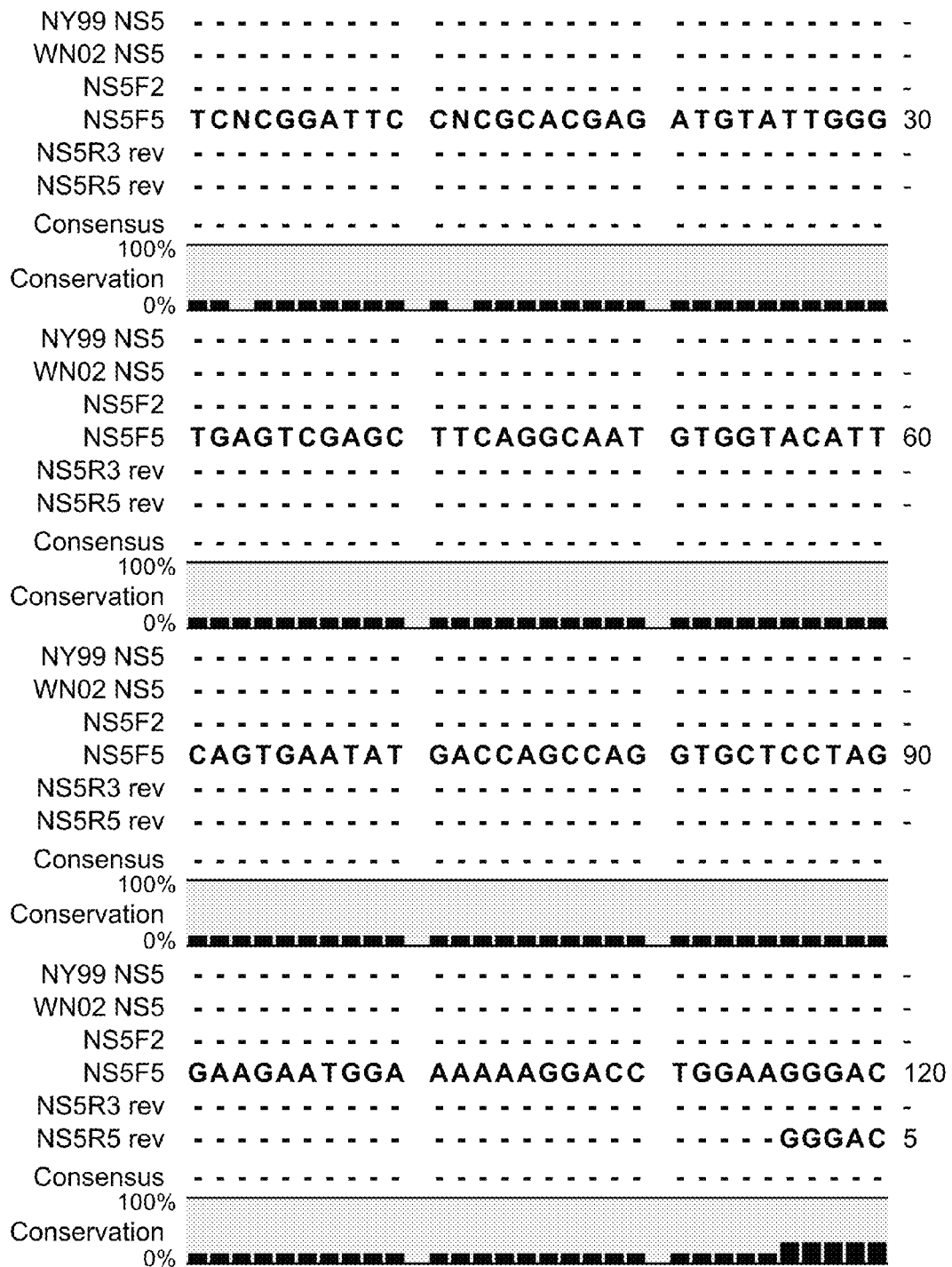
Figure 14B:
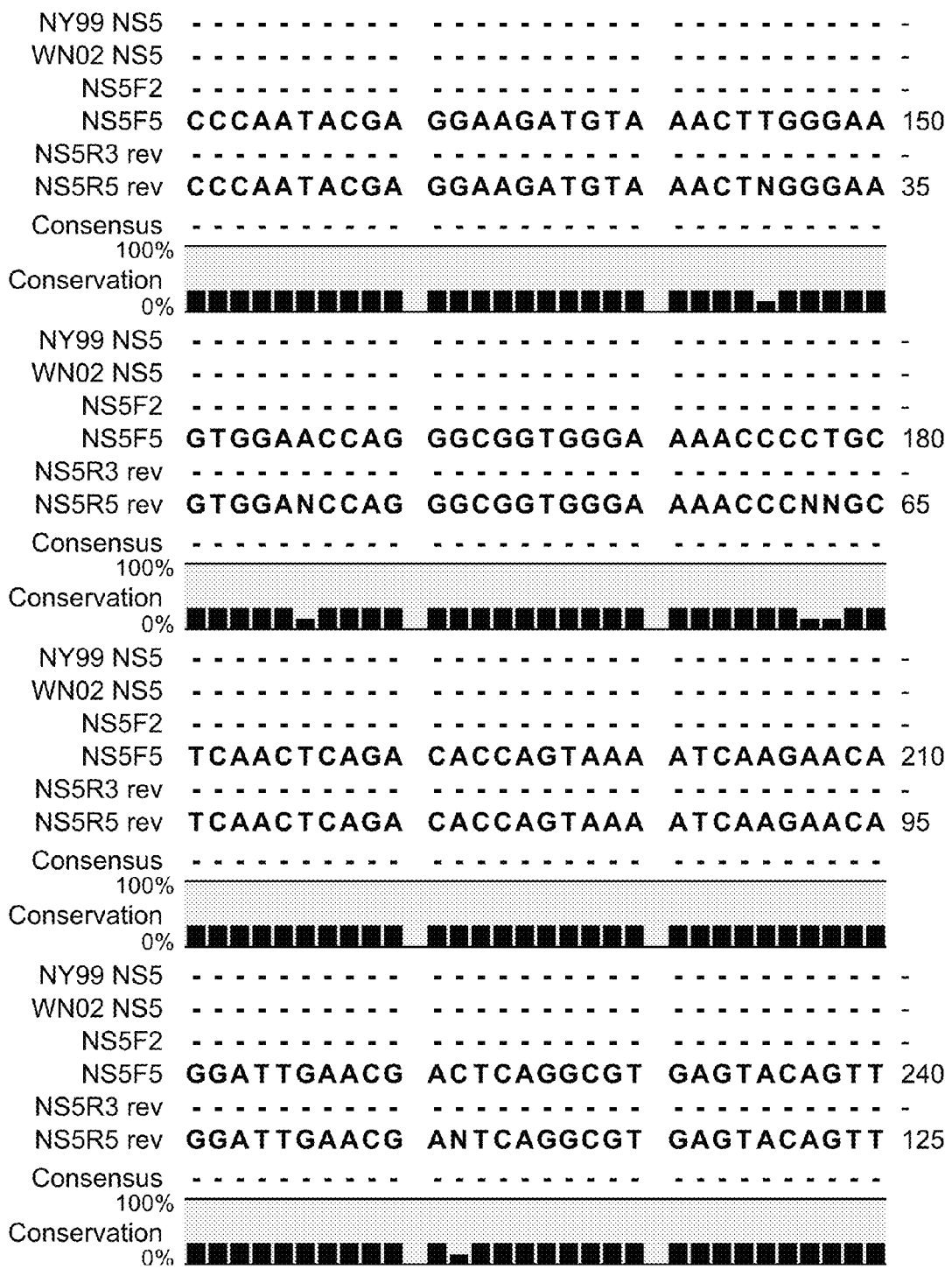
Figure 14E:
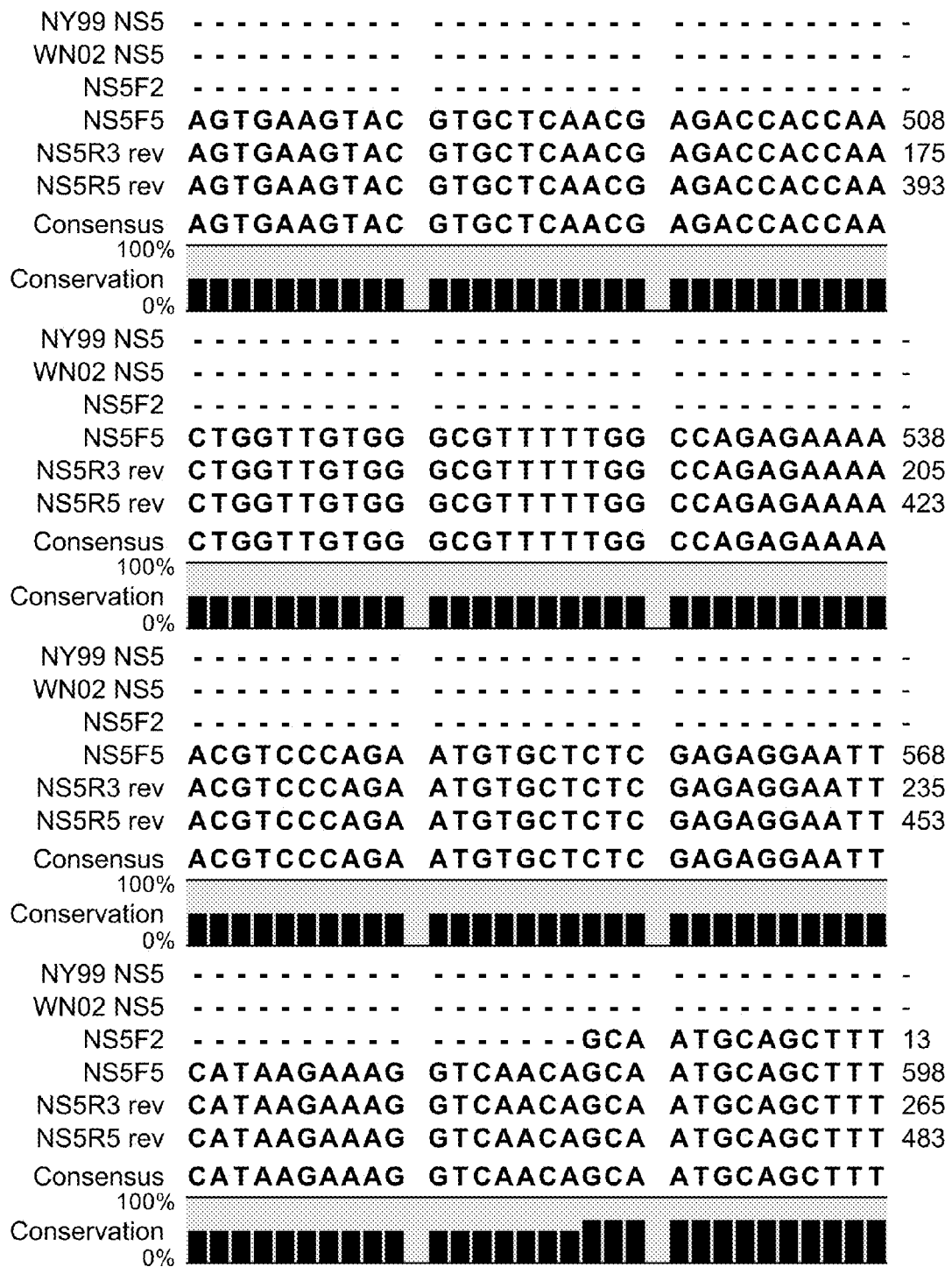
Figure 14F:
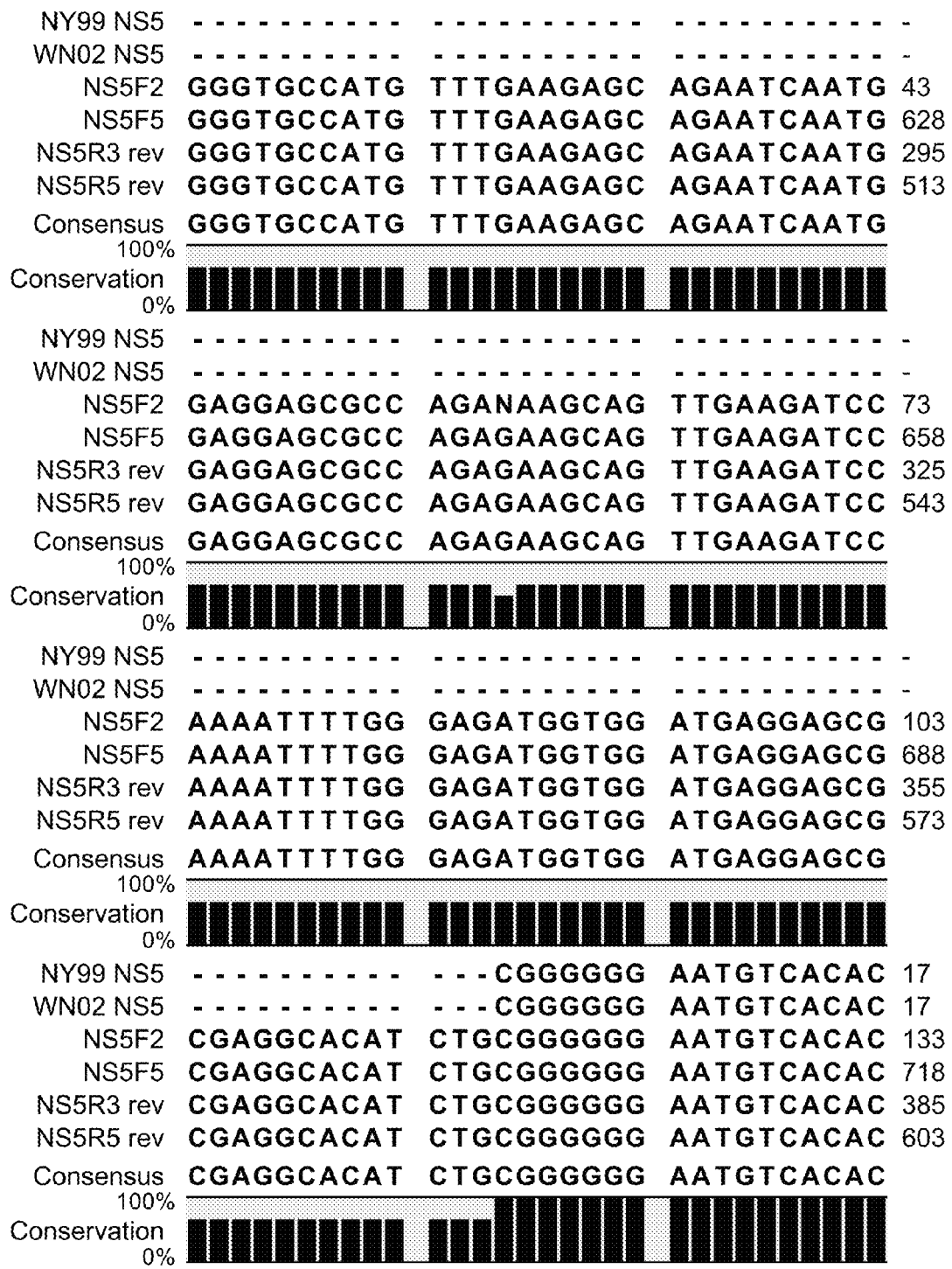
Figure 14H:
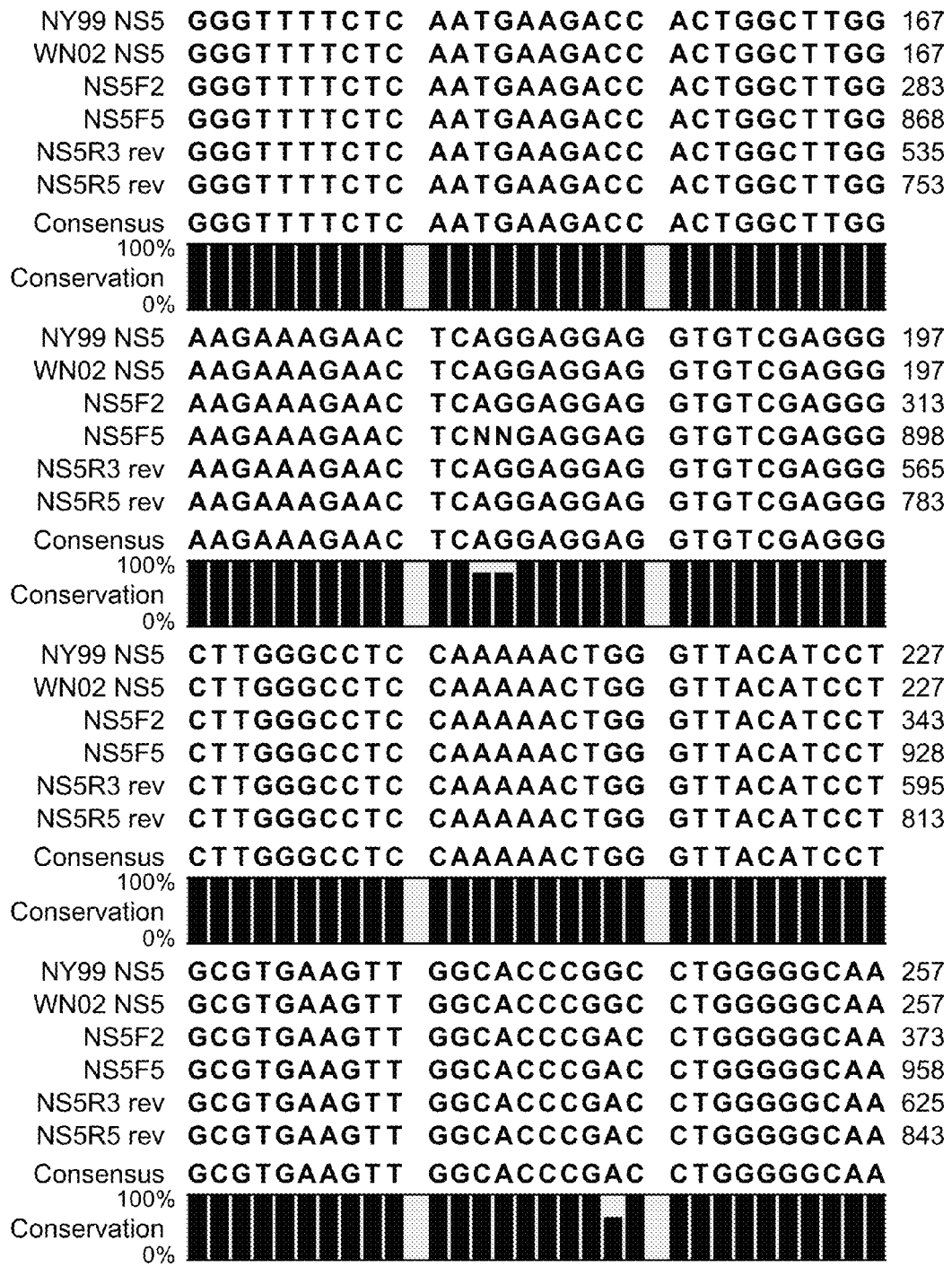
Figure 14L:
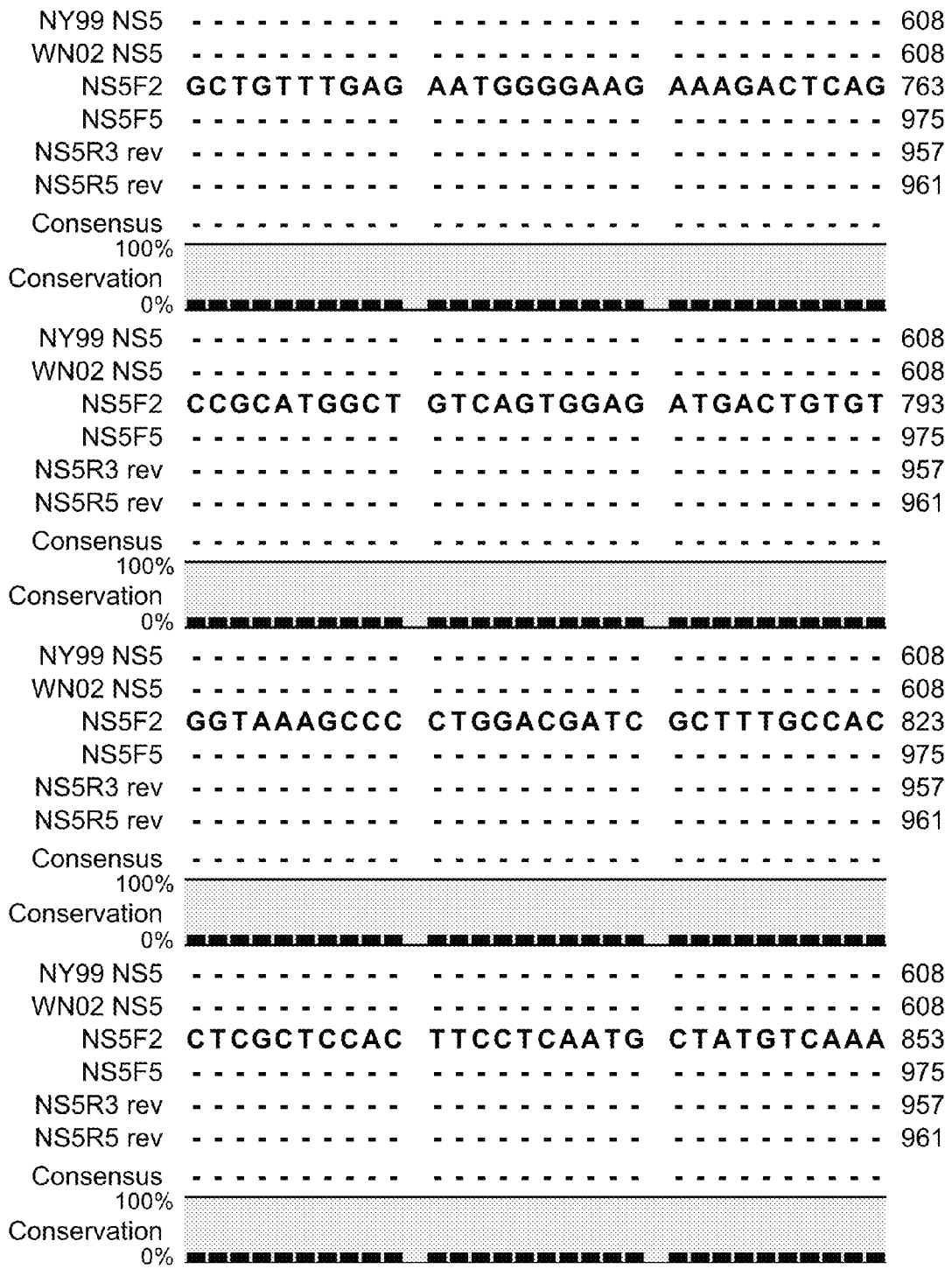
Figure 15F:
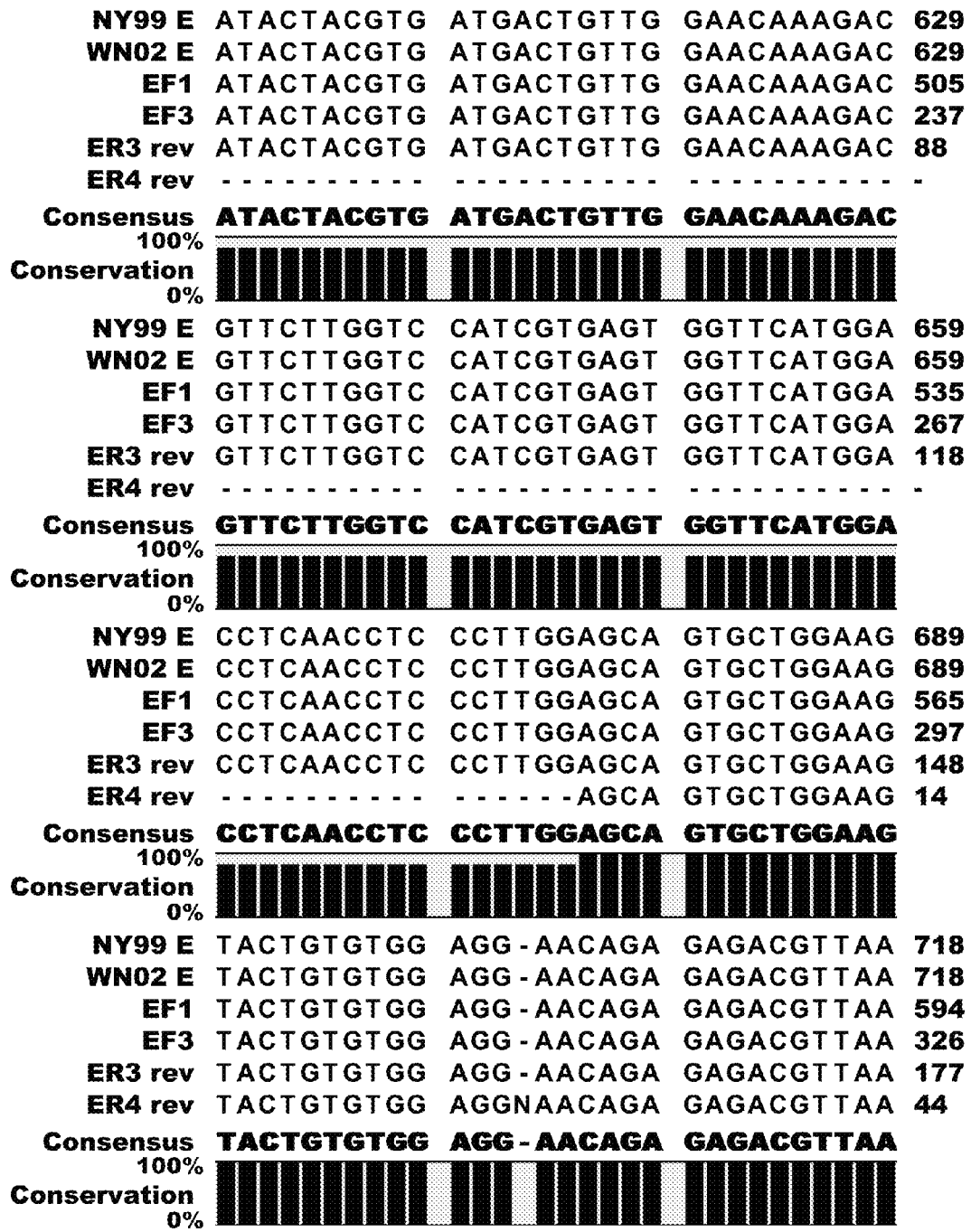
FIG. 15A through 15O is a nucleotide alignment of the H WN05 region of WNV isolates (SEQ ID NOS 17-22, respectively, in order of appearance)
Figure 15H:
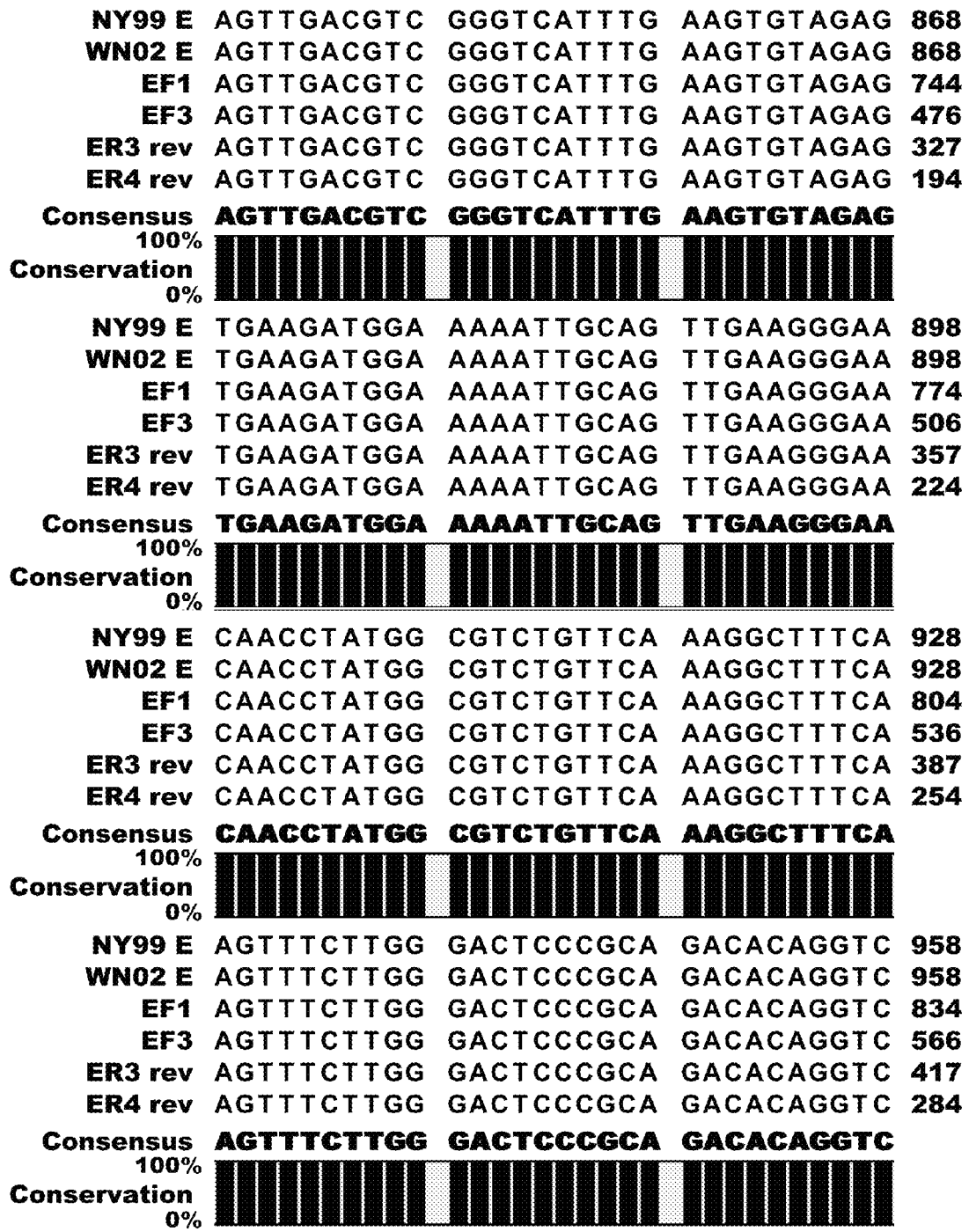
Figure 15I:
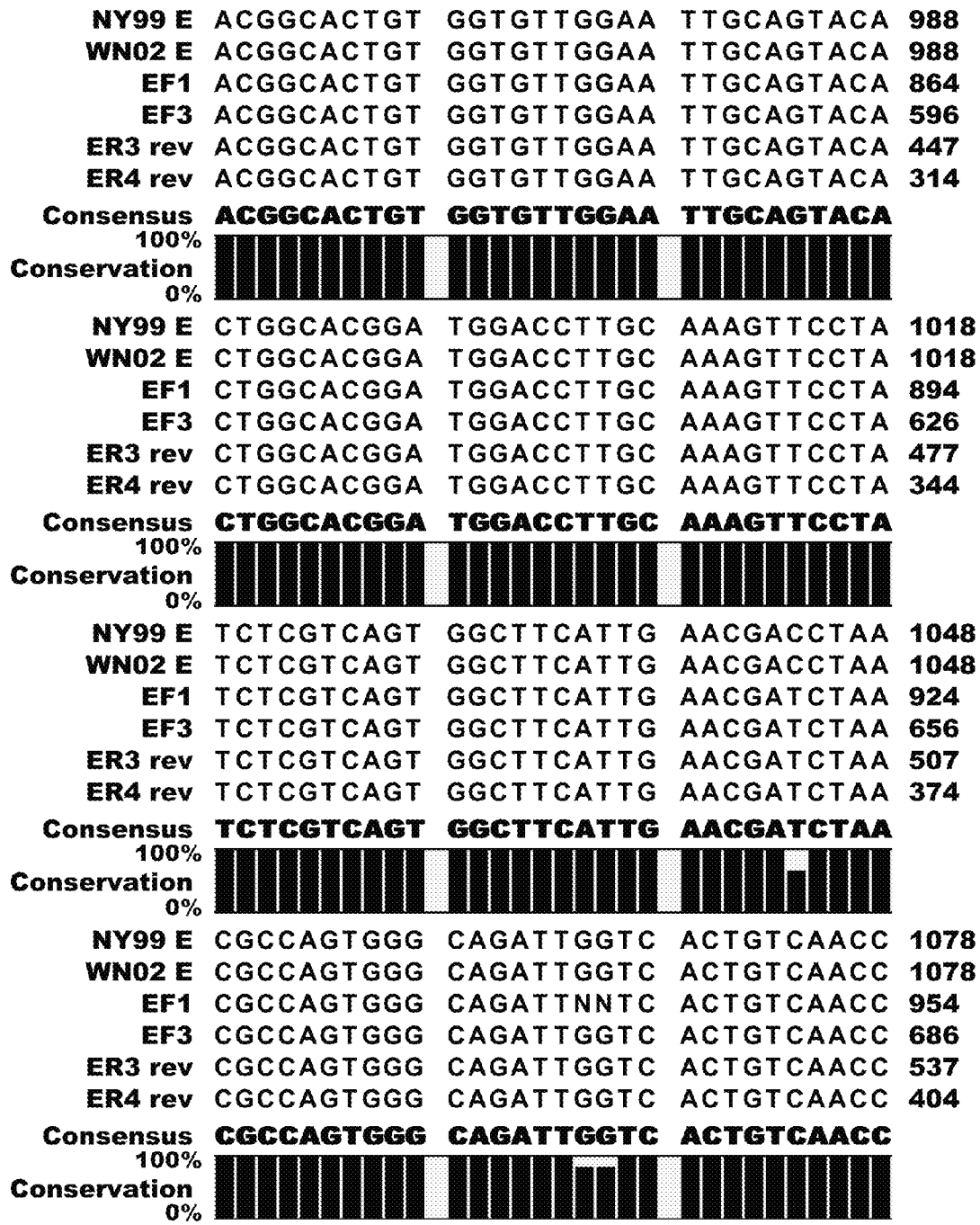
Figure 16A:
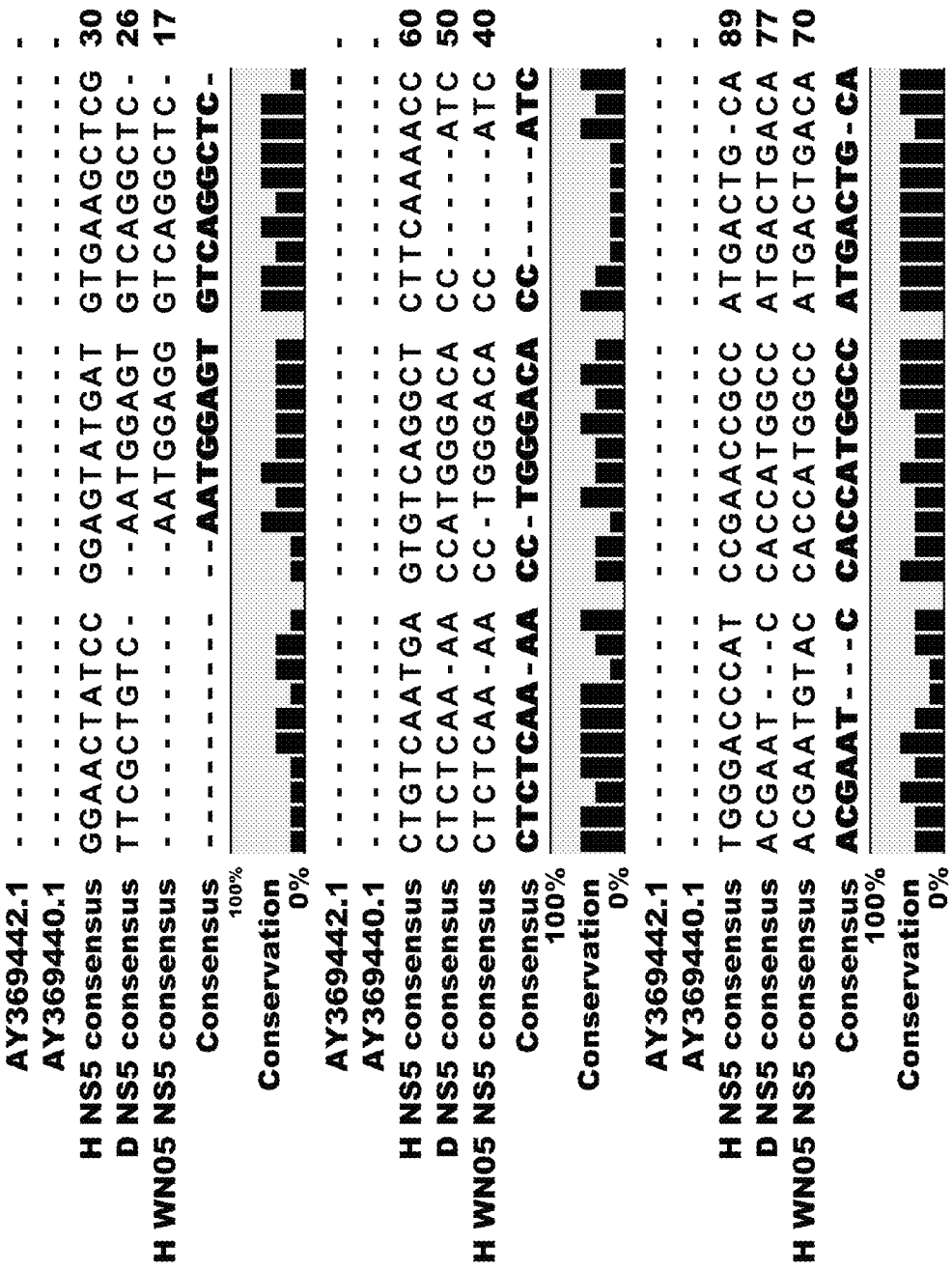
Figure 16E:
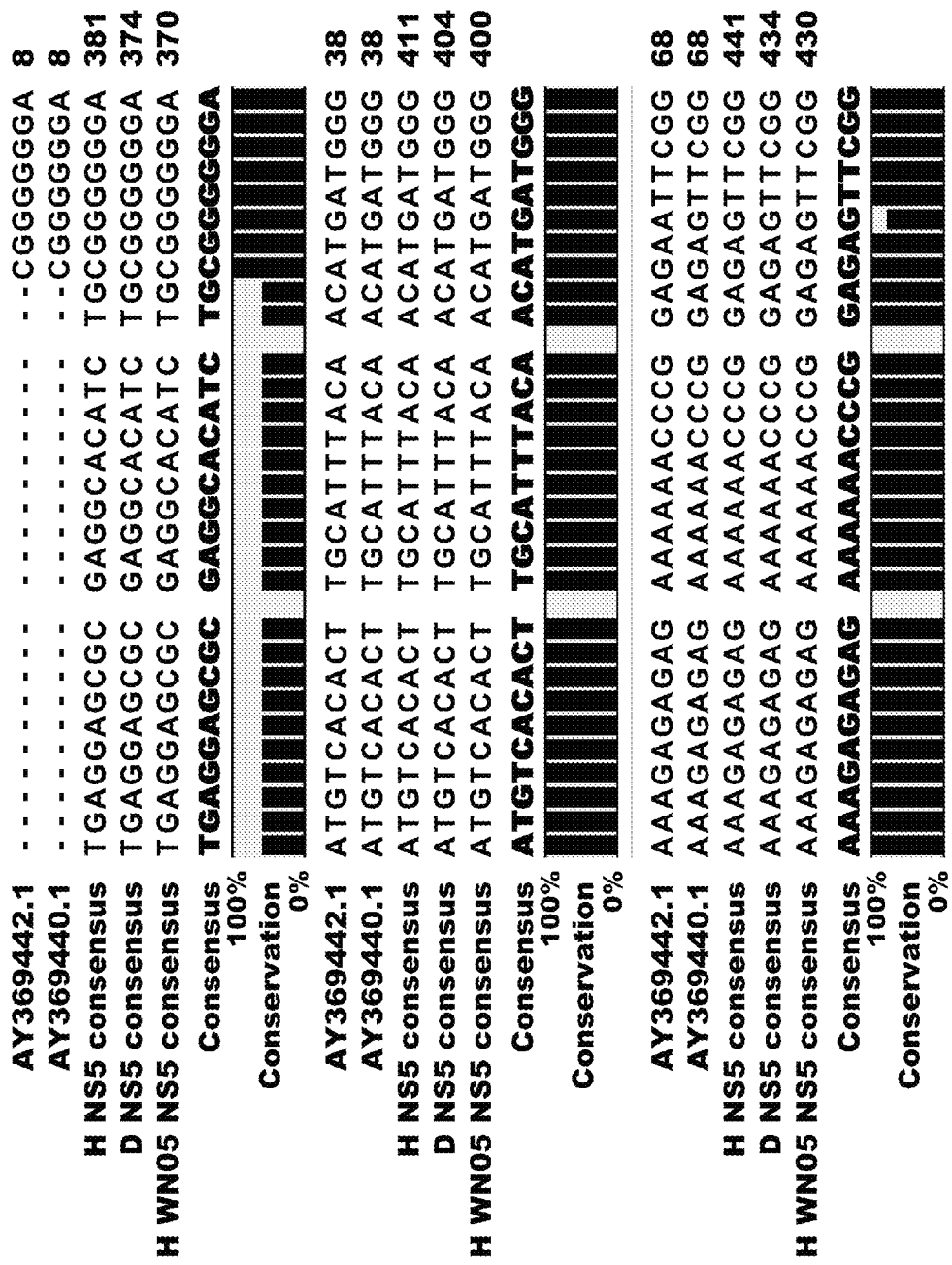
Figure 16F:
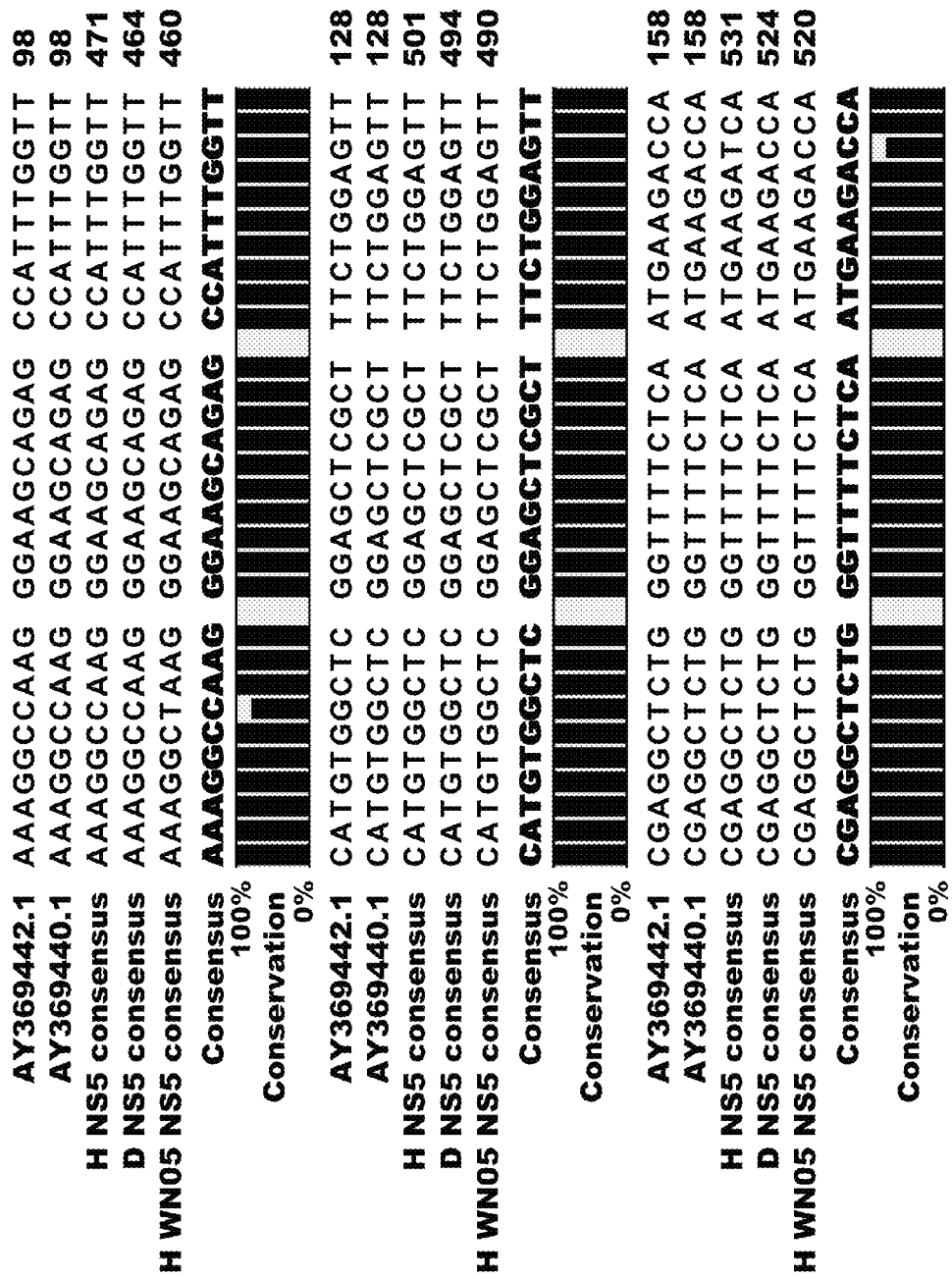
Figure 16H:
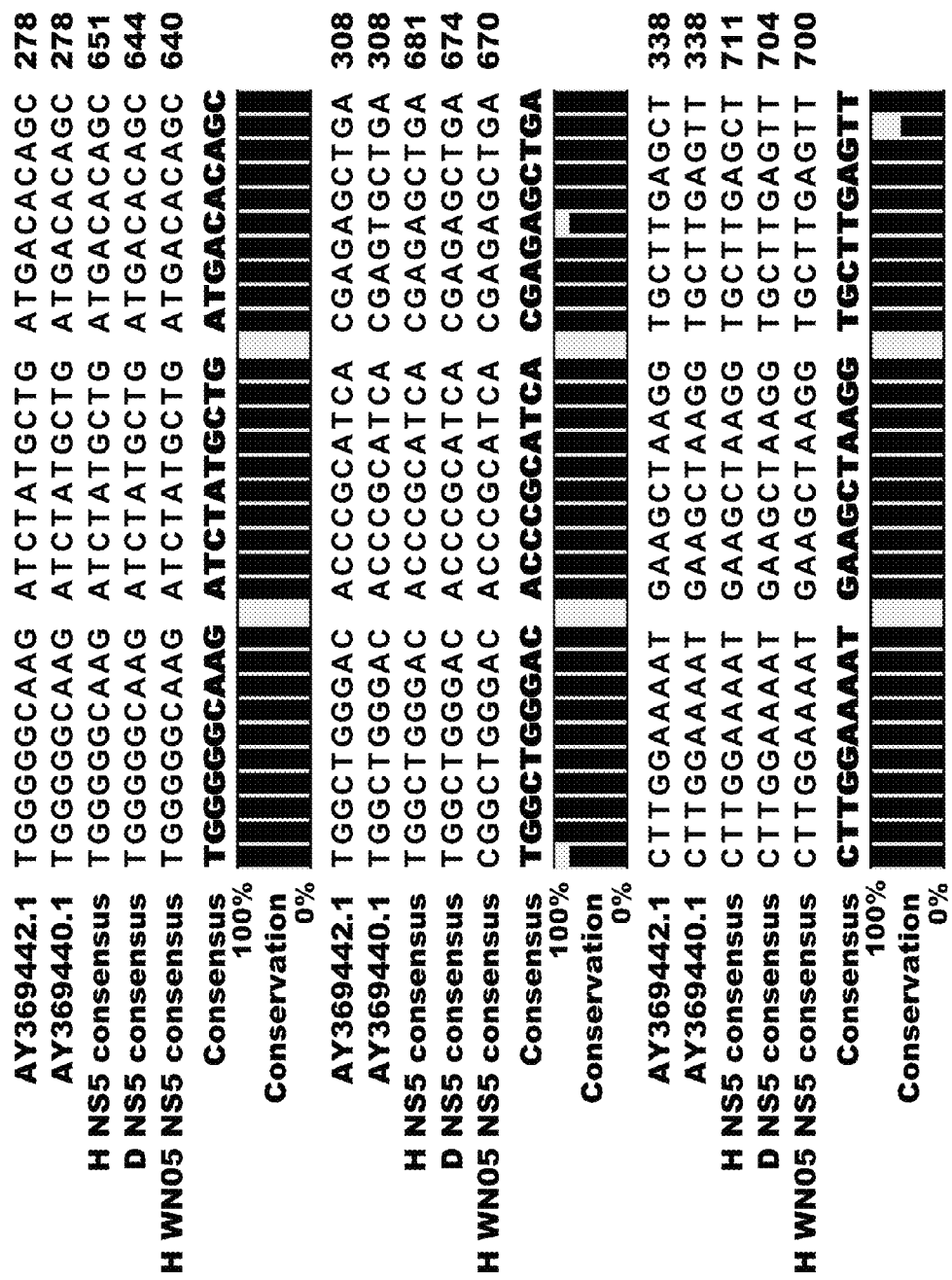
Figure 16J:
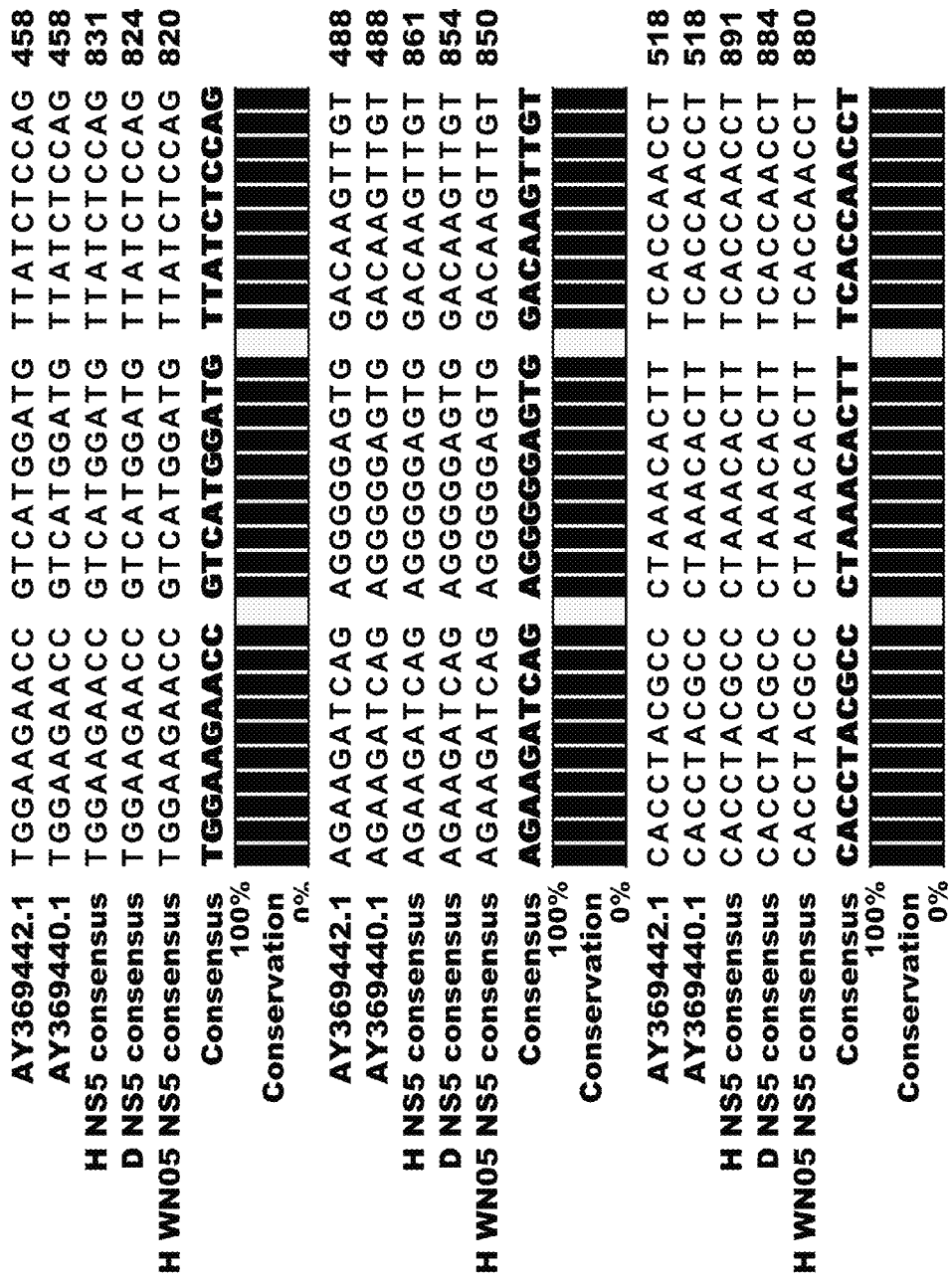
Figure 16K:
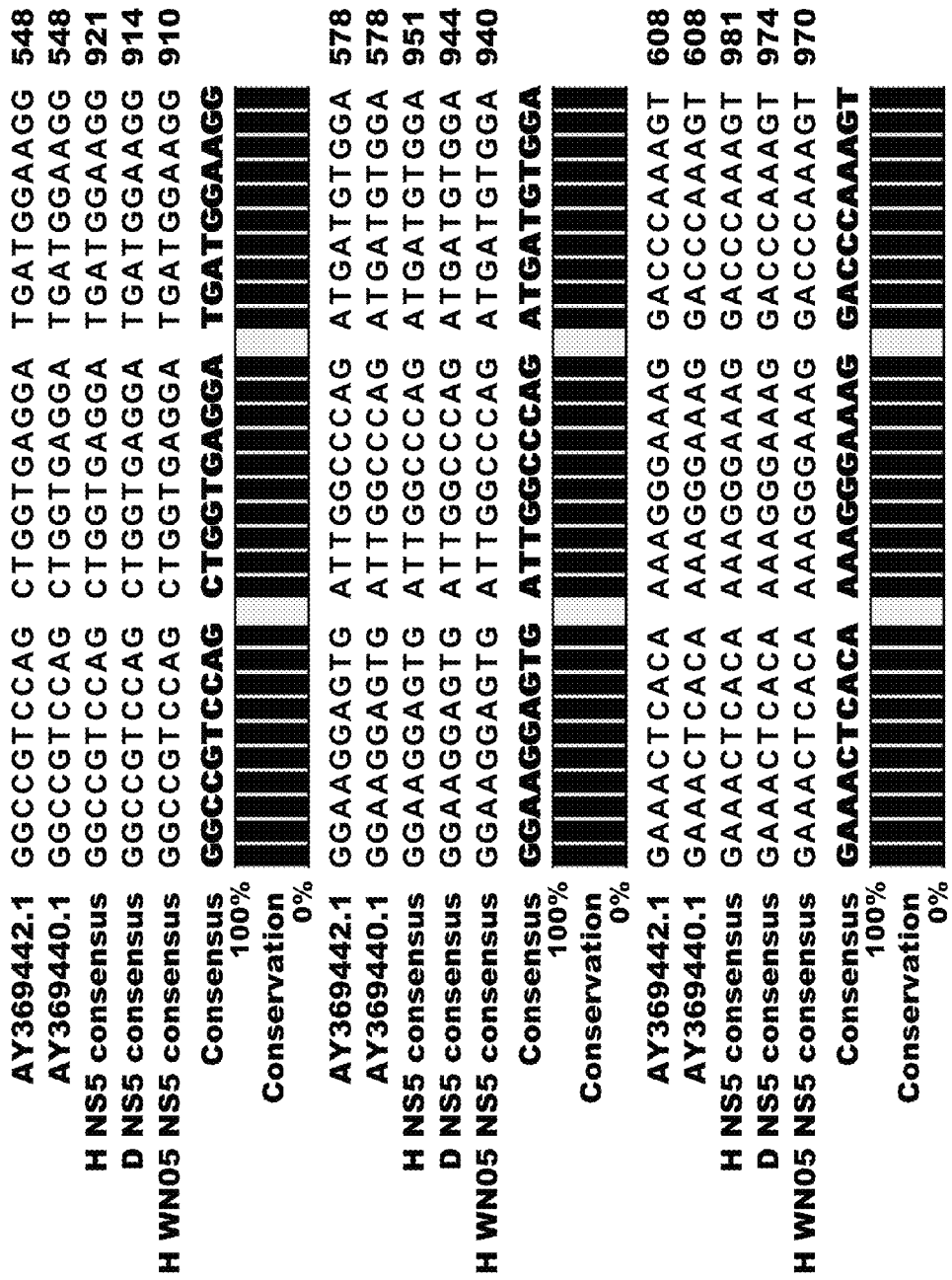
Figure 17C:
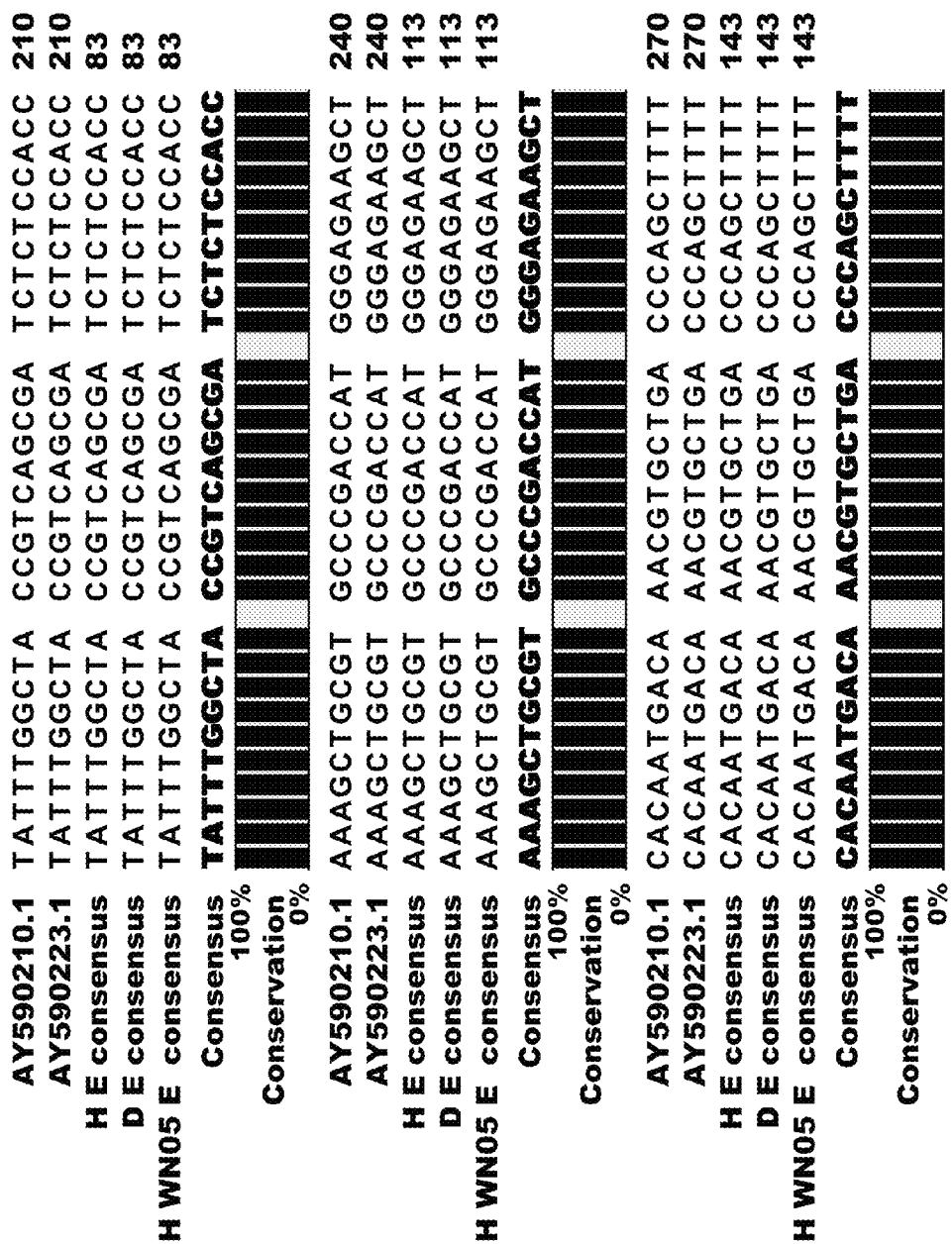
FIG. 17A through 17Q is a nucleotide alignment of the E region of WNV isolates (SEQ ID NOS 7-11, respectively, in order of appearance).
Figure 17D:
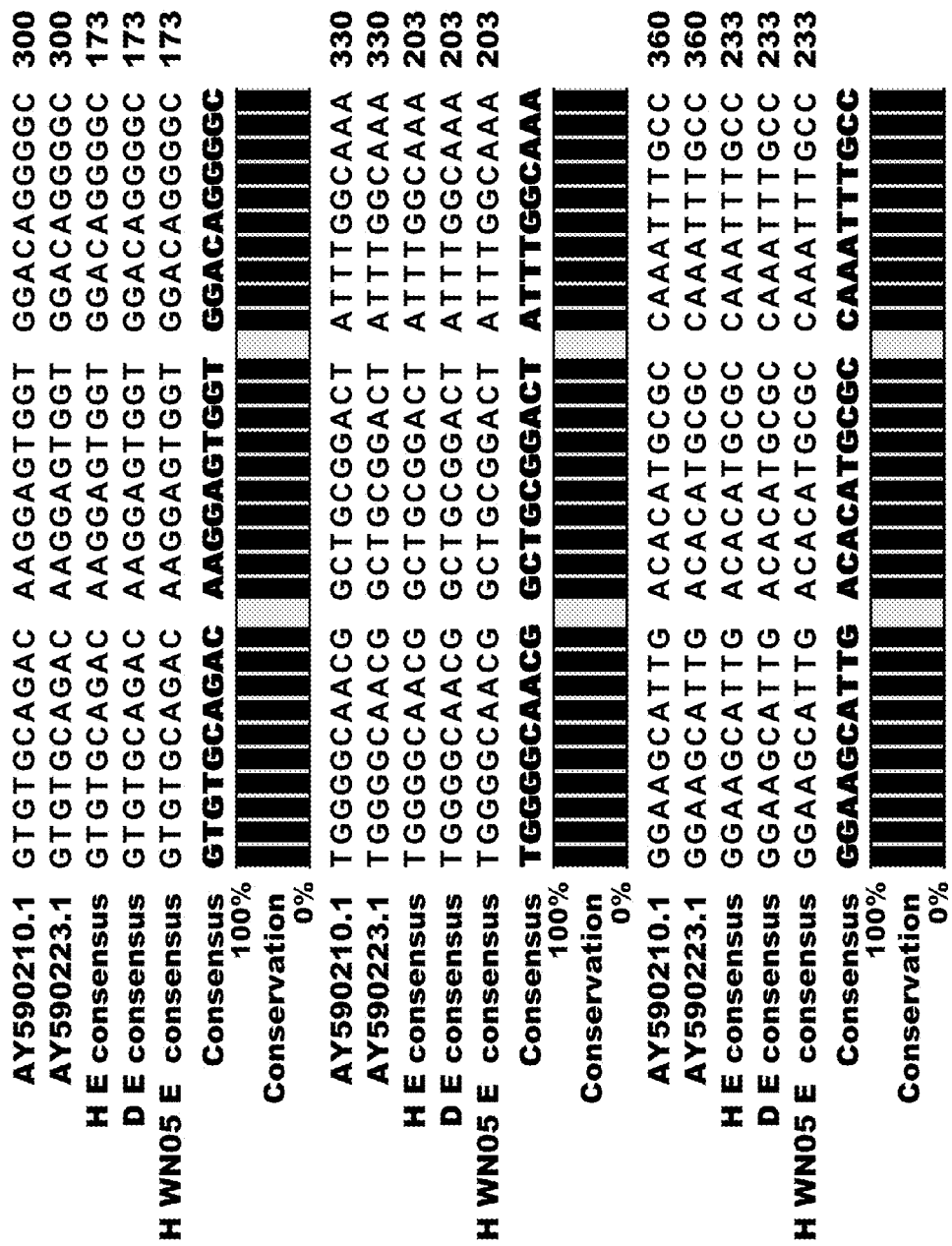
Figure 17E:
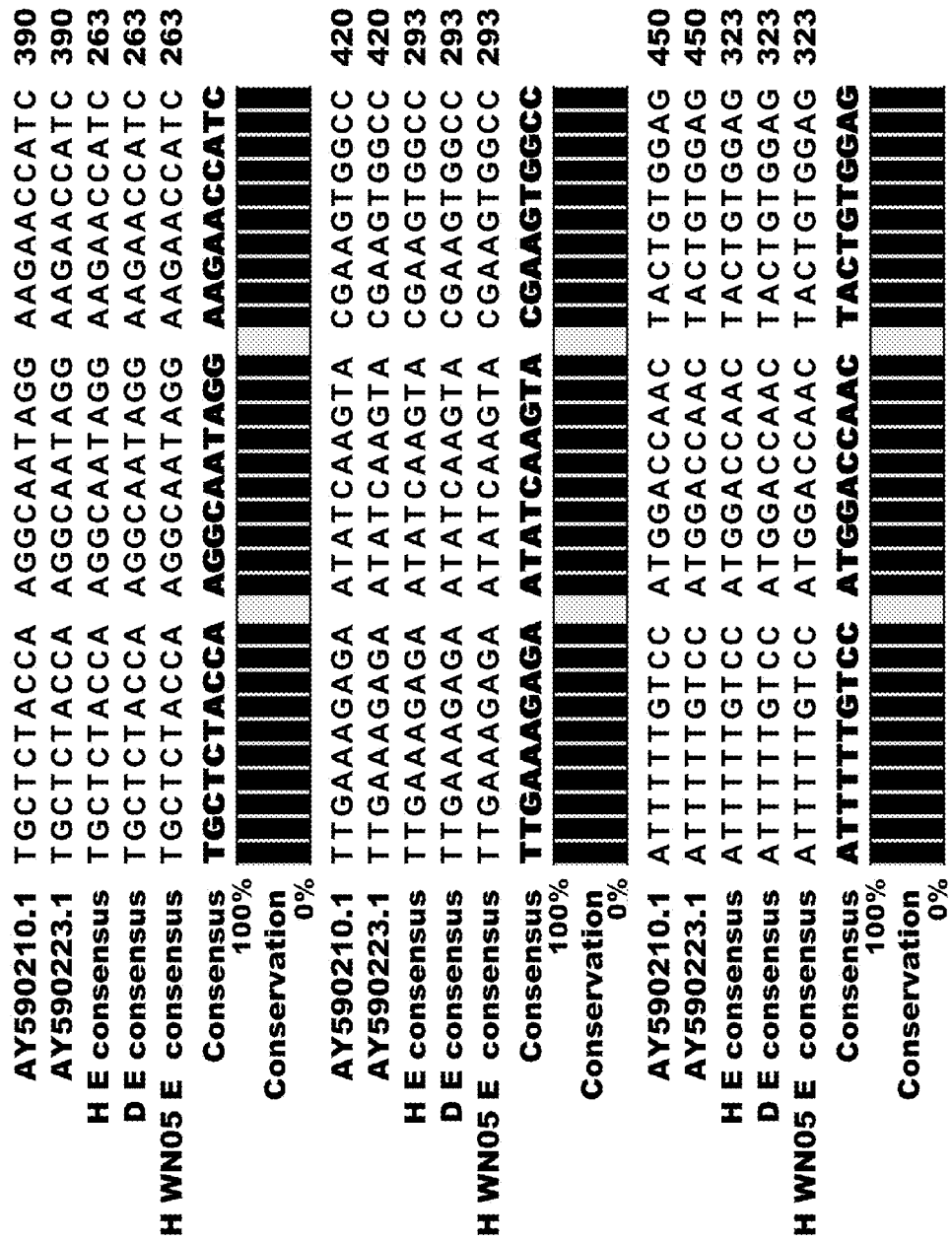
Figure 17F:
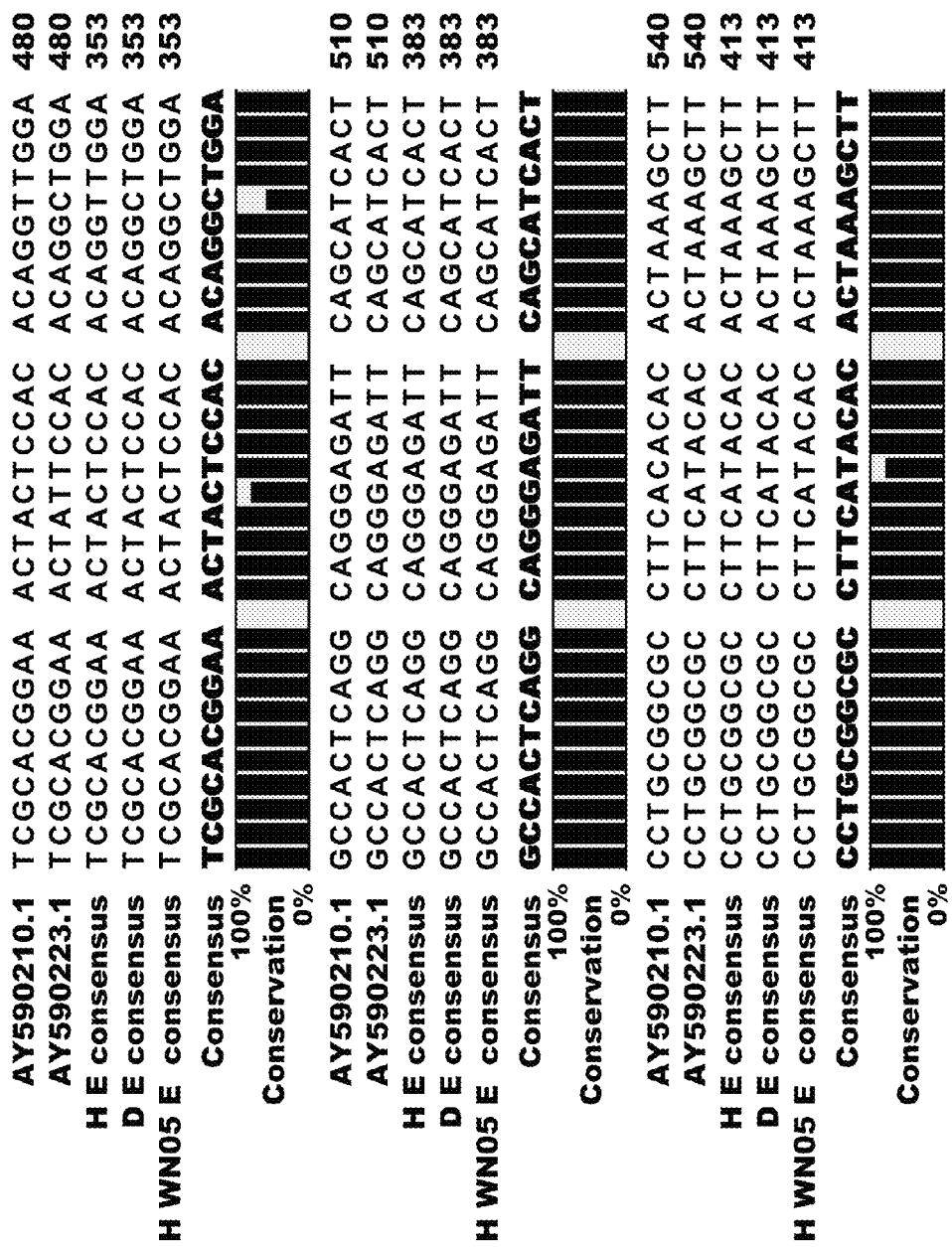
Figure 17G:
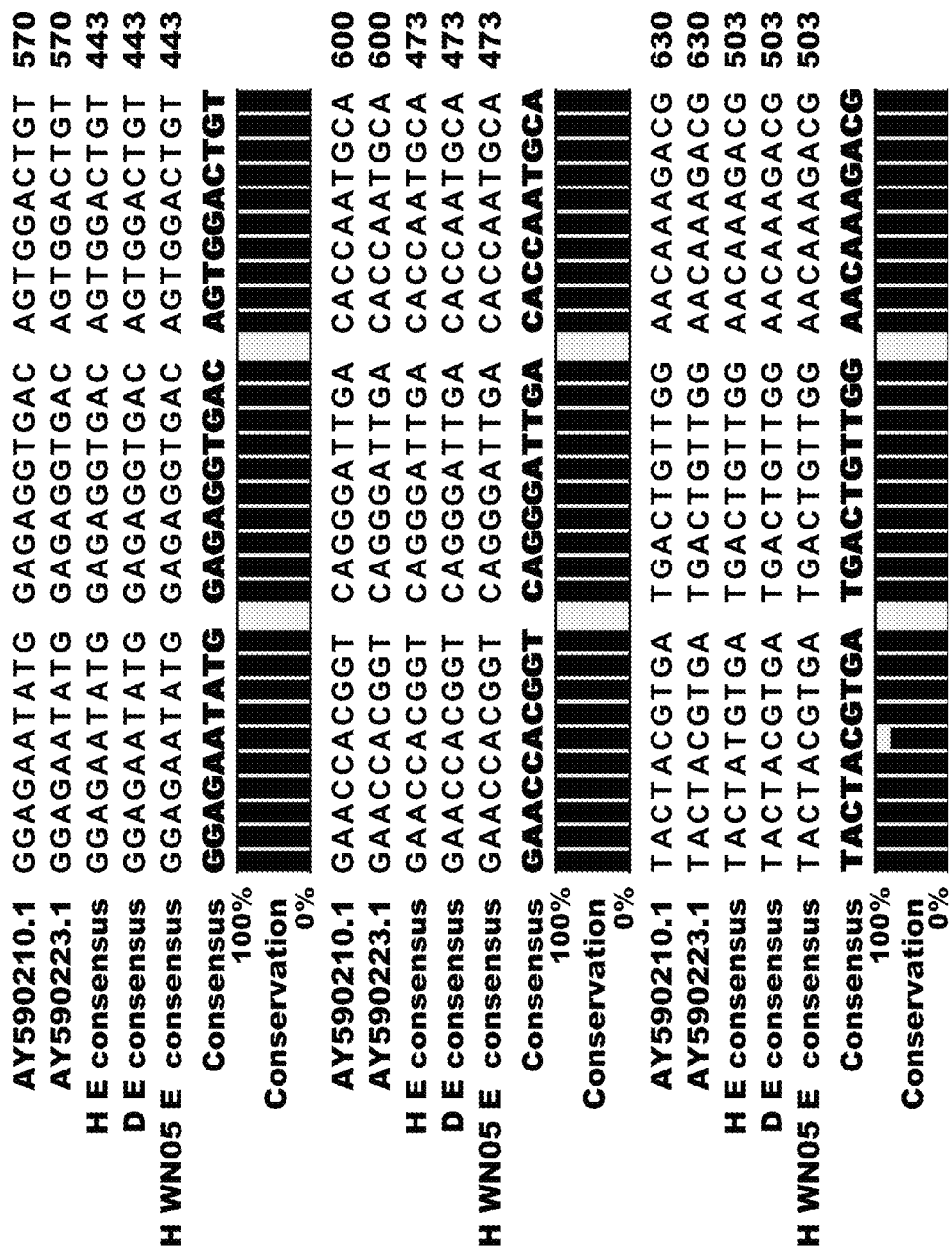
Figure 17H:
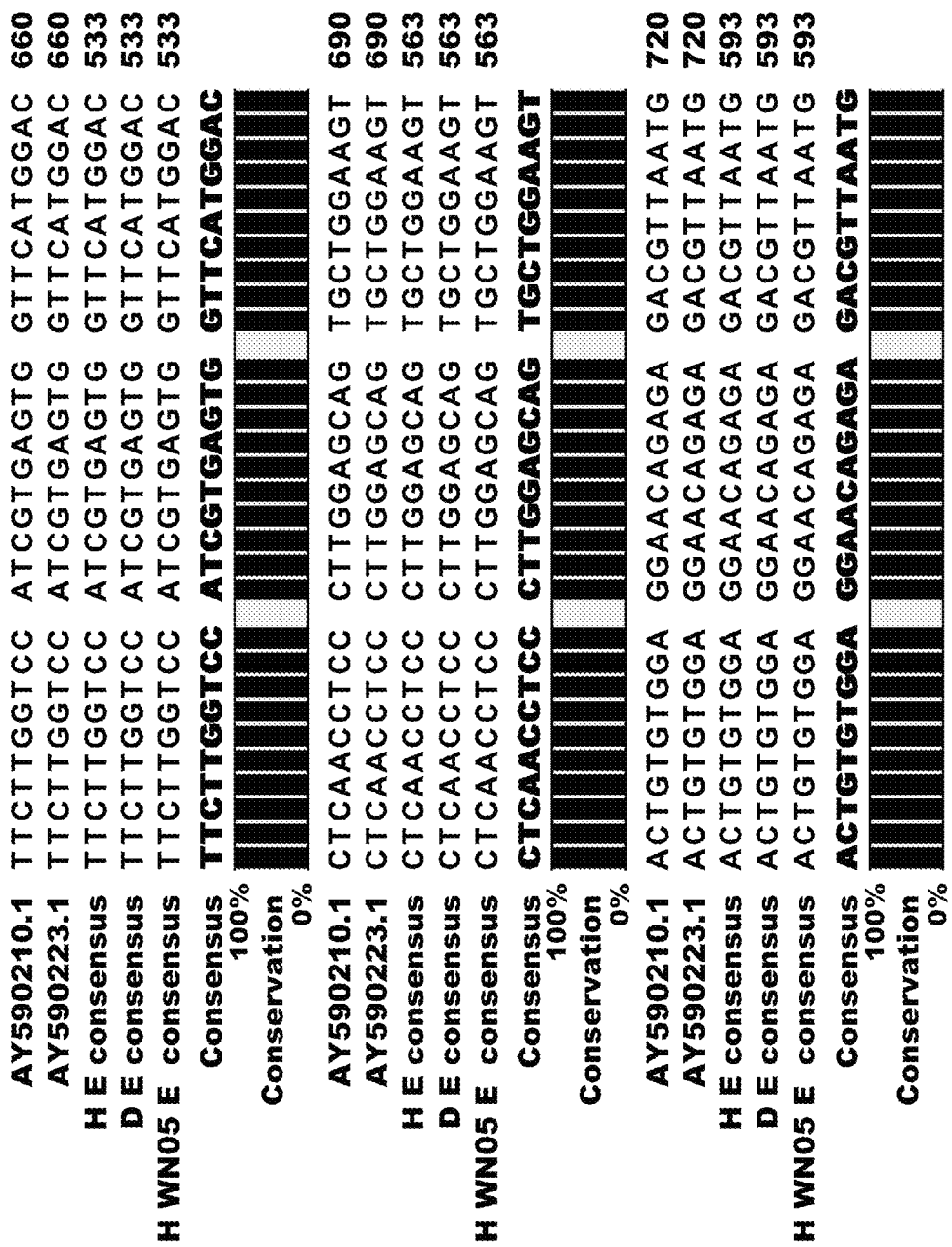
Figure 17I:
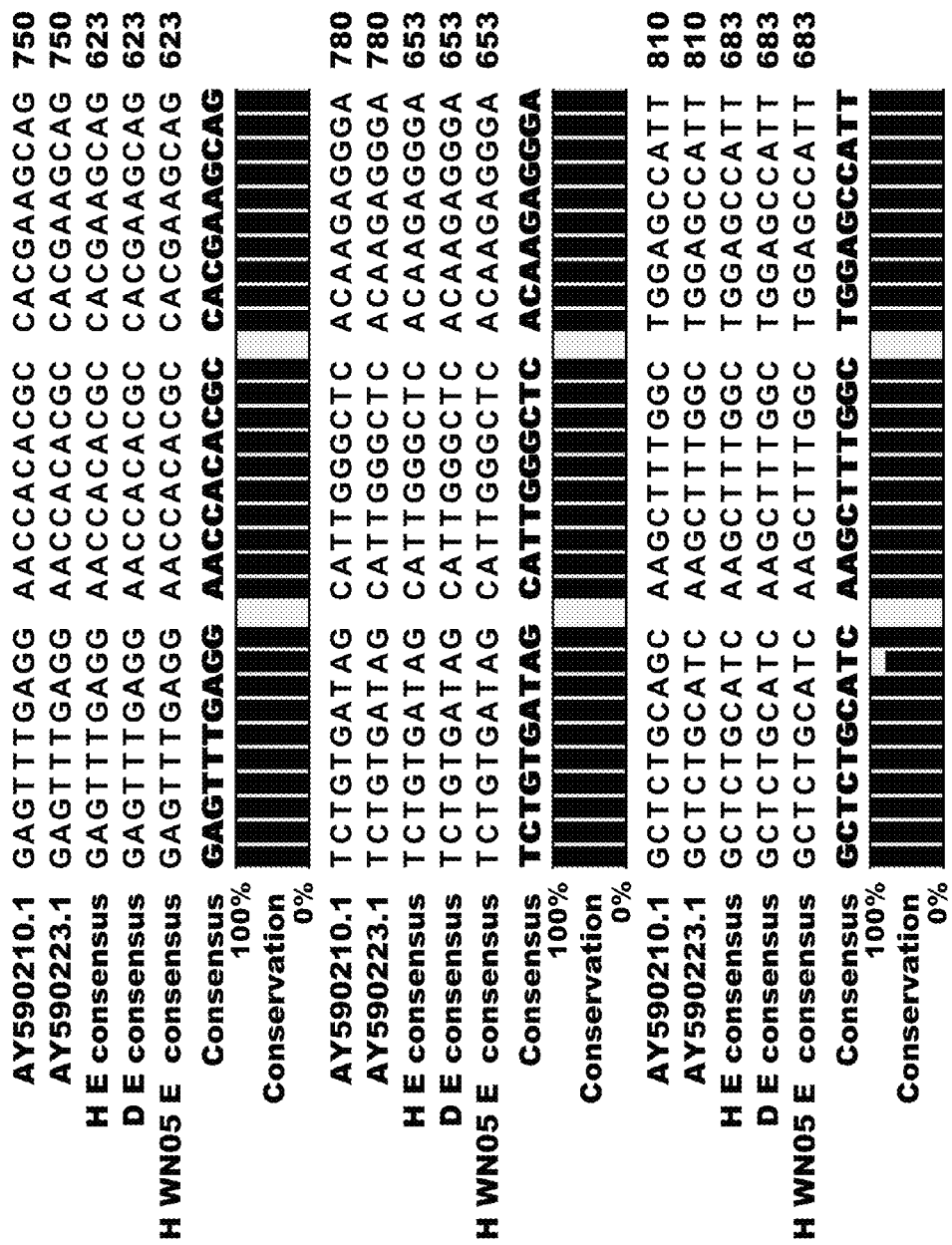
Figure 17J:
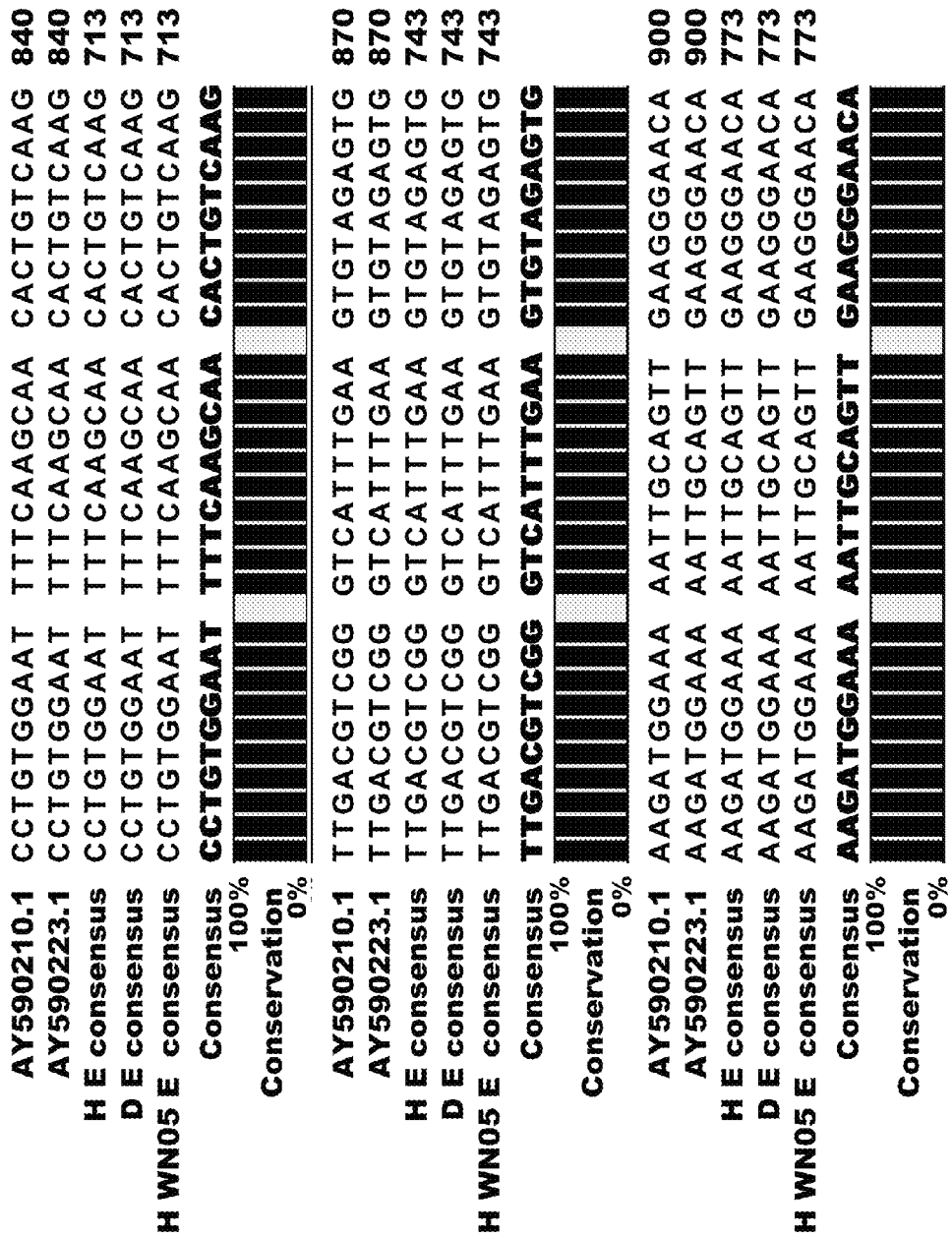
Figure 17K:
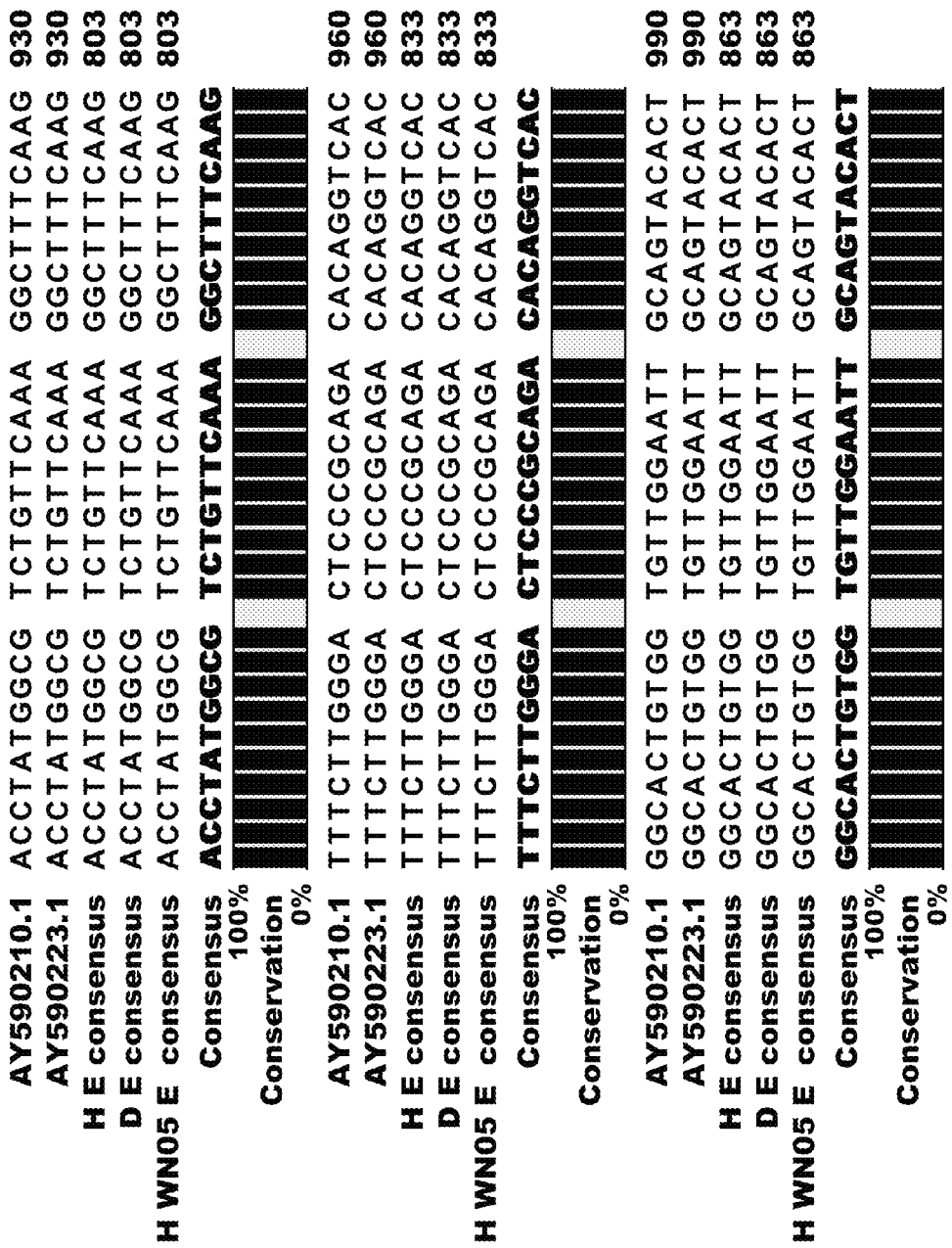
Figure 17L:
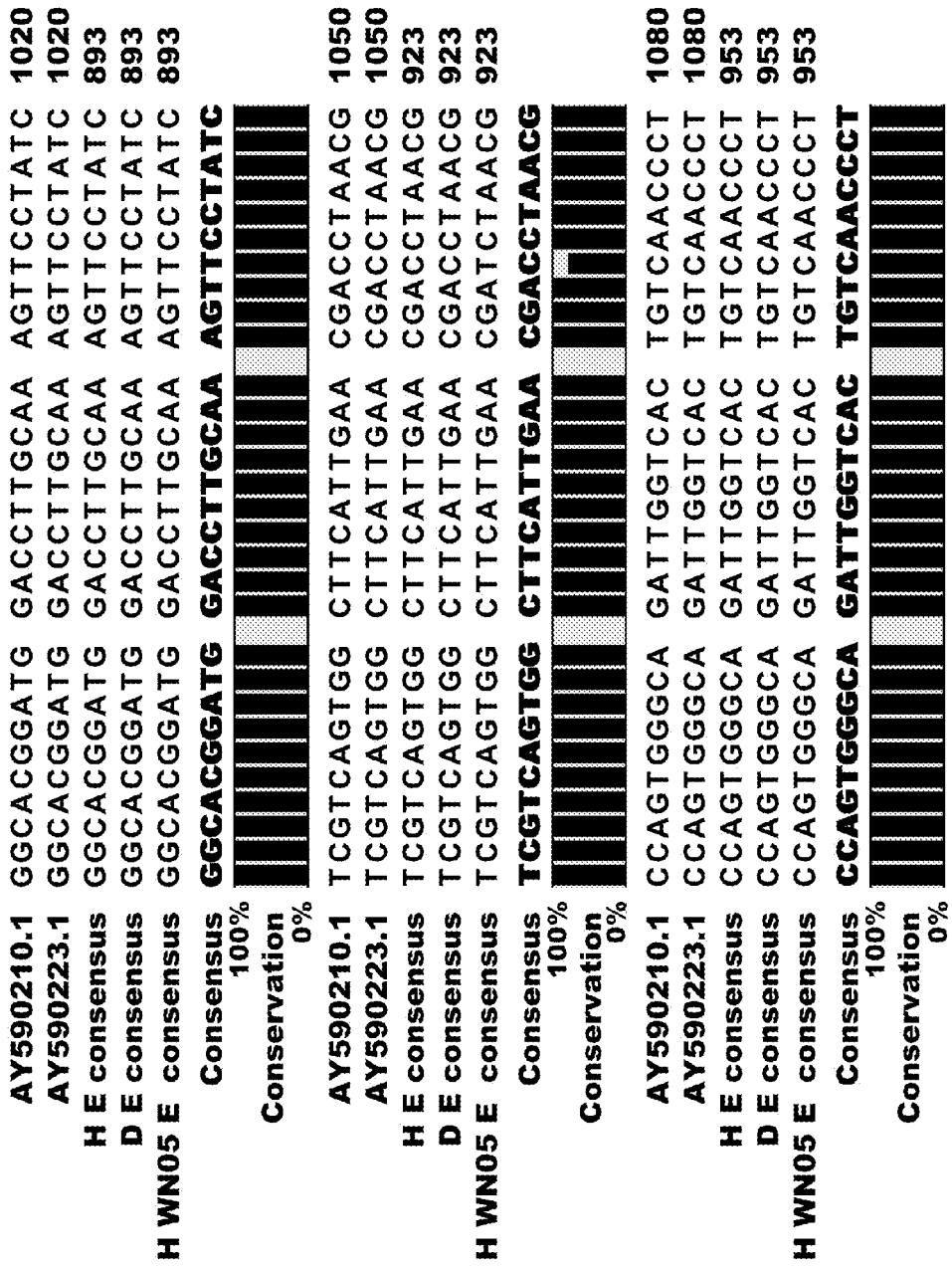
Figure 17M:
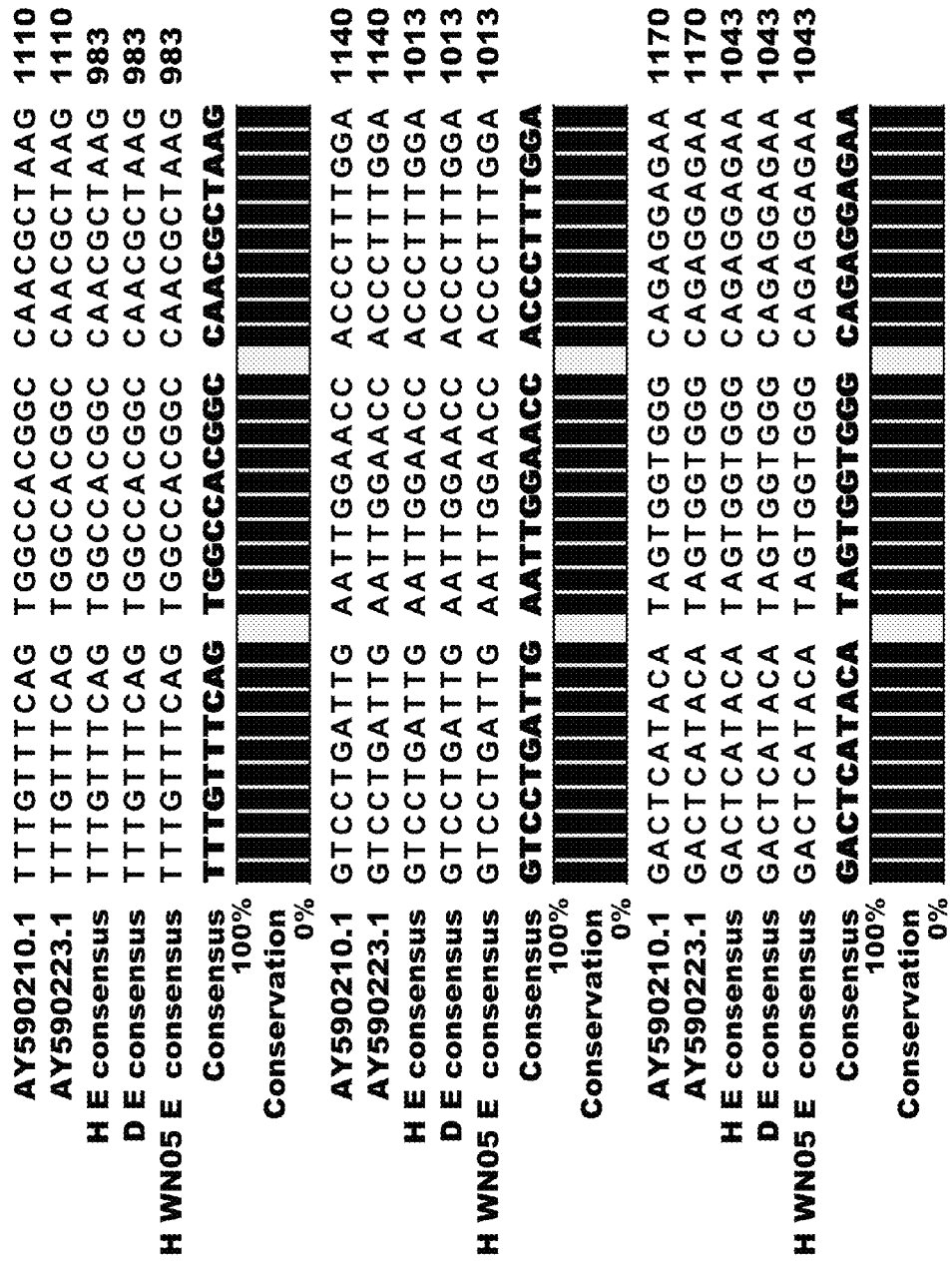
Figure 17N:
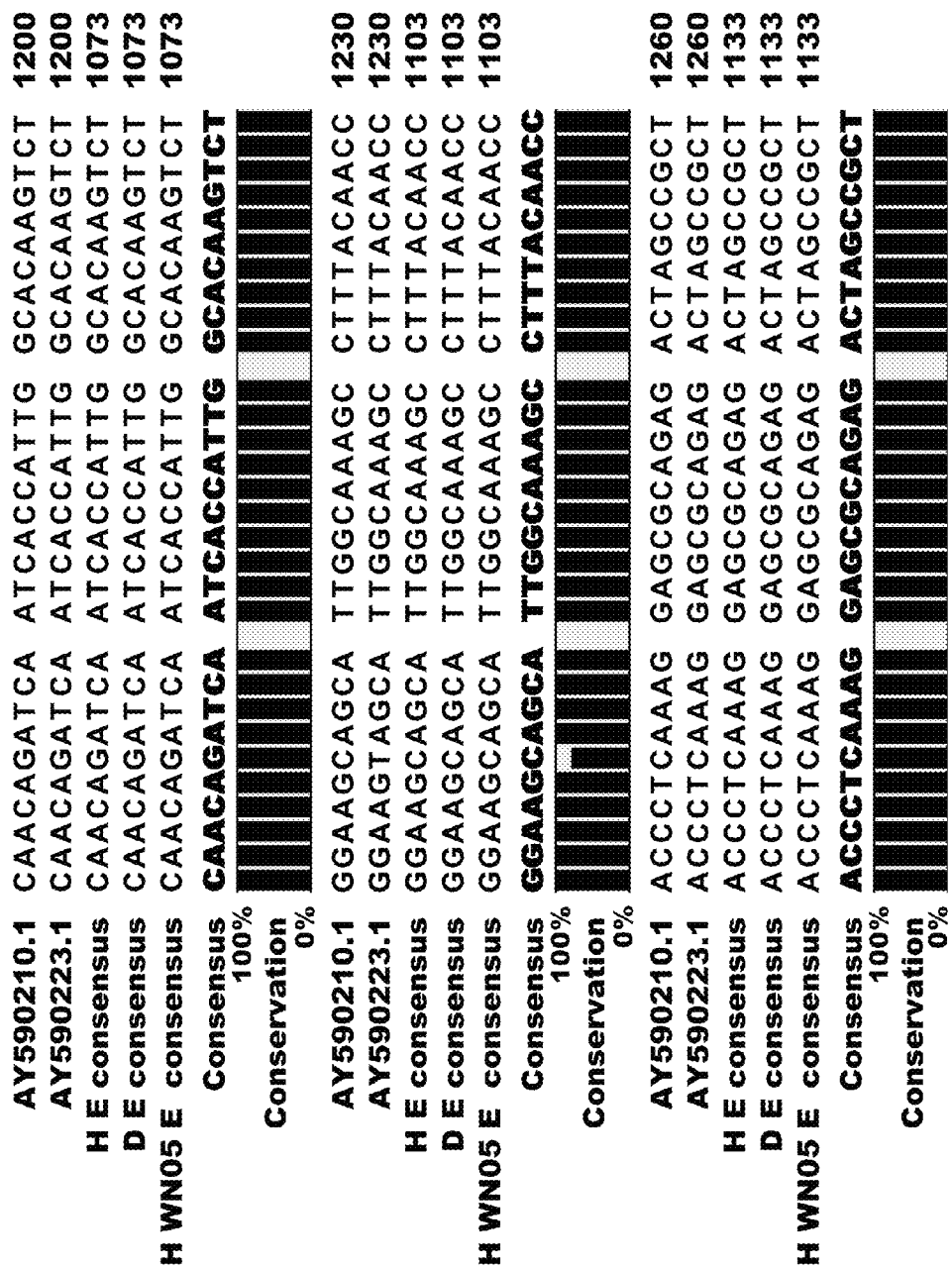
Figure 170:
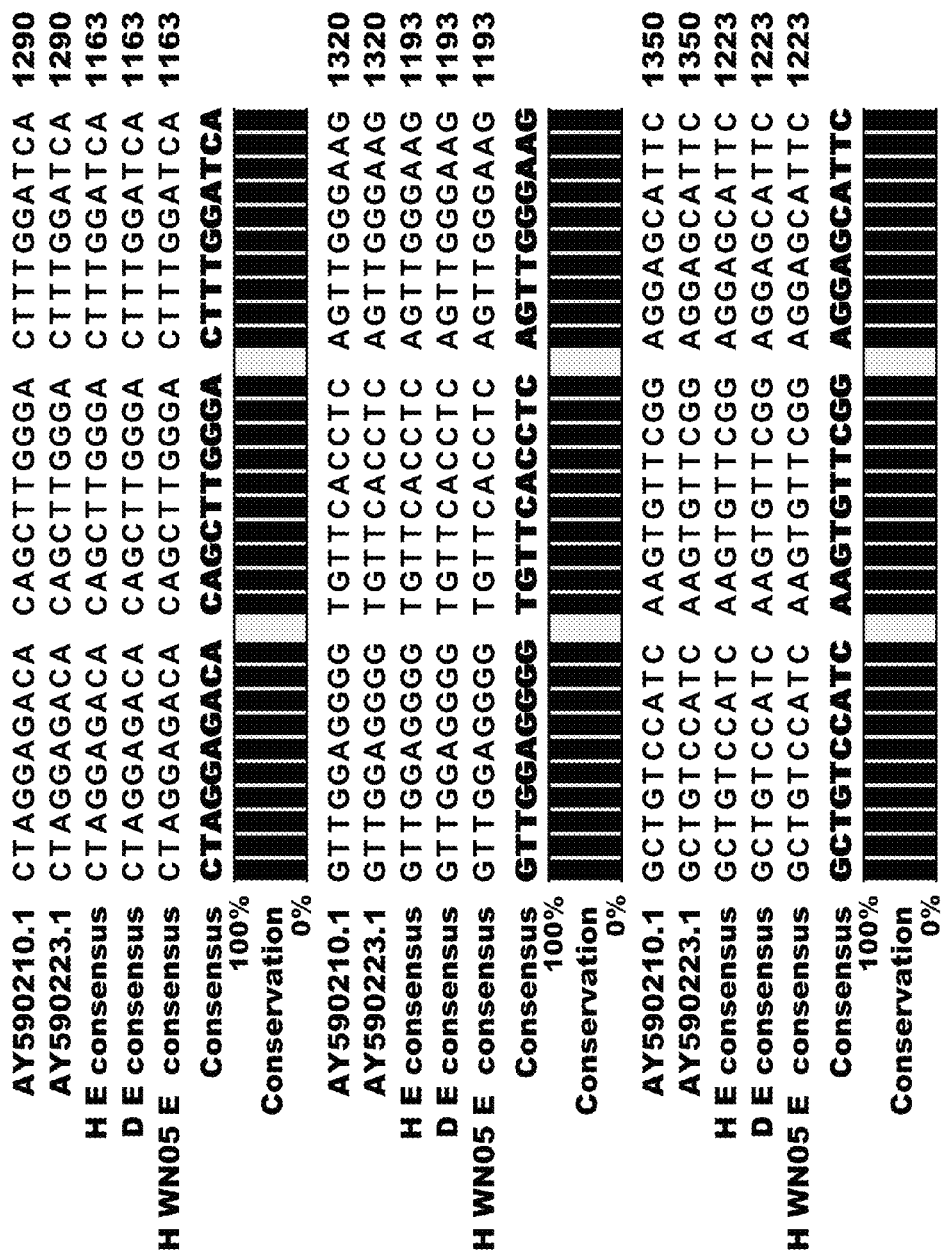
Figure 17P:
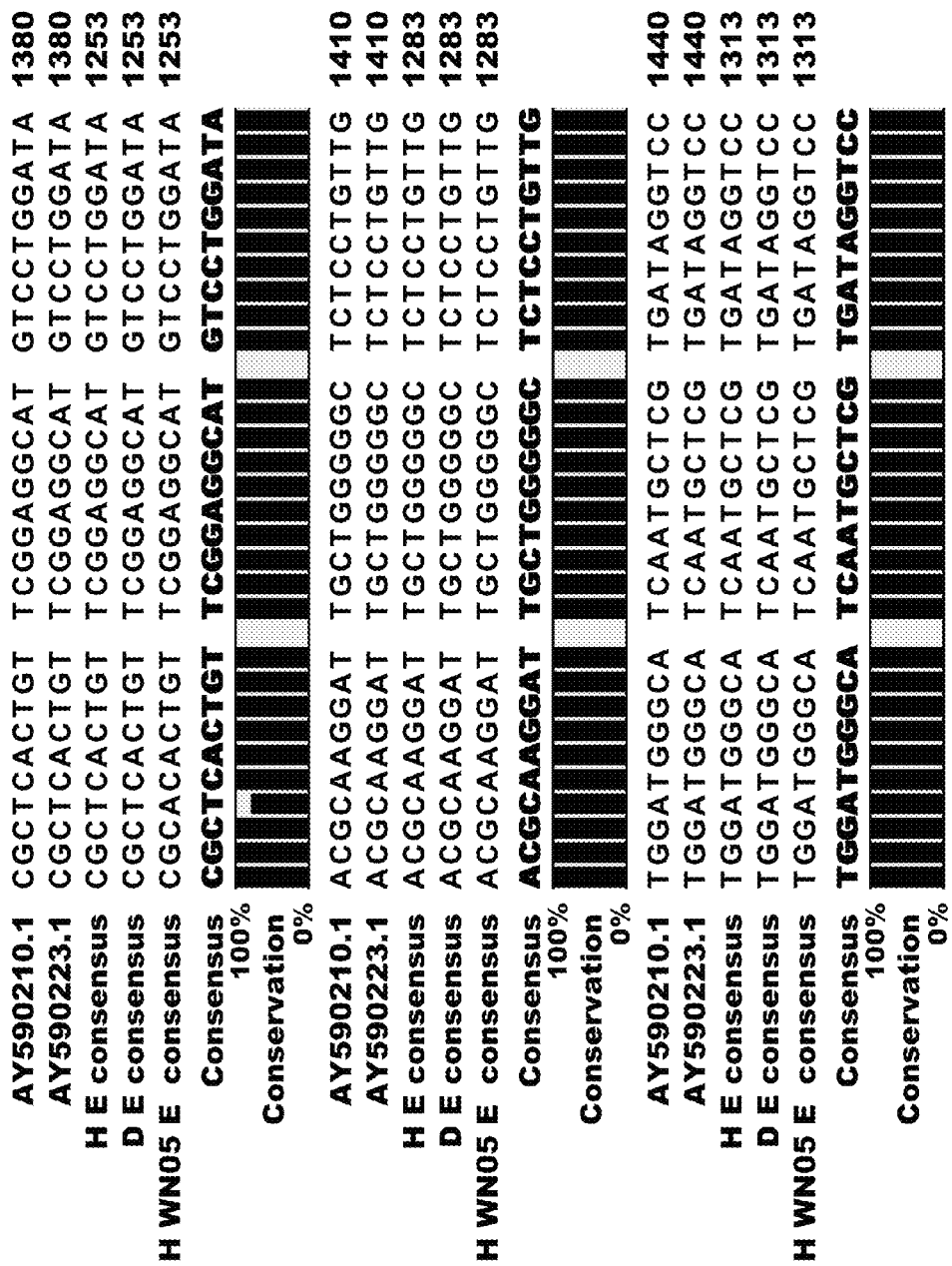
Figure 17Q:
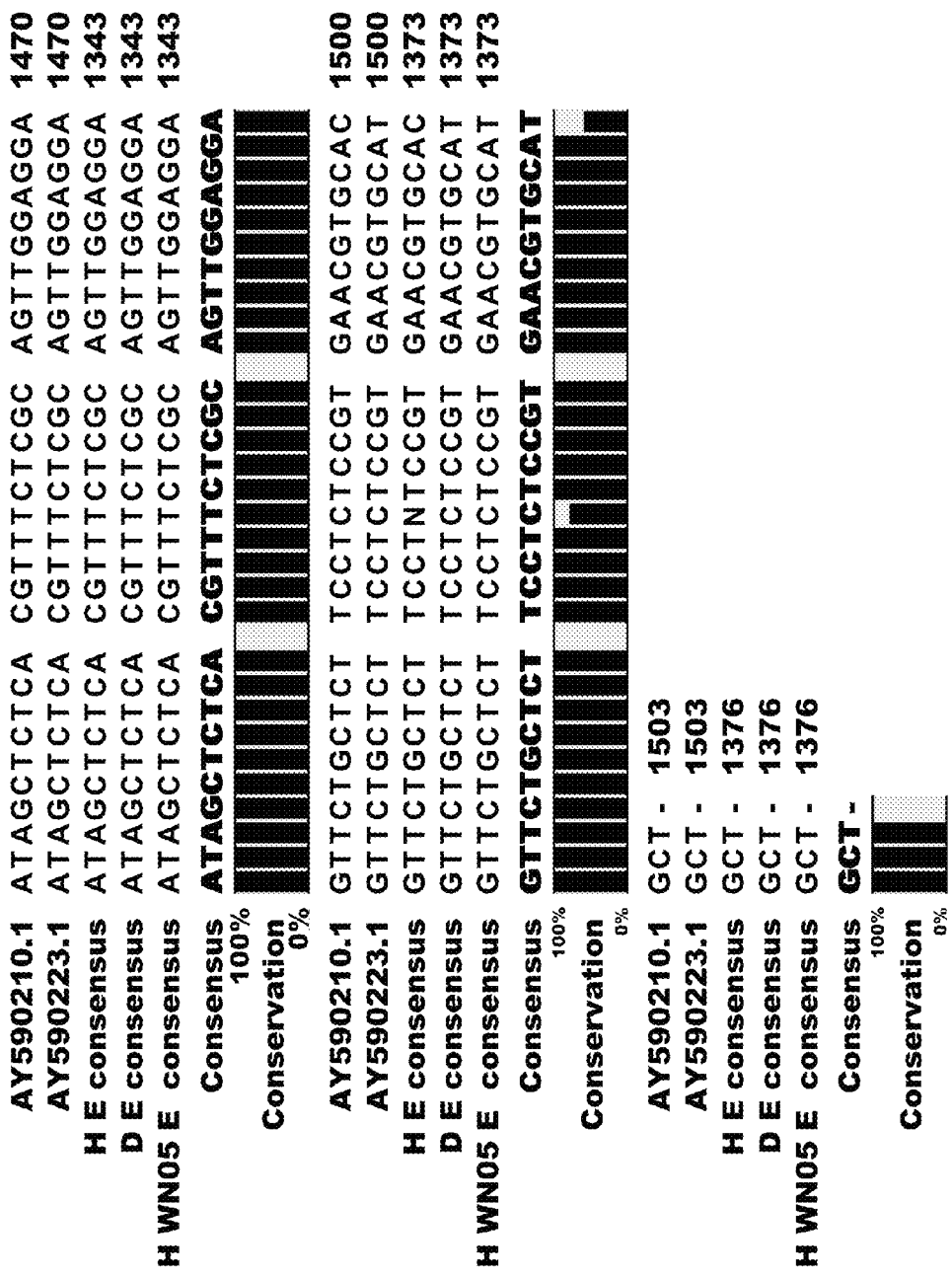

The critical Envelope (E) protein and Non-Structural 5 (NS5) protein was sequenced in these WNV isolates using standard laboratory techniques to determine genetic differences in nucleotide sequence as contrasted with WNV NY99. Notably, the North American Dominant isolates, of which specific examples are North American Equine E159 (NAEE159) and North American Donkey E159(NADE159), displayed the changes which characterize North American Dominant WNV isolates and distinguish them from NY99 WNV, namely, the U to C mutation and C to U mutation at positions 1442 and 2466, respectively, of the nucleotide sequence encoding the E protein and the C to U mutation at position 9352 in the sequence encoding the NS5 protein. FIGS. 10-17 show the sequence alignments of various regions of isolates. The alignments in the E region are relative to publically available reference sequences for a NY 99 isolate (deposited in GenBank as AY590210) and a North American Dominant isolate (WN 02 isolate) deposited in GenBank as AY590223. The alignments in the NS5 region are also relative to publically available reference sequences for a NY 99 isolate (deposited in GenBank as AY369442) and a North American Dominant isolate (WN 02 isolate) deposited in GenBank as AY369440). As shown by these alignments, North American Dominant WNV isolates have the same sequence changes relative to the NY 99 isolate as those defined in the definition for a North American Dominant WNV isolate. These sequences are provided herein as SEQ ID NOS. 1-22, the full length genome of a WN99 isolate is provided as SEQ ID NO. 23, and the protein encoded by the full length genome of SEQ ID NO. 23 is provided as SEQ ID NO. 24.

What is claimed is:

1. An immunogenic composition comprising a strain of killed or inactivated West Nile Virus, wherein said West Nile Virus strain is Horse Origin 2005, also known as NAEE 159, deposited at the United States Department of Agriculture Isolate under accession number 405330 and also deposited with the ATCC under accession number PTA-9409; and one or more of the antigenic components selected from the group consisting of Equine Influenza Virus, deposited with the ATCC under accession numbers ATCC Accession No. PTA-9522, PTA-9523, and PTA-9524, Eastern Equine Encephalomyelitis Virus, deposited with the ATCC under accession number PTA-9412; Western Equine Encephalomyelitis Virus, deposited with the ATCC under accession number PTA-9410; Venezuelan Equine Encephalomyelitis Virus, deposited with the ATCC under accession number PTA-9411; Equine Herpes Virus Type 1, deposited with the ATCC under accession number PTA-9525, Equine Herpes Virus Type 4, deposited with the ATCC under accession number PTA-9526; and Tetanus toxoid.

2. A method for reducing the incidence or lessening the severity of clinical symptoms associated with or caused by West Nile Virus and one or more of the pathogens selected from the group consisting of Equine Influenza Virus and/or Equine Herpes Virus Type 1 and/or Equine Herpes Virus type 4 in a horse or a herd of horses comprising the step of administering the immunogenic composition corresponding to the mixture of antigenic components selected in claim 1 to a horse in need thereof.

3. The method according to claim 2, wherein the incidence of clinical symptoms caused by West Nile Virus and one or more of said pathogens in a herd of horses is reduced from about 10%-50% as compared to a herd not receiving said immunogenic composition.

4. A method of providing a duration of immunity of at least 12 months against West Nile Virus by administering at least one dose of a killed or inactivated West Nile Virus to a horse or herd of horses in need thereof, wherein said West Nile Virus strain is Horse Origin 2005, also known as NAEE I59, deposited at the United States Department of Agriculture Isolate under accession number 405330 and also deposited with the ATCC under accession number PTA-9409.

* * * * *

SEQUENCE LISTING

<160> NUMBER OF SEQ ID NOS: 40

<210> SEQ ID NO 1
<211> LENGTH: 608
<212> TYPE: DNA
<213> ORGANISM: West Nile virus

<400> SEQUENCE: 1 cgggggggaat gtcacacttg catttacaac atgatgggaa agagagagaa aaaacccgga    60

| | |
|---|---|
| gaattcggaa aggccaaggg aagcagagcc atttggttca tgtggctcgg agctcgcttt | 120 |
| ctggagttcg aggctctggg ttttctcaat gaagaccact ggcttggaag aaagaactca | 180 |
| ggaggaggtg tcgagggctt gggcctccaa aaactgggtt acatcctgcg tgaagttggc | 240 |
| acccggcctg ggggcaagat ctatgctgat gacacagctg gctgggacac ccgcatcacg | 300 |
| agagctgact tggaaaatga agctaaggtg cttgagctgc ttgatgggga acatcggcgt | 360 |
| cttgccaggg ccatcattga gctcacctat cgtcacaaag ttgtgaaagt gatgcgcccg | 420 |
| gctgctgatg aagaaccgt catggatgtt atctccagag aagatcagag ggggagtgga | 480 |
| caagttgtca cctacgccct aaacactttc accaacctgg ccgtccagct ggtgaggatg | 540 |
| atggaagggg aaggagtgat tggcccagat gatgtggaga aactcacaaa agggaaagga | 600 |
| cccaaagt | 608 |

<210> SEQ ID NO 2
<211> LENGTH: 608
<212> TYPE: DNA
<213> ORGANISM: West Nile virus

<400> SEQUENCE: 2

| | |
|---|---|
| cgggggaat gtcacacttg catttacaac atgatgggaa agagagagaa aaacccgga | 60 |
| gagttcggaa aggccaaggg aagcagagcc atttggttca tgtggctcgg agctcgcttt | 120 |
| ctggagttcg aggctctggg ttttctcaat gaagaccact ggcttggaag aaagaactca | 180 |
| ggaggaggtg tcgagggctt gggcctccaa aaactgggtt acatcctgcg tgaagttggc | 240 |
| acccggcctg ggggcaagat ctatgctgat gacacagctg gctgggacac ccgcatcacg | 300 |
| agtgctgact tggaaaatga agctaaggtg cttgagttgc ttgatgggga acatcggcgt | 360 |
| cttgccaggg ccatcattga gctcacctat cgtcacaaag ttgtgaaagt gatgcgcccg | 420 |
| gctgctgatg aagaaccgt catggatgtt atctccagag aagatcagag ggggagtgga | 480 |
| caagttgtca cctacgccct aaacactttc accaacctgg ccgtccagct ggtgaggatg | 540 |
| atggaagggg aaggagtgat tggcccagat gatgtggaga aactcacaaa agggaaagga | 600 |
| cccaaagt | 608 |

<210> SEQ ID NO 3
<211> LENGTH: 909
<212> TYPE: DNA
<213> ORGANISM: West Nile virus
<220> FEATURE:
<221> NAME/KEY: modified_base
<222> LOCATION: (57)..(57)
<223> OTHER INFORMATION: a, c, g or t

<400> SEQUENCE: 3

| | |
|---|---|
| gcaatgcagc tttgggtgcc atgtttgaag agcagaatca atggaggagc gccaganaag | 60 |
| cagttgaaga tccaaaattt tgggagatgg tggatgagga gcgcgaggca catctgcggg | 120 |
| gggaatgtca cacttgcatt tacaacatga tgggaaagag agaaaaaa cccggagagt | 180 |
| tcggaaaggc taagggaagc agagccattt ggttcatgtg gctcggagct cgctttctgg | 240 |
| agttcgaggc tctgggtttt ctcaatgaag accactggct tggaagaaag aactcaggag | 300 |
| gaggtgtcga gggcttggc ctccaaaaac tgggttacat cctgcgtgaa gttggcaccc | 360 |
| gacctggggg caagatctat gctgatgaca cagccggctg ggacacccgc atcacgagag | 420 |
| ctgacttgga aaatgaagct aaggtgcttg agttgcttga tggggaacat cggcgtcttg | 480 |
| ccagggccat cattgagctc acctatcgtc acaaagttgt gaaagtgatg cgcccggctg | 540 |

```
ctgatggaag aaccgtcatg gatgttatct ccagagaaga tcagagggg agtggacaag        600 ttgtcaccta cgcccaaac actttcacca acctggccgt ccagctggtg aggatgatgg        660
aaggggaagg agtgattggc ccagatgatg tggagaaact cacaaaaggg aaaggaccca       720
aagtcaggac ctggctgttt gagaatgggg aagaaagact cagccgcatg gctgtcagtg       780
gagatgactg tgtggtaaag cccctggacg atcgctttgc cacctcgctc cacttcctca      840
atgctatgtc aaaggttcgc aaagacatcc aagagtggaa accgtcaact ggatggtatg      900
attggcagc                                                              909
```

```
<210> SEQ ID NO 4
<211> LENGTH: 975
<212> TYPE: DNA
<213> ORGANISM: West Nile virus
<220> FEATURE:
<221> NAME/KEY: modified_base
<222> LOCATION: (3)..(3)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (813)..(813)
<223> OTHER INFORMATION: a, c, g or t
<220> FEATURE:
<221> NAME/KEY: modified_base
<222> LOCATION: (881)..(882)
<223> OTHER INFORMATION: a, c, g or t

<400> SEQUENCE: 4
tcncggattc cncgcacgag atgtattggg tgagtcgagc ttcaggcaat gtggtacatt         60
cagtgaatat gaccagccag gtgctcctag gaagaatgga aaaaggacc tggaagggac        120 cccaatacga ggaagatgta aacttgggaa gtggaaccag ggcggtggga aaacccctgc       180
tcaactcaga caccagtaaa atcaagaaca ggattgaacg actcaggcgt gagtacagtt       240
cgacgtggca ccacgatgag aaccacccat atagaacctg gaactatcac ggcagttatg      300
atgtgaagcc cacaggctcc gccagttcgc tggttaatgg agtggtcagg ctcctctcaa      360
aaccatggga caccatcacg aatgttacca ccatggccat gactgacact actcccttcg      420
ggcagcagcg agtgttcaaa gagaaggtgg acacgaaagc tcctgaaccg ccagaaggag       480
tgaagtacgt gctcaacgag accaccaact ggttgtgggc gtttttggcc agagaaaaac      540
gtcccagaat gtgctctcga gaggaattca taagaaaggt caacagcaat gcagctttgg      600
gtgccatgtt tgaagagcag aatcaatgga ggagcgccag agaagcagtt gaagatccaa      660
aattttggga gatggtggat gaggagcgcg aggcacatct gcggggggaa tgtcacactt      720
gcatttacaa catgatggga aagagagaga aaaacccgg agagttcgga aaggctaagg       780
gaagcagagc catttggttc atgtggctcg ganctcgctt tctggagttc gaggctctgg      840
gttttctcaa tgaagaccac tggcttggaa gaaagaactc nngaggaggt gtcgagggct     900
tgggcctcca aaaactgggt tacatcctgc gtgaagttgg caccgaccct ggggcaaga      960 tctatgctga tgaca                                                       975
```

```
<210> SEQ ID NO 5
<211> LENGTH: 957
<212> TYPE: DNA
<213> ORGANISM: West Nile virus
<220> FEATURE:
```

<221> NAME/KEY: modified_base
<222> LOCATION: (8)..(8)
<223> OTHER INFORMATION: a, c, g or t
<220> FEATURE:
<221> NAME/KEY: modified_base
<222> LOCATION: (31)..(31)
<223> OTHER INFORMATION: a, c, g or t
<220> FEATURE:
<221> NAME/KEY: modified_base
<222> LOCATION: (51)..(51)
<223> OTHER INFORMATION: a, c, g or t
<220> FEATURE:
<221> NAME/KEY: modified_base
<222> LOCATION: (83)..(83)
<223> OTHER INFORMATION: a, c, g or t
<220> FEATURE:
<221> NAME/KEY: modified_base
<222> LOCATION: (130)..(130)
<223> OTHER INFORMATION: a, c, g or t

<400> SEQUENCE: 5

```
aatggagngg tcaggctcct ctcaaaaccc ntgggacacc atcacgaatg ntaccaccat      60
ggccatgact gacactactc ccnttcgggc agcagcgagt gttcaaagag aaggtggaca     120
cgaaagctcn tgaaccgcca gaaggagtga agtacgtgct caacgagacc accaactggt    180
tgtgggcgtt tttggccaga gaaaaacgtc ccagaatgtg ctctcgagag gaattcataa    240
gaaaggtcaa cagcaatgca gctttgggtg ccatgtttga agagcagaat caatggagga    300
gcgccagaga agcagttgaa gatccaaaat tttgggagat ggtggatgag gagcgcgagg    360
cacatctgcg gggggaatgt cacacttgca tttacaacat gatgggaaag agagagaaaa    420
aacccggaga gttcggaaag gctaagggaa gcagagccat ttggttcatg tggctcggag    480
ctcgcttttct ggagttcgag gctctggtt ttctcaatga agaccactgg cttggaagaa    540
agaactcagg aggaggtgtc gagggcttgg gcctccaaaa actgggttac atcctgcgtg    600
aagttggcac ccgacctggg ggcaagatct atgctgatga cacagccggc tgggacaccc    660
gcatcacgag agctgacttg gaaaatgaag ctaaggtgct tgagttgctt gatgggaac    720
atcggcgtct tgccagggcc atcattgagc tcacctatcg tcacaaagtt gtgaaagtga    780
tgcgcccggc tgctgatgga agaaccgtca tggatgttat ctccagagaa gatcagaggg    840
ggagtggaca agttgtcacc tacgccctaa acactttcac caacctggcc gtccagctgg    900
tgaggatgat ggaaggggaa ggagtgattg cccagatga tgtggagaaa ctcacaa       957
```

<210> SEQ ID NO 6
<211> LENGTH: 961
<212> TYPE: DNA
<213> ORGANISM: West Nile virus
<220> FEATURE:
<221> NAME/KEY: modified_base
<222> LOCATION: (30)..(30)
<223> OTHER INFORMATION: a, c, g or t
<220> FEATURE:
<221> NAME/KEY: modified_base
<222> LOCATION: (41)..(41)
<223> OTHER INFORMATION: a, c, g or t
<220> FEATURE:
<221> NAME/KEY: modified_base
<222> LOCATION: (62)..(63)
<223> OTHER INFORMATION: a, c, g or t
<220> FEATURE:
<221> NAME/KEY: modified_base
<222> LOCATION: (107)..(107)
<223> OTHER INFORMATION: a, c, g or t

<400> SEQUENCE: 6

```
gggaccccaa tacgaggaag atgtaaactn gggaagtgga nccagggcgg tgggaaaacc      60
```

```
cnngctcaac tcagacacca gtaaaatcaa gaacaggatt gaacgantca ggcgtgagta    120
cagttcgacg tggcaccacg atgagaacca cccatataga acctggaact atcacggcag    180
ttatgatgtg aagcccacag gctccgccag ttcgctggtt aatggagtgg tcaggctcct    240
ctcaaaacca tggacaccca tcacgaatgt taccaccatg ccatgactg acactactcc     300 cttcgggcag cagcgagtgt tcaaagagaa ggtggacacg aaagctcctg aaccgccaga    360
aggagtgaag tacgtgctca acgagaccac caactggttg tgggcgtttt tggccagaga    420
aaaacgtccc agaatgtgct ctcgagagga attcataaga aggtcaaca gcaatgcagc     480 tttgggtgcc atgtttgaag agcagaatca atggaggagc gccagagaag cagttgaaga    540
tccaaaattt tgggagatgg tggatgagga gcgcgaggca catctgcggg gggaatgtca    600
cacttgcatt tacaacatga tgggaaagag agagaaaaaa cccggagagt tcggaaaggc    660
taagggaagc agagccattt ggttcatgtg gctcggagct cgctttctgg agttcgaggc    720
tctgggtttt ctcaatgaag accactggct tggaagaaag aactcaggag gaggtgtcga    780
gggcttgggc ctccaaaaac tgggttacat cctgcgtgaa gttggcaccc gacctggggg    840
caagatctat gctgatgaca cagccggctg ggacacccgc atcacgagag ctgacttgga    900
aaatgaagct aaggtgcttg agttgcttga tgggaacat cggcgtcttg ccagggccat      960
c                                                                    961

<210> SEQ ID NO 7
<211> LENGTH: 1503
<212> TYPE: DNA
<213> ORGANISM: West Nile virus

<400> SEQUENCE: 7
ttcaactgcc ttggaatgag caacagagac ttcttggaag gagtgtctgg agcaacatgg     60
gtggatttgg ttctcgaagg cgacagctgc gtgactatca tgtctaagga caagcctacc    120
atcgatgtga agatgatgaa tatggaggcg gccaacctgg cagaggtccg cagttattgc    180
tatttggcta ccgtcagcga tctctccacc aaagctgcgt gcccgaccat gggagaagct    240
cacaatgaca acgtgctga cccagctttt gtgtgcagac aaggagtggt ggacaggggc    300
tggggcaacg gctgcggact atttggcaaa ggaagcattg acacatgcgc caaatttgcc    360
tgctctacca aggcaatagg aagaaccatc ttgaaagaga tatcaagta cgaagtggcc    420 atttttgtcc atggaccaac tactgtggag tcgcacggaa actactccac acaggttgga    480
gccactcagg cagggagatt cagcatcact cctgcgcgc cttcacacac actaaagctt    540
ggagaatatg gagaggtgac agtggactgt gaaccacggt cagggattga caccaatgca    600
tactacgtga tgactgttgg aacaaagacg ttccttggtc catcgtgagtg gttcatggac    660 ctcaacctcc cttggagcag tgctggaagt actgtgtgga ggaacagaga gacgttaatg    720
gagtttgagg aaccacacgc cacgaagcag tctgtgatag cattgggctc acaagaggga    780
gctctgcagc aagctttggc tggagccatt cctgtggaat tttcaagcaa cactgtcaag    840
ttgacgtcgg tcatttgaa gtgtagagtg aagatgaaa aattgcagtt gaagggaaca    900
acctatggcg tctgttcaaa ggcttttcaag ttcttggga ctcccgcaga cacaggtcac    960
ggcactgtgg tgttggaatt gcagtacact ggcacggatg gaccttgcaa agttcctatc    1020
tcgtcagtgg cttcattgaa cgacctaacg ccagtgggca gattggtcac tgtcaaccct    1080
tttgtttcag tggccacggc caacgctaag gtcctgattg aattggaacc acccttggga    1140
```

```
gactcataca tagtggtggg cagaggagaa caacagatca atcaccattg cacaagtct     1200 ggaagcagca ttggcaaagc ctttacaacc accctcaaag gagcgcagag actagccgct    1260
ctaggagaca cagcttggga cttiggatca gttggagggg tgttcacctc agttgggaag    1320
gctgtccatc aagtgttcgg aggagcattc cgctcactgt tcggaggcat gtcctggata    1380
acgcaaggat tgctgggggc tctcctgttg tggatgggca tcaatgctcg tgataggtcc    1440
atagctctca cgtttctcgc agttggagga gttctgctct tcctctccgt gaacgtgcac    1500
gct                                                                  1503

<210> SEQ ID NO 8
<211> LENGTH: 1503
<212> TYPE: DNA
<213> ORGANISM: West Nile virus

<400> SEQUENCE: 8
ttcaactgcc ttggaatgag caacagagac ttcttggaag gagtgtctgg agcaacatgg      60
gtggatttgg ttctcgaagg cgacagctgc gtgactatca tgtctaagga caagcctacc     120
atcgatgtga agatgatgaa tatggaggcg gccaacctgg cagaggtccg cagttattgc     180
tatttggcta ccgtcagcga tctctccacc aaagctgcgt gcccgaccat gggagaagct     240
cacaatgaca acgtgctga cccagctttt gtgtgcagac aaggagtggt ggacaggggc      300
tggggcaacg gctgcggact atttggcaaa ggaagcattg acacatgcgc caaatttgcc     360
tgctctacca aggcaatagg aagaaccatc ttgaaagaga atatcaagta cgaagtggcc     420 attttttgtcc atggaccaac tactgtggag tcgcacggaa actattccac acaggctgga     480
gccactcagg cagggagatt cagcatcact cctgcggcgc ttcatacac actaaagctt      540 ggagaatatg gagaggtgac agtggactgt gaaccacggt cagggattga caccaatgca     600
tactacgtga tgactgttgg aacaaagacg ttcttggtcc atcgtgagtg gttcatggac     660
ctcaacctcc cttggagcag tgctggaagt actgtgtgga ggaacagaga gacgttaatg     720
gagtttgagg aaccacacgc cacgaagcag tctgtgatag cattgggctc acaagaggga     780
gctctgcatc aagcttttgc tggagccatt cctgtggaat tttcaagcaa cactgtcaag     840
ttgacgtcgg gtcattigaa gtgtagagtg aagatggaaa aattgcagtt gaagggaaca     900
acctatggcg tctgttcaaa ggcttttcaag ttcttggga ctcccgcaga cacaggtcac      960
ggcactgtgg tgttggaatt gcagtacact ggcacggatg gaccttgcaa agttcctatc    1020
tcgtcagtgg cttcattgaa cgacctaacg ccagtgggca gattggtcac tgtcaaccct    1080
tttgtttcag tggccacggc caacgctaag gtcctgattg aattggaacc accctttgga    1140
gactcataca tagtggtggg cagaggagaa caacagatca atcaccattg cacaagtct     1200 ggaagtagca ttggcaaagc ctttacaacc accctcaaag gagcgcagag actagccgct    1260
ctaggagaca cagcttggga ctttggatca gttggagggg tgttcacctc agttgggaag    1320
gctgtccatc aagtgttcgg aggagcattc cgctcactgt tcggaggcat gtcctggata    1380
acgcaaggat tgctgggggc tctcctgttg tggatgggca tcaatgctcg tgataggtcc    1440
atagctctca cgtttctcgc agttggagga gttctgctct tcctctccgt gaacgtgcat    1500
gct                                                                  1503

<210> SEQ ID NO 9
<211> LENGTH: 1376
<212> TYPE: DNA
<213> ORGANISM: West Nile virus
```

```
<220> FEATURE:
<221> NAME/KEY: modified_base
<222> LOCATION: (1358)..(1358)
<223> OTHER INFORMATION: a, c, g or t

<400> SEQUENCE: 9
gatgtggaga gaatatggag gcggccaacc tggcagaggt ccgcagttat tgctatttgg      60
ctaccgtcag cgatctctcc accaaagctg cgtgcccgac catgggagaa gctcacaatg    120
acaaacgtgc tgacccagct tttgtgtgca gacaaggagt ggtggacagg ggctggggca    180
acggctgcgg actatttggc aaaggaagca ttgacacatg cgccaaattt gcctgctcta    240
ccaaggcaat aggaagaacc atcttgaaag agaatatcaa gtacgaagtg gccattttttg    300
tccatggacc aactactgtg gagtcgcacg gaaactactc cacacaggtt ggagccactc    360
aggcagggag attcagcatc actcctgcgg cgccttcata cactaaaag cttggagaat    420
atggagaggt gacagtggac tgtgaaccac ggtcagggat tgacaccaat gcatactatg    480
tgatgactgt tggaacaaag acgttcttgg tccatcgtga gtggttcatg gacctcaacc    540
tcccttggag cagtgctgga agtactgtgt ggaggaacag agagacgtta atggagtttg    600
aggaaccaca cgccacgaag cagtctgtga tagcattggg ctcacaagag ggagctctgc    660
atcaagcttt ggctggagcc attcctgtgg aatttcaag caacactgtc aagttgacgt    720
cgggtcattt gaagtgtaga gtgaagatgg aaaaattgca gttgaaggga acaacctatg    780
gcgtctgttc aaaggctttc aagtttcttg ggactccgc agacacaggt cacggcactg    840
tggtgttgga attgcagtac actggcacgg atggaccttg caaagttcct atctcgtcag    900
tggcttcatt gaacgaccta acgccagtgg gcagattggt cactgtcaac cctttttgttt    960
cagtggccac ggccaacgct aaggtcctga ttgaattgga accacccttt ggagactcat   1020
acatagtggt gggcagagga gaacaacaga tcaatcacca ttggcacaag tctgaaagca   1080
gcattggcaa agccttttaca accacccctca aaggagcgca gagactagcc gctctaggag   1140
acacagcttg ggacttttgga tcagttggag gggtgttcac ctcagttggg aaggctgtcc   1200
atcaagtgtt cggaggagca ttccgctcac tgttcggagg catgtcctgg ataacgcaag   1260
gattgctggg ggctctcctg ttgtggatgg gcatcaatgc tcgtgatagg tccatagctc   1320
tcacgtttct cgcagttgga ggagttctgc tcttcctntc cgtgaacgtg cacgct       1376

<210> SEQ ID NO 10
<211> LENGTH: 1376
<212> TYPE: DNA
<213> ORGANISM: West Nile virus

<400> SEQUENCE: 10
gatgtggaga gaatatggag gcggccaacc tggcagaggt ccgcagttat tgctatttgg      60
ctaccgtcag cgatctctcc accaaagctg cgtgcccgac catgggagaa gctcacaatg    120
acaaacgtgc tgacccagct tttgtgtgca gacaaggagt ggtggacagg ggctggggca    180
acggctgcgg actatttggc aaaggaagca ttgacacatg cgccaaattt gcctgctcta    240
ccaaggcaat aggaagaacc atcttgaaag agaatatcaa gtacgaagtg gccattttttg    300
tccatggacc aactactgtg gagtcgcacg gaaactactc cacacaggct ggagccactc    360
aggcagggag attcagcatc actcctgcgg cgccttcata cactaaaag cttggagaat    420
atggagaggt gacagtggac tgtgaaccac ggtcagggat tgacaccaat gcatactacg    480
tgatgactgt tggaacaaag acgttcttgg tccatcgtga gtggttcatg gacctcaacc    540
```

-continued

```
tcccttggag cagtgctgga agtactgtgt ggaggaacag agagacgtta atggagtttg      600
aggaaccaca cgccacgaag cagtctgtga tagcattggg ctcacaagag ggagctctgc      660
atcaagcttt ggctggagcc attcctgtgg aattttcaag caacactgtc aagttgacgt      720
cgggtcattt gaagtgtaga gtgaagatgg aaaaattgca gttgaaggga acaacctatg      780
gcgtctgttc aaaggctttc aagtttcttg gactcccgc agacacaggt cacggcactg       840
tggtgttgga attgcagtac actggcacgg atggaccttg caaagttcct atctcgtcag      900
tggcttcatt gaacgaccta cgccagtggg gcagattggt cactgtcaac ccttttgttt      960
cagtggccac ggccaacgct aaggtcctga ttgaattgga accacccttt ggagactcat     1020
acatagtggt gggcagagga gaacaacaga tcaatcacca ttggcacaag tctggaagca     1080
gcattggcaa agcctttaca accaccctca aggagcgca gagactagcc gctctaggag       1140
acacagcttg ggactttgga tcagttggag gggtgttcac ctcagttggg aaggctgtcc     1200
atcaagtgtt cggaggagca ttccgctcac tgttcggagg catgtcctgg ataacgcaag     1260
gattgctggg ggctctcctg ttgtggatgg gcatcaatgc tcgtgatagg tccatagctc     1320
tcacgtttct cgcagttgga ggagttctgc tcttcctctc cgtgaacgtg catgct        1376
```

<210> SEQ ID NO 11
<211> LENGTH: 1376
<212> TYPE: DNA
<213> ORGANISM: West Nile virus

<400> SEQUENCE: 11

```
gatgtggaga gaatatggag gcggccaacc tggcagaggt ccgcagttat tgctatttgg       60
ctaccgtcag cgatctctcc accaaagctg cgtgcccgac catgggagaa gctcacaatg      120
acaaacgtgc tgacccagct tttgtgtgca gacaaggagt ggtggacagg ggctgggca       180
acggctgcgg actatttggc aaaggaagca ttgacacatg cgccaaattt gcctgctcta      240
ccaaggcaat aggaagaacc atcttgaaag agaatatcaa gtacgaagtg ccattttg       300
tccatggacc aactactgtg gagtcgcacg gaaactactc cacacaggct ggagccactc      360
aggcagggag attcagcatc actcctgcgg cgccttcata cactaaaag cttggagaat      420
atggagaggt gacagtggac tgtgaaccac ggtcagggat tgacaccaat gcatactacg      480
tgatgactgt tggaacaaag acgttcttgg tccatcgtga gtggttcatg acctcaacc       540
tcccttggag cagtgctgga agtactgtgt ggaggaacag agagacgtta atggagtttg      600
aggaaccaca cgccacgaag cagtctgtga tagcattggg ctcacaagag ggagctctgc      660
atcaagcttt ggctggagcc attcctgtgg aattttcaag caacactgtc aagttgacgt      720
cgggtcattt gaagtgtaga gtgaagatgg aaaaattgca gttgaaggga acaacctatg      780
gcgtctgttc aaaggctttc aagtttcttg gactcccgc agacacaggt cacggcactg       840
tggtgttgga attgcagtac actggcacgg atggaccttg caaagttcct atctcgtcag      900
tggcttcatt gaacgatcta cgccagtggg gcagattggt cactgtcaac ccttttgttt      960
cagtggccac ggccaacgct aaggtcctga ttgaattgga accacccttt ggagactcat     1020
acatagtggt gggcagagga gaacaacaga tcaatcacca ttggcacaag tctggaagca     1080
gcattggcaa agcctttaca accaccctca aggagcgca gagactagcc gctctaggag       1140
acacagcttg ggactttgga tcagttggag gggtgttcac ctcagttggg aaggctgtcc     1200
atcaagtgtt cggaggagca ttccgcacac tgttcggagg catgtcctgg ataacgcaag     1260
gattgctggg ggctctcctg ttgtggatgg gcatcaatgc tcgtgatagg tccatagctc     1320
```
tcacgtttct cgcagttgga ggagttctgc tcttcctctc cgtgaacgtg catgct      1376

<210> SEQ ID NO 12
<211> LENGTH: 608
<212> TYPE: DNA
<213> ORGANISM: West Nile virus

<400> SEQUENCE: 12 cgggggaat gtcacacttg catttacaac atgatgggaa agagagagaa aaacccgga    60 gaattcggaa aggccaaggg aagcagagcc atttggttca tgtggctcgg agctcgcttt  120
ctggagttcg aggctctggg ttttctcaat gaagaccact ggcttggaag aaagaactca  180
ggaggaggtg tcgagggctt gggcctccaa aaactgggtt acatcctgcg tgaagttggc  240
acccggcctg ggggcaagat ctatgctgat gacacagctg gctgggacac ccgcatcacg  300
agagctgact tggaaaatga agctaaggtg cttgagctgc ttgatgggga acatcggcgt  360
cttgccaggg ccatcattga gctcacctat cgtcacaaag ttgtgaaagt gatgcgcccg  420
gctgctgatg aagaaccgt catggatgtt atctccagag aagatcagag ggggagtgga  480
caagttgtca cctacgccct aaacactttc accaacctgg ccgtccagct ggtgaggatg  540
atggaagggg aaggagtgat tggcccagat gatgtggaga aactcacaaa agggaaagga  600
cccaaagt                                                          608

<210> SEQ ID NO 13
<211> LENGTH: 608
<212> TYPE: DNA
<213> ORGANISM: West Nile virus

<400> SEQUENCE: 13 cgggggaat gtcacacttg catttacaac atgatgggaa agagagagaa aaacccgga    60 gagttcggaa aggccaaggg aagcagagcc atttggttca tgtggctcgg agctcgcttt  120
ctggagttcg aggctctggg ttttctcaat gaagaccact ggcttggaag aaagaactca  180
ggaggaggtg tcgagggctt gggcctccaa aaactgggtt acatcctgcg tgaagttggc  240
acccggcctg ggggcaagat ctatgctgat gacacagctg gctgggacac ccgcatcacg  300
agtgctgact tggaaaatga agctaaggtg cttgagttgc ttgatgggga acatcggcgt  360
cttgccaggg ccatcattga gctcacctat cgtcacaaag ttgtgaaagt gatgcgcccg  420
gctgctgatg aagaaccgt catggatgtt atctccagag aagatcagag ggggagtgga  480
caagttgtca cctacgccct aaacactttc accaacctgg ccgtccagct ggtgaggatg  540
atggaagggg aaggagtgat tggcccagat gatgtggaga aactcacaaa agggaaagga  600
cccaaagt                                                          608

<210> SEQ ID NO 14
<211> LENGTH: 981
<212> TYPE: DNA
<213> ORGANISM: West Nile virus

<400> SEQUENCE: 14
ggaactatcc ggagtatgat gtgaagctcg ctgtcaatga gtgtcaggct cttcaaaacc   60
tgggacccat ccgaaccgcc atgactgcac tactcccttc gggcagcagc gagtgttcaa  120
agagaaggtg gacacgaaag ctcgaaccgc cagaaggagt gaagtacgtg ctcaacgaga  180
ccaccaactg gttgtgggcg ttttggcca gagaaaaacg tcccagaatg tgctctcgag  240

| | |
|---|---|
| agatagaaag gtcaacagca atgcagcttt gggtgccatg tttgaagagc agaatcaatg | 300 |
| gaggagcgcc agagaagcag ttgaagatcc aaaattttgg gagatggtgg atgaggagcg | 360 |
| cgaggcacat ctgcggggg aatgtcacac ttgcatttac aacatgatgg gaaagagaga | 420 |
| gaaaaaaccc ggagagttcg gaaaggccaa gggaagcaga gccatttggt tcatgtggct | 480 |
| cggagctcgc tttctggagt tcgaggctct gggttttctc aatgaagatc actggcttgg | 540 |
| aagaaagaac tcaggaggag gtgtcgaggg cttgggcctc caaaaactgg gttacatcct | 600 |
| gcgtgaagtt ggcacccggc tgggggcaa gatctatgct gatgacacag ctggctggga | 660 |
| cacccgcatc acgagagctg acttggaaaa tgaagctaag gtgcttgagc tgcttgatgg | 720 |
| ggaacatcgg cgtcttgcca gggccatcat tgagctcacc tatcgtcaca agttgtgaa | 780 |
| agtgatgcgc ccggctgctg atggaagaac cgtcatggat gttatctcca gagaagatca | 840 |
| gagggggagt ggacaagttg tcacctacgc cctaaacact ttcaccaacc tggccgtcca | 900 |
| gctggtgagg atgatggaag gggaaggagt gattggccca gatgatgtgg agaaactcac | 960 |
| aaaagggaaa ggacccaaag t | 981 |

<210> SEQ ID NO 15
<211> LENGTH: 974
<212> TYPE: DNA
<213> ORGANISM: West Nile virus

<400> SEQUENCE: 15

| | |
|---|---|
| ttcgctgtca atggagtgtc aggctcctct caaaaccatg gacaccatc acgaatccac | 60 |
| catggccatg actgacacta ctcccttcgg cagcagcga gtgttcaaag agaaggtgga | 120 |
| cacgaaagct gaaccgccag aaggagtgaa gtacgtgctc aacgagacca ccaactggtt | 180 |
| gtgggcgttt ttggccagag aaaaacgtcc cagaatgtgc tctcgagagg aattcatga | 240 |
| aaggtcaaca gcaatgcagc tttgggtgcc atgtttgaag agcagaatca atggaggagc | 300 |
| gccagagaag cagttgaaga tccaaaattt tgggagatgg tggatgagga gcgcgaggca | 360 |
| catctgcggg gggaatgtca cacttgcatt tacaacatga tgggaaagag agagaaaaaa | 420 |
| cccggagagt tcggaaaggc caagggaagc agagccattt ggttcatgtg gctcggagct | 480 |
| cgctttctgg agttcgaggc tctgggtttt ctcaatgaag accactggct tggaagaaag | 540 |
| aactcaggag gaggtgtcga gggcttgggc ctccaaaaac tgggttacat cctgcgtgaa | 600 |
| gttggcaccc ggcctggggg caagatctat gctgatgaca cagctggctg ggacacccgc | 660 |
| atcacgagag ctgacttgga aaatgaagct aaggtgcttg agttgcttga tgggaacat | 720 |
| cggcgtcttg ccagggccat cattgagctc acctatcgtc acaaagttgt gaaagtgatg | 780 |
| cgcccggctg ctgatggaag aaccgtcatg gatgttatct ccagaagaa tcagaggggg | 840 |
| agtggacaag ttgtcaccta cgccctaaac actttcacca acctggccgt ccagctggtg | 900 |
| aggatgatgg aaggggaagg agtgattggc ccagatgatg tggagaaact cacaaaaggg | 960 |
| aaaggaccca aagt | 974 |

<210> SEQ ID NO 16
<211> LENGTH: 970
<212> TYPE: DNA
<213> ORGANISM: West Nile virus

<400> SEQUENCE: 16

| | |
|---|---|
| aatggagggt caggctcctc tcaaaacctg gacaccatc acgaatgtac caccatggcc | 60 |
| atgactgaca ctactcccct tcgggcagcag cgagtgttca agagaaggt ggacacgaaa | 120 |

```
gctctgaacc gccagaagga gtgaagtacg tgctcaacga gaccaccaac tggttgtggg      180 cgttttttggc cagagaaaaa cgtcccagaa tgtgctctcg agaggaattc ataagaaagg     240
tcaacagcaa tgcagctttg ggtgccatgt ttgaagagca gaatcaatgg aggagcgcca     300
gagaagcagt tgaagatcca aaattttggg agatggtgga tgaggagcgc gaggcacatc     360
tgcgggggga atgtcacact tgcatttaca acatgatggg aaagagagag aaaaaacccg     420
gagagttcgg aaaggctaag ggaagcagag ccatttggtt catgtggctc ggagctcgct     480
ttctggagtt cgaggctctg gttttctca atgaagacca ctggcttgga agaaagaact      540
caggaggagg tgtcgagggc ttgggcctcc aaaaactggg ttacatcctg cgtgaagttg     600
gcacccgacc tggggggcaag atctatgctg atgacacagc cggctgggac acccgcatca    660
cgagagctga cttggaaaat gaagctaagg tgcttgagtt gcttgatggg aacatcggc      720 gtcttgccag ggccatcatt gagctcacct atcgtcacaa agttgtgaaa gtgatgcgcc    780
cggctgctga tggaagaacc gtcatggatg ttatctccag agaagatcag aggggggagtg   840 gacaagttgt cacctacgcc ctaaacactt tcaccaacct ggccgtccag ctggtgagga    900
tgatggaagg ggaaggagtg attggcccag atgatgtgga gaaactcaca aaagggaaag    960
gacccaaagt                                                            970

<210> SEQ ID NO 17
<211> LENGTH: 1503
<212> TYPE: DNA
<213> ORGANISM: West Nile virus

<400> SEQUENCE: 17
ttcaactgcc ttggaatgag caacagagac ttcttggaag gagtgtctgg agcaacatgg      60
gtggatttgg ttctcgaagg cgacagctgc gtgactatca tgtctaagga caagcctacc     120
atcgatgtga agatgatgaa tatggaggcg gccaacctgg cagaggtccg cagttattgc     180
tatttggcta ccgtcagcga tctctccacc aaagctgcgt gcccgaccat gggagaagct     240
cacaatgaca acgtgctgaa cccagctttt gtgtgcagac aaggagtggt ggacaggggc     300
tggggcaacg gctgcggact atttggcaaa ggaagcattg acacatgcgc caaatttgcc     360
tgctctacca aggcaatagg aagaaccatc ttgaaagaga atatcaagta cgaagtggcc     420 attttttgtcc atggaccaac tactgtggag tcgcacggaa actactccac acaggttgga     480
gccactcagg cagggagatt cagcatcact cctgcggcgc cttcacacac actaaagctt    540
ggagaatatg gagaggtgac agtggactgt gaaccacggt cagggattga caccaatgca    600
tactacgtga tgactgttgg aacaaagacg ttcttggtcc atcgtgagtg gttcatggac    660
ctcaacctcc cttggagcag tgctggaagt actgtgtggga ggaacagaga gacgttaatg   720
gagtttgagg aaccacacgc cacgaagcag tctgtgatag cattgggctc acaagaggga    780
gctctgcagc aagcttttgc tggagccatt cctgtgaat tttcaagcaa cactgtcaag    840
ttgacgtcgg gtcatttgaa gtgtagagtg aagatggaaa aattgcagtt gaagggaaca    900
acctatggcg tctgttcaaa ggcttttcaag tttcttggga ctcccgcaga cacaggtcac    960
ggcactgtgg tgttggaatt gcagtacact ggcacggatg gaccttgcaa agttcctatc   1020
tcgtcagtgg cttcattgaa cgacctaacg ccagtgggca gattggtcac tgtcaaccct   1080 tttgttcag tggccacggc caacgctaag gtcctgattg aattggaacc accctttgga   1140
gactcataca tagtggtggg cagaggagaa caacagatca atcaccattg gcacaagtct   1200
```

```
ggaagcagca ttggcaaagc ctttacaacc accctcaaag gagcgcagag actagccgct      1260
ctaggagaca cagcttggga cttttggatca gttggagggg tgttcacctc agttgggaag     1320
gctgtccatc aagtgttcgg aggagcattc cgctcactgt tcggaggcat gtcctggata     1380
acgcaaggat tgctgggggc ctctcctgttg tggatgggca tcaatgctcg tgataggtcc    1440
atagctctca cgtttctcgc agttggagga gttctgctct tcctctccgt gaacgtgcac     1500
gct                                                                     1503

<210> SEQ ID NO 18
<211> LENGTH: 1503
<212> TYPE: DNA
<213> ORGANISM: West Nile virus

<400> SEQUENCE: 18
ttcaactgcc ttggaatgag caacagagac ttcttggaag gagtgtctgg agcaacatgg       60
gtggatttgg ttctcgaagg cgacagctgc gtgactatca tgtctaagga caagcctacc      120
atcgatgtga agatgatgaa tatggaggcg gccaacctgg cagaggtccg cagttattgc      180
tatttggcta ccgtcagcga tctctccacc aaagctgcgt gcccgaccat gggagaagct      240
cacaatgaca acgtgctga cccagctttt gtgtgcagac aaggagtggt ggacaggggc      300
tggggcaacg gctgcggact atttggcaaa ggaagcattg cacatgcgc caaatttgcc      360 tgctctacca aggcaatagg aagaaccatc ttgaaagaga atatcaagta cgaagtggcc      420 attttgtcc atggaccaac tactgtggag tcgcacggaa actattccac acaggctgga      480
gccactcagg cagggagatt cagcatcact cctgcgcgc cttcatacac actaaagctt      540
ggagaatatg gagaggtgac agtggactgt gaaccacggt cagggattga caccaatgca      600
tactacgtga tgactgttgg aacaaagacg ttcttggtcc atcgtgagtg gttcatggac      660
ctcaacctcc cttggagcag tgctggaagt actgtgtgga ggaacagaga gacgttaatg     720
gagtttgagg aaccacacgc cacgaagcag tctgtgatag cattgggctc acaagaggga     780
gctctgcatc aagctttggc tggagccatt cctgtggaat tttcaagcaa cactgtcaag     840
ttgacgtcgg gtcatttgaa gtgtagagtg aagatggaaa aattgcagtt gaagggaaca     900
acctatggcg tctgttcaaa ggcttttcaag tttcttggga ctcccgcaga cacaggtcac     960
ggcactgtgt gttgaatt gcagtacact ggcacggatg gaccttgcaa agttcctatc     1020
tcgtcagtgg cttcattgaa cgacctaacg ccagtgggca gattggtcac tgtcaaccct    1080
tttgtttcag tggccacggc caacgctaag gtcctgattg aattggaacc acccttggga    1140
gactcataca tagtggtggg cagaggagaa caacagatca atcaccattg gcacaagtct     1200
ggaagtagca ttggcaaagc ctttacaacc accctcaaag gagcgcagag actagccgct    1260
ctaggagaca cagcttggga cttttggatca gttggagggg tgttcacctc agttgggaag    1320
gctgtccatc aagtgttcgg aggagcattc cgctcactgt tcggaggcat gtcctggata    1380
acgcaaggat tgctgggggc ctctcctgttg tggatgggca tcaatgctcg tgataggtcc   1440
atagctctca cgtttctcgc agttggagga gttctgctct tcctctccgt gaacgtgcat    1500
gct                                                                    1503

<210> SEQ ID NO 19
<211> LENGTH: 968
<212> TYPE: DNA
<213> ORGANISM: West Nile virus
<220> FEATURE:
<221> NAME/KEY: modified_base
```

```
<222> LOCATION: (7)..(7)
<223> OTHER INFORMATION: a, c, g or t
<220> FEATURE:
<221> NAME/KEY: modified_base
<222> LOCATION: (10)..(10)
<223> OTHER INFORMATION: a, c, g or t
<220> FEATURE:
<221> NAME/KEY: modified_base
<222> LOCATION: (13)..(13)
<223> OTHER INFORMATION: a, c, g or t
<220> FEATURE:
<221> NAME/KEY: modified_base
<222> LOCATION: (941)..(942)
<223> OTHER INFORMATION: a, c, g or t

<400> SEQUENCE: 19
gatgtgngan gangaatatg gaggcggcca acctggcaga ggtccgcagt tattgctatt      60
tggctaccgt cagcgatctc tccaccaaag ctgcgtgccc gaccatggga gaagctcaca     120
atgacaaacg tgctgaccca gcttttgtgt gcagacaagg agtggtggac aggggctggg     180
gcaacggctg cggactattt ggcaaaggaa gcattgacac atgcgccaaa tttgcctgct     240
ctaccaaggc aataggaaga accatcttga aagagaatat caagtacgaa gtggccattt     300
ttgtccatgg accaactact gtggagtcgc acggaaacta ctccacacag gctggagcca     360
ctcaggcagg gagattcagc atcactcctg cggcgccttc atacacacta aagcttggag     420
aatatggaga ggtgacagtg gactgtgaac cacggtcagg gattgacacc aatgcatact     480
acgtgatgac tgttggaaca aagacgttct tggtccatcg tgagtggttc atggacctca     540
acctcccttg gagcagtgct ggaagtactg tgtggaggaa cagagagacg ttaatggagt     600
ttgaggaacc acacgccacg aagcagtctg tgatagcatt gggctcacaa gagggagctc     660
tgcatcaagc tttggctgga gccattcctg tggaatttte aagcaacact gtcaagttga     720
cgtcgggtca tttgaagtgt agagtgaaga tggaaaaatt gcagttgaag ggaacaacct     780
atggcgtctg ttcaaaggct ttcaagtttc ttgggactcc cgcagacaca ggtcacggca     840
ctgtggtgtt ggaattgcag tacactggca cggatggacc ttgcaaagtt cctatctcgt     900
cagtggcttc attgaacgat ctaacgccag tgggcagatt nntcactgtc aacccttttg     960
tttcagtg                                                              968

<210> SEQ ID NO 20
<211> LENGTH: 979
<212> TYPE: DNA
<213> ORGANISM: West Nile virus
<220> FEATURE:
<221> NAME/KEY: modified_base
<222> LOCATION: (4)..(4)
<223> OTHER INFORMATION: a, c, g or t
<220> FEATURE:
<221> NAME/KEY: modified_base
<222> LOCATION: (6)..(6)
<223> OTHER INFORMATION: a, c, g or t
<220> FEATURE:
<221> NAME/KEY: modified_base
<222> LOCATION: (10)..(10)
<223> OTHER INFORMATION: a, c, g or t
<220> FEATURE:
<221> NAME/KEY: modified_base
<222> LOCATION: (974)..(974)
<223> OTHER INFORMATION: a, c, g or t

<400> SEQUENCE: 20
cttnanagan atcaagtacg aagtggccat ttttgtccat ggaccaacta ctgtggagtc      60
gcacggaaac tactccacac aggctggagc cactcaggca gggagattca gcatcactcc     120
```

-continued

```
tgcggcgcct tcatacacac taaagcttgg agaatatgga gaggtgacag tggactgtga      180
accacggtca gggattgaca ccaatgcata ctacgtgatg actgttggaa caaagacgtt      240
cttggtccat cgtgagtggt tcatggacct caacctccct tggagcagtg ctggaagtac      300
tgtgtggagg aacagagaga cgttaatgga gtttgaggaa ccacacgcca cgaagcagtc      360
tgtgatagca ttgggctcac aagagggagc tctgcatcaa gctttggctg gagccattcc      420
tgtggaattt tcaagcaaca ctgtcaagtt gacgtcgggt catttgaagt gtagagtgaa      480
gatggaaaaa ttgcagttga agggaacaac ctatggcgtc tgttcaaagg ctttcaagtt      540
tcttgggact cccgcagaca caggtcacgg cactgtggtg ttggaattgc agtacactgg      600
cacggatgga ccttgcaaag ttcctatctc gtcagtggct tcattgaacg atctaacgcc      660
agtgggcaga ttggtcactg tcaacccttt tgtttcagtg ccacggcca acgctaaggt      720 cctgattgaa ttgaaccac cctttggaga ctcatacata gtggtgggca gaggagaaca      780
acagatcaat caccattggc acaagtctgg aagcagcatt ggcaaagcct ttacaaccac      840
cctcaaagga gcgcagagac tagccgctct aggagacaca gcttgggact ttggatcagt      900
tggaggggtg ttcacctcag ttgggaaggc tgtccatcaa gtgttcggag gagcattccg      960
cacactgttc ggangcatg                                                  979
```

<210> SEQ ID NO 21
<211> LENGTH: 1004
<212> TYPE: DNA
<213> ORGANISM: West Nile virus
<220> FEATURE:
<221> NAME/KEY: modified_base
<222> LOCATION: (4)..(4)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (14)..(15)
<223> OTHER INFORMATION: a, c, g or t
<220> FEATURE:
<221> NAME/KEY: modified_base
<222> LOCATION: (17)..(17)
<223> OTHER INFORMATION: a, c, g or t
<220> FEATURE:
<221> NAME/KEY: modified_base
<222> LOCATION: (32)..(32)
<223> OTHER INFORMATION: a, c, g or t
<220> FEATURE:
<221> NAME/KEY: modified_base
<222> LOCATION: (35)..(35)
<223> OTHER INFORMATION: a, c, g or t

<400> SEQUENCE: 21

```
agantatgga gngnngncag tggactgtga anccncggtc agggattgac accaatgcat       60
actacgtgat gactgttgga acaaagacgt tcttggtcca tcgtgagtgg ttcatggacc      120
tcaacctccc ttggagcagt gctggaagta ctgtgtggag gaacagagag acgttaatgg      180
agtttgagga accacacgcc acgaagcagt ctgtgatagc attgggctca caagagggag      240
ctctgcatca agctttggct ggagccattc ctgtggaatt ttcaagcaac actgtcaagt      300
tgacgtcggg tcatttgaag tgtagagtga agatggaaaa attgcagttg aagggaacaa      360
cctatggcgt ctgttcaaag ctttcaagt tcttgggact cccgcagaca caggtcacg       420 gcactgtggt gttggaattg cagtacactg gcacggatgg accttgcaaa gttcctatct      480
cgtcagtggc ttcattgaac gatctaacgc cagtgggcag attggtcact gtcaacccctt      540
```

```
ttgtttcagt ggccacggcc aacgctaagg tcctgattga attggaacca ccctttggag    600
actcatacat agtggtgggc agaggagaac aacagatcaa tcaccattgg cacaagtctg    660
gaagcagcat tggcaaagcc tttacaacca ccctcaaagg agcgcagaga ctagccgctc    720
taggagacac agcttgggac tttggatcag ttggaggggt gttcacctca gttgggaagg    780
ctgtccatca agtgttcgga ggagcattcc gcacactgtt cggaggcatg tcctggataa    840
cgcaaggatt gctgggggct ctcctgttgt ggatgggcat caatgctcgt gataggtcca    900
tagctctcac gtttctcgca gttggaggag ttctgctctt cctctccgtg aacgtgcatg    960
ctgacactgg gtgtgccata gacatcagcc ggcaagagct gaga                    1004
```

<210> SEQ ID NO 22
<211> LENGTH: 1006
<212> TYPE: DNA
<213> ORGANISM: West Nile virus
<220> FEATURE:
<221> NAME/KEY: modified_base
<222> LOCATION: (28)..(28)
<223> OTHER INFORMATION: a, c, g or t
<220> FEATURE:
<221> NAME/KEY: modified_base
<222> LOCATION: (996)..(996)
<223> OTHER INFORMATION: a, c, g or t
<220> FEATURE:
<221> NAME/KEY: modified_base
<222> LOCATION: (1004)..(1004)
<223> OTHER INFORMATION: a, c, g or t

<400> SEQUENCE: 22

```
agcagtgctg gaagtactgt gtggaggnaa cagagagacg ttaatggagt ttgaggaacc     60
acacgccacg aagcagtctg tgatagcatt gggctcacaa gagggagctc tgcatcaagc    120
tttggctgga gccattcctg tggaatttc aagcaacact gtcaagttga cgtcgggtca    180
tttgaagtgt agagtgaaga tggaaaaatt gcagttgaag ggaacaacct atggcgtctg    240
ttcaaaggct ttcaagtttc ttgggactcc cgcagacaca ggtcacggca ctgtggtgtt    300
ggaattgcag tacactggca cggatggacc ttgcaaagtt cctatctcgt cagtggcttc    360
attgaacgat ctaacgccag tgggcagatt ggtcactgtc aaccctttg tttcagtggc    420 cacggccaac gctaaggtcc tgattgaatt ggaaccaccc tttggagact catacatagt    480
ggtgggcaga ggagaacaac agatcaatca ccattggcac aagtctggaa gcagcattgg    540
caaagccttt acaaccaccc tcaaaggagc gcagagacta gccgctctag gagacacagc    600
ttgggacttt ggatcagttg gaggggtgtt cacctcagtt gggaaggctg tccatcaagt    660
gttcggagga gcattccgca cactgttcgg aggcatgtcc tggataacgc aaggattgct    720
gggggctctc ctgttgtgga tgggcatcaa tgctcgtgat aggtccatag ctctcacgtt    780
tctcgcagtt ggaggagttc tgctcttcct ctccgtgaac gtgcatgctg acactgggtg    840
tgccatagac atcagccggc aagagctgag atgtggaagt ggagtgttca tacacaatga    900
tgtggaggct tggatggacc ggtacaagta ttaccctgaa acgccacaag gcctagccaa    960
gatcattcag aaagctcata aggaaggagt gtgcgntcta cganca             1006
```

<210> SEQ ID NO 23
<211> LENGTH: 11029
<212> TYPE: DNA
<213> ORGANISM: West Nile virus

<400> SEQUENCE: 23

-continued

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagttttaa gaaggaacta     360
gggaccttga ccagtgctat caatcggcgg agctcaaaac aaaagaaaag aggaggaaag     420
accggaattg cagtcatgat tggcctgatc gccagcgtag gagcagttac cctctctaac     480
ttccaaggga aggtgatgat gacggtaaat gctactgacg tcacagatgt catcacgatt     540
ccaacagctg ctggaaagaa cctatgcatt gtcagagcaa tggatgtggg atacatgtgc     600
gatgatacta tcacttatga atgcccagta ctgtcggctg gtaatgatcc agaagacatc     660
gactgttggt gcacaaagtc agcagtctac gtcaggtatg gaagatgcac caagacacgc     720
cactcaagac gcagtcggag gtcactgaca gtgcagacac acggagaaag cactctagcg     780
aacaagaagg gggcttggat ggacagcacc aaggccacaa ggtatttggt aaaaacagaa     840
tcatggatct tgaggaaccc tggatatgcc ctggtggcag ccgtcattgg ttggatgctt     900
gggagcaaca ccatgcagag agttgtgttt gtcgtgctat tgcttttggt ggccccagct     960
tacagcttca actgccttgg aatgagcaac agagacttct tggaaggagt gtctggagca    1020
acatgggtgg atttggttct cgaaggcgac agctgcgtga ctatcatgtc taaggacaag    1080
cctaccatcg atgtgaagat gatgaatatg gaggcggcca acctggcaga ggtccgcagt    1140
tattgctatt tggctaccgt cagcgatctc tccaccaaag ctgcgtgccc gaccatggga    1200
gaagctcaca tgacaaacg tgctgaccca gcttttgtgt gcagacaagg agtggtggac    1260
aggggctggg gcaacggctg cggactattt ggcaaaggaa gcattgacac atgcgccaaa    1320
tttgcctgct ctaccaaggc aataggaaga accatcttga agagaatat caagtacgaa    1380 gtggccattt ttgtccatgg accaactact gtggagtcgc acggaaacta ctccacacag    1440
gttggagcca ctcaggcagg gagactcagc atcactcctg cggcgccttc atacacacta    1500
aagcttggag aatatggaga ggtgacagtg gactgtgaac cacggtcagg gattgacacc    1560
aatgcatact acgtgatgac tgttggaaca aagacgttct tggtccatcg tgagtggttc    1620
atggacctca acctcccttg gagcagtgct ggaagtactg tgtggaggaa cagagagacg    1680
ttaatggagt tgaggaacc acacgccacg aagcagtctg tgatagcatt gggctcacaa    1740
gagggagctc tgcatcaagc tttggctgga gccattcctg tggaattttc aagcaacact    1800
gtcaagttga cgtcgggtca tttgaagtgt agagtgaaga tggaaaaatt gcagttgaag    1860
ggaacaacct atggcgtctg ttcaaaggct ttcaagtttc ttgggactcc cgcagacaca    1920
ggtcacggca ctgtggtgtt ggaattgcag tacactggca cggatggacc ttgcaaagtt    1980
cctatctcgt cagtggcttc attgaacgac ctaacgccag tgggcagatt ggtcactgtc    2040 aaccctttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc gcagagacta    2220
gccgctctag agacacagc ttgggacttt ggatcagttg gagggtgtt cacctcagtt    2280 gggaaggctg tccatcaagt gttcggagga gcattccgct cactgttcgg aggcatgtcc    2340
tggataacgc aaggattgct ggggctctc ctgttgtgga tgggcatcaa tgctcgtgat    2400
```

```
aggtccatag ctctcacgtt tctcgcagtt ggaggagttc tgctcttcct ctccgtgaac    2460
gtgcacgctg acactgggtg tgccatagac atcagccggc aagagctgag atgtggaagt    2520
ggagtgttca tacacaatga tgtggaggct tggatggacc ggtacaagta ttaccctgaa    2580
acgccacaag gcctagccaa gatcattcag aaagctcata aggaaggagt gtgcggtcta    2640
cgatcagttt ccagactgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
tggggaaaga gtattttatt tgcaccagaa ctcgccaaca caccttttgt ggttgatggt    2880
ccggagacca aggaatgtcc gactcagaat cgcgcttgga atagcttaga agtggaggat    2940
tttggatttg gtctcaccag cactcggatg ttcctgaagg tcagagagag caacacaact    3000
gaatgtgact cgaagatcat tggaacggct gtcaagaaca acttggcgat ccacagtgac    3060
ctgtcctatt ggattgaaag caggctcaat gatacgtgga agcttgaaag gcagttctg     3120 ggtgaagtca aatcatgtac gtggcctgag acgcatacct tgtgggcga tggaatcctt     3180 gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc caggaactac ggtcaccctg agtgagagct cgggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgacccct tcagttggg cc cttctggtc gtgttcttgg ccacccagga ggtccttcgc    3600
aagaggtgga cagccaagat cagcatgcca gctatactga ttgctctgct agtcctggtg    3660 tttggggggca ttacttacac tgatgtgtta cgctatgtca tcttggtggg ggcagctttc    3720
gcagaatcta attcgggagg agacgtggta cacttggcgc tcatggcgac cttcaagata    3780
caaccagtgt ttatggtggc atcgtttctc aaagcgagat ggaccaacca ggagaacatt    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagccgca aaaaagaaag gagcaagtct gctatgcttg    4140
gctctagcct caacaggact tttcaacccc atgatccttg ctgctggact gattgcatgt    4200
gatcccaacc gtaaacgcgg atggcccgca actgaagtga tgcagctgt cggcctaatg    4260 tttgccatcg tcggagggct ggcagagctt gacattgact ccatggccat tccaatgact    4320 atcgcgggc tcatgtttgc tgctttcgtg atttctggga atcaacaga tatgtggatt    4380 gagagaacgg cggacattct ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac ccctggca     4560 atcttgccct cagtagttgg attttggata actctccaat acacaaagag aggaggcgtg    4620
ttgtgggaca ctccctcacc aaaggagtac aaaaagggg acacgaccac cggcgtctac    4680
aggatcatga ctcgtgggct gctcggcagt tatcaagcag gagcgggcgt gatggttgaa    4740
```

```
ggtgttttcc acacccttttg gcatacaaca aaaggagccg ctttgatgag cggagagggc    4800
cgcctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggctttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg cgccggtaa acaaggagg     5220
attctgccac agatcatcaa agaggccata aacagaagac tgagaacagc cgtgctagcg    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc taggggaggc ggcggcaata ttcatgacag ccacccccacc aggcacttca    5580
gatccattcc cagagtccaa ttcaccaatt tccgacttac agactgagat cccggatcga    5640
gcttggaact ctggatacga atggatcaca gaatacaccg ggaagacggt ttggtttgtg    5700
cctagtgtca gatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atgggggcta acttcaaggc gagcagggtg    5880
attgacagcc ggaagagtgt gaaaccaacc atcataacag aaggagaagg gagagtgatc    5940
ctgggagaac catctgcagt gacagcagct agtgccgccc agacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattcta ccaaccagag cgtgagaagg tatataccat ggatgggga    6180
taccggctca gaggagaaga gagaaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca caacgaagt ggaagtcatc    6360
acgaagcttg gtgaaaggaa gattctgagg ccgcgctgga ttgatgccag ggtgtactcg    6420
gatcaccagg cactaaaggc gttcaaggac ttcgcctcgg gaaaacgttc tcagataggg    6480
ctcattgagg ttctgggaaa gatgcctgag cacttcatgg ggaagacatg ggaagcactt    6540
gacaccatgt acgttgtggc cactgcagag aaaggaggaa gagctcacag aatggccctg    6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac cttttttctgt tggatggctg aagttccagg aacgaagatc    6780
gccggaatgt tgctgctctc ccttctcttg atgattgtgc taattcctga gccagagaag    6840
caacgttcgc agacagacaa ccagctagcc gtgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttctggac    7020
ttgaggccca caacagcctg gtcactgtac gctgtgacaa cagcggtcct cactccactg    7080
ctaaagcatt tgatcacgtc agattacatc aacacctcat tgacctcaat aaacgttcag    7140
```

```
gcaagtgcac tattcacact cgcgcgaggc ttcccctccg tcgatgttgg agtgtcggct    7200
ctcctgctag cagccggatg ctggggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
gccacggacg tcccagaatt agagcgcacc acacccatca tgcagaagaa agttggacag    7440
atcatgctga tcttggtgtc tctagctgca gtagtagtga acccgtctgt gaagacagta    7500
cgagaagccg aattttgat cacggccgca gcggtgacgc tttgggagaa tggagcaagc    7560
tctgtttgga acgcaacaac tgccatcgga ctctgccaca tcatgcgtgg gggttggttg    7620
tcatgtctat ccataacatg gacactcata agaacatgg aaaaaccagg actaaaaga    7680 ggtggggcaa aaggacgcac cttgggagag gttttggaaag aaagactcaa ccagatgaca    7740
aaagaagagt tcactaggta ccgcaaagag gccatcatcg aagtcgatcg ctcagcggca    7800
aaacacgcca ggaaagaagg caatgtcact ggagggcatc cagtctctag ggcacagca    7860 aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caaagggcgg tcccggacat gaagagcccc aactagtgca aagttatgga    8040
tggaacattg tcaccatgaa gagtggagtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgtcccta catgccgaaa gtcatagaga agatggagct gctccaacgc    8280
cggtatgggg ggggactggt cagaaaccca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggaccccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga gcccacagg ctccgccagt    8640 tcgctggtca atgagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggttgt gggcgttttt ggccagaaa aaacgtccca gaatgtgctc tcgagaggaa    8880
ttcataagaa aggtcaacag caatgcagct ttgggtgcca tgtttgaaga gcagaatcaa    8940
tggaggagcg ccagagaagc agttgaagat ccaaaatttt gggagatggt ggatgaggag    9000
cgcgaggcac atctgcgggg ggaatgtcac acttgcattt acaacatgat gggaaagaga    9060
gagaaaaaac ccgagagtt cggaaaggcc aagggaagca gagccatttg gttcatgtgg    9120
ctcggagctc gctttctgga gttcgaggct ctgggttttc tcaatgaaga ccactggctt    9180
ggaagaaaga actcaggagg aggtgtcgag ggcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gctgcttgat    9360
ggggaacatc ggcgtcttgc cagggccatc attgagctca cctatcgtca caaagttgtg    9420
aaagtgatgc gcccggctgc tgatggaaga accgtcatgg atgttatctc cagagaagat    9480
```

```
cagaggggga gtggacaagt tgtcacctac gccctaaaca ctttcaccaa cctggccgtc    9540
cagctggtga ggatgatgga aggggaagga gtgattggcc cagatgatgt ggagaaactc    9600
acaaaaggga aaggacccaa agtcaggacc tggctgtttg agaatgggga agaaagactc    9660
agccgcatgg ctgtcagtgg agatgactgt gtggtaaagc ccctggacga tcgctttgcc    9720
acctcgctcc acttcctcaa tgctatgtca aaggttcgca agacatcca agagtggaaa    9780 ccgtcaactg gatggtatga ttggcagcag gttccatttt gctcaaacca tttcactgaa    9840
ttgatcatga agatggaag aacactggtg gttccatgcc gaggacagga tgaattggta    9900
ggcagagctc gcatatctcc aggggccgga tggaacgtcc gcgacactgc ttgtctggct    9960
aagtcttatg cccagatgtg gctgcttctg tacttccaca agagacct gcggctcatg    10020 gccaacgcca tttgctccgc tgtccctgtg aattgggtcc ctaccggaag aaccacgtgg    10080
tccatccatg caggaggaga gtggatgaca acagaggaca tgttggaggt ctggaaccgt    10140
gtttggatag aggagaatga atggatgaa gacaaaaccc cagtggagaa atggagtgac    10200
gtcccatatt caggaaaacg agaggacatc tggtgtggca gcctgattgg cacaagagcc    10260
cgagccacgt gggcagaaaa catccaggtg gctatcaacc aagtcagagc aatcatcgga    10320
gatgagaagt atgtggacta catgagttca ctaaagagat atgaagacac aacttttggtt    10380 gaggacacag tactgtagat atttaatcaa ttgtaaatag acaatataag tatgcataaa    10440
agtgtagttt tatagtagta tttagtggtg ttagtgtaaa tagttaagaa aattttgagg    10500
agaaagtcag gccgggaagt tcccgccacc ggaagttgag tagacggtgc tgcctgcgac    10560
tcaaccccag gaggactggg tgaacaaagc cgcgaagtga tccatgtaag ccctcagaac    10620
cgtctcggaa ggaggacccc acatgttgta acttcaaagc ccaatgtcag accacgctac    10680
ggcgtgctac tctgcggaga gtgcagtctg cgatagtgcc ccaggaggac tgggttaaca    10740
aaggcaaacc aacgccccac gcggccctag ccccggtaat ggtgttaacc agggcgaaag    10800
gactagaggt tagaggagac cccgcggttt aaagtgcacg gcccagcctg gctgaagctg    10860
taggtcaggg gaaggactag aggttagtgg agaccccgtg ccacaaaaca ccacaacaaa    10920
acagcatatt gacacctggg atagactagg agatcttctg ctctgcacaa ccagccacac    10980
ggcacagtgc gccgacaatg gtggctggtg gtgcgagaac acaggatct                11029
```

<210> SEQ ID NO 24
<211> LENGTH: 3433
<212> TYPE: PRT
<213> ORGANISM: West Nile virus

<400> SEQUENCE: 24

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
```

```
            100                 105                 110
Val Met Ile Gly Leu Ile Ala Ser Val Gly Val Thr Leu Ser Asn
            115                 120                 125
Phe Gln Gly Lys Val Met Met Thr Val Asn Ala Thr Asp Val Thr Asp
            130                 135                 140
Val Ile Thr Ile Pro Thr Ala Ala Gly Lys Asn Leu Cys Ile Val Arg
145                 150                 155                 160
Ala Met Asp Val Gly Tyr Met Cys Asp Thr Ile Thr Tyr Glu Cys
                165                 170                 175
Pro Val Leu Ser Ala Gly Asn Asp Pro Glu Asp Ile Asp Cys Trp Cys
                180                 185                 190
Thr Lys Ser Ala Val Tyr Val Arg Tyr Gly Arg Cys Thr Lys Thr Arg
                195                 200                 205
His Ser Arg Arg Ser Arg Arg Ser Leu Thr Val Gln Thr His Gly Glu
                210                 215                 220
Ser Thr Leu Ala Asn Lys Lys Gly Ala Trp Met Asp Ser Thr Lys Ala
225                 230                 235                 240
Thr Arg Tyr Leu Val Lys Thr Glu Ser Trp Ile Leu Arg Asn Pro Gly
                245                 250                 255
Tyr Ala Leu Val Ala Ala Val Ile Gly Trp Met Leu Gly Ser Asn Thr
                260                 265                 270
Met Gln Arg Val Val Phe Val Val Leu Leu Leu Val Ala Pro Ala
                275                 280                 285
Tyr Ser Phe Asn Cys Leu Gly Met Ser Asn Arg Asp Phe Leu Glu Gly
                290                 295                 300
Val Ser Gly Ala Thr Trp Val Asp Leu Val Leu Glu Gly Asp Ser Cys
305                 310                 315                 320
Val Thr Ile Met Ser Lys Asp Lys Pro Thr Ile Asp Val Lys Met Met
                325                 330                 335
Asn Met Glu Ala Ala Asn Leu Ala Glu Val Arg Ser Tyr Cys Tyr Leu
                340                 345                 350
Ala Thr Val Ser Asp Leu Ser Thr Lys Ala Ala Cys Pro Thr Met Gly
                355                 360                 365
Glu Ala His Asn Asp Lys Arg Ala Asp Pro Ala Phe Val Cys Arg Gln
                370                 375                 380
Gly Val Val Asp Arg Gly Trp Gly Asn Gly Cys Gly Leu Phe Gly Lys
385                 390                 395                 400
Gly Ser Ile Asp Thr Cys Ala Lys Phe Ala Cys Ser Thr Lys Ala Ile
                405                 410                 415
Gly Arg Thr Ile Leu Lys Glu Asn Ile Lys Tyr Glu Val Ala Ile Phe
                420                 425                 430
Val His Gly Pro Thr Thr Val Glu Ser His Gly Asn Tyr Ser Thr Gln
                435                 440                 445
Val Gly Ala Thr Gln Ala Gly Arg Leu Ser Ile Thr Pro Ala Ala Pro
                450                 455                 460
Ser Tyr Thr Leu Lys Leu Gly Glu Tyr Gly Glu Val Thr Val Asp Cys
465                 470                 475                 480
Glu Pro Arg Ser Gly Ile Asp Thr Asn Ala Tyr Tyr Val Met Thr Val
                485                 490                 495
Gly Thr Lys Thr Phe Leu Val His Arg Glu Trp Phe Met Asp Leu Asn
                500                 505                 510
Leu Pro Trp Ser Ser Ala Gly Ser Thr Val Trp Arg Asn Arg Glu Thr
                515                 520                 525
```

```
Leu Met Glu Phe Glu Glu Pro His Ala Thr Lys Gln Ser Val Ile Ala
    530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
    850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
    930                 935                 940
```

-continued

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
            965                 970                 975

Thr Ala Val Lys Asn Asn Leu Ala Ile His Ser Asp Leu Ser Tyr Trp
        980                 985                 990

Ile Glu Ser Arg Leu Asn Asp Thr Trp Lys Leu Glu Arg Ala Val Leu
    995                 1000                1005

Gly Glu Val Lys Ser Cys Thr Trp Pro Glu Thr His Thr Leu Trp
1010                1015                1020

Gly Asp Gly Ile Leu Glu Ser Asp Leu Ile Ile Pro Val Thr Leu
1025                1030                1035

Ala Gly Pro Arg Ser Asn His Asn Arg Arg Pro Gly Tyr Lys Thr
1040                1045                1050

Gln Asn Gln Gly Pro Trp Asp Glu Gly Arg Val Glu Ile Asp Phe
1055                1060                1065

Asp Tyr Cys Pro Gly Thr Thr Val Thr Leu Ser Glu Ser Cys Gly
1070                1075                1080

His Arg Gly Pro Ala Thr Arg Thr Thr Thr Glu Ser Gly Lys Leu
1085                1090                1095

Ile Thr Asp Trp Cys Cys Arg Ser Cys Thr Leu Pro Pro Leu Arg
1100                1105                1110

Tyr Gln Thr Asp Ser Gly Cys Trp Tyr Gly Met Glu Ile Arg Pro
1115                1120                1125

Gln Arg His Asp Glu Lys Thr Leu Val Gln Ser Gln Val Asn Ala
1130                1135                1140

Tyr Asn Ala Asp Met Ile Asp Pro Phe Gln Leu Gly Leu Leu Val
1145                1150                1155

Val Phe Leu Ala Thr Gln Glu Val Leu Arg Lys Arg Trp Thr Ala
1160                1165                1170

Lys Ile Ser Met Pro Ala Ile Leu Ile Ala Leu Leu Val Leu Val
1175                1180                1185

Phe Gly Gly Ile Thr Tyr Thr Asp Val Leu Arg Tyr Val Ile Leu
1190                1195                1200

Val Gly Ala Ala Phe Ala Glu Ser Asn Ser Gly Gly Asp Val Val
1205                1210                1215

His Leu Ala Leu Met Ala Thr Phe Lys Ile Gln Pro Val Phe Met
1220                1225                1230

Val Ala Ser Phe Leu Lys Ala Arg Trp Thr Asn Gln Glu Asn Ile
1235                1240                1245

Leu Leu Met Leu Ala Ala Val Phe Phe Gln Met Ala Tyr His Asp
1250                1255                1260

Ala Arg Gln Ile Leu Leu Trp Glu Ile Pro Asp Val Leu Asn Ser
1265                1270                1275

Leu Ala Val Ala Trp Met Ile Leu Arg Ala Ile Thr Phe Thr Thr
1280                1285                1290

Thr Ser Asn Val Val Pro Leu Leu Ala Leu Leu Thr Pro Gly
1295                1300                1305

Leu Arg Cys Leu Asn Leu Asp Val Tyr Arg Ile Leu Leu Leu Met
1310                1315                1320

Val Gly Ile Gly Ser Leu Ile Arg Glu Lys Arg Ser Ala Ala Ala
1325                1330                1335

Lys Lys Lys Gly Ala Ser Leu Leu Cys Leu Ala Leu Ala Ser Thr

-continued

```
            1340                1345                1350

Gly Leu Phe Asn Pro Met Ile Leu Ala Ala Gly Leu Ile Ala Cys
    1355                1360                1365

Asp Pro Asn Arg Lys Arg Gly Trp Pro Ala Thr Glu Val Met Thr
    1370                1375                1380

Ala Val Gly Leu Met Phe Ala Ile Val Gly Gly Leu Ala Glu Leu
    1385                1390                1395

Asp Ile Asp Ser Met Ala Ile Pro Met Thr Ile Ala Gly Leu Met
    1400                1405                1410

Phe Ala Ala Phe Val Ile Ser Gly Lys Ser Thr Asp Met Trp Ile
    1415                1420                1425

Glu Arg Thr Ala Asp Ile Ser Trp Glu Ser Asp Ala Glu Ile Thr
    1430                1435                1440

Gly Ser Ser Glu Arg Val Asp Val Arg Leu Asp Asp Gly Asn
    1445                1450                1455

Phe Gln Leu Met Asn Asp Pro Gly Ala Pro Trp Lys Ile Trp Met
    1460                1465                1470

Leu Arg Met Val Cys Leu Ala Ile Ser Ala Tyr Thr Pro Trp Ala
    1475                1480                1485

Ile Leu Pro Ser Val Val Gly Phe Trp Ile Thr Leu Gln Tyr Thr
    1490                1495                1500

Lys Arg Gly Gly Val Leu Trp Asp Thr Pro Ser Pro Lys Glu Tyr
    1505                1510                1515

Lys Lys Gly Asp Thr Thr Thr Gly Val Tyr Arg Ile Met Thr Arg
    1520                1525                1530

Gly Leu Leu Gly Ser Tyr Gln Ala Gly Ala Gly Val Met Val Glu
    1535                1540                1545

Gly Val Phe His Thr Leu Trp His Thr Thr Lys Gly Ala Ala Leu
    1550                1555                1560

Met Ser Gly Glu Gly Arg Leu Asp Pro Tyr Trp Gly Ser Val Lys
    1565                1570                1575

Glu Asp Arg Leu Cys Tyr Gly Gly Pro Trp Lys Leu Gln His Lys
    1580                1585                1590

Trp Asn Gly Gln Asp Glu Val Gln Met Ile Val Val Glu Pro Gly
    1595                1600                1605

Lys Asn Val Lys Asn Val Gln Thr Lys Pro Gly Val Phe Lys Thr
    1610                1615                1620

Pro Glu Gly Glu Ile Gly Ala Val Thr Leu Asp Phe Pro Thr Gly
    1625                1630                1635

Thr Ser Gly Ser Pro Ile Val Asp Lys Asn Gly Asp Val Ile Gly
    1640                1645                1650

Leu Tyr Gly Asn Gly Val Ile Met Pro Asn Gly Ser Tyr Ile Ser
    1655                1660                1665

Ala Ile Val Gln Gly Glu Arg Met Asp Glu Pro Ile Pro Ala Gly
    1670                1675                1680

Phe Glu Pro Glu Met Leu Arg Lys Lys Gln Ile Thr Val Leu Asp
    1685                1690                1695

Leu His Pro Gly Ala Gly Lys Thr Arg Arg Ile Leu Pro Gln Ile
    1700                1705                1710

Ile Lys Glu Ala Ile Asn Arg Arg Leu Arg Thr Ala Val Leu Ala
    1715                1720                1725

Pro Thr Arg Val Val Ala Ala Glu Met Ala Glu Ala Leu Arg Gly
    1730                1735                1740
```

```
Leu Pro Ile Arg Tyr Gln Thr Ser Ala Val Pro Arg Glu His Asn
    1745             1750                1755

Gly Asn Glu Ile Val Asp Val Met Cys His Ala Thr Leu Thr His
    1760             1765                1770

Arg Leu Met Ser Pro His Arg Val Pro Asn Tyr Asn Leu Phe Val
    1775             1780                1785

Met Asp Glu Ala His Phe Thr Asp Pro Ala Ser Ile Ala Ala Arg
    1790             1795                1800

Gly Tyr Ile Ser Thr Lys Val Glu Leu Gly Glu Ala Ala Ala Ile
    1805             1810                1815

Phe Met Thr Ala Thr Pro Pro Gly Thr Ser Asp Pro Phe Pro Glu
    1820             1825                1830

Ser Asn Ser Pro Ile Ser Asp Leu Gln Thr Glu Ile Pro Asp Arg
    1835             1840                1845

Ala Trp Asn Ser Gly Tyr Glu Trp Ile Thr Glu Tyr Thr Gly Lys
    1850             1855                1860

Thr Val Trp Phe Val Pro Ser Val Lys Met Gly Asn Glu Ile Ala
    1865             1870                1875

Leu Cys Leu Gln Arg Ala Gly Lys Lys Val Val Gln Leu Asn Arg
    1880             1885                1890

Lys Ser Tyr Glu Thr Glu Tyr Pro Lys Cys Lys Asn Asp Asp Trp
    1895             1900                1905

Asp Phe Val Ile Thr Thr Asp Ile Ser Glu Met Gly Ala Asn Phe
    1910             1915                1920

Lys Ala Ser Arg Val Ile Asp Ser Arg Lys Ser Val Lys Pro Thr
    1925             1930                1935

Ile Ile Thr Glu Gly Glu Gly Arg Val Ile Leu Gly Glu Pro Ser
    1940             1945                1950

Ala Val Thr Ala Ala Ser Ala Ala Gln Arg Arg Gly Arg Ile Gly
    1955             1960                1965

Arg Asn Pro Ser Gln Val Gly Asp Glu Tyr Cys Tyr Gly Gly His
    1970             1975                1980

Thr Asn Glu Asp Asp Ser Asn Phe Ala His Trp Thr Glu Ala Arg
    1985             1990                1995

Ile Met Leu Asp Asn Ile Asn Met Pro Asn Gly Leu Ile Ala Gln
    2000             2005                2010

Phe Tyr Gln Pro Glu Arg Glu Lys Val Tyr Thr Met Asp Gly Glu
    2015             2020                2025

Tyr Arg Leu Arg Gly Glu Glu Arg Lys Asn Phe Leu Glu Leu Leu
    2030             2035                2040

Arg Thr Ala Asp Leu Pro Val Trp Leu Ala Tyr Lys Val Ala Ala
    2045             2050                2055

Ala Gly Val Ser Tyr His Asp Arg Arg Trp Cys Phe Asp Gly Pro
    2060             2065                2070

Arg Thr Asn Thr Ile Leu Glu Asp Asn Asn Glu Val Glu Val Ile
    2075             2080                2085

Thr Lys Leu Gly Glu Arg Lys Ile Leu Arg Pro Arg Trp Ile Asp
    2090             2095                2100

Ala Arg Val Tyr Ser Asp His Gln Ala Leu Lys Ala Phe Lys Asp
    2105             2110                2115

Phe Ala Ser Gly Lys Arg Ser Gln Ile Gly Leu Ile Glu Val Leu
    2120             2125                2130
```

-continued

```
Gly Lys Met Pro Glu His Phe Met Gly Lys Thr Trp Glu Ala Leu
    2135                2140                2145
Asp Thr Met Tyr Val Val Ala Thr Ala Glu Lys Gly Gly Arg Ala
    2150                2155                2160
His Arg Met Ala Leu Glu Glu Leu Pro Asp Ala Leu Gln Thr Ile
    2165                2170                2175
Ala Leu Ile Ala Leu Leu Ser Val Met Thr Met Gly Val Phe Phe
    2180                2185                2190
Leu Leu Met Gln Arg Lys Gly Ile Gly Lys Ile Gly Leu Gly Gly
    2195                2200                2205
Ala Val Leu Gly Val Ala Thr Phe Phe Cys Trp Met Ala Glu Val
    2210                2215                2220
Pro Gly Thr Lys Ile Ala Gly Met Leu Leu Leu Ser Leu Leu Leu
    2225                2230                2235
Met Ile Val Leu Ile Pro Glu Pro Glu Lys Gln Arg Ser Gln Thr
    2240                2245                2250
Asp Asn Gln Leu Ala Val Phe Leu Ile Cys Val Met Thr Leu Val
    2255                2260                2265
Ser Ala Val Ala Ala Asn Glu Met Gly Trp Leu Asp Lys Thr Lys
    2270                2275                2280
Ser Asp Ile Ser Ser Leu Phe Gly Gln Arg Ile Glu Val Lys Glu
    2285                2290                2295
Asn Phe Ser Met Gly Glu Phe Leu Leu Asp Leu Arg Pro Ala Thr
    2300                2305                2310
Ala Trp Ser Leu Tyr Ala Val Thr Thr Ala Val Leu Thr Pro Leu
    2315                2320                2325
Leu Lys His Leu Ile Thr Ser Asp Tyr Ile Asn Thr Ser Leu Thr
    2330                2335                2340
Ser Ile Asn Val Gln Ala Ser Ala Leu Phe Thr Leu Ala Arg Gly
    2345                2350                2355
Phe Pro Phe Val Asp Val Gly Val Ser Ala Leu Leu Leu Ala Ala
    2360                2365                2370
Gly Cys Trp Gly Gln Val Thr Leu Thr Val Thr Val Thr Ala Ala
    2375                2380                2385
Thr Leu Leu Phe Cys His Tyr Ala Tyr Met Val Pro Gly Trp Gln
    2390                2395                2400
Ala Glu Ala Met Arg Ser Ala Gln Arg Arg Thr Ala Ala Gly Ile
    2405                2410                2415
Met Lys Asn Ala Val Val Asp Gly Ile Val Ala Thr Asp Val Pro
    2420                2425                2430
Glu Leu Glu Arg Thr Thr Pro Ile Met Gln Lys Lys Val Gly Gln
    2435                2440                2445
Ile Met Leu Ile Leu Val Ser Leu Ala Ala Val Val Val Asn Pro
    2450                2455                2460
Ser Val Lys Thr Val Arg Glu Ala Gly Ile Leu Ile Thr Ala Ala
    2465                2470                2475
Ala Val Thr Leu Trp Glu Asn Gly Ala Ser Ser Val Trp Asn Ala
    2480                2485                2490
Thr Thr Ala Ile Gly Leu Cys His Ile Met Arg Gly Gly Trp Leu
    2495                2500                2505
Ser Cys Leu Ser Ile Thr Trp Thr Leu Ile Lys Asn Met Glu Lys
    2510                2515                2520
Pro Gly Leu Lys Arg Gly Gly Ala Lys Gly Arg Thr Leu Gly Glu
```

2525                    2530                    2535

Val Trp Lys Glu Arg Leu Asn Gln Met Thr Lys Glu Glu Phe Thr
    2540                    2545                    2550

Arg Tyr Arg Lys Glu Ala Ile Ile Glu Val Asp Arg Ser Ala Ala
    2555                    2560                    2565

Lys His Ala Arg Lys Glu Gly Asn Val Thr Gly Gly His Pro Val
    2570                    2575                    2580

Ser Arg Gly Thr Ala Lys Leu Arg Trp Leu Val Glu Arg Arg Phe
    2585                    2590                    2595

Leu Glu Pro Val Gly Lys Val Ile Asp Leu Gly Cys Gly Arg Gly
    2600                    2605                    2610

Gly Trp Cys Tyr Tyr Met Ala Thr Gln Lys Arg Val Gln Glu Val
    2615                    2620                    2625

Arg Gly Tyr Thr Lys Gly Gly Pro Gly His Glu Glu Pro Gln Leu
    2630                    2635                    2640

Val Gln Ser Tyr Gly Trp Asn Ile Val Thr Met Lys Ser Gly Val
    2645                    2650                    2655

Asp Val Phe Tyr Arg Pro Ser Glu Cys Cys Asp Thr Leu Leu Cys
    2660                    2665                    2670

Asp Ile Gly Glu Ser Ser Ser Ser Ala Glu Val Glu Glu His Arg
    2675                    2680                    2685

Thr Ile Arg Val Leu Glu Met Val Glu Asp Trp Leu His Arg Gly
    2690                    2695                    2700

Pro Arg Glu Phe Cys Val Lys Val Leu Cys Pro Tyr Met Pro Lys
    2705                    2710                    2715

Val Ile Glu Lys Met Glu Leu Leu Gln Arg Arg Tyr Gly Gly Gly
    2720                    2725                    2730

Leu Val Arg Asn Pro Leu Ser Arg Asn Ser Thr His Glu Met Tyr
    2735                    2740                    2745

Trp Val Ser Arg Ala Ser Gly Asn Val Val His Ser Val Asn Met
    2750                    2755                    2760

Thr Ser Gln Val Leu Leu Gly Arg Met Glu Lys Arg Thr Trp Lys
    2765                    2770                    2775

Gly Pro Gln Tyr Glu Glu Asp Val Asn Leu Gly Ser Gly Thr Arg
    2780                    2785                    2790

Ala Val Gly Lys Pro Leu Leu Asn Ser Asp Thr Ser Lys Ile Lys
    2795                    2800                    2805

Asn Arg Ile Glu Arg Leu Arg Arg Glu Tyr Ser Ser Thr Trp His
    2810                    2815                    2820

His Asp Glu Asn His Pro Tyr Arg Thr Trp Asn Tyr His Gly Ser
    2825                    2830                    2835

Tyr Asp Val Lys Pro Thr Gly Ser Ala Ser Ser Leu Val Asn Gly
    2840                    2845                    2850

Val Val Arg Leu Leu Ser Lys Pro Trp Asp Thr Ile Thr Asn Val
    2855                    2860                    2865

Thr Thr Met Ala Met Thr Asp Thr Thr Pro Phe Gly Gln Gln Arg
    2870                    2875                    2880

Val Phe Lys Glu Lys Val Asp Thr Lys Ala Pro Glu Pro Pro Glu
    2885                    2890                    2895

Gly Val Lys Tyr Val Leu Asn Glu Thr Thr Asn Trp Leu Trp Ala
    2900                    2905                    2910

Phe Leu Ala Arg Glu Lys Arg Pro Arg Met Cys Ser Arg Glu Glu
    2915                    2920                    2925

-continued

```
Phe Ile Arg Lys Val Asn Ser Asn Ala Ala Leu Gly Ala Met Phe
    2930                2935                2940

Glu Glu Gln Asn Gln Trp Arg Ser Ala Arg Glu Ala Val Glu Asp
    2945                2950                2955

Pro Lys Phe Trp Glu Met Val Asp Glu Glu Arg Glu Ala His Leu
    2960                2965                2970

Arg Gly Glu Cys His Thr Cys Ile Tyr Asn Met Met Gly Lys Arg
    2975                2980                2985

Glu Lys Lys Pro Gly Glu Phe Gly Lys Ala Lys Gly Ser Arg Ala
    2990                2995                3000

Ile Trp Phe Met Trp Leu Gly Ala Arg Phe Leu Glu Phe Glu Ala
    3005                3010                3015

Leu Gly Phe Leu Asn Glu Asp His Trp Leu Gly Arg Lys Asn Ser
    3020                3025                3030

Gly Gly Gly Val Glu Gly Leu Gly Leu Gln Lys Leu Gly Tyr Ile
    3035                3040                3045

Leu Arg Glu Val Gly Thr Arg Pro Gly Gly Lys Ile Tyr Ala Asp
    3050                3055                3060

Asp Thr Ala Gly Trp Asp Thr Arg Ile Thr Arg Ala Asp Leu Glu
    3065                3070                3075

Asn Glu Ala Lys Val Leu Glu Leu Leu Asp Gly Glu His Arg Arg
    3080                3085                3090

Leu Ala Arg Ala Ile Ile Glu Leu Thr Tyr Arg His Lys Val Val
    3095                3100                3105

Lys Val Met Arg Pro Ala Ala Asp Gly Arg Thr Val Met Asp Val
    3110                3115                3120

Ile Ser Arg Glu Asp Gln Arg Gly Ser Gly Gln Val Val Thr Tyr
    3125                3130                3135

Ala Leu Asn Thr Phe Thr Asn Leu Ala Val Gln Leu Val Arg Met
    3140                3145                3150

Met Glu Gly Glu Gly Val Ile Gly Pro Asp Asp Val Glu Lys Leu
    3155                3160                3165

Thr Lys Gly Lys Gly Pro Lys Val Arg Thr Trp Leu Phe Glu Asn
    3170                3175                3180

Gly Glu Glu Arg Leu Ser Arg Met Ala Val Ser Gly Asp Asp Cys
    3185                3190                3195

Val Val Lys Pro Leu Asp Asp Arg Phe Ala Thr Ser Leu His Phe
    3200                3205                3210

Leu Asn Ala Met Ser Lys Val Arg Lys Asp Ile Gln Glu Trp Lys
    3215                3220                3225

Pro Ser Thr Gly Trp Tyr Asp Trp Gln Gln Val Pro Phe Cys Ser
    3230                3235                3240

Asn His Phe Thr Glu Leu Ile Met Lys Asp Gly Arg Thr Leu Val
    3245                3250                3255

Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315
```

```
Asn Trp Val Pro Thr Gly Arg Thr Thr Trp Ser Ile His Ala Gly
    3320            3325            3330

Gly Glu Trp Met Thr Thr Glu Asp Met Leu Glu Val Trp Asn Arg
    3335            3340            3345

Val Trp Ile Glu Glu Asn Glu Trp Met Glu Asp Lys Thr Pro Val
    3350            3355            3360

Glu Lys Trp Ser Asp Val Pro Tyr Ser Gly Lys Arg Glu Asp Ile
    3365            3370            3375

Trp Cys Gly Ser Leu Ile Gly Thr Arg Ala Arg Ala Thr Trp Ala
    3380            3385            3390

Glu Asn Ile Gln Val Ala Ile Asn Gln Val Arg Ala Ile Ile Gly
    3395            3400            3405

Asp Glu Lys Tyr Val Asp Tyr Met Ser Ser Leu Lys Arg Tyr Glu
    3410            3415            3420

Asp Thr Thr Leu Val Glu Asp Thr Val Leu
    3425            3430

<210> SEQ ID NO 25
<211> LENGTH: 945
<212> TYPE: DNA
<213> ORGANISM: West Nile virus
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (726)..(726)
<223> OTHER INFORMATION: a, c, t, g, unknown or other
<220> FEATURE:
<221> NAME/KEY: modified_base
<222> LOCATION: (831)..(833)
<223> OTHER INFORMATION: a, c, t, g, unknown or other
<220> FEATURE:
<221> NAME/KEY: modified_base
<222> LOCATION: (838)..(838)
<223> OTHER INFORMATION: a, c, t, g, unknown or other
<220> FEATURE:
<221> NAME/KEY: modified_base
<222> LOCATION: (854)..(854)
<223> OTHER INFORMATION: a, c, t, g, unknown or other
<220> FEATURE:
<221> NAME/KEY: modified_base
<222> LOCATION: (893)..(893)
<223> OTHER INFORMATION: a, c, t, g, unknown or other
<220> FEATURE:
<221> NAME/KEY: modified_base
<222> LOCATION: (907)..(907)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other
<220> FEATURE:
<221> NAME/KEY: modified_base
<222> LOCATION: (928)..(929)
<223> OTHER INFORMATION: a, c, t, g, unknown or other
<220> FEATURE:
<221> NAME/KEY: modified_base
```

<222> LOCATION: (931)..(931)
<223> OTHER INFORMATION: a, c, t, g, unknown or other
<220> FEATURE:
<221> NAME/KEY: modified_base
<222> LOCATION: (937)..(937)
<223> OTHER INFORMATION: a, c, t, g, unknown or other
<220> FEATURE:
<221> NAME/KEY: modified_base
<222> LOCATION: (941)..(943)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other

<400> SEQUENCE: 25

```
cgatgtgnga ngangaatat ggaggcggcc aacctggcag aggtccgcag ttattgctat    60
ttggctaccg tcagcgatct ctccaccaaa gctgcgtgcc cgaccatggg agaagctcac   120
aatgacaaac gtgctgaccc agcttttgtg tgcagacaag gagtggtgga caggggctgg   180
ggcaacggct gcggactatt tggcaaagga agcattgaca catgcgccaa atttgcctgc   240
tctaccaagg caataggaag aaccatcttg aaagagaata tcaagtacga agtggccatt   300
tttgtccatg gaccaactac tgtggagtcg cacggaaact actccacaca ggttggagcc   360
actcaggcag ggagattcag catcactcct gcggcgcctt catacacact aaagcttgga   420
gaatatggag aggtgacagt ggactgtgaa ccacggtcag ggattgacac caatgcatac   480
tatgtgatga ctgttggaac aaagacgttc ttggtccatc gtgagtggtt catggacctc   540
aacctcccctt ggagcagtgc tggaagtact gtgtggagga acagagagac gttaatggag   600
tttgaggaac cacacgccac gaagcagtct gtgatagcat gggctcaca agagggagct   660
ctgcatcaag ctttggctgg agccattcct gtggaatttt caagcaacac tgtcaagttg   720
acgtcnggtc atttgaagtg tagagtgaag atggaaaaat tgcagttgaa gggaacaacc   780
tatggcgtct gttcaaaggc tttcaagttt cttgggactc ccgcagacac nnntcacngc   840
actgtggtgt tggnattgca gtacactggg cacggatgga ccttgcaaag ttnctatctc   900
gtcagtngct tcattgnacg anctaacnnc ngtgggnaga nnngn              945
```

<210> SEQ ID NO 26
<211> LENGTH: 855
<212> TYPE: DNA
<213> ORGANISM: West Nile virus
<220> FEATURE:
<221> NAME/KEY: modified_base
<222> LOCATION: (649)..(649)
<223> OTHER INFORMATION: a, c, t, g, unknown or other
<220> FEATURE:
<221> NAME/KEY: modified_base
<222> LOCATION: (704)..(704)
<223> OTHER INFORMATION: a, c, t, g, unknown or other
<220> FEATURE:
<221> NAME/KEY: modified_base
<222> LOCATION: (761)..(761)
<223> OTHER INFORMATION: a, c, t, g, unknown or other
<220> FEATURE:
<221> NAME/KEY: modified_base
<222> LOCATION: (791)..(791)
<223> OTHER INFORMATION: a, c, t, g, unknown or other
<220> FEATURE:
<221> NAME/KEY: modified_base
<222> LOCATION: (823)..(823)
<223> OTHER INFORMATION: a, c, t, g, unknown or other
<220> FEATURE:
<221> NAME/KEY: modified_base
<222> LOCATION: (839)..(839)
<223> OTHER INFORMATION: a, c, t, g, unknown or other
<220> FEATURE:

```
<221> NAME/KEY: modified_base
<222> LOCATION: (844)..(844)
<223> OTHER INFORMATION: a, c, t, g, unknown or other
<220> FEATURE:
<221> NAME/KEY: modified_base
<222> LOCATION: (846)..(846)
<223> OTHER INFORMATION: a, c, t, g, unknown or other

<400> SEQUENCE: 26
caagtacgaa gtggccattt ttgtccatgg accaactact gtggagtcgc acggaaacta      60
ctccacacag gttggagcca ctcaggcagg gagattcagc atcactcctg cggcgccttc     120
atacacacta aagcttggag aatatggaga ggtgacagtg gactgtgaac cacggtcagg     180
gattgacacc aatgcatact atgtgatgac tgttggaaca aagacgttct tggtccatcg     240
tgagtggttc atggacctca acctcccttg gagcagtgct ggaagtactg tgtggaggaa     300
cagagagacg ttaatggagt tgaggaacc acacgccacg aagcagtctg tgatagcatt      360
gggctcacaa gagggagctc tgcatcaagc tttggctgga gccattcctg tggaattttc     420
aagcaacact gtcaagttga cgtcgggtca tttgaagtgt agagtgaaga tggaaaaatt     480
gcagttgaag ggaacaacct atggcgtctg ttcaaaggct ttcaagtttc ttgggactcc     540
cgcagacaca ggtcacggca ctgtggtgtt ggaattgcag tacactggca cggatggacc     600
ttgcaaagtt cctatctcgt cagtggcttc attgaacgac ctaacgccng tgggcagatt     660
ggtcactgtc aacccttttg tttcagtggc cacggccaac gctnaggtcc tgattgaatt     720
ggaaccaccc tttggagact catacatagt ggtgggcaga ngagaacaac agatcaatca     780
ccattggcac nagtctggaa gcagcattgg caaagccttt acnaccaccc tcaaagganc     840
gcananacta gccgc                                                     855

<210> SEQ ID NO 27
<211> LENGTH: 940
<212> TYPE: DNA
<213> ORGANISM: West Nile virus
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (30)..(32)
<223> OTHER INFORMATION: a, c, t, g, unknown or other
<220> FEATURE:
<221> NAME/KEY: modified_base
<222> LOCATION: (45)..(46)
<223> OTHER INFORMATION: a, c, t, g, unknown or other
<220> FEATURE:
<221> NAME/KEY: modified_base
<222> LOCATION: (130)..(130)
<223> OTHER INFORMATION: a, c, t, g, unknown or other

<400> SEQUENCE: 27
tntgatgact gtnggaacaa agacgttctn nntccatcgt gagtnnttca tggacctcaa      60
cctcccttgg agcagtgctg gaagtactgt gtggaggaac agagagacgt taatggagtt     120
tgaggaaccn cacgccacga agcagtctgt gatagcattg gctcacaag agggagctct      180 gcatcaagct ttggctggag ccattcctgt ggaattttca agcaacactg tcaagttgac     240
gtcgggtcat ttgaagtgta gagtgaagat ggaaaaattg cagttgaagg gaacaaccta     300
tggcgtctgt tcaaaggctt tcaagtttct tgggactccc gcagacacag gtcacggcac     360
```

```
tgtggtgttg gaattgcagt acactggcac ggatggacct tgcaaagttc ctatctcgtc    420
agtggcttca ttgaacgacc taacgccagt gggcagattg gtcactgtca acccttttgt    480
ttcagtggcc acggccaacg ctaaggtcct gattgaattg gaaccaccct ttggagactc    540
atacatagtg gtgggcagag gagaacaaca gatcaatcac cattggcaca agtctggaag    600
cagcattggc aaagccttta caaccaccct caaaggagcg cagagactag ccgctctagg    660
agacacagct gggactttg atcagttgg aggggtgttc acctcagttg ggaaggctgt      720
ccatcaagtg ttcggaggag cattccgctc actgttcgga ggcatgtcct ggataacgca    780
aggattgctg ggggctctcc tgttgtggat gggcatcaat gctcgtgata ggtccatagc    840
tctcacgttt ctcgcagttg gaggagttct gctcttcctt ccgtgaacg tgcacgctga     900 cactgggtgt gccatagaca tcagccggca agagctgaga                          940
```

```
<210> SEQ ID NO 28
<211> LENGTH: 1005
<212> TYPE: DNA
<213> ORGANISM: West Nile virus
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (997)..(997)
<223> OTHER INFORMATION: a, c, t, g, unknown or other

<400> SEQUENCE: 28
nagcagtgct ggnangtact gtgtggagga acagagagac gttaatggag tttgagganc     60
cacacgccac gaagcagtct gtgatagcat tgggctcaca agagggagct ctgcatcaag    120 cttttggctgg agccattcct gtggaatttt caagcaaac tgtcaagttg acgtcgggtc    180
atttgaagtg tagagtgaag atggaaaaat tgcagttgaa gggaacaacc tatggcgtct    240
gttcaaaggc tttcaagttt cttgggactc ccgcagacac aggtcacggc actgtggtgt    300
tggaattgca gtacactggc acggatggac cttgcaaagt tcctatctcg tcagtggctt    360
cattgaacga cctaacgcca gtgggcagat tggtcactgt caacccttt gtttcagtgg     420 ccacggccaa cgctaaggtc ctgattgaat tggaaccacc ctttggagac tcatacatag    480
tggtgggcag aggagaacaa cagatcaatc accattggca caagtctgga agcagcattg    540
gcaaagcctt tacaaccacc ctcaaaggag cgcagagact agccgctcta ggagacacag    600
cttgggactt tggatcagtt ggagggggtgt tcacctcagt tgggaaggct gtccatcaag    660
tgttcggagg agcattccgc tcactgttcg gaggcatgtc ctggataacg caaggattgc    720
tgggggctct cctgttgtgg atgggcatca atgctcgtga taggtccata gctctcacgt    780
ttctcgcagt tggaggagtt ctgctcttcc tttccgtgaa cgtgcacgct gacactgggt    840
gtgccataga catcagccgg caagagctga gatgtggaag tggagtgttc atacacaatg    900
```

-continued

```
atgtggaggc ttggatggac cggtacaagt attaccctga aacgccacaa ggcctagcca      960
agatcattca gaaagctcat aaggaaggag tgtgcgntct acgat                     1005
```

<210> SEQ ID NO 29
<211> LENGTH: 944
<212> TYPE: DNA
<213> ORGANISM: West Nile virus
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (886)..(886)
<223> OTHER INFORMATION: a, c, t, g, unknown or other
<220> FEATURE:
<221> NAME/KEY: modified_base
<222> LOCATION: (892)..(892)
<223> OTHER INFORMATION: a, c, t, g, unknown or other
<220> FEATURE:
<221> NAME/KEY: modified_base
<222> LOCATION: (921)..(921)
<223> OTHER INFORMATION: a, c, t, g, unknown or other
<220> FEATURE:
<221> NAME/KEY: modified_base
<222> LOCATION: (934)..(935)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (943)..(943)
<223> OTHER INFORMATION: a, c, t, g, unknown or other

<400> SEQUENCE: 29

```
cgatgtgnga ngangaatat ggaggcggcc aacctggcag aggtccgcag ttattgctat       60
ttggctaccg tcagcgatct ctccaccaaa gctgcgtgcc cgaccatggg agaagctcac      120
aatgacaaac gtgctgaccc agcttttgtg tgcagacaag gagtggtgga caggggctgg      180
ggcaacggct gcggactatt tggcaaagga agcattgaca catgcgccaa atttgcctgc      240
tctaccaagg caataggaag aaccatcttg aaagagaata tcaagtacga agtggccatt      300
tttgtccatg gaccaactac tgtggagtcg cacggaaact actccacaca ggctggagcc      360
actcaggcag ggagattcag catcactcct gcggcgcctt catacacact aaagcttgga      420
gaatatggag aggtgacagt ggactgtgaa ccacggtcag ggattgacac caatgcatac      480
tacgtgatga ctgttggaac aaagacgttc ttggtccatc gtgagtggtt catggacctc      540
aacctccctt ggagcagtgc tggaagtact gtgtggagga acagagagac gttaatggag      600
tttgaggaac cacacgccac gaagcagtct gtgatagcat gggctcaca  agagggagct      660 ctgcatcaag ctttgctgg  agccattcct gtggaatttt caagcaacac tgtcaagttg      720
acgtcgggtc atttgaagtg tagagtgaag atggaaaaat tgcagttgaa gggaacaacc      780
tatggcgtct gttcaaaggc tttcaagttt cttgggactc ccgcagacac aggtcacggc      840
actgtggtgt tggaattgca gtacactggc acgatggac  cttgcnaagt tnctatctcg      900
tcagtggctt cattgaacga nctaacgcca gtgnnagant ggnc                      944
```

<210> SEQ ID NO 30
<211> LENGTH: 997
<212> TYPE: DNA
<213> ORGANISM: West Nile virus
<220> FEATURE:
<221> NAME/KEY: modified_base
<222> LOCATION: (839)..(839)
<223> OTHER INFORMATION: a, c, t, g, unknown or other
<220> FEATURE:
<221> NAME/KEY: modified_base
<222> LOCATION: (863)..(863)
<223> OTHER INFORMATION: a, c, t, g, unknown or other
<220> FEATURE:
<221> NAME/KEY: modified_base
<222> LOCATION: (873)..(873)
<223> OTHER INFORMATION: a, c, t, g, unknown or other
<220> FEATURE:
<221> NAME/KEY: modified_base
<222> LOCATION: (916)..(916)
<223> OTHER INFORMATION: a, c, t, g, unknown or other
<220> FEATURE:
<221> NAME/KEY: modified_base
<222> LOCATION: (919)..(919)
<223> OTHER INFORMATION: a, c, t, g, unknown or other
<220> FEATURE:
<221> NAME/KEY: modified_base
<222> LOCATION: (933)..(933)
<223> OTHER INFORMATION: a, c, t, g, unknown or other
<220> FEATURE:
<221> NAME/KEY: modified_base
<222> LOCATION: (947)..(947)
<223> OTHER INFORMATION: a, c, t, g, unknown or other
<220> FEATURE:
<221> NAME/KEY: modified_base
<222> LOCATION: (958)..(958)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other
<220> FEATURE:
<221> NAME/KEY: modified_base
<222> LOCATION: (976)..(978)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (989)..(989)
<223> OTHER INFORMATION: a, c, t, g, unknown or other
<220> FEATURE:
<221> NAME/KEY: modified_base
<222> LOCATION: (991)..(991)
<223> OTHER INFORMATION: a, c, t, g, unknown or other

<400> SEQUENCE: 30

| | | | | | |
|---|---|---|---|---|---|
| caagtacgaa | gtggccattt | ttgtccatgg | accaactact | gtggagtcgc | acggaaacta | 60 |
| ctccacacag | gctggagcca | ctcaggcagg | gagattcagc | atcactcctg | cggcgccttc | 120 |
| atacacacta | aagcttggag | aatatggaga | ggtgacagtg | gactgtgaac | cacggtcagg | 180 |
| gattgacacc | aatgcatact | acgtgatgac | tgttggaaca | aagacgttct | tggtccatcg | 240 |
| tgagtggttc | atggacctca | acctcccttg | gagcagtgct | ggaagtactg | tgtggaggaa | 300 |
| cagagagacg | ttaatggagt | ttgaggaacc | acacgccacg | aagcagtctg | tgatagcatt | 360 |
| gggctcacaa | gagggagctc | tgcatcaagc | tttggctgga | gccattcctg | tggaattttc | 420 |

-continued

```
aagcaacact gtcaagttga cgtcgggtca tttgaagtgt agagtgaaga tggaaaaatt    480
gcagttgaag ggaacaacct atggcgtctg ttcaaaggct ttcaagtttc ttgggactcc    540
cgcagacaca ggtcacggca ctgtggtgtt ggaattgcag tacactggca cggatggacc    600
ttgcaaagtt cctatctcgt cagtggcttc attgaacgac ctaacgccag tgggcagatt    660
ggtcactgtc aacccttttg tttcagtggc cacggccaac gctaaggtcc tgattgaatt    720
ggaaccaccc tttggagact catacatagt ggtgggcaga ggagaacaac agatcaatca    780
ccattggcac aagtctggaa gcagcattgg caaagccttt acaaccaccc tcaaagganc    840
gcagagacta gccgctctag ganacacagc ttnggacttt ggatcagttg gagggtgtt    900 cacctcagtt gggaanggnt gtccatcaag tgntcggagg agcattnccg ctcactgntc    960
ggaggcatgt ncnggnnnac gcaaggntng ntggggg    997
```

<210> SEQ ID NO 31
<211> LENGTH: 941
<212> TYPE: DNA
<213> ORGANISM: West Nile virus
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (21)..(22)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (30)..(35)
<223> OTHER INFORMATION: a, c, t, g, unknown or other
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: modified_base
<222> LOCATION: (56)..(56)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (68)..(69)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (131)..(131)
<223> OTHER INFORMATION: a, c, t, g, unknown or other
<220> FEATURE:
<221> NAME/KEY: modified_base
<222> LOCATION: (133)..(133)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (197)..(197)
<223> OTHER INFORMATION: a, c, t, g, unknown or other
<220> FEATURE:
<221> NAME/KEY: modified_base
<222> LOCATION: (238)..(238)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (299)..(299)
<223> OTHER INFORMATION: a, c, t, g, unknown or other

<400> SEQUENCE: 31

```
atgcnnacta cgtgatgact nnganaagan nnnnntccat cgtgagnnnc atggancTca    60
ncctnccnng gagcagtgct ggaagtactg ngtggaggaa cagagagacg ttaatggagt   120
ttgagnaacc ncncgccacg aagcagtctg tgatagcatt gggctcacaa gagggagctn   180
tgcatcaagc tttggcngga gccattcctg tggaattttc aagcaacact gtcaagtnga   240
cgtcggntca tttgaagtgt agagtgaaga tggaaaaatt gcagttgaag ggaacaacnt   300
atggcgtctg ttcaaaggct ttcaagtttc ttgggactcc cgcagacaca ggtcacggca   360
ctgtggtgtt ggaattgcag tacactggca cggatggacc ttgcaaagtt cctatctcgt   420
cagtggcttc attgaacgac ctaacgccag tgggcagatt ggtcactgtc aacccttttg   480
tttcagtggc cacggccaac gctaaggtcc tgattgaatt ggaaccaccc tttgagact    540
catacatagt ggtgggcaga ggagaacaac agatcaatca ccattggcac aagtctggaa   600
gcagcattgg caaagccttt acaaccaccc tcaaaggagc gcagagacta gccgctctag   660
gagacacagc ttgggacttt ggatcagttg gaggggtgtt cacctcagtt gggaaggctg   720
tccatcaagt gttcggagga gcattccgct cactgttcgg aggcatgtcc tggataacgc   780
aaggattgct gggggctctc ctgttgtgga tgggcatcaa tgctcgtgat aggtccatag   840
ctctcacgtt tctcgcagtt ggaggagttc tgctcttcct ctccgtgaac gtgcatgctg   900
acactgggtg tgccatagac atcagccggc aagagctgag a                      941
```

<210> SEQ ID NO 32
<211> LENGTH: 931
<212> TYPE: DNA
<213> ORGANISM: West Nile virus
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:

<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (154)..(154)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other

<400> SEQUENCE: 32

```
cagtnngtga tancntnggc tcananaggn agntntgcat caagctttgg cnggagccat      60
tnctgtggaa ttttcaagca acactgtcaa gttgacgtcg ggtcatttga agtgtagagt     120
gaagatggaa aaattgcagt tgaagggaac aacntatggc gtctgttcaa aggctttcaa    180
gtttcttggg actcccgcag acacaggtca cggcactgtg gtgtnggaat tgcagtacac    240
tggcacggat ggaccttgca aagttcctat ctcgtcagtg gcttcattga acgacctaac    300
gccagtgggc agattggtca ctgtcaaccc ttttgtttca gtggccacgg ccaacgctaa    360
ggtcctgatt gaattggaac cacccttggg agactcatac atagtggtgg cagaggaga    420
acaacagatc aatcaccatt ggcacaagtc tggaagcagc attggcaaag cctttacaac    480
caccctcaaa ggagcgcaga gactagccgc tctaggagac acagcttggg actttggatc    540
agttggaggg gtgttcacct cagttgggaa ggctgtccat caagtgttcg gaggagcatt    600
ccgctcactg ttcggaggca tgtcctggat aacgcaagga ttgctggggg ctctcctgtt    660
gtggatgggc atcaatgctc gtgataggtc catagctctc acgtttctcg cagttggagg    720
agttctgctc ttcctctccg tgaacgtgca tgctgacact gggtgtgcca tagacatcag    780
ccggcaagag ctgagatgtg gaagtggagt gttcatacac aatgatgtgg aggcttggat    840
ggaccggtac aagtattacc ctgaaacgcc acaaggccta gccaagatca ttcagaaagc    900
tcataaggaa ggagtgtgcg gtctacgatc a                                   931
```

<210> SEQ ID NO 33
<211> LENGTH: 967
<212> TYPE: DNA
<213> ORGANISM: West Nile virus
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (673)..(673)
<223> OTHER INFORMATION: a, c, t, g, unknown or other
<220> FEATURE:
<221> NAME/KEY: modified_base
<222> LOCATION: (859)..(861)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (940)..(941)
<223> OTHER INFORMATION: a, c, t, g, unknown or other
<220> FEATURE:
<221> NAME/KEY: modified_base
<222> LOCATION: (959)..(959)
<223> OTHER INFORMATION: a, c, t, g, unknown or other
<220> FEATURE:
<221> NAME/KEY: modified_base
<222> LOCATION: (961)..(961)
<223> OTHER INFORMATION: a, c, t, g, unknown or other

<400> SEQUENCE: 33
cacagcaatg cagctttggg tgccntgttt gaagagcaga atcaatggag gagcgccaga 60
gaagcagttg aagatccaaa attttgggag atggtggatg aggagcgcga ggcacatctg 120
cggggggaat gtcacacttg catttacaac atgatgggaa agagagagaa aaaacccgga 180
gagttcggaa aggccaaggg aagcagagcc atttggttca tgtggctcgg agctcgcttt 240
ctggagttcg aggctctggg ttttctcaat gaagaccact ggcttggaag aaagaactca 300
ggaggaggtg tcgagggctt gggcctccaa aaactgggtt acatcctgcg tgaagttggc 360
acccggcctg ggggcaagat ctatgctgat gacacagctg gctgggacac ccgcatcacg 420
agagctgact tggaaaatga agctaaggtg cttgagttgc ttgatgggga acatcggcgt 480
cttgccaggg ccatcattga gctcacctat cgtcacaaag ttgtgaaagt gatgcgcccg 540
gctgctgatg gaagaaccgt catggatgtt atctccagag aagatcagag ggggagtgga 600
caagttgtca cctacgccct aaacactttc accaacctgg ccgtccagct ggtgaggatg 660
atggaagggg aanggagtga ttggcccaga tgatgtggag aaactcacaa aagggaaagg 720
acccaaagtc aggacctggc tgtttgagaa tggggaagaa agactcagcc gcatggctgt 780
cagtggagat gactgtgtgg taaagcccct ggacgatcgc tttgccacct cgctccactt 840
cctcaatgct atgtcaaann ntcgcaaaga catccaagag tggaaaccgt caactggatg 900
gtatgattgg cagcnggttc cattttgctc aaaccatttn nctgaattga tcatgaaana 960 nggaaga 967

<210> SEQ ID NO 34
<211> LENGTH: 955
<212> TYPE: DNA
<213> ORGANISM: West Nile virus
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (815)..(815)
<223> OTHER INFORMATION: a, c, t, g, unknown or other
<220> FEATURE:
<221> NAME/KEY: modified_base
<222> LOCATION: (874)..(876)
<223> OTHER INFORMATION: a, c, t, g, unknown or other
<220> FEATURE:

```
<221> NAME/KEY: modified_base
<222> LOCATION: (882)..(886)
<223> OTHER INFORMATION: a, c, t, g, unknown or other
<220> FEATURE:
<221> NAME/KEY: modified_base
<222> LOCATION: (903)..(905)
<223> OTHER INFORMATION: a, c, t, g, unknown or other
<220> FEATURE:
<221> NAME/KEY: modified_base
<222> LOCATION: (928)..(928)
<223> OTHER INFORMATION: a, c, t, g, unknown or other
<220> FEATURE:
<221> NAME/KEY: modified_base
<222> LOCATION: (938)..(938)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (947)..(947)
<223> OTHER INFORMATION: a, c, t, g, unknown or other

<400> SEQUENCE: 34
tctcncggat tccncgcacg agatgtattg ggtgagtcga gcttcaggca atgtggtaca      60
ttcagtgaat atgaccagcc aggtgctcct aggaagaatg gaaaaaagga cctggaaggg     120
accccaatac gaggaagatg taaacttggg aagtggaacc agggcggtgg gaaaccccct    180
gctcaactca gacaccagta aaatcaagaa caggattgaa cgactcaggc gtgagtacag    240
ttcgacgtgg caccacgatg agaaccaccc atatagaacc tggaactatc acggcagtta   300
tgatgtgaag cccacaggct ccgccagttc gctggtcaat ggagtggtca ggctcctctc    360
aaaaccatgg gacaccatca cgaatgttac caccatggcc atgactgaca ctactcccctt   420 cgggcagcag cgagtgttca agagaaggt ggacacgaaa gctcctgaac cgccagaagg      480
agtgaagtac gtgctcaacg agaccaccaa ctggttgtgg gcgttttgg ccagagaaaa     540 acgtcccaga atgtgctctc gagaggaatt cataagaaag gtcaacagca atgcagcttt    600
gggtgccatg tttgaagagc agaatcaatg gaggagcgcc agagaagcag ttgaagatcc    660
aaaattttgg gagatggtgg atgaggagcg cgaggcacat ctgcggggg aatgtcacac     720 ttgcatttac aacatgatgg gaaagagaga gaaaaaaccc ggagagttcg gaaaggccaa    780
gggaagcaga gccatttggt tcatgtggct cgganctcgc tttctggagt tcgaggctct   840
gggttttctc aatgaagacc actggcttgg aagnnnaact cnnnnngagg tgtcgagggc    900
ttnnnctcca aaaactgggt tacatccngc gtgaagtngc accngnctg ggggc          955

<210> SEQ ID NO 35
<211> LENGTH: 971
<212> TYPE: DNA
<213> ORGANISM: West Nile virus
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (59)..(61)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
```

<220> FEATURE:
<221> NAME/KEY: modified_base
<222> LOCATION: (137)..(139)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other

<400> SEQUENCE: 35

```
ttcgctngtc aatggagtng tcaggctcct ctcaaaacca tgggacacca tcacgaatnn      60
nccaccatgg ccatgactga cactactccc nttcgggcag cagcgagtgt tcaaagagaa     120
ggtggacacg aaagctnnng aaccgccaga aggagtgaag tacgtgctca acgagaccac     180
caactggttg tgggcgtttt tggccagaga aaaacgtccc agaatgtgct ctcgagagga     240
attcatnaga aaggtcaaca gcaatgcagc tttgggtgcc atgtttgaag agcagaatca     300
atggaggagc gccagagaag cagttgaaga tccaaaattt tgggagatgg tggatgagga     360
gcgcgaggca catctgcggg gggaatgtca cacttgcatt tacaacatga tgggaaagag     420
agagaaaaaa cccggagagt tcggaaaggc caagggaagc agagccattt ggttcatgtg     480
gctcggagct cgctttctgg agttcgaggc tctgggtttt ctcaatgaag accactggct     540
tggaagaaag aactcaggag gaggtgtcga gggcttgggc ctccaaaaac tgggttacat     600
cctgcgtgaa gttggcaccc ggcctggggg caagatctat gctgatgaca cagctggctg     660
ggacacccgc atcacgagag ctgacttgga aaatgaagct aaggtgcttg agttgcttga     720
tgggaacat cggcgtcttg ccagggccat cattgagctc acctatcgtc acaaagttgt      780
gaaagtgatg cgcccggctg ctgatggaag aaccgtcatg gatgttatct ccagagaaga     840
tcagaggggg agtggacaag ttgtcaccta cgccctaaac actttcacca acctggccgt     900
ccagctggtg aggatgatgg aaggggaagg agtgattggc ccagatgatg tggagaaact     960
cacaaagggg a                                                          971
```

<210> SEQ ID NO 36
<211> LENGTH: 971
<212> TYPE: DNA
<213> ORGANISM: West Nile virus
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (73)..(73)
<223> OTHER INFORMATION: a, c, t, g, unknown or other
<220> FEATURE:

<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (103)..(103)
<223> OTHER INFORMATION: a, c, t, g, unknown or other
<220> FEATURE:
<221> NAME/KEY: modified_base
<222> LOCATION: (157)..(157)
<223> OTHER INFORMATION: a, c, t, g, unknown or other
<220> FEATURE:
<221> NAME/KEY: modified_base
<222> LOCATION: (159)..(160)
<223> OTHER INFORMATION: a, c, t, g, unknown or other
<220> FEATURE:
<221> NAME/KEY: modified_base
<222> LOCATION: (970)..(970)
<223> OTHER INFORMATION: a, c, t, g, unknown or other

<400> SEQUENCE: 36

```
gggaccccaa tacnngaaga tgtaaacttg ggaagnnanc nngggcggtg ggaaaccnng    60
ntcaactcag acnccagtaa aatcaaganc aggattgaac gantcaggcg tgagtacagt   120
tcgacgtggc accacgatga gaaccaccca tatagancnn ggaactatca cggcagttat   180
gatgtgaagc ccacaggctc cgccagttcg ctggtcaatg gagtggtcag gctcctctca   240
aaaccatggg acaccatcac gaatgttacc accatggcca tgactgacac tactcccttc   300
gggcagcagc gagtgttcaa agagaaggtg gacacgaaag ctcctgaacc gccagaagga   360
gtgaagtacg tgctcaacga gaccaccaac tggttgtggg cgttttggc cagagaaaaa   420
cgtcccagaa tgtgctctcg agaggaattc ataagaaagg tcaacagcaa tgcagctttg   480
ggtgccatgt ttgaagagca gaatcaatgg aggagcgcca gagaagcagt tgaagatcca   540
aaatttggg agatggtgga tgaggagcgc gaggcacatc tgcggggga atgtcacact   600
tgcatttaca acatgatggg aaagagagag aaaaacccg gagagttcgg aaaggccaag   660
ggaagcagag ccatttggtt catgtggctc ggagctcgct ttctggagtt cgaggctctg   720
ggttttctca atgaagacca ctggcttgga agaaagaact caggaggagg tgtcgagggc   780
ttgggcctcc aaaaactggg ttacatcctg cgtgaagttg gcacccggcc tggggcaag   840
atctatgctg atgacacagc tggctgggac acccgcatca cgagagctga cttggaaaat   900
gaagctaagg tgcttgagtt gcttgatggg gaacatcggc gtcttgccag ggccatcatt   960
gagctcaccn a                                                        971
```

<210> SEQ ID NO 37
<211> LENGTH: 945
<212> TYPE: DNA
<213> ORGANISM: West Nile virus
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (673)..(673)
<223> OTHER INFORMATION: a, c, t, g, unknown or other
<220> FEATURE:
<221> NAME/KEY: modified_base
<222> LOCATION: (859)..(859)
<223> OTHER INFORMATION: a, c, t, g, unknown or other
<220> FEATURE:
<221> NAME/KEY: modified_base

```
<222> LOCATION: (884)..(884)
<223> OTHER INFORMATION: a, c, t, g, unknown or other
<220> FEATURE:
<221> NAME/KEY: modified_base
<222> LOCATION: (915)..(917)
<223> OTHER INFORMATION: a, c, t, g, unknown or other

<400> SEQUENCE: 37
cacagcaatg cagctttggg tgccntgttt gaagagcaga atcaatggag gagcgccaga      60
gaagcagttg aagatccaaa attttgggag atggtggatg aggagcgcga ggcacatctg     120
cgggggaat gtcacacttg catttacaac atgatgggaa agagagagaa aaaacccgga      180
gagttcggaa aggccaaggg aagcagagcc atttggttca tgtggctcgg agctcgcttt     240
ctggagttcg aggctctggg tttctcaat gaagatcact ggcttggaag aaagaactca      300
ggaggaggtg tcgagggctt gggcctccaa aaactgggtt acatcctgcg tgaagttggc     360
acccggcctg ggggcaagat ctatgctgat gacacagctg gctgggacac ccgcatcacg     420
agagctgact tggaaaatga agctaaggtg cttgagctgc ttgatgggga acatcggcgt     480
cttgccaggg ccatcattga gctcacctat cgtcacaaag ttgtgaaagt gatgcgcccg     540
gctgctgatg gaagaaccgt catggatgtt atctccagag aagatcagag ggggagtgga     600
caagttgtca cctacgcnct aaacactttc accaacctgg ccgtccagct ggtgaggatg     660
atggaagggg aaggagtga ttggcccaga tgatgtggag aaactcacaa aagggaaagg      720
acccaaagtc aggacctggc tgtttgagaa tggggaagaa agactcagcc gcatggctgt     780
cagtggagat gactgtgtgg taaagccccct ggacgatcgc tttgccacct cgctccactt    840
cctcaatgct atgtcaaang ttcgcaaaga catccaagag tggnaaccgt caactggatg     900
gtatgattgg cagcnnntcc attttgctca aaccatttca ctgaa                     945

<210> SEQ ID NO 38
<211> LENGTH: 1027
<212> TYPE: DNA
<213> ORGANISM: West Nile virus
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (841)..(841)
<223> OTHER INFORMATION: a, c, t, g, unknown or other
<220> FEATURE:
<221> NAME/KEY: modified_base
<222> LOCATION: (883)..(885)
<223> OTHER INFORMATION: a, c, t, g, unknown or other
<220> FEATURE:
<221> NAME/KEY: modified_base
<222> LOCATION: (887)..(887)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (950)..(950)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other
<220> FEATURE:
```

-continued

<221> NAME/KEY: modified_base
<222> LOCATION: (985)..(986)
<223> OTHER INFORMATION: a, c, t, g, unknown or other
<220> FEATURE:
<221> NAME/KEY: modified_base
<222> LOCATION: (991)..(992)
<223> OTHER INFORMATION: a, c, t, g, unknown or other
<220> FEATURE:
<221> NAME/KEY: modified_base
<222> LOCATION: (997)..(997)
<223> OTHER INFORMATION: a, c, t, g, unknown or other
<220> FEATURE:
<221> NAME/KEY: modified_base
<222> LOCATION: (1007)..(1007)
<223> OTHER INFORMATION: a, c, t, g, unknown or other
<220> FEATURE:
<221> NAME/KEY: modified_base
<222> LOCATION: (1013)..(1013)
<223> OTHER INFORMATION: a, c, t, g, unknown or other
<220> FEATURE:
<221> NAME/KEY: modified_base
<222> LOCATION: (1016)..(1018)
<223> OTHER INFORMATION: a, c, t, g, unknown or other
<220> FEATURE:
<221> NAME/KEY: modified_base
<222> LOCATION: (1024)..(1024)
<223> OTHER INFORMATION: a, c, t, g, unknown or other

<400> SEQUENCE: 38
tctcncggat tccncgcacg agatgtattg ggtgagtcga gcttcaggca atgtggtaca 60
ttcagtgaat atgaccagcc aggtgctcct aggaagaatg gaaaaaagga cctggaaggg 120
accccaatac gaggaagatg taaacttggg aagtggaacc agggcggtgg gaaaacccct 180
gctcaactca gacaccagta aaatcaagaa caggattgaa cgactcaggc gtgagtacag 240
ttcgacgtgg caccacgatg agaaccaccc atatagaacc tggaactatc acggcagtta 300
tgatgtgaag cccacaggct ccgccagttc gctggtcaat ggagtggtca ggctcctctc 360
aaaaccatgg gacaccatga cgaatgttac caccatggcc atgactgaca ctactccctt 420
cgggcagcag cgagtgttca aagagaaggt ggacacgaaa gctcctgaac cgccagaagg 480
agtgaagtac gtgctcaacg agaccaccaa ctggttgtgg gcgtttttgg ccagagaaaa 540
acgtcccaga atgtgctctc gagaggaatt cataagaaag gtcaacagca atgcagcttt 600
gggtgccatg tttgaagagc agaatcaatg gaggagcgcc agagaagcag ttgaagatcc 660
aaaattttgg gagatggtgg atgaggagcg cgaggcacat ctgcgggggg aatgtcacac 720
ttgcatttac aacatgatgg gaaagagaga gaaaaaaccc ggagagttcg gaaaggccaa 780
gggaagcaga gccatttggt tcatgtggct cggagctcgc tttctggagt tcgaggctct 840
nggttttctc aatgaagatc actggcttgg aagaaagaac tcnnnangag gtgtcgaggg 900
cttgggcctc caaaaactgg gttacatcct gcgtgaagtt ggcacccngn cctgggggca 960
agatctatgc tgatgacnca gctgnntggg nnacccncat cacgagngct ganttnnnaa 1020 atgnagc 1027

<210> SEQ ID NO 39
<211> LENGTH: 1019
<212> TYPE: DNA
<213> ORGANISM: West Nile virus
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other -continued

```
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (29)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(42)
<223> OTHER INFORMATION: a, c, t, g, unknown or other
<220> FEATURE:
<221> NAME/KEY: modified_base
<222> LOCATION: (44)..(47)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (94)..(94)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (105)..(108)
<223> OTHER INFORMATION: a, c, t, g, unknown or other
<220> FEATURE:
<221> NAME/KEY: modified_base
<222> LOCATION: (116)..(116)
<223> OTHER INFORMATION: a, c, t, g, unknown or other
<220> FEATURE:
<221> NAME/KEY: modified_base
<222> LOCATION: (118)..(118)
<223> OTHER INFORMATION: a, c, t, g, unknown or other
<220> FEATURE:
<221> NAME/KEY: modified_base
<222> LOCATION: (128)..(128)
<223> OTHER INFORMATION: a, c, t, g, unknown or other
<220> FEATURE:
<221> NAME/KEY: modified_base
<222> LOCATION: (139)..(139)
<223> OTHER INFORMATION: a, c, t, g, unknown or other
<220> FEATURE:
<221> NAME/KEY: modified_base
<222> LOCATION: (186)..(187)
```

<223> OTHER INFORMATION: a, c, t, g, unknown or other
<220> FEATURE:
<221> NAME/KEY: modified_base
<222> LOCATION: (295)..(295)
<223> OTHER INFORMATION: a, c, t, g, unknown or other
<220> FEATURE:
<221> NAME/KEY: modified_base
<222> LOCATION: (920)..(920)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other

<400> SEQUENCE: 39

```
ggaactatcn cggnagtnat gatgtgaann nacnggntnn nncnnnntcg ctgntcaatg    60
nagtgntcag gctcntntca aaaccccntgg gacnccatcn cgaannnncc accatngncc   120
atgactgnca ctactcccnt tcgggcagca gcgagtgttc aaagagaagg tggacacgaa   180
agctcnngaa ccgccagaag gagtgaagta cgtgctcaac gagaccacca actggttgtg   240
ggcgttttg gccagagaaa aacgtcccag aatgtgctct cgagaggaat tcatnagaaa    300
ggtcaacagc aatgcagctt tgggtgccat gtttgaagag cagaatcaat ggaggagcgc   360
cagagaagca gttgaagatc caaaattttg ggagatggtg gatgaggagc gcgaggcaca   420
tctgcggggg gaatgtcaca cttgcattta caacatgatg ggaaagagag agaaaaaacc   480
cggagagttc ggaaaggcca agggaagcag agccatttgg ttcatgtggc tcggagctcg   540
ctttctggag ttcgaggctc tgggttttct caatgaagat cactggcttg aagaaagaa    600
ctcaggagga ggtgtcgagg gcttgggcct ccaaaaactg ggttacatcc tgcgtgaagt   660
tggcacccgg cctgggggca agatctatgc tgatgacaca gctggctggg acacccgcat   720
cacgagagct gacttggaaa atgaagctaa ggtgcttgag ctgcttgatg ggaacatcg    780
gcgtcttgcc agggccatca ttgagctcac ctatcgtcac aaagttgtga agtgatgcg    840
cccggctgct gatggaagaa ccgtcatgga tgttatctcc agagaagatc agaggggag    900
tggacaagtt gtcacctacn cnctaaacac tttcaccaac ctggccgtcc agctggtgag   960
gatgatggaa ggggaaggag tgattggccc agatgatgtg gagaaactca caaaaggga   1019
```

<210> SEQ ID NO 40
<211> LENGTH: 1015
<212> TYPE: DNA
<213> ORGANISM: West Nile virus
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (34)..(38)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (73)..(73)
<223> OTHER INFORMATION: a, c, t, g, unknown or other
<220> FEATURE:
<221> NAME/KEY: modified_base
<222> LOCATION: (83)..(84)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (104)..(105)
<223> OTHER INFORMATION: a, c, t, g, unknown or other
<220> FEATURE:
<221> NAME/KEY: modified_base
<222> LOCATION: (119)..(119)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (491)..(496)
<223> OTHER INFORMATION: a, c, t, g, unknown or other

<400> SEQUENCE: 40
tgncancnng ngctcnnngn ngaatgnaaa aaannnnngg nangggaccc cnntacgagg      60
aagatgtaaa ctngggaagt ggnnccnggg cggtgggaaa accnngctca actcagacnc     120
cagtaaaatc aagaacagga ttgaacgact caggcgtgag tacagttcga cgtggcacca    180
cgatgagaac cacccatata gaacctggaa ctatcacggc agttatgatg tgaagcccac    240
aggntccgcc agttcgctgg tcaatggagt ggtcaggctc ctctcaaaac catgggacac    300
catcacgaat gttaccacca tggccatgac tgacactact cccttcgggc agcagcgagt    360
gttcaaagag aaggtggaca cgaaagctcc tgaaccgcca gaaggagtga agtacgtgct    420
caacgagacc accaactggt tgtgggcgtt tttggccaga gaaaaacgtc ccagaatgtg    480
ctctcgagag nnnnnnataa gaaaggtcaa cagcaatgca gctttgggtg ccatgtttga    540
agagcagaat caatggagga gcgccagaga agcagttgaa gatccaaaat tttgggagat    600
ggtggatgag gagcgcgagg cacatctgcg gggggaatgt cacacttgca tttacaacat    660
gatgggaaag agagagaaaa aacccggaga gttcggaaag gccaagggaa gcagagccat    720
ttggttcatg tggctcggag ctcgctttct ggagttcgag gctctgggtt ttctcaatga    780
agatcactgg cttggaagaa agaactcagg aggaggtgtc gagggcttgg gcctccaaaa    840

-continued

```
actgggttac atcctgcgtg aagttggcac ccggcctggg ggcaagatct atgctgatga      900
cacagctggc tgggacaccc gcatcacgag agctgacttg gaaaatgaag ctaaggtgct      960
tgagctgctt gatggggaac atcggcgtct tgccagggcc atcattgagc tcacc         1015
```